United States Patent
Tong et al.

(10) Patent No.: US 7,320,986 B2
(45) Date of Patent: Jan. 22, 2008

(54) FUSED TRI AND TETRA-CYCLIC PYRAZOLE KINASE INHIBITORS

(75) Inventors: Yunsong Tong, Grayslake, IL (US); Akiyo K. Claiborne, Mundelein, IL (US); Gaoquan Li, Park City, IL (US); Nan-Horng Lin, Vernon Hills, IL (US); Hing L. Sham, Vernon Hills, IL (US); Thomas J. Sowin, Wadsworth, IL (US); Zhi-Fu Tao, Gurnee, IL (US)

(73) Assignee: Abbott Labortories, Abbott Park, IL (US)

( * ) Notice: Subject to any disclaimer, the term of this patent is extended or adjusted under 35 U.S.C. 154(b) by 514 days.

(21) Appl. No.: 10/792,564

(22) Filed: Mar. 3, 2004

(65) Prior Publication Data

US 2004/0259904 A1 Dec. 23, 2004

Related U.S. Application Data

(60) Provisional application No. 60/452,702, filed on Mar. 7, 2003.

(51) Int. Cl.
*A61K 31/4745* (2006.01)
*A61K 31/4162* (2006.01)
*C07D 487/14* (2006.01)

(52) U.S. Cl. .................. 514/292; 514/406; 546/82; 548/359.5

(58) Field of Classification Search ........... 514/292, 514/406; 548/359.5; 546/82
See application file for complete search history.

(56) References Cited

U.S. PATENT DOCUMENTS

| 2,969,371 | A |   | 1/1961  | Braun et al.    |         |
|-----------|---|---|---------|-----------------|---------|
| 2,969,373 | A |   | 1/1961  | Loev et al.     |         |
| 3,004,983 | A |   | 10/1961 | Loev            |         |
| 3,843,665 | A | * | 10/1974 | Coombs et al.   | 546/275.7 |
| 3,843,666 | A |   | 10/1974 | Coombs et al.   |         |
| 3,932,430 | A | * | 1/1976  | Habeck et al.   | 546/275.7 |
| 6,291,504 | B1|   | 9/2001  | Nugiel et al.   | 514/403 |
| 6,297,238 | B1|   | 10/2001 | Doyle et al.    | 514/232.8 |
| 6,407,103 | B2|   | 6/2002  | Nugiel et al.   | 514/232.8 |
| 6,462,036 | B1| * | 10/2002 | Doyle et al.    | 514/218 |
| 2001/0027195 | A1 | | 10/2001 | Nugiel et al. | 514/232.8 |
| 2002/0183334 | A1 | | 12/2002 | Bacon et al.  |         |

FOREIGN PATENT DOCUMENTS

| JP | 60130521 | 7/1985 |
|----|----------|--------|
| WO | 9917769  | 4/1999 |
| WO | 9917770  | 4/1999 |
| WO | 99/54308 | 10/1999 |
| WO | 00/27822 | 5/2000 |
| WO | 0027822  | 5/2000 |
| WO | 0059901  | 10/2000 |
| WO | 01/87846 | 11/2001 |
| WO | 0187846  | 11/2001 |
| WO | 02/44174 | 6/2002 |
| WO | 02/46182 | 6/2002 |
| WO | 02/070494 | 9/2002 |
| WO | 03/004491 | 1/2003 |
| WO | 03/007883 | 1/2003 |
| WO | 03/033499 | 4/2003 |
| WO | 03/070236 | 8/2003 |

OTHER PUBLICATIONS

Nugiel et al., "Indenopyrazoles as novel cyclin dependent kinase (CDK) inhibitors," J. Med. Chem. 44:1334-1336 (2001).

Nugiel et al., "Synthesis and evaluation of indenopyrazoles as cyclin-dependent kinase inhibitors. 2. Probing the indeno ring substituent pattern," J. Med. Chem. 45:5224-5232 (2002).

Yue et al., "Synthesis and evaluation of indenopyrazoles as cyclin-dependent kinase inhibitors. 3. Structure activity relationships at $C3^{1,2}$," J. Med. Chem. 45:5233-5248 (2002).

Braun, et al., Journal of Organic Chemistry, 24, 648-650, (1959).

Braun et al, Journal of the American Chemical Society, 80, 4919-4921 (1958).

Nishida Seigj, Patent Abstracts of Japan, 009(287), C-314 (1985).

* cited by examiner

*Primary Examiner*—Kamal A. Saeed
(74) *Attorney, Agent, or Firm*—Patricia Coleman James

(57) ABSTRACT

Compounds having the formula (I)

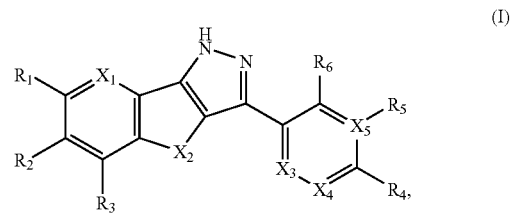

are useful for inhibiting protein kinases. Also disclosed are methods of making the compounds, compositions containing the compounds, and methods of treatment using the compounds.

4 Claims, No Drawings

FUSED TRI AND TETRA-CYCLIC PYRAZOLE KINASE INHIBITORS

This Application claims benefit under 35 U.S.C. § 119(e) of U.S. provisional Application No. 60/452,702, filed Mar. 7, 2003.

TECHNICAL FIELD

The present invention relates to fused pyrazoles, to methods of making the compounds, to compositions containing the compounds, and to methods of treatment using the compounds.

BACKGROUND OF THE INVENTION

Protein kinases are important in the progression of many disease states that are induced by the inappropriate proliferation of cells. These kinases are often found to be upregulated in many hyperproliferative states such as cancer. These kinases may also be important in cell signaling, where their inappropriate activation induces cells to proliferate (e.g., EGFR, ERBB2, VEGFR, FGFR, PDGFR, c-Met, IGF-1R, RET, TIE2). Alternatively, kinases may be involved in signal transduction within cells (e.g., c-Src, PKC, Akt, PKA, c-Abl, PDK-1) where these signal transduction genes are recognized proto-oncogenes. Many of these kinases control cell cycle progression near the G1-S transition (e.g., Cdk2, Cdk4), at the G2-M transition (e.g., Wee1, Myt1, Chk1, Cdc2) or at the spindle checkpoint (Plk, Auroral or 2, Bub1 or 3). Furthermore, kinases are intimately linked to the DNA damage response (e.g., ATM, ATR, Chk1, Chk2). Deregulation of these cellular functions: cell signaling, signal transduction, cell cycle control, and DNA repair, are all hallmarks of hyperproliferative diseases, particularly cancer. Therefore, pharmacological modulation of one or more kinases would be useful in slowing or stopping diseases that are induced by the inappropriate proliferation of cells such as cancer.

SUMMARY OF THE INVENTION

In the principle embodiment, the present invention relates to compounds of formula (I)

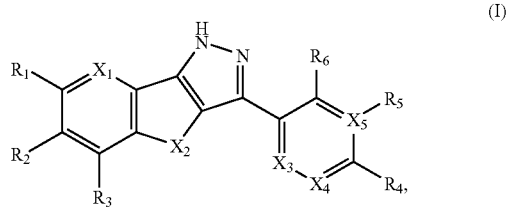

(I)

or a pharmaceutically acceptable salt, ester, amide, or prodrug thereof, wherein $R_1$ and $R_2$ are independently selected from the group consisting of hydrogen, alkenyl, alkenyloxy, alkoxy, alkoxyalkoxy, alkoxyalkoxyalkynyl, alkoxyalkyl, alkoxycarbonyl, alkoxycarbonylalkyl, alkoxysulfonyl, alkyl, alkylcarbonyl, alkylcarbonyloxy, alkylsulfinyl, alkylsulfonyl, alkylthio, alkylthioalkyl, alkynyl, carboxy, carboxyalkyl, cyano, cycloalkenylalkoxy, cycloalkylalkoxy, cycloalkylalkyl, cycloalkylcarbonyl, cycloalkyloxy, formyl, haloalkoxy, haloalkoxyalkynyl, haloalkyl, halogen, heteroarylalkoxy, heteroarylalkoxyalkoxy, heteroarylalkyl, heteroarylalkynyl, heteroaryloxyalkyl, heterocycle, heterocyclealkoxy, heterocyclealkyl, heterocyclecarbonyl, heterocycleoxy, hydroxy, hydroxyalkoxy, hydroxyalkyl, hydroxyalkynyl, hydroxysulfonyl, hydroxysulfonylalkyl, mercapto, mercaptoalkyl, nitro, —$NR_AR_B$, $(NR_AR_B)$alkoxy, $(NR_AR_B)$alkyl, $(NR_AR_B)$alkynyl, $(NR_AR_B)$carbonyl, $(NR_AR_B)$carbonylalkoxy, $(NR_AR_B)$carbonylalkyl, and $(NR_GR_H)$alkoxy; or $R_1$ and $R_2$ together with the carbon atoms to which they are attached form a 5, 6, 7, or 8-membered nonaromatic ring wherein the ring contains 0, 1, or 2 heteroatoms selected from the group consisting of O, $N(R_C)$, and $N(R_D)$, wherein the nonaromatic ring is substituted with 0, 1, or 2 substituents selected from the group consisting of alkyl and hydroxy;

$R_3$ is selected from the group consisting of hydrogen, alkenyl, alkenyloxy, alkoxy, alkoxyalkyl, alkoxycarbonyl, alkoxycarbonylalkyl, alkyl, alkylcarbonyl, alkylthio, alkylthioalkyl, alkynyl, carboxy, carboxyalkyl, cyano, formyl, haloalkoxy, haloalkyl, halogen, hydroxy, hydroxyalkyl, mercapto, nitro, —$NR_ER_F$, $(NR_ER_F)$alkoxy $(NR_ER_F)$alkyl, $(NR_ER_F)$carbonyl, and $(NR_ER_F)$carbonylalkyl;

$R_4$ is selected from the group consisting of hydrogen, alkoxycarbonyl, alkylcarbonylalkoxy, aryl, arylalkoxy, arylalkyl, aryloxy, carboxy, cyano, halogen, heteroaryl, heteroarylalkoxy, heteroarylalkyl, heteroaryloxy, heterocycle, heterocyclealkoxy, heterocyclealkyl, heterocycleoxy, hydroxy, —$NR_ER_F$, and $(NR_ER_F)$carbonyl;

$R_5$ is absent or selected from the group consisting of hydrogen, alkoxycarbonyl, carboxy, halogen, heteroaryl, hydroxy, nitro, —$NR_ER_F$, and $(NR_ER_F)$carbonyl; or $R_4$ and $R_5$, together with the atoms to which they are attached, form a phenyl ring optionally substituted with 1, 2, 3, or 4 substituents independently selected from the group consisting of alkenyl, alkoxy, alkoxyalkyl, alkoxycarbonyl, alkoxycarbonylalkyl, alkoxysulfonyl, alkyl, alkylcarbonyl, alkylcarbonyloxy, alkylsulfinyl, alkylsulfonyl, alkylthio, alkylthioalkyl, alkynyl, carboxy, carboxyalkyl, cyano, formyl, haloalkoxy, haloalkyl, halogen, hydroxy, hydroxyalkyl, mercapto, nitro, —$NR_GR_H$, $(NR_GR_H)$alkoxy, $(NR_GR_H)$alkyl, $(NR_GR_H)$carbonyl, and $(NR_GR_H)$sulfonyl; or $R_4$ and $R_5$, together with the atoms to which they are attached, form a heterocycle optionally substituted with 1, 2, or 3 substituents independently selected from the group consisting of alkenyl, alkoxy, alkoxyalkyl, alkoxycarbonyl, alkyl, alkylcarbonyl, alkylcarbonyloxy, alkylthio, alkynyl, carboxy, cyano, formyl, haloalkoxy, haloalkyl, halogen, hydroxy, hydroxyalkyl, mercapto, nitro, oxo, —$NR_GR_H$, $(NR_GR_H)$alkoxy, $(NR_GR_H)$alkyl, and $(NR_GR_H)$carbonyl;

provided that when $R_5$ is hydrogen, $R_4$ is other than hydrogen;

$R_6$ is selected from the group consisting of hydrogen, lower alkoxy, lower alkyl, halogen, hydroxy, and —$NR_ER_F$;

$R_A$ and $R_B$ are independently selected from the group consisting of hydrogen, alkenyl, alkoxyalkyl, alkoxyalkylcarbonyl, alkoxycarbonyl, alkoxycarbonylalkyl, alkoxycarbonylalkylcarbonyl, alkoxysulfonyl, alkoxysulfonylalkyl, alkoxysulfonylalkylcarbonyl, alkyl, alkylcarbonyl, alkynyl, aryl, carboxyalkyl, carboxyalkylcarbonyl, cyanoalkyl, cycloalkyl, cycloalkylalkyl, cycloalkylalkylcarbonyl, cycloalkylcarbonyl, cycloalkylcarbonylalkyl, cycloalkylcarbonylalkylcarbonyl, heteroaryl, heteroarylalkyl, heterocycle, heterocyclealkyl, heterocyclealkylcarbonyl, heterocyclecarbonyl, heterocyclecarbonylalkyl, heterocyclecarbonylalkylcarbonyl, hydroxyalkyl, hydroxyalkylcarbonyl, hydroxysulfonyl, hydroxysulfonylalkyl, hydroxysulfonylalkylcarbonyl, $(NR_ER_F)$alkyl, $(NR_ER_F)$alkylcarbonyl, $(NR_ER_F)$carbonyl, (NR_ER_F)carbonylalkyl, (NR_ER_F)carbonylalkylcarbonyl, (NR_ER_F)sulfonyl, (NR_ER_F)sulfonylalkyl, and (NR_ER_F)sulfonylalkylcarbonyl;

R_C and R_D are independently selected from the group consisting of hydrogen, alkoxycarbonyl, alkyl, and alkylcarbonyl;

R_E and R_F are independently selected from the group consisting of hydrogen, alkyl, alkylcarbonyl, cycloalkyl, heteroarylalkyl, and hydroxyalkyl;

X_1, X_3, and X_4 are independently selected from the group consisting of CH and N;

X_2 is selected from the group consisting of CH(R_7), C(R_7)(R_8), C=O, N(R_8);

X_5 is selected from the group consisting of C and N;

R_7 is selected from the group consisting of hydrogen, alkoxy, alkyl, hydroxy, lower alkoxy, lower alkyl, and hydroxyalkyl; and R_8 is selected from the group consisting of hydrogen, alkoxycarbonyl, alkyl, alkylcarbonyl, and hydroxyalkyl.

In another embodiment, the present invention relates to pharmaceutical compositions comprising a compound of formula (I), or a therapeutically acceptable salt thereof, in combination with a therapeutically acceptable carrier.

In another embodiment, the present invention relates to a method for inhibiting protein kinases in a patient in recognized need of such treatment comprising administering to the patient a therapeutically acceptable amount of a compound of formula (I), or a therapeutically acceptable salt thereof.

In another embodiment, the present invention relates to a method for treating cancer in a patient in recognized need of such treatment comprising administering to the patient a therapeutically acceptable amount of a compound of formula (I), or a therapeutically acceptable salt thereof.

DETAILED DESCRIPTION OF THE INVENTION

In the principle emobidment, the present invention relates to compounds of formula (I)

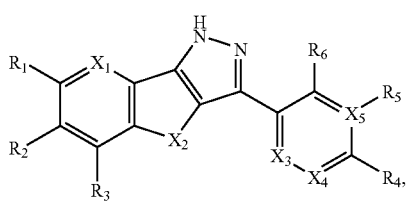

or a pharmaceutically acceptable salt, ester, amide, or prodrug thereof, wherein R_1 and R_2 are independently selected from the group consisting of hydrogen, alkenyl, alkenyloxy, alkoxy, alkoxyalkoxy, alkoxyalkoxyalkynyl, alkoxyalkyl, alkoxycarbonyl, alkoxycarbonylalkyl, alkoxysulfonyl, alkyl, alkylcarbonyl, alkylcarbonyloxy, alkylsulfinyl, alkylsulfonyl, alkylthio, alkylthioalkyl, alkynyl, carboxy, carboxyalkyl, cyano, cycloalkenylalkoxy, cycloalkylalkoxy, cycloalkylalkyl, cycloalkylcarbonyl, cycloalkyloxy, formyl, haloalkoxy, haloalkoxyalkynyl, haloalkyl, halogen, heteroarylalkoxy, heteroarylalkoxyalkoxy, heteroarylalkyl, heteroarylalkynyl, heteroaryloxyalkyl, heterocycle, heterocyclealkoxy, heterocyclealkyl, heterocyclecarbonyl, heterocycleoxy, hydroxy, hydroxyalkoxy, hydroxyalkyl, hydroxyalkynyl, hydroxysulfonyl, hydroxysulfonylalkyl, mercapto, mercaptoalkyl, nitro, —NR_AR_B, (NR_AR_B)alkoxy, (NR_AR_B)alkyl, (NR_AR_B)alkynyl, (NR_AR_B)carbonyl, (NR_AR_B)carbonylalkoxy, (NR_AR_B)carbonylalkyl, and (NR_GR_H)alkoxy; or R_1 and R_2 together with the carbon atoms to which they are attached form a 5, 6, 7, or 8 -membered nonaromatic ring wherein the ring contains 0, 1, or 2 heteroatoms selected from the group consisting of O, N(R_C), and N(R_D), wherein the nonaromatic ring is substituted with 0, 1, or 2 substituents selected from the group consisting of alkyl and hydroxy;

R_3 is selected from the group consisting of hydrogen, alkenyl, alkenyloxy, alkoxy, alkoxyalkyl, alkoxycarbonyl, alkoxycarbonylalkyl, alkyl, alkylcarbonyl, alkylthio, alkylthioalkyl, alkynyl, carboxy, carboxyalkyl, cyano, formyl, haloalkoxy, haloalkyl, halogen, hydroxy, hydroxyalkyl, mercapto, nitro, —NR_ER_F, (NR_ER_F)alkoxy (NR_ER_F)alkyl, (NR_ER_F)carbonyl, and (NR_ER_F)carbonylalkyl;

R_4 is selected from the group consisting of hydrogen, alkoxycarbonyl, alkylcarbonylalkoxy, aryl, arylalkoxy, arylalkyl, aryloxy, carboxy, cyano, halogen, heteroaryl, heteroarylalkoxy, heteroarylalkyl, heteroaryloxy, heterocycle, heterocyclealkoxy, heterocyclealkyl, heterocycleoxy, hydroxy, —NR_ER_F, and (NR_ER_F)carbonyl;

R_5 is absent or selected from the group consisting of hydrogen, alkoxycarbonyl, carboxy, halogen, heteroaryl, hydroxy, nitro, —NR_ER_F, and (NR_ER_F)carbonyl; or R_4 and R_5, together with the atoms to which they are attached, form a phenyl ring optionally substituted with 1, 2, 3, or 4 substituents independently selected from the group consisting of alkenyl, alkoxy, alkoxyalkyl, alkoxycarbonyl, alkoxycarbonylalkyl, alkoxysulfonyl, alkyl, alkylcarbonyl, alkylcarbonyloxy, alkylsulfinyl, alkylsulfonyl, alkylthio, alkylthioalkyl, alkynyl, carboxy, carboxyalkyl, cyano, formyl, haloalkoxy, haloalkyl, halogen, hydroxy, hydroxyalkyl, mercapto, nitro, —NR_GR_H, (NR_GR_H)alkoxy, (NR_GR_H)alkyl, (NR_GR_H)carbonyl, and (NR_GR_H)sulfonyl; or R_4 and R_5, together with the atoms to which they are attached, form a heterocycle optionally substituted with 1, 2, or 3 substituents independently selected from the group consisting of alkenyl, alkoxy, alkoxyalkyl, alkoxycarbonyl, alkyl, alkylcarbonyl, alkylcarbonyloxy, alkylthio, alkynyl, carboxy, cyano, formyl, haloalkoxy, haloalkyl, halogen, hydroxy, hydroxyalkyl, mercapto, nitro, oxo, —NR_GR_H, (NR_GR_H)alkoxy, (NR_GR_H)alkyl, and (NR_GR_H)carbonyl;

provided that when R_5 is hydrogen, R_4 is other than hydrogen;

R_6 is selected from the group consisting of hydrogen, lower alkoxy, lower alkyl, halogen, hydroxy, and —NR_ER_F;

R_A and R_B are independently selected from the group consisting of hydrogen, alkenyl, alkoxyalkyl, alkoxyalkylcarbonyl, alkoxycarbonyl, alkoxycarbonylalkyl, alkoxycarbonylalkylcarbonyl, alkoxysulfonyl, alkoxysulfonylalkyl, alkoxysulfonylalkylcarbonyl, alkyl, alkylcarbonyl, alkynyl, aryl, carboxyalkyl, carboxyalkylcarbonyl, cycloalkyl, cycloalkylalkyl, cycloalkylalkylcarbonyl, cycloalkylcarbonyl, cycloalkylcarbonylalkyl, cycloalkylcarbonylalkylcarbonyl, heteroaryl, heteroarylalkyl, heterocycle, heterocyclealkyl, heterocyclealkylcarbonyl, heterocyclecarbonyl, heterocyclecarbonylalkyl, heterocyclecarbonylalkylcarbonyl, hydroxyalkyl, hydroxyalkylcarbonyl, hydroxysulfonyl, hydroxysulfonylalkyl, hydroxysulfonylalkylcarbonyl, (NR_ER_F)alkyl, (NR_ER_F)alkylcarbonyl, (NR_ER_F)carbonyl, (NR_ER_F)carbonylalkyl, (NR_ER_F)carbonylalkylcarbonyl, (NR_ER_F)sulfonyl, (NR_ER_F)sulfonylalkyl, and (NR_ER_F)sulfonylalkylcarbonyl;

$R_C$ and $R_D$ are independently selected from the group consisting of hydrogen, alkoxycarbonyl, alkyl, and alkylcarbonyl;

$R_E$ and $R_F$ are independently selected from the group consisting of hydrogen, alkyl, alkylcarbonyl, cycloalkyl, heteroarylalkyl, and hydroxyalkyl;

$X_1$, $X_3$, and $X_4$ are independently selected from the group consisting of CH and N;

$X_2$ is selected from the group consisting of $CH(R_7)$, $C(R_7)(R_8)$, C=O, $N(R_8)$;

$X_5$ is selected from the group consisting of C and N;

$R_7$ is selected from the group consisting of hydrogen, alkoxy, alkyl, hydroxy, lower alkoxy, lower alkyl, and hydroxyalkyl; and $R_8$ is selected from the group consisting of hydrogen, alkoxycarbonyl, alkyl, alkylcarbonyl, and hydroxyalkyl.

In another embodiment, the present invention relates to a compound of formula (I) wherein $X_1$, $X_3$, and $X_4$ are CH; $X_2$ is $CH(R_7)$; $X_5$ is C; $R_1$ and $R_2$ are independently selected from the group consisting of hydrogen, alkenyloxy, alkoxy, alkoxyalkyl, heterocyclealkyl, hydroxy, hydroxyalkyl, $(NR_AR_B)$alkyl, and $(NR_AR_B)$carbonyl; $R_3$ is hydrogen; $R_4$ is selected from the group consisting of hydrogen, alkoxycarbonyl, aryl, carboxy, cyano, heteroaryl, hydroxy, —$NR_ER_F$, and $(NR_ER_F)$carbonyl; $R_5$ is selected from the group consisting of hydrogen and —$NR_ER_F$; $R_6$ is hydrogen; $R_7$ is hydrogen; $R_A$ is selected from the group consisting of hydrogen and alkyl; $R_B$ is selected from the group consisting of hydrogen, alkyl, cycloalkyl, heteroarylalkyl, heterocycle, and hydroxyalkyl; $R_E$ is selected from the group consisting of hydrogen and alkyl; and $R_F$ is selected from the group consisting of hydrogen, alkyl, and alkylcarbonyl.

In another embodiment, the present invention relates to a compound of formula (I) wherein $X_1$, $X_3$, and $X_4$ are CH; $X_2$ is $CH(R_7)$; $X_5$ is C; $R_1$ and $R_2$ are independently selected from the group consisting of hydrogen, alkenyloxy, alkoxy, alkoxyalkyl, hydroxy, hydroxyalkyl, $(NR_AR_B)$alkyl, $(NR_AR_B)$carbonyl, and heterocyclealkyl, wherein the heterocycle of heterocyclealkyl is selected from the group consisting of 4-morpholinyl and 4-hydroxy-1-piperidinyl; $R_3$ is hydrogen; $R_4$ is selected from the group consisting of hydrogen, alkoxycarbonyl, carboxy, cyano, heteroaryl, hydroxy, —$NR_ER_F$, $(NR_ER_F)$carbonyl, and aryl, wherein the aryl is phenyl substituted with 1, 2, or 3 substituents selected from the group consisting of alkoxy, formyl, halogen, hydroxy, hydroxyalkyl, and —$NR_GR_H$; $R_5$ is selected from the group consisting of hydrogen and —$NR_ER_F$; $R_6$ is hydrogen; $R_7$ is hydrogen; $R_A$ is selected from the group consisting of hydrogen and alkyl; $R_B$ is selected from the group consisting of hydrogen, alkyl, hydroxyalkyl, and cycloalkyl, wherein the cycloalkyl is cyclohexyl substituted with 1 substituent selected from the group consisting of alkyl and hydroxy; $R_E$ is selected from the group consisting of hydrogen and alkyl; and $R_F$ is selected from the group consisting of hydrogen, alkyl, and alkylcarbonyl.

In another embodiment, the present invention relates to a compound of formula (I) wherein $X_1$, $X_3$, and $X_4$ are CH; $X_2$ is $CH(R_7)$; $X_5$ is C; $R_1$, $R_3$, $R_5$, and $R_6$ are hydrogen; $R_2$ is selected from the group consisting of alkenyloxy, alkoxyalkyl, hydroxy, hydroxyalkyl, $(NR_AR_B)$alkyl, $(NR_AR_B)$carbonyl, and heterocyclealkyl, wherein the heterocycle of heterocyclealkyl is selected from the group consisting of 4-morpholinyl and 4-hydroxy-1-piperidinyl; $R_4$ is selected from the group consisting of alkoxycarbonyl, carboxy, cyano, hydroxy, and $(NR_ER_F)$carbonyl; $R_7$ is hydrogen; $R_A$ is selected from the group consisting of alkyl, hydroxyalkyl, and cycloalkyl, wherein the cycloalkyl is cyclohexyl substituted with 1 substituent selected from the group consisting of alkyl and hydroxy; and $R_B$, $R_E$ and $R_F$ are hydrogen.

In another embodiment, the present invention relates to a compound of formula (I) wherein $X_1$, $X_3$, and $X_4$ are CH; $X_2$ is $CH(R_7)$; $X_5$ is C; $R_1$, $R_3$, $R_5$, and $R_6$ are hydrogen; $R_2$ is selected from the group consisting of hydrogen, alkenyloxy, alkoxyalkyl, hydroxy, hydroxyalkyl, $(NR_AR_B)$alkyl, $(NR_AR_B)$carbonyl, and heterocyclealkyl, wherein the heterocycle of heterocyclealkyl is selected from the group consisting of 4-morpholinyl and 4-hydroxy-1-piperidinyl; $R_4$ is aryl wherein the aryl is phenyl substituted with 1, 2, or 3 substituents selected from the group consisting of alkoxy, formyl, halogen, hydroxy, hydroxyalkyl, and —$NR_GR_H$; $R_7$ is hydrogen; $R_A$ is selected from the group consisting of alkyl, hydroxyalkyl, and cycloalkyl, wherein the cycloalkyl is cyclohexyl substituted with 1 substituent selected from the group consisting of alkyl and hydroxy; and $R_B$, $R_E$, and $R_F$ are hydrogen.

In another embodiment, the present invention relates to a compound of formula (I) wherein $X_1$, $X_3$, and $X_4$ are CH; $X_2$ is $CH(R_7)$; $X_5$ is C; $R_1$, $R_3$, $R_5$, and $R_6$ are hydrogen; $R_2$ is selected from the group consisting of hydrogen, alkenyloxy, alkoxyalkyl, hydroxy, hydroxyalkyl, $(NR_AR_B)$alkyl, $(NR_AR_B)$carbonyl, and heterocyclealkyl, wherein the heterocycle of heterocyclealkyl is selected from the group consisting of 4-morpholinyl and 4-hydroxy-1-piperidinyl; $R_4$ is heteroaryl; $R_7$ is hydrogen; $R_A$ is selected from the group consisting of alkyl, hydroxyalkyl, and cycloalkyl, wherein the cycloalkyl is cyclohexyl substituted with 1 substituent selected from the group consisting of alkyl and hydroxy; and $R_B$ is selected from the group consisting of hydrogen and alkyl.

In another embodiment, the present invention relates to a compound of formula (I) wherein $X_1$, $X_3$, and $X_4$ are CH; $X_2$ is $CH(R_7)$; $X_5$ is C; $R_1$, $R_3$, $R_5$, and $R_6$ are hydrogen; $R_2$ is alkenyloxy; $R_4$ is heteroaryl wherein the heteroaryl is tetraazolyl; and $R_7$ is hydrogen.

In another embodiment, the present invention relates to a compound of formula (I) wherein $X_1$, $X_3$, and $X_4$ are CH; $X_2$ is $CH(R_7)$; $X_5$ is C; $R_1$, $R_3$, and $R_6$ are hydrogen; $R_2$ is selected from the group consisting of alkenyloxy, alkoxyalkyl, hydroxy, hydroxyalkyl, $(NR_AR_B)$alkyl, $(NR_AR_B)$carbonyl, and heterocyclealkyl, wherein the heterocycle of heterocyclealkyl is selected from the group consisting of 4-morpholinyl and 4-hydroxy-1-piperidinyl; $R_4$ is selected from the group consisting of hydrogen, carboxy, and cyano; $R_5$ is selected from the group consisting of alkoxycarbonyl, carboxy, hydroxy, hydroxyalkyl, $NR_ER_F$, and $(NR_ER_F)$carbonyl; $R_7$ is hydrogen; $R_A$ is selected from the group consisting of alkyl, hydroxyalkyl, and cycloalkyl, wherein the cycloalkyl is cyclohexyl substituted with 1 substituent selected from the group consisting of alkyl and hydroxy; $R_B$ is selected from the group consisting of hydrogen and alkyl; $R_E$ is selected from the group consisting of hydrogen and alkyl; and $R_F$ is selected from the group consisting of hydrogen, alkyl, and alkylcarbonyl.

In another embodiment, the present invention relates to a compound of formula (I) wherein $X_1$, $X_3$, and $X_4$ are CH; $X_2$ is $CH(R_7)$; $X_5$ is C; $R_1$, $R_3$, and $R_6$ are hydrogen; $R_2$ is selected from the group consisting of alkenyloxy, alkoxyalkyl, hydroxy, hydroxyalkyl, $(NR_AR_B)$alkyl, $(NR_AR_B)$carbonyl, and heterocyclealkyl, wherein the heterocycle of heterocyclealkyl is selected from the group consisting of 4-morpholinyl and 4-hydroxy-1-piperidinyl; $R_4$ is selected from the group consisting of hydrogen, carboxy, and cyano; $R_5$ is —$NR_ER_F$; $R_A$ is selected from the group consisting of alkyl, hydroxyalkyl, and cycloalkyl, wherein the cycloalkyl is cyclohexyl substituted with 1 substituent selected from the group consisting of alkyl and hydroxy; $R_B$ is selected from the group consisting of hydrogen and alkyl; $R_E$ is selected from the group consisting of hydrogen and alkyl; and $R_F$ is selected from the group consisting of hydrogen, alkyl, and alkylcarbonyl.

In another embodiment, the present invention relates to a compound of formula (I) wherein $X_1$, $X_3$, and $X_4$ are CH; $X_2$ is CH($R_7$); $X_5$ is C; $R_2$, $R_3$, $R_5$, and $R_6$ are hydrogen; $R_1$ is selected from the group consisting of alkenyloxy, alkoxyalkyl, hydroxy, hydroxyalkyl, $(NR_AR_B)$alkyl, $(NR_AR_B)$carbonyl, and heterocyclealkyl, wherein the heterocycle of heterocyclealkyl is selected from the group consisting of 4-morpholinyl and 4-hydroxy-1-piperidinyl; $R_4$ is selected from the group consisting of alkoxycarbonyl, carboxy, cyano, hydroxy, hydroxyalkyl, —$NR_ER_F$, and $(NR_ER_F)$carbonyl; $R_7$ is hydrogen; $R_4$ is selected from the group consisting of alkyl, hydroxyalkyl, and cycloalkyl, wherein the cycloalkyl is cyclohexyl substituted with 1 substituent selected from the group consisting of alkyl and hydroxy; $R_B$ is selected from the group consisting of hydrogen and alkyl; $R_E$ is selected from the group consisting of hydrogen and alkyl; and $R_F$ is selected from the group consisting of hydrogen, alkyl, and alkylcarbonyl.

In another embodiment, the present invention relates to a compound of formula (I) wherein $X_1$, $X_3$, and $X_4$ are CH; $X_2$ is CH($R_7$); $X_5$ is C; $R_2$, $R_3$, $R_5$, and $R_6$ are hydrogen; $R_1$ is selected from the group consisting of alkenyloxy, alkoxyalkyl, hydroxy, hydroxyalkyl, $(NR_AR_B)$alkyl, $(NR_AR_B)$carbonyl, and heterocyclealkyl, wherein the heterocycle of heterocyclealkyl is selected from the group consisting of 4-morpholinyl and 4-hydroxy-1-piperidinyl; $R_4$ is aryl wherein the aryl is phenyl substituted with 1, 2, or 3 substituents selected from the group consisting of alkoxy, formyl, halogen, hydroxy, hydroxyalkyl, and —$NR_GR_H$; $R_7$ is hydrogen; $R_4$ is selected from the group consisting of alkyl, hydroxyalkyl, and cycloalkyl, wherein the cycloalkyl is cyclohexyl substituted with 1 substituent selected from the group consisting of alkyl and hydroxy; $R_B$ is selected from the group consisting of hydrogen and alkyl; $R_E$ is selected from the group consisting of hydrogen and alkyl; and $R_F$ is selected from the group consisting of hydrogen, alkyl, and alkylcarbonyl.

In another embodiment, the present invention relates to a compound of formula (I) wherein $X_1$, $X_3$, and $X_4$ are CH; $X_2$ is CH($R_7$); $X_5$ is C; $R_2$, $R_3$, and $R_6$ are hydrogen; $R_1$ is selected from the group consisting of alkenyloxy, alkoxyalkyl, hydroxy, hydroxyalkyl, $(NR_AR_B)$alkyl, $(NR_AR_B)$carbonyl, and heterocyclealkyl, wherein the heterocycle of heterocyclealkyl is selected from the group consisting of 4-morpholinyl and 4-hydroxy-1-piperidinyl; $R_4$ is selected from the group consisting of hydrogen, carboxy, and cyano; $R_5$ is selected from the group consisting of alkoxycarbonyl, carboxy, hydroxy, hydroxyalkyl, $NR_ER_F$, and $(NR_ER_F)$carbonyl; $R_7$ is hydrogen; $R_4$ is selected from the group consisting of alkyl, hydroxyalkyl, and cycloalkyl, wherein the cycloalkyl is cyclohexyl substituted with 1 substituent selected from the group consisting of alkyl and hydroxy; $R_B$ is selected from the group consisting of hydrogen and alkyl; $R_E$ is selected from the group consisting of hydrogen and alkyl; and $R_F$ is selected from the group consisting of hydrogen, alkyl, and alkylcarbonyl.

In another embodiment, the present invention relates to a compound of formula (I) wherein $X_1$, $X_3$, and $X_4$ are CH; $X_2$ is CH($R_7$); $X_5$ is C; $R_1$ and $R_2$ are alkoxy; $R_3$ and $R_6$ are hydrogen; $R_4$ is selected from the group consisting of alkoxycarbonyl, carboxy, cyano, hydroxy, —$NR_ER_F$, and $(NR_ER_F)$carbonyl; $R_5$ is selected from the group consisting of hydrogen and carboxy; $R_7$ is hydrogen; $R_E$ is selected from the group consisting of hydrogen and alkyl; and $R_F$ is selected from the group consisting of hydrogen, alkyl, and alkylcarbonyl.

In another embodiment, the present invention relates to a compound of formula (I) wherein $X_1$, $X_3$, and $X_4$ are CH; $X_2$ is CH($R_7$); $X_5$ is C; $R_1$ and $R_2$ are alkoxy; $R_3$, $R_5$, and $R_6$ are hydrogen; $R_4$ is aryl wherein the aryl is phenyl substituted with 1, 2, or 3 substituents selected from the group consisting of alkoxy, formyl, halogen, hydroxy, hydroxyalkyl, and —$NR_GR_H$; $R_7$ is hydrogen; $R_E$ is selected from the group consisting of hydrogen and alkyl; and $R_F$ is selected from the group consisting of hydrogen, alkyl, and alkylcarbonyl.

In another embodiment, the present invention relates to a compound of formula (I) wherein $X_1$, $X_3$, and $X_4$ are CH; $X_2$ is CH($R_7$); $X_5$ is C; $R_1$ and $R_2$ are alkoxy; $R_3$, $R_5$, and $R_6$ are hydrogen; $R_4$ is heteroaryl; and $R_7$ is hydrogen.

In another embodiment, the present invention relates to a compound of formula (I) wherein $X_1$, $X_3$, and $X_4$ are CH; $X_2$ is CH($R_7$); $X_5$ is C; $R_1$ and $R_2$ are alkoxy; $R_3$, $R_5$, and $R_6$ are hydrogen; $R_4$ is heteroaryl wherein the heteraryl is tetraazolyl; and $R_7$ is hydrogen.

In another embodiment, the present invention relates to a compound of formula (I) wherein $X_1$, $X_3$, and $X_4$ are CH; $X_2$ is CH($R_7$); $X_5$ is C; $R_1$, $R_2$, $R_3$, $R_5$, and $R_6$ are hydrogen; $R_4$ is selected from the group consisting of alkoxycarbonyl, carboxy, cyano, hydroxy, hydroxyalkyl, —$NR_ER_F$, and $(NR_ER_F)$carbonyl; and $R_7$ is selected from the group consisting of alkoxy and hydroxy.

In another embodiment, the present invention relates to a compound of formula (I) wherein $X_1$ is CH; $X_2$ is CH($R_7$); $X_3$ is N; $X_4$ is CH; $X_5$ is C; $R_1$, $R_3$, $R_5$, and $R_6$ are hydrogen; $R_2$ is selected from the group consisting of alkenyloxy, alkoxyalkyl, hydroxy, hydroxyalkyl, $(NR_AR_B)$alkyl, $(NR_AR_B)$carbonyl, and heterocyclealkyl, wherein the heterocycle of heterocyclealkyl is selected from the group consisting of 4-morpholinyl and 4-hydroxy-1-piperidinyl; $R_4$ is selected from the group consisting of hydrogen, alkoxycarbonyl, carboxy, cyano, hydroxy, hydroxyalkyl, —$NR_ER_F$, and $(NR_ER_F)$carbonyl; $R_7$ is hydrogen; $R_4$ is selected from the group consisting of alkyl, hydroxyalkyl, and cycloalkyl, wherein the cycloalkyl is cyclohexyl substituted with 1 substituent selected from the group consisting of alkyl and hydroxy; $R_B$ is selected from the group consisting of hydrogen and alkyl; $R_E$ is selected from the group consisting of hydrogen and alkyl; and $R_F$ is selected from the group consisting of hydrogen, alkyl, and alkylcarbonyl.

In another embodiment, the present invention relates to a compound of formula (I) wherein $X_1$, $X_3$, and $X_4$ are CH; $X_2$ is CH($R_7$); $X_5$ is C; $R_1$ and $R_2$ together with the carbon atoms to which they are attached form a 5 or 6-membered non-aromatic ring wherein the ring contains 0, 1, or 2 heteroatoms selected from the group consisting of O, N($R_C$), and N($R_D$); $R_3$, $R_5$, and $R_6$ are hydrogen; $R_4$ is selected from the group consisting of hydrogen, alkoxycarbonyl, carboxy, cyano, hydroxy, hydroxyalkyl, —$NR_ER_F$, and $(NR_ER_F)$carbonyl; $R_7$ is hydrogen; $R_4$ is selected from the group consisting of alkyl, hydroxyalkyl, and cycloalkyl, wherein the cycloalkyl is cyclohexyl substituted with 1 substituent selected from the group consisting of alkyl and hydroxy; $R_B$ is selected from the group consisting of hydrogen and alkyl; $R_E$ is selected from the group consisting of hydrogen and alkyl; $R_F$ is selected from the group consisting of hydrogen, alkyl, and alkylcarbonyl; and $R_C$ and $R_D$ are as defined in formula (I).

In another embodiment, the present invention relates to a compound of formula (I) wherein $X_1$, $X_3$, and $X_4$ are CH; $X_2$ is $CH(R_7)$; $X_5$ is C; $R_1$ and $R_2$ together with the carbon atoms to which they are attached form a 5 or 6-membered non-aromatic ring wherein the ring contains 2 heteroatoms selected from the group consisting of O, $N(R_C)$, and $N(R_D)$; $R_3$, $R_5$, and $R_6$ are hydrogen; $R_4$ is selected from the group consisting of hydrogen, alkoxycarbonyl, carboxy, cyano, hydroxy, hydroxyalkyl, —$NR_ER_F$, and ($NR_ER_F$)carbonyl; $R_7$ is hydrogen; $R_A$ is selected from the group consisting of alkyl, hydroxyalkyl, and cycloalkyl, wherein the cycloalkyl is cyclohexyl substituted with 1 substituent selected from the group consisting of alkyl and hydroxy; $R_B$ is selected from the group consisting of hydrogen and alkyl; $R_E$ is selected from the group consisting of hydrogen and alkyl; $R_F$ is selected from the group consisting of hydrogen, alkyl, and alkylcarbonyl; and $R_C$ and $R_D$ are as defined in formula (I).

In another embodiment, the present invention relates to a compound of formula (I) wherein $X_1$, $X_3$, and $X_4$ are CH; $X_2$ is $CH(R_7)$; $X_5$ is C; $R_1$ and $R_2$ together with the carbon atoms to which they are attached form a 5 or 6-membered non-aromatic ring wherein the ring contains 0, 1, or 2 heteroatoms selected from the group consisting of O, $N(R_C)$, and $N(R_D)$; $R_3$, $R_5$, and $R_6$ are hydrogen; $R_4$ is aryl wherein the aryl is phenyl substituted with 1, 2, or 3 substituents selected from the group consisting of alkoxy, formyl, halogen, hydroxy, hydroxyalkyl, and —$NR_GR_H$; $R_7$ is hydrogen; $R_A$ is selected from the group consisting of alkyl, hydroxyalkyl, and cycloalkyl, wherein the cycloalkyl is cyclohexyl substituted with 1 substituent selected from the group consisting of alkyl and hydroxy; $R_B$ is selected from the group consisting of hydrogen and alkyl; $R_E$ is selected from the group consisting of hydrogen and alkyl; and $R_F$ is selected from the group consisting of hydrogen, alkyl, and alkylcarbonyl; and $R_C$ and $R_D$ are as defined in formula (I).

In another embodiment, the present invention relates to a compound of formula (I) wherein $X_1$, $X_3$, and $X_4$ are CH; $X_2$ is $CH(R_7)$; $X_5$ is C; $R_1$ and $R_2$ together with the carbon atoms to which they are attached form a 5 or 6-membered non-aromatic ring wherein the ring contains 2 heteroatoms selected from the group consisting of O, $N(R_C)$, and $N(R_D)$; $R_3$, $R_5$, and $R_6$ are hydrogen; $R_4$ is aryl wherein the aryl is phenyl substituted with 1, 2, or 3 substituents selected from the group consisting of alkoxy, formyl, halogen, hydroxy, hydroxyalkyl, and —$NR_GR_H$; $R_7$ is hydrogen; $R_A$ is selected from the group consisting of alkyl, hydroxyalkyl, and cycloalkyl, wherein the cycloalkyl is cyclohexyl substituted with 1 substituent selected from the group consisting of alkyl and hydroxy; $R_B$ is selected from the group consisting of hydrogen and alkyl; $R_E$ is selected from the group consisting of hydrogen and alkyl; and $R_F$ is selected from the group consisting of hydrogen, alkyl, and alkylcarbonyl; and $R_C$ and $R_D$ are as defined in formula (I).

In another embodiment, the present invention relates to a compound of formula (I) wherein $X_1$, $X_3$, and $X_4$ are CH; $X_2$ is $CH(R_7)$; $X_5$ is C; $R_1$ is selected from the group consisting of hydrogen, alkoxy, alkyl, hydroxyalkoxy, and hydroxyalkyl; $R_2$ is selected from the group consisting of alkoxy, alkoxyalkoxyalkynyl, alkyl, haloalkoxyalkynyl, heteroarylalkoxy, heteroarylalkynyl, heteroaryloxyalkyl, heteroaryloxy, heterocyclealkoxy, heterocyclecarbonyl, heterocycleoxy, heterocycleoxyalkyl, hydroxyalkoxy, hydroxalkyl, hydroxyalkynyl, ($NR_AR_B$)alkynyl, and ($NR_AR_B$)carbonyl; $R_3$ is selected from the group consisting of hydrogen, —$NR_ER_F$, and hydroxyalkyl; $R_4$ is aryl wherein the aryl is phenyl substituted with 1 or 2 substituents selected from the group consisting of alkoxy, carboxy, cyano, halogen, and hydroxy; $R_5$ and $R_6$ are hydrogen; $R_E$ and $R_F$ are independently selected from the group consisting of hydrogen, alkyl, and alkylcarbonyl; and $R_A$ and $R_B$ are as defined in formula (I).

In another embodiment, the present invention relates to a compound of formula (I) wherein $X_1$, $X_3$, and $X_4$ are CH; $X_2$ is $CH(R_7)$; $X_5$ is C; $R_1$ and $R_2$ together with the carbon atoms to which they are attached form a 5 or 6-membered non-aromatic ring wherein the ring contains 2 heteroatoms selected from the group consisting of O, $N(R_C)$, and $N(R_D)$; $R_3$, $R_5$, and $R_6$ are hydrogen; $R_4$ is aryl wherein the aryl is phenyl substituted with 1 or 2 substituents selected from the group consisting of alkoxy, carboxy, cyano, halogen, and hydroxy; $R_5$ and $R_6$ are hydrogen; $R_E$ and $R_F$ are independently selected from the group consisting of hydrogen, alkyl, and alkylcarbonyl; and $R_A$ and $R_B$ are as defined in formula (I).

In another embodiment, the present invention relates to a compound of formula (I) wherein $X_1$, $X_3$, and $X_4$ are CH; $X_2$ is C=O; $X_5$ is C; $R_1$ is selected from the group consisting of hydrogen, alkoxy, alkyl, hydroxyalkoxy, and hydroxyalkyl; $R_2$ is selected from the group consisting of alkoxy, alkoxyalkoxyalkynyl, alkyl, haloalkoxyalkynyl, heteroarylalkoxy, heteroarylalkynyl, heteroaryloxyalkyl, heteroaryloxy, heterocyclealkoxy, heterocyclecarbonyl, heterocycleoxy, heterocycleoxyalkyl, hydroxyalkoxy, hydroxalkyl, hydroxyalkynyl, ($NR_AR_B$)alkynyl, and ($NR_AR_B$)carbonyl; $R_3$ is selected from the group consisting of hydrogen, —$NR_ER_F$, and hydroxyalkyl; $R_4$ is aryl wherein the aryl is phenyl substituted with 1 or 2 substituents selected from the group consisting of alkoxy, carboxy, cyano, halogen, and hydroxy; $R_5$ and $R_6$ are hydrogen; $R_E$ and $R_F$ are independently selected from the group consisting of hydrogen, alkyl, and alkylcarbonyl; and $R_A$ and $R_B$ are as defined in formula (I).

In another embodiment, the present invention relates to a compound of formula (I) wherein $X_1$ and $X_4$ are CH; $X_2$ is $CH(R_7)$; $X_3$ is N; $X_5$ is C; $R_1$ is selected from the group consisting of hydrogen, alkoxy, alkyl, hydroxyalkoxy, and hydroxyalkyl; $R_2$ is selected from the group consisting of alkoxy, alkoxyalkoxyalkynyl, alkyl, haloalkoxyalkynyl, heteroarylalkoxy, heteroarylalkynyl, heteroaryloxyalkyl, heteroaryloxy, heterocyclealkoxy, heterocyclecarbonyl, heterocycleoxy, heterocycleoxyalkyl, hydroxyalkoxy, hydroxalkyl, hydroxyalkynyl, ($NR_AR_B$)alkynyl, and ($NR_AR_B$)carbonyl; $R_3$ is selected from the group consisting of hydrogen, —$NR_ER_F$, and hydroxyalkyl; $R_4$ is selected from the group consisting of cyano, halogen, and aryl wherein the aryl is phenyl optionally substituted with 1 or 2 substituents independently selected from alkoxy and hydroxy; $R_5$ and $R_6$ are hydrogen; $R_7$ is selected from the group consisting of hydrogen, lower alkoxy, lower alkyl, and hydroxy; $R_E$ and $R_F$ are independently selected from the group consisting of hydrogen, alkyl, and alkylcarbonyl; and $R_A$ and $R_B$ are as defined in formula (I).

In another embodiment, the present invention relates to a compound of formula (I) wherein $X_1$ and $X_4$ are CH; $X_2$ is C=O; $X_3$ is N; $X_5$ is C; $R_1$ is selected from the group consisting of hydrogen, alkoxy, alkyl, hydroxyalkoxy, and hydroxyalkyl; $R_2$ is selected from the group consisting of alkoxy, alkoxyalkoxyalkynyl, alkyl, haloalkoxyalkynyl, heteroarylalkoxy, heteroarylalkynyl, heteroaryloxyalkyl, heteroaryloxy, heterocyclealkoxy, heterocyclecarbonyl, heterocycleoxy, heterocycleoxyalkyl, hydroxyalkoxy, hydroxalkyl, hydroxyalkynyl, ($NR_AR_B$)alkynyl, and ($NR_AR_B$)carbonyl; $R_3$ is selected from the group consisting of hydrogen, —$NR_ER_F$, and hydroxyalkyl; $R_4$ is selected from the group consisting of cyano, halogen, and aryl wherein the aryl is phenyl optionally substituted with 1 or 2 substituents independently selected from alkoxy and hydroxy; $R_5$ and $R_6$ are hydrogen; $R_E$ and $R_F$ are independently selected from the group consisting of hydrogen, alkyl, and alkylcarbonyl; and $R_A$ and $R_B$ are as defined in formula (I).

In another embodiment, the present invention relates to a compound of formula (I) wherein $X_1$ and $X_3$ are CH; $X_2$ is $CH(R_7)$; $X_4$ is N; $X_5$ is C; $R_1$ is selected from the group consisting of hydrogen, alkoxy, alkyl, hydroxyalkoxy, and hydroxyalkyl; $R_2$ is selected from the group consisting of alkoxy, alkoxyalkoxyalkynyl, alkyl, haloalkoxyalkynyl, heteroarylalkoxy, heteroarylalkynyl, heteroaryloxyalkyl, heteroaryloxy, heterocyclealkoxy, heterocyclecarbonyl, heterocycleoxy, heterocycleoxyalkyl, hydroxyalkoxy, hydroxyalkyl, hydroxyalkynyl, $(NR_AR_B)$alkynyl, and $(NR_AR_B)$carbonyl; $R_3$ is selected from the group consisting of hydrogen, —$NR_ER_F$, and hydroxyalkyl; $R_4$ is selected from the group consisting of cyano, halogen, and aryl wherein the aryl is phenyl optionally substituted with 1 or 2 substituents independently selected from alkoxy and hydroxy; $R_5$ and $R_6$ are hydrogen; $R_7$ is selected from the group consisting of hydrogen, lower alkoxy, lower alkyl, and hydroxy; $R_E$ and $R_F$ are independently selected from the group consisting of hydrogen, alkyl, and alkylcarbonyl; and $R_A$ and $R_B$ are as defined in formula (I).

In another embodiment, the present invention relates to a compound of formula (I) wherein $X_1$ and $X_3$ are CH; $X_2$ is C=O; $X_4$ is N; $X_5$ is C; $R_1$ is selected from the group consisting of hydrogen, alkoxy, alkyl, hydroxyalkoxy, and hydroxyalkyl; $R_2$ is selected from the group consisting of alkoxy, alkoxyalkoxyalkynyl, alkyl, haloalkoxyalkynyl, heteroarylalkoxy, heteroarylalkynyl, heteroaryloxyalkyl, heteroaryloxy, heterocyclealkoxy, heterocyclecarbonyl, heterocycleoxy, heterocycleoxyalkyl, hydroxyalkoxy, hydroxyalkyl, hydroxyalkynyl, $(NR_AR_B)$alkynyl, and $(NR_AR_B)$carbonyl; $R_3$ is selected from the group consisting of hydrogen, —$NR_ER_F$, and hydroxyalkyl; $R_4$ is selected from the group consisting of cyano, halogen, and aryl wherein the aryl is phenyl optionally substituted with 1 or 2 substituents independently selected from alkoxy and hydroxy; $R_5$ and $R_6$ are hydrogen; $R_E$ and $R_F$ are independently selected from the group consisting of hydrogen, alkyl, and alkylcarbonyl; and $R_A$ and $R_B$ are as defined in formula (I).

In another embodiment, the present invention relates to a compound of formula (I) wherein $X_1$ and $X_3$ are CH; $X_2$ is CH($R_7$); $X_4$ and $X_5$ are N; $R_1$ is selected from the group consisting of hydrogen, alkoxy, alkyl, hydroxyalkoxy, and hydroxyalkyl; $R_2$ is selected from the group consisting of alkoxy, alkoxyalkoxyalkynyl, alkyl, haloalkoxyalkynyl, heteroarylalkoxy, heteroarylalkynyl, heteroaryloxyalkyl, heteroaryloxy, heterocyclealkoxy, heterocyclecarbonyl, heterocycleoxy, heterocycleoxyalkyl, hydroxyalkoxy, hydroxyalkyl, hydroxyalkynyl, $(NR_AR_B)$alkynyl, and $(NR_AR_B)$carbonyl; $R_3$ is selected from the group consisting of hydrogen, —$NR_ER_F$, and hydroxyalkyl; $R_4$ is selected from the group consisting of cyano, halogen, and aryl wherein the aryl is phenyl optionally substituted with 1 or 2 substituents independently selected from alkoxy and hydroxy; $R_5$ is absent; $R_6$ is hydrogen; $R_7$ is selected from the group consisting of hydrogen, lower alkoxy, lower alkyl, and hydroxy; $R_E$ and $R_F$ are independently selected from the group consisting of hydrogen, alkyl, and alkylcarbonyl; and $R_A$ and $R_B$ are as defined in formula (I).

In another embodiment, the present invention relates to a compound of formula (I) wherein $X_1$ and $X_3$ are CH; $X_2$ is C=O; $X_4$ and $X_5$ are N; $R_1$ is selected from the group consisting of hydrogen, alkoxy, alkyl, hydroxyalkoxy, and hydroxyalkyl; $R_2$ is selected from the group consisting of alkoxy, alkoxyalkoxyalkynyl, alkyl, haloalkoxyalkynyl, heteroarylalkoxy, heteroarylalkynyl, heteroaryloxyalkyl, heteroaryloxy, heterocyclealkoxy, heterocyclecarbonyl, heterocycleoxy, heterocycleoxyalkyl, hydroxyalkoxy, hydroxyalkyl, hydroxyalkynyl, $(NR_AR_B)$alkynyl, and $(NR_AR_B)$carbonyl; $R_3$ is selected from the group consisting of hydrogen, —$NR_ER_F$, and hydroxyalkyl; $R_4$ is selected from the group consisting of cyano, halogen, and aryl wherein the aryl is phenyl optionally substituted with 1 or 2 substituents independently selected from alkoxy and hydroxy; $R_5$ is absent; $R_6$ is hydrogen; $R_E$ and $R_F$ are independently selected from the group consisting of hydrogen, alkyl, and alkylcarbonyl; and $R_A$ and $R_B$ are as defined in formula (I).

In another embodiment, the present invention relates to a compound of formula (I) wherein $X_1$ and $X_4$ are CH; $X_2$ is CH($R_7$); $X_3$ and $X_5$ are N; $R_1$ is selected from the group consisting of hydrogen, alkoxy, alkyl, hydroxyalkoxy, and hydroxyalkyl; $R_2$ is selected from the group consisting of alkoxy, alkoxyalkoxyalkynyl, alkyl, haloalkoxyalkynyl, heteroarylalkoxy, heteroarylalkynyl, heteroaryloxyalkyl, heteroaryloxy, heterocyclealkoxy, heterocyclecarbonyl, heterocycleoxy, heterocycleoxyalkyl, hydroxyalkoxy, hydroxyalkyl, hydroxyalkynyl, $(NR_AR_B)$alkynyl, and $(NR_AR_B)$carbonyl; $R_3$ is selected from the group consisting of hydrogen, —$NR_ER_F$, and hydroxyalkyl; $R_4$ is selected from the group consisting of cyano, halogen, and aryl wherein the aryl is phenyl optionally substituted with 1 or 2 substituents independently selected from alkoxy and hydroxy; $R_5$ is absent; $R_6$ is hydrogen; $R_7$ is selected from the group consisting of hydrogen, lower alkoxy, lower alkyl, and hydroxy; $R_E$ and $R_F$ are independently selected from the group consisting of hydrogen, alkyl, and alkylcarbonyl; and $R_A$ and $R_B$ are as defined in formula (I).

In another embodiment, the present invention relates to a compound of formula (I) wherein $X_1$ and $X_4$ are CH; $X_2$ is C=O; $X_3$ and $X_5$ are N; $R_1$ is selected from the group consisting of hydrogen, alkoxy, alkyl, hydroxyalkoxy, and hydroxyalkyl; $R_2$ is selected from the group consisting of alkoxy, alkoxyalkoxyalkynyl, alkyl, haloalkoxyalkynyl, heteroarylalkoxy, heteroarylalkynyl, heteroaryloxyalkyl, heteroaryloxy, heterocyclealkoxy, heterocyclecarbonyl, heterocycleoxy, heterocycleoxyalkyl, hydroxyalkoxy, hydroxyalkyl, hydroxyalkynyl, $(NR_AR_B)$alkynyl, and $(NR_AR_B)$carbonyl; $R_3$ is selected from the group consisting of hydrogen, —$NR_ER_F$, and hydroxyalkyl; $R_4$ is selected from the group consisting of cyano, halogen, and aryl wherein the aryl is phenyl optionally substituted with 1 or 2 substituents independently selected from alkoxy and hydroxy; $R_5$ is absent; $R_6$ is hydrogen; $R_E$ and $R_F$ are independently selected from the group consisting of hydrogen, alkyl, and alkylcarbonyl; and $R_A$ and $R_B$ are as defined in formula (I).

In another embodiment, the present invention relates to a compound of formula (I) wherein $X_1$, $X_3$, and $X_4$ are CH; $X_2$ is CH($R_7$); $X_5$ is C; $R_1$ is selected from the group consisting of hydrogen, alkoxy, alkyl, hydroxyalkoxy, and hydroxyalkyl; $R_2$ is selected from the group consisting of alkoxy, alkoxyalkoxyalkynyl, alkyl, haloalkoxyalkynyl, heteroarylalkoxy, heteroarylalkynyl, heteroaryloxyalkyl, heteroaryloxy, heterocyclealkoxy, heterocyclecarbonyl, heterocycleoxy, heterocycleoxyalkyl, hydroxyalkoxy, hydroxyalkyl, hydroxyalkynyl, $(NR_AR_B)$alkynyl, and $(NR_AR_B)$carbonyl; $R_3$ is selected from the group consisting of hydrogen, —$NR_ER_F$, and hydroxyalkyl; $R_4$ and $R_5$ together with the atoms to which they are attached, form a phenyl ring optionally substituted with 1 or 2 substituents independently selected from alkoxy, carboxy, cyano, halogen, and hydroxy; $R_7$ is selected from the group consisting of hydrogen, lower alkoxy, lower alkyl, and hydroxy; $R_E$ and $R_F$ are independently selected from the group consisting of hydrogen, alkyl, and alkylcarbonyl; and $R_A$ and $R_B$ are as defined in formula (I).

In another embodiment, the present invention relates to a compound of formula (I) wherein $X_1$, $X_3$, and $X_4$ are CH; $X_2$ is C=O; $X_5$ is C; $R_1$ is selected from the group consisting of hydrogen, alkoxy, alkyl, hydroxyalkoxy, and hydroxyalkyl; $R_2$ is selected from the group consisting of alkoxy, alkoxyalkoxyalkynyl, alkyl, haloalkoxyalkynyl, heteroarylalkoxy, heteroarylalkynyl, heteroaryloxyalkyl, heteroaryloxy, heterocyclealkoxy, heterocyclecarbonyl, heterocycleoxy, heterocycleoxyalkyl, hydroxyalkoxy, hydroxalkyl, hydroxyalkynyl, $(NR_AR_B)$alkynyl, and $(NR_AR_B)$carbonyl; $R_3$ is selected from the group consisting of hydrogen, —$NR_E R_F$, and hydroxyalkyl; $R_4$ is selected from the group consisting of cyano, halogen, and aryl wherein the aryl is phenyl optionally substituted with 1 or 2 substituents independently selected from alkoxy and hydroxy; $R_5$ is absent; $R_6$ is hydrogen; $R_E$ and $R_F$ are independently selected from the group consisting of hydrogen, alkyl, and alkylcarbonyl; and $R_A$ and $R_B$ are as defined in formula (I).

Definition of Terms

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl (allyl), 2-methyl-2-propenyl, 3-butenyl, 4-pentenyl, 5-hexenyl, 2-heptenyl, 2-methyl-1-heptenyl, and 3-decenyl.

The term "alkenyloxy" as used herein, means an alkenyl group, as defined herein, appended to the parent molecular moiety through an oxygen atom. Representative examples of alkenyloxy include, but are not limited to, allyloxy, 2-butenyloxy and 3-butenyloxy.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through an alkoxy group, as defined herein. Representative examples of alkoxyalkoxy include, but are not limited to, 2-(methoxy)ethoxy, 2-(ethoxy)ethoxy, 2-(tert-butoxy)ethoxy, and 3-(methoxy)butoxy.

The term "alkoxyalkoxyalkynyl" as used herein, means an alkoxyalkoxy group, as defined herein, appended to the parent molecular moiety through an alkynyl group, as defined herein. Representative examples of alkoxyalkoxyalkynyl include, but are not limited to, 3-(2-isopropoxyethoxy)prop-1-ynyl, 3-(2-methoxyethoxy)prop-1-ynyl, and 4-(2-isopropoxyethoxy)but-1-ynyl.

The term "alkoxyalkyl" as used herein, means an alkoxy group, as defined herein, appended to the parent molecular moiety through an alkyl group, as defined herein. Representative examples of alkoxyalkyl include, but are not limited to, methoxymethyl, ethoxymethyl, 2-ethoxyethyl, tert-butoxymethyl, and 2-methoxyethyl.

The term "alkoxyalkylcarbonyl" as used herein, means an alkoxyalkyl group, as defined herein, appended to the parent molecular moiety through a carbonyl group, as defined herein. Representative examples of alkoxyalkylcarbonyl include, but are not limited to, 3-methoxypropanoyl and 5-methoxypentanoyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxycarbonylalkylcarbonyl" as used herein, means an alkoxycarbonylalkyl group, as defined herein, appended to the parent molecular moiety through a carbonyl group, as defined herein. Representative examples of alkoxycarbonylalkylcarbonyl include, but are not limited to, 5-methoxy-5-oxopentanoyl, 5-ethoxy-5-oxopentanoyl, and 4-methoxy-4-oxobutanoyl.

The term "alkoxysulfonyl" as used herein, means an alkoxy group, as defined herein, appended appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkoxysulfonylalkyl" as used herein, means an alkoxysulfonyl group, as defined herein, appended appended to the parent molecular moiety through an alkyl group, as defined herein. Representative examples of alkoxysulfonylalkyl include, but are not limited to, 3-(methoxysulfonyl)propyl, 3-(ethoxysulfonyl)propyl, and 2-(methoxysulfonyl)ethyl.

The term "alkoxysulfonylalkylcarbonyl" as used herein, means an alkoxysulfonylalkyl group, as defined herein, appended appended to the parent molecular moiety through an alkyl group, as defined herein. Representative examples of alkoxysulfonylalkylcarbonyl include, but are not limited to, 3-(methoxysulfonyl)propanoyl, 3-(ethoxysulfonyl)propanoyl, and 4-(methoxysulfonyl)butanoyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkoxy" as used herein, means an alkylcarbonyl group, as defined herein, appended to the parent molecular moiety through an alkoxy group, as defined herein. Representative examples of alkylcarbonylalkoxy include, but are not limited to, acetyl, 2-oxopropoxy, 2-oxobutoxy, and 3-oxobutoxy, 4-oxopentyloxy.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, appended to the parent molecular moiety through an alkyl group, as defined herein. Representative examples of alkylthioalkyl include, but are not limited, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means a monocyclic-ring system or a bicyclic-fused ring system wherein one or more of the fused rings are aromatic. Representative examples of aryl include, but are not limited to, indenyl, naphthyl, phenyl, and tetrahydronaphthyl.

The aryl groups of the present invention are substituted with 0, 1, 2, 3, 4, or 5 substituents independently selected from alkenyl, alkoxy, alkoxyalkyl, alkoxycarbonyl, alkoxycarbonylalkyl, alkoxysulfonyl, alkyl, alkylcarbonyl, alkylcarbonyloxy, alkylsulfinyl, alkylsulfonyl, alkylthio, alkylthioalkyl, alkynyl, carboxy, carboxyalkyl, cyano, formyl, haloalkoxy, haloalkyl, halogen, hydroxy, hydroxyalkyl, mercapto, nitro, —$NR_GR_H$, ($NR_GR_H$)alkoxy, ($NR_GR_H$)alkyl, ($NR_GR_H$)carbonyl, and ($NR_GR_H$)sulfonyl. The aryl groups of the present invention may be optionally substituted with one heterocycle, as defined herein. The heterocycle may be optionally substituted with 1, 2, 3, 4, or 5 substituents independently selected from alkenyl, alkoxy, alkoxyalkyl, alkoxycarbonyl, alkoxycarbonylalkyl, alkoxysulfonyl, alkyl, alkylcarbonyl, alkylcarbonyloxy, alkylsulfinyl, alkylsulfonyl, alkylthio, alkylthioalkyl, alkynyl, carboxy, carboxyalkyl, cyano, formyl, haloalkoxy, haloalkyl, halogen, hydroxy, hydroxyalkyl, mercapto, nitro, —$NR_GR_H$, ($NR_GR_H$)alkoxy, ($NR_GR_H$)alkyl, ($NR_GR_H$)carbonyl, and ($NR_GR_H$)sulfonyl The term "arylalkoxy" as used herein, means an aryl group, as defined herein, appended to the parent molecular moiety through an alkoxy group, as defined herein. Representative examples of arylalkoxy include, but are not limited to, 2-phenylethoxy, 3-phenylpropoxy, and 5-phenylpentyloxy.

The term "arylalkyl" as used herein, means an aryl group, as defined herein, appended to the parent molecular moiety through an alkyl group, as defined herein. Representative examples of arylalkyl include, but are not limited to, 4 carboxyphenylmethyl, 2-(4-hydroxyphenyl)ethyl, and 3-(4-carboxyphenyl)propyl.

The term "aryloxy" as used herein, means an aryl group, as defined herein, appended to the parent molecular moiety through an oxygen atom. Representative examples of aryloxy include, but are not limited to, 4-carboxyphenoxy, 4-hydroxyphenoxy, and 3,4-dihydroxyphenoxy.

The term "carboxy" as used herein, means a —$CO_2H$ group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "carboxyalkylcarbonyl" as used herein, means a carboxyalkyl group, as defined herein, appended to the parent molecular moiety through a carbonyl group, as defined herein. Representative examples of carboxyalkylcarbonyl include, but are not limited to, 4-carboxybutanoyl, 3-carboxypropanoyl, and 5-carboxypentanoyl.

The term "cyano" as used herein, means a —CN group.

The term "cycloalkyl" as used herein, means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The cycloalkyl groups of the present invention are substituted with 0, 1, 2, 3, or 4 substituents selected from alkenyl, alkoxy, alkoxyalkyl, alkoxycarbonyl, alkyl, alkylcarbonyl, alkylcarbonyloxy, alkynyl, carboxy, cyano, formyl, haloalkoxy, haloalkyl, halogen, hydroxy, hydroxyalkyl, —$NR_GR_H$, ($NR_GR_H$)alkoxy, ($NR_GR_H$)alkyl, and ($NR_GR_H$)carbonyl.

The term "cycloalkenyl," as used herein, means a non-aromatic, partially unsaturated monocyclic, bicyclic, or tricyclic ring system having four to eight carbon atoms and zero heteroatoms. Representative examples of cycloalkenyl groups include, but are not limited to, cyclohexenyl and cyclopentenyl.

The term "cycloalkenylalkoxy" as used herein, means a cycloalkenyl group, as defined herein, appended to the parent molecular moiety through an alkoxy group, as defined herein.

The term "cycloalkylalkoxy" as used herein, means a cycloalkyl group, as defined herein, appended to the parent molecular moiety through an alkoxy group, as defined herein. Representative examples of cycloalkylalkoxy include, but are not limited to, cyclopropylmethoxy, 2-cyclobutylethoxy, cyclopentylmethoxy, cyclohexylmethoxy, 2-cyclohexylethoxy, 3-cyclohexylpropoxy, 4-cyclohexylbutoxy, 4-(4-aminocyclohexyl)butoxy, 4-(4-dimethylaminocyclohexyl)butoxy, 4-(4-hydroxycyclohexyl)butoxy, and 4-cycloheptylbutoxy.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, 2-cyclohexylethyl, 3-cyclohexylpropyl, 4-cyclohexylbutyl, 4-(4-aminocyclohexyl)butyl, 4-(4-dimethylaminocyclohexyl)butyl, 4-(4-hydroxycyclohexyl)butyl, and 4-cycloheptylbutyl.

The term "cycloalkylalkylcarbonyl" as used herein, means a cycloalkylalkyl group, as defined herein, appended to the parent molecular moiety through a carbonyl group, as defined herein. Representative examples of cycloalkylalkylcarbonyl include, but are not limited to, 4-cyclohexylbutanoyl, 3-cyclohexylpropanoyl, and 5-cyclohexylpentanoyl.

The term "cycloalkylcarbonyl" as used herein, means a cycloalkyl group, as defined herein, appended to the parent molecular moiety through a carbonyl group, as defined herein. Representative examples of cycloalkylcarbonyl include, but are not limited to, cyclohexylcarbonyl and cyclopentylcarbonyl.

The term "cycloalkyloxy" as used herein, means a cycloalkyl group, as defined herein, appended to the parent molecular moiety through an oxygen atom. Representative examples of cycloalkyloxy include, but are not limited to, cyclohexyloxy and cyclopentyloxy.

The term "cycloalkylcarbonylalkyl" as used herein, means a cycloalkylcarbonyl group, as defined herein, appended to the parent molecular moiety through an alkyl group, as defined herein. Representative examples of cycloalkylcarbonylalkyl include, but are not limited to, 4-cyclohexyl-4-oxobutyl and 3-cyclohexyl-3-oxopropyl.

The term "cycloalkylcarbonylalkylcarbonyl" as used herein, means a cycloalkylcarbonylalkyl group, as defined herein, appended to the parent molecular moiety through a carbonyl group, as defined herein. Representative examples of cycloalkylcarbonylalkylcarbonyl include, but are not limited to, 4-cyclohexyl-4-oxobutanoyl and 3-cyclohexyl-3-oxopropanoyl.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Additionally, the alkyl group may optionally be substituted with at least one halogen atom. Representative examples of haloalkoxy include, but are not limited to, chloromethoxy, 2-fluoroethoxy, trifluoromethoxy, pentafluoroethoxy,and 3-chloro-2-(hydroxymethyl)-2-methylpropoxy.

The term "haloalkoxyalkynyl" as used herein, means a haloalkoxy group, as defined herein, appended to the parent molecular moiety through an alkynyl group, as defined herein. Representative examples of haloalkoxyalkynyl include, but are not limited to, 3-(2,2,2-trifluoroethoxy) prop-1-ynyl and 3-(trifluoromethoxy)prop-1-ynyl.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, refers to an aromatic five- or six-membered ring wherein 1, 2, 3, or 4 heteroatoms are independently selected from N, O, or S. The five membered rings have two double bonds and the six membered rings have three double bonds. The heteroaryl groups are connected to the parent molecular moiety through a carbon or nitrogen atom. The term "heteroaryl" also includes bicyclic systems where a heteroaryl ring is fused to a phenyl group or an additional heteroaryl group. Representative examples of heteroaryl include, but are not limited to, benzothienyl, benzoxadiazolyl, cinnolinyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, quinolinyl, tetraazolyl, thiadiazolyl, thiazolyl, thienopyridinyl, thienyl, triazolyl, and triazinyl.

The heteroaryl groups of the present invention are substituted with 0, 1, 2, 3, or 4 substituents independently selected from alkenyl, alkoxy, alkoxyalkyl, alkoxycarbonyl, alkoxycarbonylalkyl, alkoxysulfonyl, alkyl, alkylcarbonyl, alkylcarbonyloxy, alkylsulfinyl, alkylsulfonyl, alkylthio, alkynyl, carboxy, carboxyalkyl, cyano, formyl, haloalkoxy, haloalkyl, halogen, hydroxy, hydroxyalkyl, mercapto, nitro, —NR$_G$R$_H$, (NR$_G$R$_H$)alkoxy, (NR$_G$R$_H$)alkyl, (NR$_G$R$_H$)carbonyl, and (NR$_G$R$_H$)sulfonyl.

The term "heteroarylalkoxy" as used herein, means a heteroaryl group, as defined herein, appended to the parent molecular moiety through an alkoxy group, as defined herein. Representative examples of heteroarylalkoxy include, but are not limited to, 5-hydroxy-2-pyridinylmethyl, 2-(5-hydroxy-2-pyridinyl)ethyl, and 5-hydroxy-2-pyrimidinylmethyl.

The term "heteroarylalkoxyalkoxy" as used herein, means a heteroarylalkoxy group, as defined herein, appended to the parent molecular moiety through an alkoxy group, as defined herein.

The term "heteroarylalkyl" as used herein, means a heteroaryl group, as defined herein, appended to the parent molecular moiety through an alkyl group, as defined herein. Representative examples of heteroarylalkyl include, but are not limited to, 5-carboxy-2-pyridinylmethyl, 5-hydroxy-2-pyridinylmethyl, 2-(5-hydroxy-2-pyridinyl)ethyl, and 3-(5-hydroxy-2-pyridinyl)propyl.

The term "heteroarylalkynyl" as used herein, means a heteroaryl group, as defined herein, appended to the parent molecular moiety through an alkynyl group, as defined herein. Representative examples of heteroarylalkynyl include, but are not limited to, pyridin-2-ylethynyl, pyridin-3-ylethynyl, 4-pyridin-2-ylbut-1-ynyl, and 4-pyrazin-2-yl-pent-1-ynyl.

The term "heteroaryloxy" as used herein, means a heteroaryl group, as defined herein, appended to the parent molecular moiety through an oxygen atom. Representative examples of heteroaryloxy include, but are not limited to, 5-carboxy-2-pyridinyloxy, 5-hydroxy-2-pyridinyloxy, and 5-hydroxy-2-pyrimidinyloxy.

The term "heteroaryloxyalkyl" as used herein, means a heteroaryloxy group, as defined herein, appended to the parent molecular moiety through an alkyl group. Representative examples of heteroaryloxyalkyl include, but are not limited to, pyridinyl-5-carboxy-2-pyridinyloxymethyl, 5-hydroxy-2-pyridinyloxymethyl, and 5-hydroxy-2-pyrimidinyloxy.

The term "heterocycle," as used herein, refers to a three, four, five, six, seven or eight membered ring containing one, two, or three heteroatoms independently selected from the group consisting of nitrogen, oxygen, and sulfur. The three membered ring has zero double bonds. The four and five membered rings have zero or one double bond. The six membered ring has zero, one, or two double bonds. The seven and eight membered rings have zero, one, two, or three double bonds. The heterocycle groups of the present invention can be attached to the parent molecular moiety through a carbon atom or a nitrogen atom. Representative examples of heterocycle include, but are not limited to, azetidinyl, azepanyl, aziridinyl, azocanyl, 1,4-diazepan-2-yl, 1,4-dioxanyl, morpholinyl, piperazinyl, piperidinyl, pyrrolidinyl, thiomorpholinyl, and 1,1-dioxidothiomorpholinyl.

The heterocycles of the present invention are substituted with 0, 1, 2, 3, or 4 substituents independently selected from alkenyl, alkoxy, alkoxyalkyl, alkoxycarbonyl, alkyl, alkylcarbonyl, alkylcarbonyloxy, alkylthio, alkynyl, carboxy, cyano, formyl, haloalkoxy, haloalkyl, halogen, hydroxy, hydroxyalkyl, mercapto, nitro, oxo, —NR$_G$R$_H$, (NR$_G$R$_H$) alkoxy, (NR$_G$R$_H$)alkyl, and (NR$_G$R$_H$)carbonyl. The heterocycles of the present invention may be optionally substituted with one aryl group, as defined herein. The aryl group may be optionally substituted with 1, 2, 3, 4, or 5 substituents independently selected from alkenyl, alkoxy, alkoxyalkyl, alkoxycarbonyl, alkoxycarbonylalkyl, alkoxysulfonyl, alkyl, alkylcarbonyl, alkylcarbonyloxy, alkylsulfinyl, alkylsulfonyl, alkylthio, alkylthioalkyl, alkynyl, carboxy, carboxyalkyl, cyano, formyl, haloalkoxy, haloalkyl, halogen, hydroxy, hydroxyalkyl, mercapto, nitro, —NR$_G$R$_H$, (NR$_G$R$_H$)alkoxy, (NR$_G$R$_H$)alkyl, (NR$_G$R$_H$)carbonyl, and (NR$_G$R$_H$)sulfonyl.

The term "heterocyclealkoxy" as used herein, means a heterocycle, as defined herein, appended to the parent molecular moiety through an alkoxy group, as defined herein. Representative examples of heterocyclealkoxy include, but are not limited to, 4-morpholinylmethoxy, 2-(4-morpholinyl)ethoxy, 4-thiomorpholinylmethoxy, 2-(4-thiomorpholinyl)ethoxy, 1-piperidinylmethoxy, 2-(1-piperidinyl)ethoxy, 4-hydroxy-1-piperidinylmethoxy, 2-(4-hydroxy-1-piperidinyl)ethoxy, 3-hydroxy-1-pyrrolidinylmethoxy, 3-hydroxy-1-azetidinylmethoxy, and 4-hydroxy-1-azepanylmethoxy.

The term "heterocyclealkyl" as used herein, means a heterocycle, as defined herein, appended to the parent molecular moiety through an alkyl group, as defined herein. Representative examples of heterocyclealkyl include, but are not limited to, 4-morpholinylmethyl, 2-(4-morpholinyl)ethyl, 4-thiomorpholinylmethyl, 2-(4-thiomorpholinyl)ethyl, 1-piperidinylmethyl, 2-(1-piperidinyl)ethyl, 4-hydroxy-1-piperidinylmethyl, 2-(4-hydroxy-1-piperidinyl)ethyl, 3-hydroxy-1-pyrrolidinylmethyl, 3-hydroxy-1-azetidinylmethyl, 3-hydroxy-1-azepanylmethyl, and 4-hydroxy-1-azepanylmethyl.

The term "heterocyclealkylcarbonyl" as used herein, means a heterocyclealkyl, as defined herein, appended to the parent molecular moiety through a carbonyl group, as defined herein. Representative examples of heterocyclealkylcarbonyl include, but are not limited to, 4-(1-piperidinyl)butanoyl, 3-(1-piperidinyl)propanoyl, 4-(4-morpholinyl)butanoyl, and 3-(4-morpholinyl)propanoyl.

The term "heterocyclecarbonyl" as used herein, means a heterocycle, as defined herein, appended to the parent molecular moiety through a carbonyl group, as defined herein. Representative examples of heterocyclecarbonyl include, but are not limited to, 4-morpholinylcarbonyl, 4-thiomorpholinylcarbonyl, 1-piperidinylcarbonyl, (4-hydroxy-1-piperidinyl)carbonyl, and 3-hydroxy-1-pyrrolidinylcarbonyl.

The term "heterocyclecarbonylalkyl" as used herein, means a heterocyclecarbonyl, as defined herein, appended to the parent molecular moiety through an alkyl group, as defined herein. Representative examples of heterocyclecarbonylalkyl include, but are not limited to, 2-(4-morpholinyl)-2-oxoethyl, 3-(4-morpholinyl)-3-oxopropyl, and 2-(1-piperidinyl)-2-oxoethyl.

The term "heterocyclecarbonylalkylcarbonyl" as used herein, means a heterocyclecarbonylalkyl, as defined herein, appended to the parent molecular moiety through a carbonyl group, as defined herein. Representative examples of heterocyclecarbonylalkylcarbonyl include, but are not limited to, 5-(4-morpholinyl)-5-oxopentanoyl, 4-(4-morpholinyl)-4-oxobutanoyl, and 5-(1-piperidinyl)-5-oxopentanoyl.

The term "heterocycleoxy" as used herein, means a heterocycle group, as defined herein, appended to the parent molecular moiety through an oxygen atom. Representative examples of heterocycleoxy include, but are not limited to, 4 piperidinyloxy, 3-pyrrolidinyloxy, 3-azetidinyloxy, and tetrahydrofuran-3-yloxy.

The term "hydroxy" as used herein, means an —OH group.

The term "hydroxyalkoxy" as used herein, means at least one hydroxy group, as defined herein, is appended to the parent molecular moiety through an alkoxy group, as defined herein. Representative examples of hydroxyalkoxy include, but are not limited to, 2-hydroxyethoxy, 3-hydroxypropoxy, 2,3-dihydroxypropoxy, 2,3-dihydroxypentoxy, and 3-hydroxy-2,2-dimethylpropoxy.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypropyl, 2,3-dihydroxypentyl, 2-ethyl-4-hydroxyheptyl, and 3-hydroxy-2,2-dimethylpropyl.

The term "hydroxyalkynyl" as used herein, means at least one hydroxy group, as defined herein, is appended to the parent molecular moiety through an alkynyl group, as defined herein. Representative examples of hydroxyalkynyl include, but are not limited to, 4-hydroxy-4-methylpent-1-ynyl, 4-hydroxybut-1-ynyl, and 3-hydroxyprop-1-ynyl.

The term "hydroxyalkylcarbonyl" as used herein, means a hydroxyalkyl group, as defined herein, is appended to the parent molecular moiety through a carbonyl group, as defined herein. Representative examples of hydroxyalkylcarbonyl include, but are not limited to, glycoloyl, 3-hydroxypropanoyl, and 4-hydroxybutanoyl.

The term "hydroxysulfonyl" as used herein, means a HOS(O)$_2$— group.

The term "hydroxysulfonylalkyl" as used herein, means a hydroxysulfonyl group, as defined herein, is appended to the parent molecular moiety through an alkyl group, as defined herein. Representative examples of hydroxysulfonylalkyl include, but are not limited to, 4-sulfobutyl, 3-sulfopropyl, and 2-sulfoethyl.

The term "hydroxysulfonylalkylcarbonyl" as used herein, means a hydroxysulfonylalkyl group, as defined herein, is appended to the parent molecular moiety through a carbonyl group, as defined herein. Representative examples of hydroxysulfonylalkylcarbonyl include, but are not limited to, 4-sulfobutanoyl and 3-sulfopropanoyl.

The term "lower alkoxy" as used herein, is a subset of alkoxy as defined herein and means a lower alkyl group, as defined herein, appended to the parent molecular moiety through an oxygen atom, as defined herein. Representative examples of lower alkoxy include, but are not limited to, methoxy, ethoxy, propoxy, and 2-propoxy.

The term "lower alkyl" as used herein, is a subset of alkyl as defined herein and means a straight or branched chain hydrocarbon group containing from 1 to 3 carbon atoms. Examples of lower alkyl are methyl, ethyl, n-propyl, and iso-propyl.

The term "mercapto" as used herein, means a —SH group.

The term "mercaptoalkyl" as used herein, means a mercapto group, as defined herein, is appended to the parent molecular moiety through an alkyl group, as defined herein. Representative examples of mercaptoalkyl include, but are not limited to, hydroxymethyl, 2-mercaptoethyl, 3-mercaptopropyl, and 4-mercaptobutyl.

The term "nitro" as used herein, means a —NO$_2$ group.

The term "—NR$_A$R$_B$" as used herein, means two groups, R$_A$ and R$_B$, which are appended to the parent molecular moiety through a nitrogen atom. R$_A$ and R$_B$ are each independently selected from the group consisting of hydrogen, alkenyl, alkoxyalkyl, alkoxyalkylcarbonyl, alkoxycarbonyl, alkoxycarbonylalkyl, alkoxycarbonylalkylcarbonyl, alkoxysulfonyl, alkoxysulfonylalkyl, alkoxysulfonylalkylcarbonyl, alkyl, alkylcarbonyl, alkynyl, aryl, carboxyalkyl, carboxyalkylcarbonyl, cycloalkyl, cycloalkylalkyl, cycloalkylalkylcarbonyl, cycloalkylcarbonyl, cycloalkylcarbonylalkyl, cycloalkylcarbonylalkylcarbonyl, heteroaryl, heteroarylalkyl, heterocycle, heterocyclealkyl, heterocyclealkylcarbonyl, heterocyclecarbonyl, heterocyclecarbonylalkyl, heterocyclecarbonylalkylcarbonyl, hydroxyalkyl, hydroxyalkylcarbonyl, hydroxysulfonyl, hydroxysulfonylalkyl, hydroxysulfonylalkylcarbonyl, $(NR_ER_F)$alkyl, $(NR_ER_F)$alkylcarbonyl, $(NR_ER_F)$carbonyl, $(NR_ER_F)$carbonylalkyl, $(NR_ER_F)$carbonylalkylcarbonyl, $(NR_ER_F)$sulfonyl, $(NR_ER_F)$sulfonylalkyl, and $(NR_ER_F)$sulfonylalkylcarbonyl. Representative examples of —$NR_AR_B$ include, but are not limited to, amino, methylamino, dimethylamino, cyclohexylamino, (trans)-4-methylcyclohexylamino, (cis)-4-methylcyclohexylamino, (trans)-4-hydroxycyclohexylamino, and (cis)-4-hydroxycyclohexylamino.

The term "$(NR_AR_B)$alkoxy" as used herein, means a —$NR_AR_B$ group, as defined herein, appended to the parent molecular moiety through an alkoxy group, as defined herein. Representative examples of $(NR_AR_B)$alkoxy include, but are not limited to aminomethoxy, 2-aminoethoxy, methylaminomethoxy, 2-(methylamino)ethoxy, dimethylaminomethoxy, 2-(dimethylamino)ethoxy, cyclohexylaminomethoxy, (trans)-4-methylcyclohexylaminomethoxy, (cis)-4-methylcyclohexylaminomethoxy, (trans)-4-hydroxycyclohexylaminomethoxy, and (cis)-4-hydroxycyclohexylaminomethoxy.

The term "$(NR_AR_B)$alkyl" as used herein, means a —$NR_AR_B$ group, as defined herein, appended to the parent molecular moiety through an alkyl group, as defined herein. Representative examples of $(NR_AR_B)$alkyl include, but are not limited to aminomethyl, 2-aminoethyl, methylaminomethyl, 2-methylamino)ethyl, dimethylaminomethyl, 2-(dimethylamino)ethyl, cyclohexylaminomethyl, (trans)-4-methylcyclohexylaminomethyl, (cis)-4-methylcyclohexylaminomethyl, (trans)-4-hydroxycyclohexylaminomethyl, and (cis)-4-hydroxycyclohexylaminomethyl.

The term "$(NR_AR_B)$alkynyl" as used herein, means a —$NR_AR_B$ group, as defined herein, appended to the parent molecular moiety through an alkynyl group, as defined herein. Representative examples of $(NR_AR_B)$alkynyl include, but are not limited to 3-aminoprop-1-ynyl, 3-(dimethylamino)prop-1-ynyl, and 4-aminopent-1-ynyl.

The term "$(NR_AR_B)$carbonyl" as used herein, means a —$NR_AR_B$ group, as defined herein, appended to the parent molecular moiety through a carbonyl group, as defined herein. Representative examples of $(NR_AR_B)$carbonyl include, but are not limited to, aminocarbonyl, (methylamino)carbonyl, (dimethylamino)carbonyl, and (ethylmethylamino)carbonyl.

The term "$(NR_AR_B)$carbonylalkyl" as used herein, means a $(NR_AR_B)$carbonyl group, as defined herein, appended to the parent molecular moiety through an alkyl group, as defined herein. Representative examples of $(NR_AR_B)$carbonylalkyl include, but are not limited to, aminocarbonylmethyl, (methylamino)carbonylmethyl, (dimethylamino)carbonylmethyl, and (ethylmethylamino)carbonylmethyl.

The term "—$NR_ER_F$" as used herein, means two groups, $R_E$ and $R_F$, which are appended to the parent molecular moiety through a nitrogen atom. $R_E$ and $R_F$ are each independently selected from the group consisting of hydrogen, alkyl, alkylcarbonyl, cycloalkyl, heteroarylalkyl, and hydroxyalkyl. Representative examples of —$NR_ER_F$ include, but are not limited to, amino, methylamino, dimethylamino, acetylamino, and acetylmethylamino.

The term "$(NR_ER_F)$alkoxy" as used herein, means a —$NR_ER_F$ group, as defined herein, appended to the parent molecular moiety through an alkoxy group, as defined herein. Representative examples of $(NR_ER_F)$alkoxy include, but are not limited to aminomethoxy, 2-aminoethoxy, methylaminomethoxy, 2-(methylamino)ethoxy, dimethylaminomethoxy, and 2-(dimethylamino)ethoxy.

The term "$(NR_ER_F)$alkyl" as used herein, means a —$NR_ER_F$ group, as defined herein, appended to the parent molecular moiety through an alkyl group, as defined herein. Representative examples of $(NR_ER_F)$alkyl include, but are not limited to aminomethyl, 2-aminoethyl, 3-aminopropyl, methylaminomethyl, 2-(methylamino)ethyl, dimethylaminomethyl, and 2-(dimethylamino)ethyl.

The term "$(NR_ER_F)$alkylcarbonyl" as used herein, means a $(NR_ER_F)$alkyl group, as defined herein, appended to the parent molecular moiety through a carbonyl group, as defined herein. Representative examples of $(NR_ER_F)$alkylcarbonyl include, but are not limited to aminoacetyl, 3-aminopropanoyl, 3-dimethylaminopropanoyl, and 4-aminobutanoyl.

The term "$(NR_ER_F)$carbonyl" as used herein, means a —$NR_ER_F$ group, as defined herein, appended to the parent molecular moiety through a carbonyl group, as defined herein. Representative examples of $(NR_ER_F)$carbonyl include, but are not limited to, aminocarbonyl, (methylamino)carbonyl, (dimethylamino)carbonyl, and (ethylmethylamino)carbonyl.

The term "$(NR_ER_F)$carbonylalkyl" as used herein, means a $(NR_ER_F)$carbonyl group, as defined herein, appended to the parent molecular moiety through an alkyl group, as defined herein. Representative examples of $(NR_ER_F)$carbonylalkyl include, but are not limited to, 2-amino-2-oxoethyl, 3-amino-3-oxopropyl, and 4-amino-4-oxobutyl.

The term "$(NR_ER_F)$carbonylalkylcarbonyl" as used herein, means a $(NR_ER_F)$carbonylalkyl group, as defined herein, appended to the parent molecular moiety through a carbonyl group, as defined herein. Representative examples of $(NR_ER_F)$carbonylalkylcarbonyl include, but are not limited to, 3-amino-3-oxopropanoyl and 4-amino-4-oxobutanoyl.

The term "$(NR_ER_F)$sulfonyl" as used herein, means a —$NR_ER_F$ group, as defined herein, appended to the parent molecular moiety through a sulfonyl group, as defined herein. Representative examples of $(NR_ER_F)$sulfonyl include, but are not limited to, aminosulfonyl, (methylamino)sulfonyl, (dimethylamino)sulfonyl, and (ethylmethylamino)sulfonyl.

The term "$(NR_ER_F)$sulfonylalkyl" as used herein, means a $(NR_ER_F)$sulfonyl group, as defined herein, appended to the parent molecular moiety through an alkyl group, as defined herein. Representative examples of $(NR_ER_F)$sulfonylalkyl include, but are not limited to, 2-(aminosulfonyl)ethyl, 2-(methylaminosulfonyl)ethyl, 3-(dimethylaminosulfonyl)propyl, and 4-(ethylmethylaminosulfonyl)butyl.

The term "$(NR_ER_F)$sulfonylalkylcarbonyl" as used herein, means a $(NR_ER_F)$sulfonylalkyl group, as defined herein, appended to the parent molecular moiety through a carbonyl group, as defined herein. Representative examples of $(NR_ER_F)$sulfonylalkylcarbonyl include, but are not limited to, 3-(aminosulfonyl)propanoyl, 4-(methylaminosulfonyl)butanoyl, 4-(dimethylaminosulfonyl)butanoyl, and 4-(ethylmethylaminosulfonyl)butanoyl.

The term "—$NR_GR_H$" as used herein, means two groups, $R_G$ and $R_H$, which are appended to the parent molecular moiety through a nitrogen atom. $R_G$ and $R_H$ are each independently selected from the group consisting of hydrogen, alkyl, and alkylcarbonyl. Representative examples of —$NR_GR_H$ include, but are not limited to, amino, methylamino, dimethylamino, acetylamino, and acetylmethylamino.

The term "(NR$_G$R$_H$)alkoxy" as used herein, means at least one —NR$_G$R$_H$ group, as defined herein, appended to the parent molecular moiety through an alkoxy group, as defined herein. Representative examples of (NR$_G$R$_H$)alkoxy include, but are not limited to aminomethoxy, 2-aminoethoxy, methylaminomethoxy, 2-(methylamino)ethoxy, dimethylaminomethoxy, 2-(dimethylamino)ethoxy, and 2-(dimethylamino)-1-[(dimethylamino)methyl]ethoxy.

The term "(NR$_G$R$_H$)alkyl" as used herein, means a —NR$_G$ R$_H$ group, as defined herein, appended to the parent molecular moiety through an alkyl group, as defined herein. Representative examples of (NR$_G$R$_H$)alkyl include, but are not limited to aminomethyl, 2-aminoethyl, 3-aminopropyl, methylaminomethyl, 2-(methylamino)ethyl, dimethylaminomethyl, and 2-(dimethylamino)ethyl.

The term "(NR$_G$R$_H$)carbonyl" as used herein, means a —NR$_G$R$_H$ group, as defined herein, appended to the parent molecular moiety through a carbonyl group, as defined herein. Representative examples of (NR$_G$R$_H$)carbonyl include, but are not limited to, aminocarbonyl, (methylamino)carbonyl, (dimethylamino)carbonyl, and (ethylmethylamino)carbonyl.

The term "(NR$_G$R$_H$)sulfonyl" as used herein, means a —NR$_G$R$_H$ group, as defined herein, appended to the parent molecular moiety through a sulfonyl group, as defined herein. Representative examples of (NR$_G$R$_H$)sulfonyl include, but are not limited to, aminosulfonyl, (methylamino)sulfonyl, (dimethylamino)sulfonyl, and (ethylmethylamino)sulfonyl.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

The compounds of the present invention can exist as therapeutically acceptable salts. The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The present compounds can also exist as therapeutically acceptable prodrugs. The term "therapeutically acceptable prodrug," refers to those prodrugs which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) for example, by hydrolysis in blood. A representative example of a prodrug of the present invention includes, but is not limited to, 4'-(6,7-dimethoxy-1,4-dihydroindeno[1,2-c]pyrazol-3-yl)-1,1'-biphenyl-4-yl 1,4'-bipiperidine-1'-carboxylate.

Asymmetric centers exist in the compounds of the present invention. These centers are designated by the symbols "R" or "S," depending on the configuration of substituents around the chiral carbon atom. It should be understood that the invention encompasses all stereochemical isomeric forms, or mixtures thereof, which possess the ability to inhibit protein kinases. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

In accordance with methods of treatment and pharmaceutical compositions of the invention, the compounds can be administered alone or in combination with other anticancer agents. When using the compounds, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. The compounds can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, diglycerides, fatty acids such as oleic acid, and fixed oils such as monoglycerides or diglycerides.

The anticancer effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled;

Transdermal patches can also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents, and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes therefore.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable non-irritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The total daily dose of the compounds administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Determination of Biological Activity

The Chk1 enzymatic assay was carried out using recombinant Chk1 kinase domain protein covering amino acids from residue 1 to 289 and a polyhistidine tag at the C-terminal end. Human cdc25c peptide substrate contained a sequence from amino acid residue 204 to 225. The reaction mixture contained 25 mM of HEPES at pH 7.4, 10 mM $MgCl_2$, 0.08 mM Triton X-100, 0.5 mM DTT, 5 µM ATP, 4 nM 33P ATP, 5 µM cdc25c peptide substrate, and 6.3 nM of the recombinant Chk1 protein. Compound vehicle DMSO was maintained at 2% in the final reaction. After 30 minutes at room temperature, the reaction was stopped by addition of equal volume of 4 M NaCl and 0.1M EDTA, pH 8. A 40 µL aliquot of the reaction was added to a well in a Flash Plate (NEN Life Science Products, Boston, MA) containing 160 µL of phosphate buffered saline (PBS) without calcium chloride and magnesium chloride and incubated at room temperature for 10 minutes. The plate was then washed 3 times in PBS with 0.05% of Tween-20 and counted in a Packard TopCount counter (Packard BioScience Company, Meriden, Conn.).

Compounds of the present invention inhibited Chk1 at $IC_{50}$ values between about 0.1 nM and about 10,0000 nM. Preferred compounds inhibited Chk1 at $IC_{50}$ values between about 0.1 nM and about 250 µM. Most preferred compounds inhibited Chk1 at $IC_{50}$ values between about 0.1 nM and about 50 nM. Thus, the compounds of the invention are useful in treating disorders which are caused or exacerbated by increased protein kinase levels.

The compounds of the invention, including but not limited to those specified in the examples, possess the ability to inhibit protein kinases. As protein kinase inhibitors, such compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e., chloromas, plasmacytomas and the plaques and tumors of mycosis fungicides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents.

Synthetic Methods

Abbreviations which have been used in the descriptions of the scheme and the examples that follow are: Bu for $CH_3CH_2CH_2CH_2$—, Et for $CH_3CH_2$—; Me for $CH_3$—; $PPh_3$ for triphenylphosphine; $PCy_3$ for tricyclohexylphosphine; dba for dibenzylideneacetone; EDC or EDCI for 1-(3-dimethylaminopropyl)-3-ethylcarbodiimide hydrochloride; DCC for 1,3-dicyclohexylcarbodiimide; HOBt for 1-hydroxybenzotriazole; DMSO for dimethylsulfoxide; DME for 1,2-dimethoxyethane; THF for tetrahydrofuran; DMF for N,N-dimethylformamide; TFA for trifluoracetic acid; dppf for diphenylphosphinoferrocene; Ac for —C(O)CH$_3$, TMS for trimethylsilyl; SEM for [2-(trimethylsilyl)ethoxy]methyl; DMA for dimethylacetamide; and DIEA for diisopropylethylamine.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art.

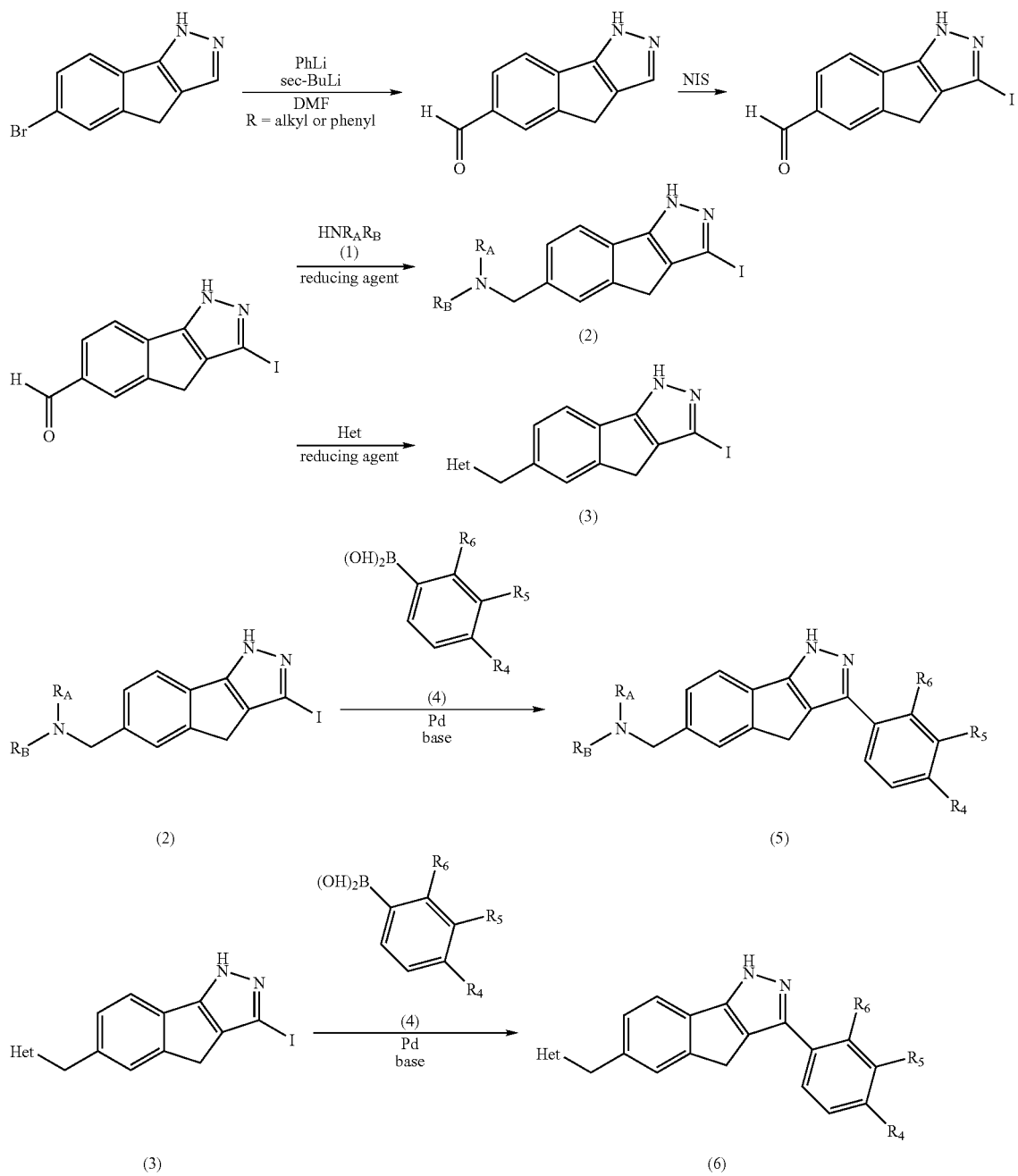

3,6-Disubstituted-1,4-dihydroindeno[1,2-c]pyrazoles of general formula (5) and (6), wherein $R_A$, $R_B$, $R_4$, $R_5$, and $R_6$ are as defined in formula (I), can be prepared as described in Scheme 1. 1,4-Dihydroindeno[1,2-c]pyrazole-6-carbaldehyde, prepared using the procedure described in U.S. Pat. No. 6,297,238, herein incorporated by reference, can be treated with N-iodosuccinimide to provide 3-iodo-1,4-dihydroindeno[1,2-c]pyrazole-6-carbaldehyde. 3-Iodo-1,4-dihydroindeno[1,2-c]pyrazole-6-carbaldehyde can be treated with amines of general formula (I) (or $H_2NOH$) and a reducing agent, including but not limited to, sodium borohydride or sodium cyanoborohydride to provide amines of general formula (2). Amines of general formula (2) can be treated with boronic acids of general formula (4) (or 4,4,5,5-tetramethyl-1,3,2-dioxaborolanes), a base, including but not limited to, cesium carbonate, sodium carbonate, or potassium carbonate, and a metal catalyst, including but not limited to, tetrakis(triphenylphoshine)palladium or bis(triphenylphoshine)palladium(II) chloride to provide 3,6-disubstituted-1,4-dihydroindeno[1,2-c]pyrazoles of general formula (5).

3-Iodo-1,4-dihydroindeno[1,2-c]pyrazole-6-carbaldehyde can also be treated with nitrogen containing heterocycles, including but not limited to, azetidine, azepane, aziridine, azocane, morpholine, mono-protected piperazine, piperidine, 4-hydroxypiperidine, pyrrolidine, thiomorpholine, or 1,1-dioxidothiomorpholine, for example, to provide compounds of general formula (3). Compounds of general formula (3) can be treated with boronic acids of general formula (4), a base, including but not limited to, cesium carbonate, sodium carbonate, or potassium carbonate, and a metal catalyst, including but not limited to, tetrakis(triphenylphoshine)palladium or bis(triphenylphoshine)palladium(II) chloride to provide 3,6-disubstituted-1,4-dihydroindeno[1,2-c]pyrazoles of general formula (6).

It is to be understood that 3,7-disubstituted-1,4-dihydroindeno[1,2-c]pyrazoles can be prepared from 1,4-dihydroindeno[1,2-c]pyrazole-7-carbaldehyde using the methodology described in Scheme 1.

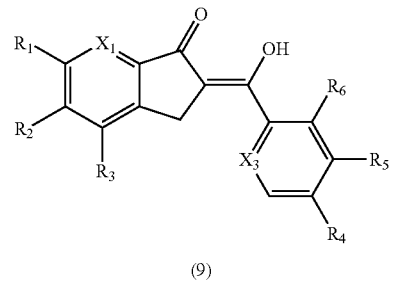

(9)

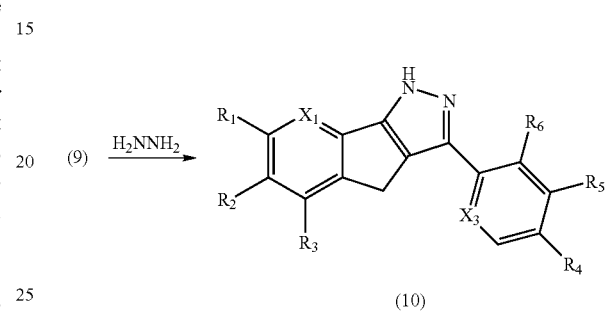

(10)

Compounds of general formula (10), wherein $X_1$, $X_3$, $R_1$, $R_2$, $R_3$, $R_4$, $R_5$, and $R_6$ are as defined in formula (I), can be prepared as described in Scheme 1. 1-Indanones or 5,6-dihydro-7H-cyclopenta[b]pyridin-7-ones, purchased or prepared using methodology known to those of skill in the art, can be treated with esters of general formula (8), 1,1'-carbonyldiimidazole, and a base, including but not limited to, lithium diisopropylamide to provide compounds of general formula (9). Compounds of general formula (9) can be treated with hydrazine and an Aid, including but not limited to, acetic acid, with heat to provide compounds of general formula (10).

Scheme 2

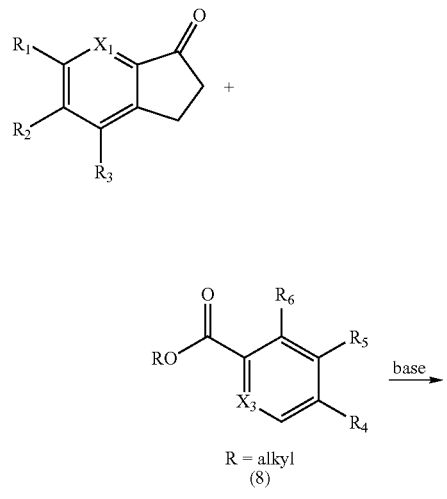

Scheme 3

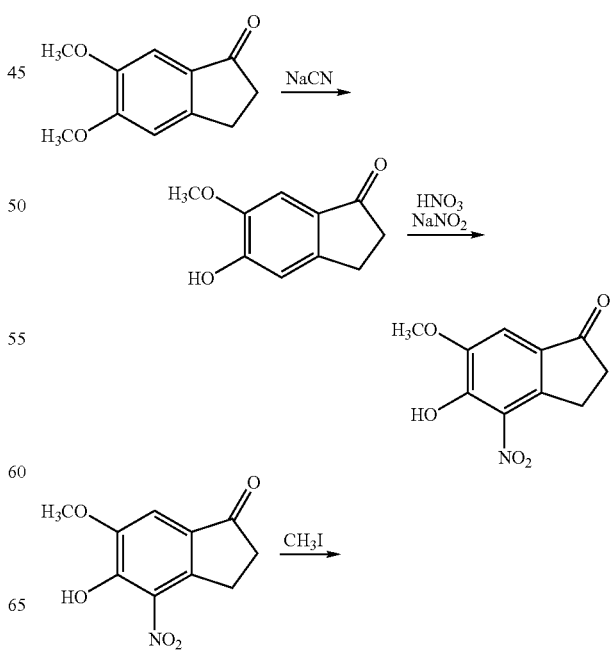

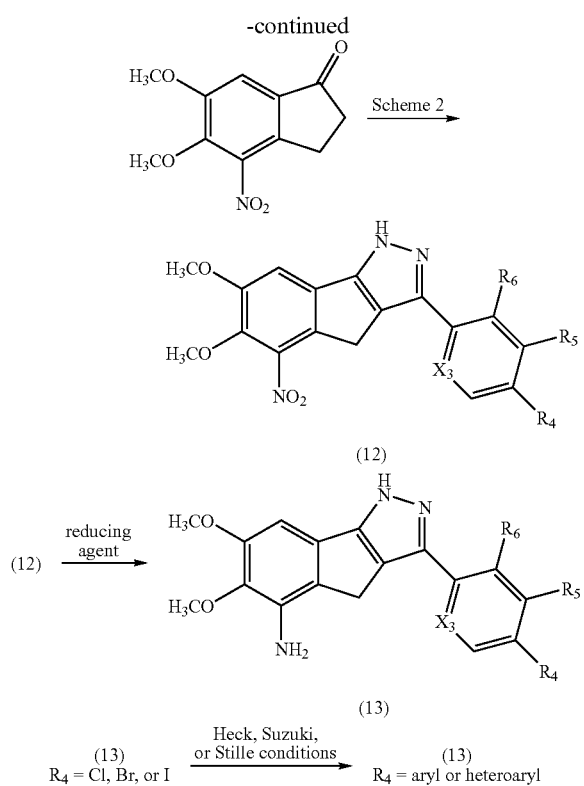

pared using known methodology, a palladium source such as tris(dibenzylidineacetone)dipalladium or palladium diacetate, and a ligand such as tri(2-furyl)phosphine or triphenyl arsine in a solvent such as DMF at 25-150° C. (Stille conditions) to provide compounds of general formula (13) wherein $R_4$ is aryl or heteroaryl as defined herein. Organotin reagents can be prepared from arylhalides, aryltriflates, heteroarylhalides, or heteroaryltriflates by reaction with distannanes like $(Me_3Sn)_2$ (hexamethyl distannane) in the presence of a palladium source like $Pd(Ph_3P)_4$ as described in Krische, Lehn, et. al., Helvetica Chimica Acta, 1909-1920:81 (11) (1998) and in Benaglia, et al., Tetrahedron Letters, 4737-4740:38 (1997) 38.

Compounds of general formula (13), wherein $R_4$ is chlorine, bromine, or iodine, can be treated with aryl or heteroaryl halides, purchased or prepared using known methodology, under Heck conditions as described in Tetrahedron 3327:36 (1980) to provide compounds of general formula (13) wherein $R_4$ is aryl or heteroaryl as defined herein.

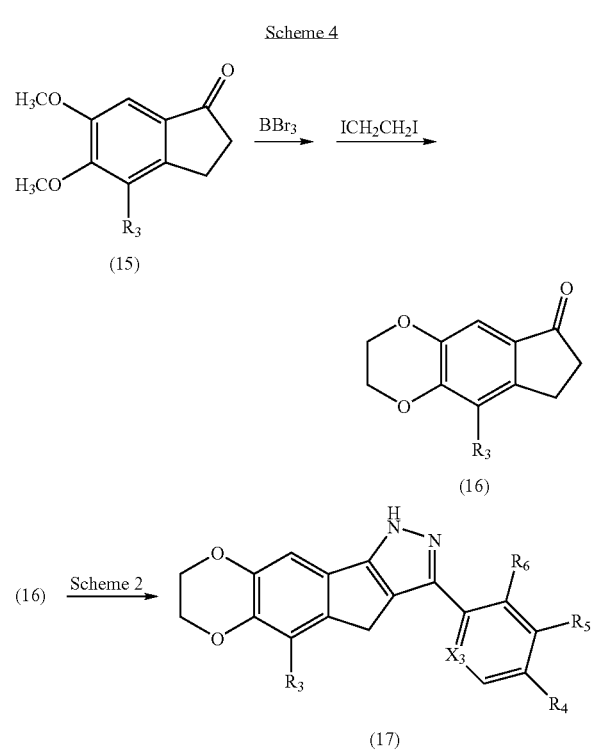

1,4-Dihydroindeno[1,2-c]pyrazoles of general formula (13), wherein $X_3$, $R_4$, $R_5$, and $R_6$ are as defined in formula (I), can be prepared as described in Scheme 3. 5,6-Dimethoxy-1-indanone, purchased from Aldrich Chemical Co., can be treated with sodium cyanide to provide 5-hydroxy-6-methoxy-1-indanone. 5-Hydroxy-6-methoxy-1-indanone can be treated with nitric acid and sodium nitrite to provide 5-hydroxy-6-methoxy-4-nitro-1-indanone. 5-Hydroxy-6-methoxy-4-nitro-1-indanone can be treated with iodomethane and then methodology described in Scheme 2 to provide compounds of general formula (12). Compounds of general formula (12) can be treated with a reducing agent, including iron metal in the presence of acetic acid, to provide amines of general formula (13).

Compounds of general formula (13) where $R_4$ is chlorine, bromine or iodine can be further elaborated under Heck, Suzuki, or Stille conditions to provide compounds of general formula (13) wherein $R_4$ is aryl or heteroaryl as defined herein. An example of suitable Suzuki conditions is described in Example 1D herein or Suzuki conditions as described in N. Miyaura, A. Suzuki, Chem. Rev., 2457-2483:95 (1995); A. Suzuki, J. Organomet. Chem., 147-168: 576 (1999), N. Miyaura, In Advances in Metal-Organic Chemistry, L. S. Liebeskind, Ed., JAI: London, 1998; Vol. 6, pp 187-243; and A. Suzuki, In Metal-Catalyzed Cross-Coupling Reactions, F. Diederich, P. J. Stang, Eds., Wiley-VCH: New York, 1998; Chapter 2; S. P. Stanforth, Tetrahedron, 263-303:54 (1998); can be used to prepare compounds, including but not limited to, 4'-(5-amino-6,7-dimethoxy-1,4-dihydroindeno[1,2-c]pyrazol-3-yl)-1,1 '-biphenyl-4-ol. Aryl and heteroaryl boronic acids and boronic esters are available commercially or can be prepared as described in the scientific literature of synthetic organic chemistry or as described in Example 11 herein.

Compounds of general formula (13), wherein $R_4$ is chlorine, bromine, or iodine, can be treated with aryl or heteroaryl stannanes ($Me_3SnR_4$, $Bu_3SnR_4$), purchased or pre-

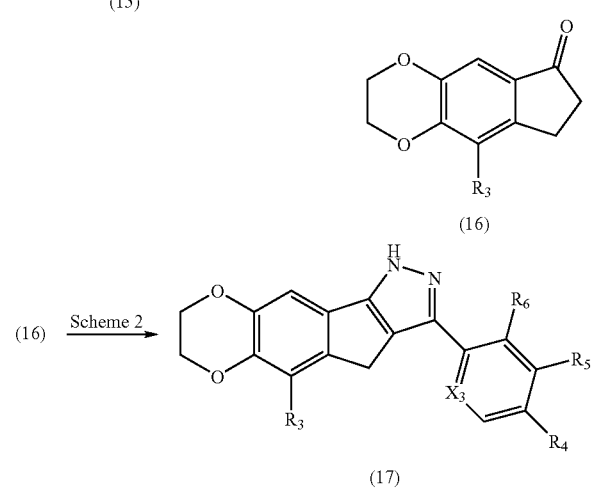

1,4,7,8-Tetrahydro[1,4]dioxino[2',3':5,6]indeno[1,2-c] pyrazoles of general formula (17), wherein $X_3$, $R_3$, $R_4$, $R_5$, and $R_6$ are as defined in formula (I), can be prepared as described in Scheme 4. 5,6-Dimethoxy indanones of general formula (15), purchased or prepared using known methodology, can be treated with tribromoborane and then 1,2-iodoethane to provide 2,3,7,8-tetrahydro-6H-indeno[5,6-b] [1,4]dioxin-6-ones of general formula (16). 2,3,7,8-Tetrahydro-6H-indeno[5,6-b][1,4]dioxin-6-ones of general formula (16) can be treated under conditions as described in Scheme 2 to provide 1,4,7,8-tetrahydro[1,4]dioxino[2',3':5, 6]indeno[1,2-c]pyrazoles of general formula (17), including but not limited to, 4'-(1,4,7,8-tetrahydro[1,4]dioxino[2',3':5, 6]indeno[1,2-c]pyrazol-3-yl)-1,1'-biphenyl-4-ol.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the present invention were named by ACD/ChemSketch version 5.0 (developed by Advanced Chemistry Development, Inc., Toronto, ON, Canada) or were given names consistent with ACD nomenclature.

EXAMPLE 1

4-(6-{[(trans-4-methylcyclohexyl)amino]methyl}-1,4-dihydroindeno[1,2-c]pyrazol-3-yl)benzoic acid

EXAMPLE 1A 1,4-Dihydro-indeno[1,2-c]pyrazole-6-carbaldehyde

To a solution of 6-bromo-1,4-dihydro-indeno[1,2-c]pyrazole (0.100 g, 0.425 mmol, see U.S. Pat. No. 6,297,238 for preparation) in THF (3 mL) at −78° C. was added 1.8 M PhLi in cyclohexane/ether (0.71 mL, 1.28 mmol) followed by 1.3 M s-BuLi in cyclohexane (0.98 mL, 1.28 mmol) 30 minutes later. The reaction mixture was stirred at −78° C. for 60 minutes and DMF (0.33 mL, 4.25 mmol) was added. The dry ice bath was removed after 30 minutes. After an additional 30 minutes, the reaction was quenched with water. The reaction mixture was extracted with EtOAc, washed with 50% brine, dried over $MgSO_4$, filtered, and concentrated. The concentrate was purified by flash chromatography eluted with EtOAc/hexane (7:3 to 8:2) to give 0.053 g (68%) of the desired product as brown solid. MS ($DCI/NH_3$) m/z: 185.0 $(M+H)^+$; $^1H$ NMR (300 MHz, $CD_3OD$) δ 3.76 (s, 2H), 7.63 (s, 1H), 7.62-7.97 (m, 2H), 8.04 (s, 1H), 10.00 (s, 1H).

EXAMPLE 1B

3-Iodo-1,4-dihydro-indeno[1,2-c]pyrazole-6-carbaldehyde

A suspension of Example 1A (7.90 g, 0.0429 mol) and N-iodosuccinimide (11.6 g, 0.0515 mol) in DMF (150 mL) was heated at 80° C. for 5.5 hours. The reaction was cooled and the solvent was evaporated. The concentrate was triturated with EtOAc and ether to give 7.20 g of brown solid as the desired product. The filtrate was concentrated and purified by flash chromatography eluted with EtOAc/hexane (7:3) to give 1.30 g of the desired product (combined yield: 64%). MS ($DCI/NH_3$) m/z: 310.9 $(M+H)^+$; $^1H$ NMR (300 MHz, $DMSO-d_6$) δ 3.63 (s, 0.8H), 3.68 (s, 1.2H), 7.72 (d, J=7.46 Hz, 0.5H), 7.83 (d, J=7.80 Hz, 0.5H), 7.96 (m, 1H), 8.07 (m, 1H), 10.03 (s, 1H), 13.45 (s, 0.6H), 13.72 (s, 0.4H).

EXAMPLE 1C

N-[(3-iodo-1,4-dihydroindeno[1,2-c]pyrazol-6-yl)methyl]-N-(trans-4-methylcyclohexyl)amine and N-[(3-iodo-1,4-dihydroindeno[1,2-c]pyrazol-6-yl)methyl]-N-(cis-4-methylcyclohexyl)amine To a suspension of Example 1B (7.18 g, 0.0232 mol) in EtOH (500 mL) were added 4-methylcyclohexylamine hydrochloride (8.66 g, 0.0579 mol) and potassium carbonate (4.81 g, 0.0348 mol). The mixture was heated to reflux overnight and cooled to room temperature. To the above yellow suspension was added $NaBH_4$ (1.76 g, 0.0464 mol) in two portions and the reaction mixture stirred overnight. After filtration of the solid, the filtrate was concentrated and purified by flash chromatography eluted with EtOAc/MeOH/$NH_4OH$ (10:0.2:0.02 to 10:1:0.1) to give 2.20 g of the cis product (higher Rf) as yellow solid and 3.60 g of the trans product as yellow solid. cis isomer: MS ($DCI/NH_3$) m/z: 408.0 $(M+H)^+$; $^1H$ NMR (300 MHz, $CD_3OD$) δ 0.96 (d, J=6.78 Hz, 3H), 1.35-1.70 (m, 9H), 2.56 (m, 1H), 3.53 (s, 2H), 3.81 (s, 1H), 7.35 (d, J=7.80 Hz, 1H), 7.54 (s, 1H), 7.58 (d, J=7.46 Hz, 1H). trans isomer: MS ($DCI/NH_3$) m/z: 408.0 $(M+H)^+$; $^1H$ NMR (300 MHz, $CD_3OD$) δ 0.88 (d, J=6.44 Hz, 3H), 1.09-1.24 (m, 2H), 1.28-1.53 (m, 2H), 1.62 (m, 1H), 1.67-1.79 (m, 2H), 1.93-2.05 (m, 2H), 2.48 (m, 1H), 3.53 (s, 2H), 3.84 (s, 2H), 7.34 (d, J=7.80 Hz, 1H), 7.53 (s, 1H), 7.58 (d, J=7.80 Hz, 1H).

EXAMPLE 1D 4-(6-{[(trans-4-methylcyclohexyl)amino]methyl}-1,4-dihydroindeno[1,2-c]pyrazol-3-yl)benzoic acid A mixture of Example 1C (trans, 45.0 mg, 0.110 mmol), 4 carboxybenzene boronic acid (20.1 mg, 0.121 mmol), $Na_2CO_3$ (1 M, 0.26 mL, 0.264 mmol), and $Pd(PPh_3)_2Cl_2$ (7.70 mg, 0.0110 mmol) in DME/EtOH/$H_2O$ (7:2:3, 1.2 mL) in a capped 2 mL vial was heated at 160° C. for 450 seconds in a Smith Synthesizer (300W). The reaction was cooled using 40 psi pressurized air. Solvents were evaporated and the crude product was purified using preparative HPLC to give 25.0 mg (26%) of the desired product as pale yellow foam. The purification was processed on a Waters Symmetry C8 column (25 mm×100 mm, 7 μm particle size) using a gradient of 10% to 100% acetonitrile: 0.1% aqueous TFA over 8 min (10 min run time) at a flow rate of 40 mL/min. MS ($DCI/NH_3$) m/z: 402.2 $(M+H)^+$; $^1H$ NMR (300 MHz, $CD_3OD$) δ 0.95 (d, J=6.44 Hz, 3H), 1.00-1.20 (m, 2H), 1.33-1.60 (m, 3H), 1.81-1.98 (m, 2H), 2.15-2.30 (m, 2H), 3.15 (m, 1H), 3.96 (s, 2H), 4.31 (s, 2H), 7.52 (m, 1H), 7.71 (m, 1H), 7.81 (d, J=7.80 Hz, 1H), 7.90 (d, J=8.81 Hz, 2H), 8.15 (d, J=8.48 Hz, 2H).

EXAMPLE 2

4-(6-{[(cis-4-methylcyclohexyl)amino]methyl}-1,4-dihydroindeno[1,2-c]pyrazol-3-yl)benzoic acid The desired product was prepared using the procudure in Example 1D replacing the trans product from Example 1C with the cis product from Example 1C. MS ($DCI/NH_3$) m/z: 402 $(M+H)^+$; $^1H$ NMR (300 MHz, $CD_3OD$) δ 1.04 (d, J=7.12 Hz, 3H), 1.50-1.98 (m, 9H), 3.23 (m, 1H), 3.98 (s, 2H), 4.31 (s, 2H), 7.53 (d, J=9.15 Hz, 1H), 7.73 (s, 1H), 7.82 (d, J=7.80 Hz, 1H), 7.91 (d, J=8.81 Hz, 2H), 8.15 (d, J=8.48 Hz, 2H).

EXAMPLE 3 ethyl 4-(6-{[(trans-4-methylcyclohexyl)amino]methyl}-1,4-dihydroindeno[1,2-c]pyrazol-3-yl)benzoate To a degassed suspension of Example 1C (trans, 45.0 mg, 0.110 mmol) in DME/EtOH/$H_2O$ (7:3:2) were added 4-(4,4,5,5-tetramethyl-[1,3,2]dioxaborolan-2-yl)-benzoic acid ethyl ester (31.8 μL, 0.121 mmol), $Na_2CO_3$ (1M, 0.11 mL), and $Pd(PPh_3)_2Cl_2$ (7.7 mg, 0.0110 mmol). The reaction mixture was heated overnight at 85° C. in a sealed vial. The mixture was concentrated and the residue was extracted with EtOAc, washed with brine, dried over MgSO$_4$, filtered, and concentrated. The residue was purified using preparative HPLC (see condition in Example 1D) to give 8.8 mg (12%) of the desired product as white foam. MS (DCI/NH$_3$) m/z: 430.2 (M+H)$^+$; $^1$H NMR (300 MHz, CD$_3$OD) δ 0.95 (d,J=6.78 Hz, 3H), 1.09 (m, 2H), 1.42 (t, J=7.12 Hz, 3H), 1.42-1.57 (m, 3H), 1.82-1.94 (m, 2H), 2.16-2.29 (m, 2H), 3.15 (m, 1H), 3.98 (s, 2H), 4.30 (s, 2H), 4.40 (q, J=7.12 Hz, 2H), 7.52 (d, J=7.80 Hz, 1H), 7.72 (s, 1H), 7.82 (d, J=7.80 Hz, 1H), 7.92 (d, J=8.82 Hz, 2H), 8.15 (d, J=8.48 Hz, 2H).

EXAMPLE 4

4-(6-{[(trans-4-hydroxycyclohexyl)amino]methyl}-1,4-dihydroindeno[1,2-c]pyrazol-3-yl)benzoic acid

EXAMPLE 4A trans-4-[(3-Iodo-1,4-dihydro-indeno[1,2-c]pyrazol-6-ylmethyl)-amino]-cyclohexanol The desired product was prepared by replacing 4-tethyl-cyclohexylamine hydrochloride with trans-4-hydroxycyclo-hexylamine hydrochloride in Example 1C. MS (DCI/NH$_3$) m/z: 410.0 (M+H)$^+$; $^1$H NMR (300 MHz, CD$_3$OD) δ 1.09-1.35 (m, 4H), 1.82-2.08 (m, 4H), 2.48 (m, 1H), 3.47-3.58 (m, 3H), 3.82 (s, 2H), 7.34 (m, 1H), 7.52 (m, 1H), 7.58 (d, J=7.80 Hz, 0.8H), 7.65 (d, J=7.80 Hz, 0.2H).

EXAMPLE 4B 4-(6-{[(trans-4-hydroxycyclohexyl)amino]methyl}-1,4-dihydroindeno[1,2-c]pyrazol-3-yl)benzoic acid The desired product was prepared by replacing Example 1C with Example 4A in Example 1D. MS (DCI/NH$_3$) m/z: 404.2 (M+H)$^+$; $^1$H NMR (300 MHz, CD$_3$OD) δ 1.27-1.61 (m, 4H), 2.02-2.16 (m, 2H), 2.18-2.32 (m, 2H), 3.07-3.25 (m, 1H), 3.50-3.66 (m, 1H), 3.97 (s, 2H), 4.30 (s, 2H), 7.51 (dd, J=7.80, 1.36 Hz, 1H), 7.71 (s, 1H), 7.81 (d, J=7.80 Hz, 1H), 7.91 (d, J=8.48 Hz, 2H), 8.15 (d, J=8.48 Hz, 2H).

EXAMPLE 5

N-[3-(6-{[(trans-4-hydroxycyclohexyl)amino]me-thyl}-1,4-dihydroindeno[1,2-c]pyrazol-3-yl)phenyl] acetamide The desired product was prepared by replacing Example 1C and 4-carboxybenzene boronic acid with Example 4A and 3-acetamidobenzene boronic acid in Example 1D. MS (DCI/NH$_3$) m/z: 417.2 (M+H)$^+$; $^1$H NMR (300 MHz, CD$_3$OD) δ 1.28-1.69 (m, 4H), 2.03-2.14 (m, 2H), 2.19 (s, 3H), 2.21-2.33 (m, 2H), 3.17 (m, 1H), 3.58 (m, 1H), 3.92 (s, 2H), 4.29 (s, 2H), 7.34-7.59 (m, 4H), 7.70 (s, 1H), 7.80 (d, J=8.14 Hz, 1H), 8.24 (m, 1H).

EXAMPLE 6

4-(6-{[(trans-4-hydroxycyclohexyl)amino]methyl}-1,4-dihydroindeno[1,2-c]pyrazol-3-yl)benzamide The desired product was prepared by replacing Example 1C and 4-carboxybenzene boronic acid with Example 4A and 4-(4,4,5,5-tetramethyl-[1,3,2]dioxaborolan-2-yl)-benza-mide in Example 1D. MS (DCI/NH$_3$) m/z: 403.3 (M+H)$^+$; $^1$H NMR (300 MHz, CD$_3$CD) δ 1.29-1.59 (m, 4H), 2.03-2.15 (m, 2H), 2.20-2.32 (m, 2H), 3.17 (m, 1H), 3.56 (m, 1H), 3.97 (s, 2H), 4.30 (s, 2H), 7.52 (dd, J=7.80, 1.36 Hz, 1H), 7.72 (s, 1H), 7.82 (d, J=7.80 Hz, 1H), 7.90 (d, J=8.48 Hz, 2H), 8.02 (d, J=8.48 Hz, 2H).

EXAMPLE 7

4-[6-(4-morpholinylmethyl)-1,4-dihydroindeno[1,2-c]pyrazol-3-yl]benzoic acid

EXAMPLE 7A

3-Iodo-6-morpholin-4-ylmethyl-1,4-dihydro-indeno[1,2-c]pyrazole

A mixture of Example 1B (1.00 g, 3.22 mmol), morpho-line (0.84 mL, 9.66 mmol), and TsOH.H$_2$O (61.2 mg, 0.322 mmol) in toluene (50 mL) was heated to refluxing overnight. The solvent was evaporated. To the resulting residue were added EtOH (40 mL), THF (10 mL), and NaBH$_4$ (0.182 g, 4.83 mmol) at room temperature. The mixture was stirred overnight and the resulting solid was filtered. The filtrate was concentrated, treated with 1N HCl, and extracted with EtOAc. The aqueous layer was basified using 3N NaOH and extracted with EtOAc. The organic layer was dried over MgSO$_4$, filtered, and concentrated. The residue was purified by flash chromatography eluted with EtOAc/MeOH (95:5) to give 0.387 g (32%) of the desired product as pale yellow solid. MS (DCI/NH$_3$) m/z: 382.0 (M+H)$^+$; $^1$H NMR (300 MHz, CD$_3$OD) δ 2.44-2.51 (m, 4H), 3.53 (s, 2H), 3.57 (s, 2H), 3.66-3.72 (m, 4H), 7.34 (d, J=8.14 Hz, 1H), 7.54 (s, 1H), 7.58 (d, J=7.80 Hz, 1H).

EXAMPLE 7B

4-[6-(4-morpholinylmethyl)-1,4-dihydroindeno[1,2-c]pyrazol-3-yl]benzoic acid

The desired product was prepared by replacing Example 1C with Example 7A in Example 1D. MS (DCI/NH$_3$) m/z: 376.1 (M+H)$^+$; $^1$H NMR (500 MHz, DMSO-d$_6$) δ 3.06-3.17 (m, 2H,) 3.26 (d, J=12.17 Hz, 2H), 3.87 (t, J=11.54 Hz, 2H), 3.91-3.99 (m, 4H), 4.40 (d, J=4.37 Hz, 2H), 7.66 (d, J=7.80 Hz, 1H), 7.75 (d, J=7.80 Hz, 1H), 7.89 (s, 1H), 7.98 (d, J=8.42 Hz, 2H), 8.06 (d, J=8.42 Hz, 2H), 11.61 (s, 1H).

EXAMPLE 8 methyl 4-[6-(4-morpholinylmethyl)-1,4-dihydroin-deno[1,2-c]pyrazol-3-yl]benzoate To Example 7B (28.8 mg, 0.0643 mmol) in MeOH (3 mL) was added concentrated HCl (0.50 mL). The mixture was heated to 65° C. and stirred for 3 days. The reaction mixture was concentrated and purified using HPLC. The TFA salt of the desired product was converted into the HCl (17.0 mg, 81%) using the procedure in Example 7B. The HPLC condition is indicated as the following: Dynamx C18 (5 μm, 21.4×250 mm) column was used containing a Rainin Dynamax solvent delivery system with a Dynamax UV-D II detector. The solvent system used was a 20% to 100% acetonitrile/water containing 0.1% TFA linear gradient. The elution rate was 10 mL/min and the UV detection wave-length was set at 254 nm). MS (DCI/NH$_3$) m/z: 390 (M+H)$^+$; $^1$H NMR (400 MHz, DMSO-d$_6$) δ 3.05-3.18 (m, 2H), 3.22-3.30 (m, 2H), 3.77-3.87 (m, 2H), 3.89 (s, 3H), 3.91-4.00 (m, 4H), 4.40 (d, J=4.60 Hz, 2H), 7.63 (d, J=7.98 Hz, 1H), 7.75 (d, J=7.67 Hz, 1H), 7.86 (s, 1H), 7.99 (d, J=8.29 Hz, 2H), 8.08 (d, J=8.28 Hz, 2H), 11.29 (s, 1H).

EXAMPLE 9

4-[6-(4-morpholinylmethyl)-1,4-dihydroindeno[1,2-c]pyrazol-3-yl]benzamide

The desired product was prepared by replacing Example 1C and 4-carboxybenzene boronic acid with Example 7A and 4-(4,4,5,5-tetramethyl-[1,3,2]dioxaborolan-2-yl)-benzamide in Example 1D. The product was purified by flash chromatography eluted with EtOAc/MeOH/NH$_4$OH (10:1: 0.1). MS (DCI/NH$_3$) m/z: 375.2 (M+H)$^+$; $^1$H NMR (300 MHz, DMSO-d$_6$) δ 2.34-2.44 (m, 4H), 3.53 (s, 2H,), 3.56-3.63 (m, 4H), 3.91 (s, 2H), 7.31 (d, J=7.46 Hz, 1H), 7.42 (s, 1H), 7.52 (s, 1H), 7.64 (m, 1H), 7.87 (d, J=7.80 Hz, 2H), 8.00 (d, J=8.48 Hz, 3H), 13.29 (s, 1H).

EXAMPLE 10

N-{3-[6-(4-morpholinylmethyl)-1,4-dihydroindeno[1,2-c]pyrazol-3-yl]phenyl}acetamide The desired product was prepared by replacing Example 1C and 4-carboxybenzene boronic acid with Example 7A and 3-acetamidobenzeneboronic acid in Example 1D. MS (DCI/NH$_3$) m/z: 389.2 (M+H)$^+$; $^1$H NMR (400 MHz, DMSO-d$_6$) δ 2.10 (s, 3H), 3.06-3.17 (m, 2H), 3.22-3.32 (m, 2H), 3.78-3.90 (m, 4H), 3.95 (d, J=14.12 Hz, 2H), 4.40 (d, J=3.68 Hz, 2H), 7.41 (t, J=7.83 Hz, 1H), 7.58 (m, 3H), 7.74 (d, J=7.67 Hz, 1H), 7.88 (s, 1H), 8.13 (s, 1H), 10.18 (s, 1H), 11.37 (s, 1H).

EXAMPLE 11

2-(acetylamino)-4-[6-(4-morpholinylmethyl)-1,4-dihydroindeno[1,2-c]pyrazol-3-yl]benzoic acid

EXAMPLE 11A

N-(5-Bromo-2-methyl-phenyl)-acetamide

To a solution of 3-bromo-6-methylaniline (1.00 g, 5.37 mmol) in pyridine (8 mL) was added acetyl chloride (0.76 mL, 10.7 mmol) at 0° C. The reaction mixture was stirred at room temperature for 1 hour and concentrated. The residue was extracted with EtOAc, washed with 5% citric acid, dried over MgSO$_4$, concentrated, and triturated with ether to give 0.750 g (61%) of the desired product as off-white crystal. MS (DCI/NH$_3$) m/z: 227.9 (M+H)$^+$, 229.9 (M+2+H)$^+$; $^1$H NMR (300 MHz, CDCl$_3$) δ 2.21 (s, 6H), 6.90 (m, 1H), 7.04 (d, J=8.14 Hz, 1H), 7.20 (d, J=7.80 Hz, 1H), 8.06 (s, 1H).

EXAMPLE 11B

2-Acetylamino-4-bromo-benzoic acid

To a solution of Example 11A (0.372 g, 1.63 mmol) in pyridine (6 mL) and H$_2$O (6 mL) was added KMnO$_4$ (1.03 g, 6.52 mmol) in 2 portions at room temperature. The reaction mixture was heated to 90° C. for 4 hours and immediately filtered. The filter cake was rinsed with hot H$_2$O. The filtrate was concentrated and treated with H$_2$O. The solid material was filtered and filtrate acidified with 10% HCl until pH=3. The white precipitate was filtered, rinsed with H$_2$O, and dried in a vacuum oven to give 0.398 g (95%) of the desired product as white solid. MS (DCI/NH$_3$) m/z: 257.9 (M+H)$^+$, 259.9 (M+2+H)$^+$; $^1$H NMR (300 MHz, CD$_3$OD) δ 2.20 (s, 3H), 7.30 (dd, J=8.48, 2.03 Hz, 1H), 7.97 (d, J=8.48 Hz, 1H), 8.84 (d, J=2.03 Hz, 1H).

EXAMPLE 11C

2-Acetylamino-4-(4,4,5,5-tetramethyl-[1,3,2]dioxaborolan-2-yl)-benzoic acid methyl ester To a solution of Example 11B (45.0 mg, 0.174 mmol) in CH$_2$Cl$_2$/MeOH (2 mL/0.3 mL) was added TMSCHN$_2$. After the disappearance of strong bubbling, the reaction mixture was concentrated. The crude methyl ester product was taken into the next step without purification. A mixture of the above crude product, Pd$_2$(dba)$_3$ (3.2 mg, 0.0034 mmol), PCy$_3$ (3.9 mg, 0.014 mmol), KOAc (25.6 mg, 0.261 mmol), and bis(pinacolato)diboron (53.0 mg, 0.209 mmol) in 1,4-dioxane (1.5 mL) was heated at 85° C. overnight in a capped vial. The solvent was evaporated and the residue was extracted with EtOAc, washed with brine, dried over MgSO$_4$, filtered, concentrated, and purified by flash chromatography eluted with hexane/EtOAc (8:2 to 7:3) to give 31.0 mg (56%) of the desired product as off-white solid. MS (DCI/NH$_3$) m/z: 320.1 (M+H)$^+$; $^1$H NMR (300 MHz, DMSO-d$_6$) δ 1.31 (s, 12H), 2.11 (s, 3H), 3.85 (s, 3H), 7.45 (d, J=8.82 Hz, 1H), 7.87 (d, J=7.80 Hz, 1H), 8.42 (s, 1H), 10.42 (s, 1H).

EXAMPLE 11D 2-(acetylamino)-4-[6-(4-morpholinylmethyl)-1,4-dihydroindeno[1,2-c]pyrazol-3-yl]benzoic acid The desired product was prepared by replacing Example 1C and 4-carboxybenzene boronic acid with Example 7A and Example 11C in Example 1D. The product was purified using the HPLC condition in Example 8. MS (DCI/NH$_3$) m/z: 433.2 (M+H)$^+$; $^1$H NMR (500 MHz, CD$_3$OD) δ 2.17 (s, 3H), 3.09-3.36 (m, 2H), 3.88 (s, 2H), 3.56-4.06 (m, 6H), 4.35 (s, 2H), 7.44 (d, J=7.80 Hz, 1H), 7.50 (d, J=6.55 Hz, 1H), 7.65 (s, 1H), 7.74 (d, J=7.80 Hz, 1H), 7.83 (d, J=8.73 Hz, 1H), 8.09 (d, J=8.11 Hz, 1H), 8.99 (s, 1H).

EXAMPLE 12

4-{6-[(4-hydroxy-1-piperidinyl)methyl]-1,4-dihydroindeno[1,2-c]pyrazol-3-yl}benzoic acid

EXAMPLE 12A 1-(3-Iodo-1,4-dihydro-indeno[1,2-c]pyrazol-6-ylmethyl)-piperidin-4-ol The desired product was prepared by replacing morpholine with 4-hydroxypiperidine in Example 7A. MS (DCI/NH$_3$) m/z: 396.0 (M+H)$^+$; $^1$H NMR (300 MHz, CD$_3$OD) δ 1.48-1.65 (m, 2H), 1.77-1.91 (m, 2H), 2.12-2.31 (m, 2H), 2.742.89 (m, 2H), 3.54 (s, 2H), 3.57-3.69 (m, 1H), 3.57 (s, 2H), 7.33 (d, J=9.15 Hz, 1H), 7.52 (s, 1H), 7.58 (d, J=7.80 Hz, 1H).

EXAMPLE 12B

4-{6-[(4-hydroxy-1-piperidinyl)methyl]-1,4-dihydroindeno[1,2-c]pyrazol-3-yl}benzoic acid The desired product was prepared by replacing Example 1C with Example 12A in Example 1D. MS (DCI/NH$_3$) m/z: 390.2 (M+H)$^+$; $^1$H NMR (400 MHz, DMSO-d$_6$) δ 1.66-1.82 (m, 2H), 1.89-2.07 (m, 2H), 2.94 (m, 1H), 3.09-3.23 (m, 2H), 3.34 (m, 1H), 3.64 (m, 1H), 3.97 (s, 2H), 4.34 (dd, J=15.04, 4.60 Hz, 2H), 6.78-6.90 (m, 2H), 7.56-7.67 (m, 0.5H), 7.71-7.81 (m, 2H) 7.84 (d, J=13.81 Hz, 0.5H,) 7.97 (d, J=8.29 Hz, 1H), 8.06 (d, J=8.59 Hz, 1H), 10.55 (s, 1H).

EXAMPLE 13

4-{6-[(4-hydroxy-1-piperidinyl)methyl]-1,4-dihydroindeno[1,2-c]pyrazol-3-yl}benzamide The desired product was prepared by replacing Example 1C and 4-carboxybenzene boronic acid with Example 12A and 4-(4,4,5,5-tetramethyl-[1,3,2]dioxaborolan-2-yl)-benzamide in Example 1D. MS (DCI/NH$_3$) m/z: 389.2 (M+H)$^+$; $^1$H NMR (400 MHz, DMSO-d$_6$) δ 1.64-1.80 (m, 2H), 1.88-2.09 (m, 2H), 2.96 (m, 1H), 3.08-3.22 (m, 2H), 3.33 (m, 1H), 3.63 (m, 1H), 3.95 (s, 2H), 4.33 (dd, J=14.58, 5.06 Hz, 2H), 7.40 (s, 1H), 7.62 (dd, J=13.20, 7.67 Hz, 1H), 7.74 (d, J=7.67 Hz, 1H), 7.84 (d, J=13.20 Hz, 1H), 7.91 (d, J=8.59 Hz, 2H), 8.01 (m, 2H), 10.65 (s, 1H).

EXAMPLE 14

N-(3-{6-[(4-hydroxy-1-piperidinyl)methyl]-1,4-dihydroindeno[1,2-c]pyrazol-3-yl}phenyl)acetamide The desired product was prepared by replacing Example 1C and 4-carboxybenzene boronic acid with Example 12A and 3-acetamidobenzeneboronic acid in Example 1D. MS (DCI/NH$_3$) m/z: 403.2 (M+H)$^+$; $^1$H NMR (400 MHz, DMSO-d$_6$) δ 1.65-1.80 (m, 2H), 1.88-2.04 (m, 2H), 2.95 (m, 1H), 3.09-3.23 (m, 2H), 3.35 (m, 1H), 3.62 (m, 1H), 3.88 (s, 2H) 4.33 (dd, J=15.50, 5.06 Hz, 2H), 7.41 (t, J=7.83 Hz, 1H), 7.50-7.64 (m, 3H), 7.73 (d, J=7.67 Hz, 1H), 7.84 (d, J=14.12 Hz, 1H), 8.13 (s, 1H), 10.15 (s, 1H), 10.46 (s, 1H).

EXAMPLE 15

4-{6-[(neopentylamino)methyl]-1,4-dihydroindeno[1,2-c]pyrazol-3-yl}benzoic acid

EXAMPLE 15A (2,2-Dimethyl-propyl)-(3-iodo-1,4-dihydro-indeno[1,2-c]pyrazol-6-ylmethyl)-amine The desired product was prepared by replacing morpholine with neopentylamine in Example 7A. MS (DCI/NH$_3$) m/z: 382.1 (M+H)$^+$; $^1$H NMR (300 MHz, CD$_3$OD) δ 0.92 (s, 9H), 2.34 (s, 2H), 3.53 (s, 2H), 3.82 (s, 2H), 7.35 (d, J=7.80 Hz, 1H), 7.527.61 (m, 2H).

EXAMPLE 15B

4-{6-[(neopentylamino)methyl]-1,4-dihydroindeno[1,2-c]pyrazol-3-yl}benzoic acid

The desired product was prepared by replacing Example 1C with Example 15A in Example 1D. MS (DCI/NH$_3$) m/z: 376.2 (M+H)$^+$; $^1$H NMR (500 MHz, DMSO-d$_6$) δ 0.98 (s, 9H), 2.62-2.77 (m, 2H), 3.96 (s, 2H), 4.23 (s, 2H), 7.62 (d, J=7.80 Hz, 1H), 7.74 (d, J=7.80 Hz, 1H), 7.83 (s, 1H), 7.96 (d, J=8.42 Hz, 2H), 8.06 (d, J=8.42 Hz, 2H), 8.94 (s, 1H).

EXAMPLE 16

4-{6-[(neopentylamino)methyl]-1,4-dihydroindeno[1,2-c]pyrazol-3-yl}benzamide

The desired product was prepared by replacing Example 1C and 4-carboxybenzene boronic acid with Example 15A and 4-(4,4,5,5-tetramethyl-[1,3,2]dioxaborolan-2-yl)-benzamide in Example 1D. MS (DCI/NH$_3$) m/z: 375.2 (M+H)$^+$; $^1$H NMR (300 MHz, DMSO-d$_6$) δ 0.97 (s, 9H), 2.62-2.81 (m, 2H), 3.97 (s, 2H), 4.24 (s, 2H), 7.42 (s, 1H), 7.60 (d, J=8.48 Hz, 1H), 7.74 (d, J=7.80 Hz, 1H), 7.81 (s, 1H), 7.90 (d, J=8.48 Hz, 2H), 8.01 (d, J=8.48 Hz, 2H), 8.86 (s, 1H).

EXAMPLE 17

4-(6-{[(3-hydroxy-2,2-dimethylpropyl)amino]methyl}-1,4-dihydroindeno[1,2-c]pyrazol-3-yl)benzoic acid

EXAMPLE 17A

3-[(3-Iodo-1,4-dihydro-indeno[1,2-c]pyrazol-6-ylmethyl)-amino]-2,2-dimethyl-propan-1-ol The desired product was prepared by replacing morpholine with 3-amino-2,2-dimethyl-1-propanol in Example 7A. MS (DCI/NH$_3$) m/z: 398.1 (M+H)$^+$; $^1$H NMR (300 MHz, CD$_3$OD) δ 0.90 (s, 6H), 2.52 (s, 2H), 3.36 (s, 2H), 3.53 (s, 2H), 3.80 (s, 2H), 7.33 (d, J=6.78 Hz, 1H), 7.52 (s, 1H), 7.57 (d, J=7.80 Hz, 1H).

EXAMPLE 17B 4-(6-{[(3-hydroxy-2,2-dimethylpropyl)amino]methyl}-1,4-dihydroindeno[1,2-c]pyrazol-3-yl)benzoic acid The desired product was prepared by replacing Example 1C with Example 17A in Example 1D. MS (DCI/NH$_3$) m/z: 391.3 (M+H)$^+$; $^1$H NMR (500 MHz, DMSO-d$_6$) δ 0.91 (s, 6H), 2.77 (m, 2H), 3.23 (s, 2H), 3.96 (s, 2H), 4.23 (s, 2H,) 7.62 (d, J=7.80 Hz, 1H), 7.73 (d, J=7.80 Hz, 1H), 7.83 (s, 1H), 7.97 (d, J=8.42 Hz, 2H), 8.06 (d, J=8.42 Hz, 1H), 8.91 (s, 2H).

EXAMPLE 18

4-(6-{[(3-hydroxy-2,2-dimethylpropyl)amino]methyl}-1,4-dihydroindeno[1,2-c]pyrazol-3-yl)benzamide The desired product was prepared by replacing Example 1C and 4-carboxybenzene boronic acid with Example 17A and 4-(4,4,5,5-tetramethyl-[1,3,2]dioxaborolan-2-yl)-benzamide in Example 1D. MS (DCI/NH$_3$) m/z: 391.2 (M+H)$^+$; $^1$H NMR (500 MHz, DMSO-d$_6$) δ 0.90 (s, 6H), 2.82 (m, 2H), 3.24 (J=4.99 Hz, 2H), 3.96 (s, 2H), 4.23 (d, J=17.47 Hz, 2H), 7.49 (d, J=8.42 Hz, 0.5H) 7.54 (d, J=8.11 Hz, 0.5H), 7.66 (s, 1H), 7.75 (s, 1H), 7.90 (d, J=8.42 Hz, 1H), 8.01 (d, J=8.11 Hz, 3H), 8.53 (s, 2H).

EXAMPLE 19

4-[6-(hydroxymethyl)-1,4-dihydroindeno[1,2-c]pyrazol-3-yl]benzoic acid

EXAMPLE 19A (3-Iodo-1,4-dihydro-indeno[1,2-c]pyrazol-6-yl)-methanol

To a suspension of Example 1B (0.500 g, 1.61 mmol) in a mixture of MeOH (9 mL) and THF (3 mL) was added $NaBH_4$ (73.0 mg, 1.93 mmol) at room temperature. The mixture was stirred for 2 hours and the solvent was evaporated. The resulting concentrate was dissolved in hot $CH_2Cl_2$ with a small amount of MeOH and the desired product was recrystalized to give 0.324 g (65%) of the desired product as brown solid. MS (DCI/$NH_3$) m/z: 312.9 (M+H)$^+$; $^1$H NMR (300 MHz, $CD_3OD$) δ 3.54 (s, 2H), 4.66 (s, 2H), 7.35 (d, J=7.80 Hz, 1H), 7.55 (s, 1H), 7.59 (d, J=7.80 Hz, 1H).

EXAMPLE 19B

4-[6-(hydroxymethyl)-1,4-dihydroindeno[1,2-c]pyrazol-3-yl]benzoic acid

The desired product was prepared by replacing Example 1C with Example 19A in Example 1D. MS (DCI/$NH_3$) m/z: 307.1 (M+H)$^+$; $^1$H NMR (500 MHz, DMSO-$d_6$) δ 3.90 (s, 2H), 4.57 (s, 2H), 7.33 (d, J=7.49 Hz, 1H), 7.54 (s, 1H), 7.61 (d, J=7.80 Hz, 1H), 7.94 (d, J=8.42 Hz, 2H), 8.05 (d, J=8.42 Hz, 2H).

EXAMPLE 20

4-[6-(hydroxymethyl)-1,4-dihydroindeno[1,2-c]pyrazol-3-yl]benzamide

The desired product was prepared by replacing Example 1C and 4-carboxybenzene boronic acid with Example 19A and 4-(4,4,5,5-tetramethyl-[1,3,2]dioxaborolan-2-yl)-benzamide in Example 1D. MS (DCI/$NH_3$) m/z: 306.1 (M+H)$^+$; $^1$H NMR (500 MHz, DMSO-$d_6$) δ 3.90 (s, 2H), 4.57 (s, 2H), 7.32 (d, J=7.49 Hz, 1H), 7.54 (s, 1H), 7.61 (d, J=7.80 Hz, 1H), 7.89 (d, J=8.42 Hz, 2H), 8.00 (d, J=8.42 Hz, 2H).

EXAMPLE 21

4-[6-(methoxymethyl)-1,4-dihydroindeno[1,2-c]pyrazol-3-yl]benzoic acid

EXAMPLE 21A

3-Iodo-6-methoxymethyl-1,4-dihydro-indeno[1,2-c]pyrazole

A mixture of Example 19A (0.294 g, 0.942 mmol), LiBr (0.090 g, 1.04 mmol), and $PBr_3$ (0.14 mL, 11.49 mmol) in DMF (5 mL) was stirred at room temperature for 2 hours. Ice was added to the reaction mixture and the resulting precipitate was filtered. The solid was suspended in MeOH and treated with $Et_3N$ (1 mL). The mixture was concentrated and purified by flash chromatography eluted with EtOAc/$CH_2Cl_2$ (2:98 to 5:95) to give 0.0422 g (12%) of the desired product. MS (DCI/$NH_3$) m/z: 327.0 (M+H)$^+$; $^1$H NMR (500 MHz, $CD_3OD$) δ 3.38 (s, 3H), 3.53 (s, 2H), 4.50 (s, 2H), 7.33 (d, J=7.80 Hz, 1H), 7.52 (s, 1H), 7.59 (m, 1H).

EXAMPLE 21B

4-[6-(methoxymethyl)-1,4-dihydroindeno[1,2-c]pyrazol-3-yl]benzoic acid

The desired product was prepared by replacing Example 1C with Example 21A in Example 1D. MS (DCI/$NH_3$) m/z: 321.0 (M+H)$^+$; $^1$H NMR (400 MHz, DMSO-$d_6$) δ 3.31 (s, 3H), 3.89 (s, 2H), 4.46 (s, 2H), 7.31 (d, J=7.67 Hz, 1H), 7.52 (s, 1H), 7.63 (d, J=7.67 Hz, 1H), 7.92 (d, J=8.59 Hz, 2H), 8.04 (d, J=8.59 Hz, 2H).

EXAMPLE 22

4-[6-(allyloxy)-1,4-dihydroindeno[1,2-c]pyrazol-3-yl]benzoic acid

EXAMPLE 22A

5-Allyloxy-indan-1-one

To a solution of 5-hydroxy-1-indanone (4.27 g, 0.0288 mol) in THF/DMF (5 mL/10 mL) at 0° C. was added NaH (60%, 1.21 g, 0.0303 mol) followed by allyl bromide (2.7 mL, 0.0317 mol). The reaction was warmed to room temperature and stirred overnight The reaction mixture was quenched with water and extracted with EtOAc, washed with brine, dried over $MgSO_4$, filtered, and concentrated. The residue was purified by flash chromatography eluted with EtOAc/hexane (1:1) to give 4.29 g (79%) of the desired product as brown oil. MS (DCI/$NH_3$) m/z: 189.1 (M+H)$^+$; $^1$H NMR (300 MHz, DMSO-$d_6$) δ 2.53-2.64 (m, 2H), 2.96-3.11 (m, 2H), 4.64-4.72 (m, 2H), 5.29 (dd, J=10.51, 1.36 Hz, 1H), 5.42 (dd, J=17.29, 1.70 Hz, 1H), 6.06 (m, 1H), 6.98 (dd, J=8.48, 2.37 Hz, 1H), 7.10 (d, J=2.03 Hz, 1H) 7.56 (d, J=8.48 Hz, 1H).

EXAMPLE 22B methyl 4-[(5-(allyloxy)-1-oxo-1,3-dihydro-2H-inden-2-ylidene)(hydroxy)methyl]benzoate To a solution of Example 22A (0.222 g, 1.18 mmol) in THF (5 mL) at −78° C. was added LDA (2.0M, 0.65 mL, 1.30 mmol). After 40 minutes, a promixed suspension of CDI (0.191 g, 1.18 mmol) and terephthalic acid monomethyl ester (0.213 g, 1.18 mmol) in THF/DMF (4 mL/1 mL) was added to the above reaction mixture at −78° C. The dry ice bath was removed after 15 minutes and the reaction mixture stirred for 1 hour. The reaction was quenched with $NH_4Cl$ solution and extracted with EtOAc. The organic layer was dried over $MgSO_4$, filtered, and concentrated. The concentrate was triturated with ether to give 0.132 g (32%) of the desired product as yellow solid. MS (DCI/$NH_3$) m/z: 351.1 (M+H)$^+$; $^1$H NMR (300 MHz, $CDCl_3$) δ 3.90 (s, 2H), 3.96 (s, 3H), 4.60-4.69 (m, 2H), 5.34 (dd, J=10.51, 1.36 Hz, 1H), 5.45 (dd, J=17.29, 1.36 Hz, 1H), 6.07 (m, 1H), 6.97-7.04 (m, 2H), 7.83 (d, J=9.16 Hz, 1H), 7.97 (d, J=8.48 Hz, 2H), 8.10-8.23 (m, 2H).

EXAMPLE 22C methyl 4-[6-(allyloxy)-1,4-dihydroindeno[1,2-c]pyrazol-3-yl]benzoate A mixture of Example 22B (1.70 g, 4.85 mmol), hydrazine monohydrate (0.28 mL, 5.82 mmol), and AcOH (0.33 mL, 5.82 mmol) in EtOH (120 mL) was heated at 90° C. overnight. The reaction was cooled and the precipitate was filtered. The filter cake was rinsed with ether to give 1.56 g (93%) of the desired product as a white solid. MS (DCI/NH$_3$) m/z: 347.1 (M+H)$^+$; $^1$H NMR (300 MHz, DMSO-d$_6$) δ 3.88 (s, 5H), 4.58-4.67 (m, 2H), 5.28 (dd, J=10.51, 1.36 Hz, 1H), 5.43 (dd, J=17.12, 1.87 Hz, 1H), 6.09 (m, 1H), 6.97 (d, J=8.48 Hz, 1H), 7.21 (s, 1H), 7.59 (d, J=8.48 Hz, 1H), 7.87-8.01 (m, 2H), 8.02-8.14 (m, 2H), 13.25 (s, 1H).

EXAMPLE 22D

4-[6-(allyloxy)-1,4-dihydroindeno[1,2-c]pyrazol-3-yl]benzoic acid

A mixture of Example 22C (0.300 g, 0.866 mmol), LiOH.H$_2$O (0.109 g, 2.60 mmol) in THF/MeOH/H$_2$O (20/5/3 mL) was heated at 60° C. for 2 hours. After cooling, the reaction mixture was treated with TFA until pH=3. Solid material was filtered, rinsed with water, and dried in a vacuum oven to give 0.290 g (100%) of the desired product as white solid. MS (DCI/NH$_3$) m/z: 333.1 (M+H)$^+$; $^1$H NMR (300 MHz, DMSO-d$_6$) δ 3.87 (s, 2H), 4.63 (d, J=5.09 Hz, 2H), 5.28 (dd, J=10.51, 1.70 Hz, 1H), 5.43 (dd, J=17.12, 1.53 Hz, 1H), 6.08 (m, 1H), 6.97 (dd, J=8.48, 2.37 Hz, 1H), 7.21 (d, J=2.37 Hz, 1H), 7.56 (d, J=8.48 Hz, 1H), 7.91 (d, J=8.48 Hz, 2H), 8.04 (d, J=8.48 Hz, 2H) 13.11 (s, 1H).

EXAMPLE 23

4-[6-(allyloxy)-1,4-dihydroindeno[1,2-c]pyrazol-3-yl]benzamide

A mixture of Example 22D (50.0 mg, 0.150 mmol), HOBt (28.5 mg, 0.211 mmol), EDC (40.4 mg, 0.211 mmol), NH$_4$Cl (40.1 mg, 0.750 mmol), and Et$_3$N (0.14 mL, 0.975 mmol) in DMF (3 mL) in a capped flask was stirred at room temperature for 24 hours. The reaction mixture was diluted with EtOAc and washed with NaHCO$_3$ and brine. The organic layer was dried over MgSO$_4$, filtered, concentrated, and triturated with EtOAc to give 28.6 mg (58%) of the desired product as white powder. MS (DCI/NH$_3$) m/z: 332.1 (M+H)$^+$; $^1$H NMR (300 MHz, DMSO-d$_6$) δ 3.87 (s, 2H), 4.54-4.69 (m, 2H) 5.28 (dd, J=10.51, 1.70 Hz, 1H), 5.43 (dd, J=17.29, 1.70 Hz, 1H), 6.09 (m, 1H), 6.97 (d, J=8.48 Hz, 1H), 7.20 (s, 1H), 7.41 (m, 1H), 7.58 (m, 1H), 7.79-7.92 (m, 2H), 4.94-8.06 (m, 3H), 13.15 (s, 1H).

EXAMPLE 24 methyl 4-(6-hydroxy-1,4-dihydroindeno[1,2-c]pyrazol-3-yl)benzoate

A suspension of Example 22C (0.200 g, 0.577 mmol) in THF (16 mL) was heated until a clear solution appeared and cooled to room temperature. To this solution was added Pd(PPh$_3$)$_4$ (0.0130 g, 2%). A suspension of NaBH$_4$ in THF (2 mL) was added to the above reaction mixture in three portions at 0° C. The reaction was warmed to room temperature and stirred overnight. The reaction mixture was treated with acetone and the solvent was evaporated. The residue was treated with warm MeOH and the solid was filtered. The filtrate was concentrated and triturated with warm EtOAc. After cooling, the solid was filtered and rinsed with EtOAc to give 0.179 g (100%) of the desired product as yellow solid. MS (DCI/NH$_3$) m/z: 307.0 (M+H)$^+$; $^1$H NMR (300 MHz, DMSO-d$_6$) δ 3.60 (s, 3H), 3.86 (s, 2H), 6.43 (d, J=7.46 Hz, 1H), 6.67 (s, 1H), 7.17 (d, J=8.14 Hz, 1H), 7.89 (d, J=8.48 Hz, 2H), 7.99 (d, J=8.48 Hz, 2H).

EXAMPLE 25

4-(6-hydroxy-1,4-dihydroindeno[1,2-c]pyrazol-3-yl) benzoic acid

The desired product was prepared by replacing Example 22C with Example 24 in Example 22D. MS (DCI/NH$_3$) m/z: 292.9 (M+H)$^+$; $^1$H NMR (300 MHz, DMSO-d$_6$) δ 3.82 (s, 2H), 6.77 (dd, J=8.14, 2.03 Hz, 1H), 7.00 (s, 1H), 7.44 (d, J=8.14 Hz, 1H), 7.90 (d, J=8.4 Hz, 2H), 8.03 (d, J=8.48 Hz, 2H).

EXAMPLE 26

4-(6-{[(trans-4-hydroxycyclohexyl)amino]carbonyl}-1,4-dihydroindeno[1,2-c]pyrazol-3-yl)benzoic acid

EXAMPLE 26A

3-Iodo-1,4-dihydro-indeno[1,2-c]pyrazole-6-carboxylic acid

A mixture of Example 1B (3.00 g, 9.67 mmol), KH$_2$PO$_4$ (5.26 g, 0.0387 mol), and H$_2$NSO$_3$H (1.41 g, 0.0145 mol) in 1,4 dioxane/H$_2$O (100/30 mL) was stirred at 0° C. for 15 minutes. To this mixture was added NaClO$_2$ (1.14 g, 0.0126 mol) in H$_2$O (15 mL) dropwise. The reaction mixture was stirred for 15 minutes at 0° C. followed by the addition of NaHSO$_3$ (1.11 g, 0.0106 mol). The resulting suspension was warmed to room temperature and stirred for 1 hour. The reaction mixture was treated with Na$_2$S$_2$O$_3$ solution and concentrated under reduced pressure. The residue was treated with water and stirred for 1 hour. The mixture was filtered and the filter cake was rinsed with water and dried in a vacuum oven to provide the title compound which was used in the next step without further purification. MS (DCI/NH$_3$) m/z: 327.0 (M+H)$^+$; $^1$H NMR (300 MHz, DMSO-d$_6$) δ 3.57 (s, 2H), 7.67 (m, 1H), 7.98 (d, J=7.80 Hz, 1H), 8.10 (s, 1H).

EXAMPLE 26B

3-Iodo-1,4-dihydro-indeno[1,2-c]pyrazole-6-carboxylic acid (4-hydroxy-cyclohexyl)-amide The desired product was prepared by replacing NH$_4$Cl and Example 22D with trans-4-amino-cyclohexanol and Example 26A in Example 23. MS (DCI/NH$_3$) m/z: 424.0 (M+H)$^+$; $^1$H NMR (300 MHz, DMSO-d$_6$) δ 1.12-1.48 (m, 4H), 1.71-1.93 (m, 4H), 3.41 (m, 1H), 3.55 (s, 0.5H), 3.60 (s, 0.5H), 3.74 (m, 1H), 4.55 (d, J=4.41 Hz, 1H), 7.56 (d, J=8.14 Hz, 0.5H), 7.66 (d, J=7.80 Hz, 0.5H), 7.86 (t, J=7.97 Hz, 1H), 8.01 (d, J=5.76 Hz, 1H), 8.20 (d, J=7.80 Hz, 1H).

EXAMPLE 26C 4-(6-{[(trans-4-hydroxycyclohexyl)amino]carbonyl}-1,4-dihydroindeno[1,2-c]pyrazol-3-yl)benzoic acid The desired product was prepared by replacing Example 1C with Example 26B in Example 1D. MS (DCI/NH$_3$) m/z: 418.2 (M+H)$^+$; $^1$H NMR (500 MHz, DMSO-d$_6$) δ 1.20-1.32

(m, 2H), 1.33-1.46 (m, 2H), 1.76-1.92 (m, 4H), 3.76 (m, 1H), 3.97 (s, 2H), 7.71 (d, J=7.80 Hz, 1H), 7.88 (d, J=7.18 Hz, 1H), 7.95 (d, J=8.11 Hz, 2H), 8.03 8.08 (m, 3H), 8.20 (d, J=7.80 Hz, 1H).

EXAMPLE 27

4-{6-[(neopentylamino)carbonyl]-1,4-dihydroindeno[1,2-c]pyrazol-3-yl}benzoic acid

EXAMPLE 27A

3-Iodo-1,4-dihydro-indeno[1,2-c]pyrazole-6-carboxylic acid (2,2-dimethyl-propyl)-amide The desired product was prepared by replacing $NH_4Cl$ and Example 22D with neopentylamine and Example 26A in Example 23. MS (DCI/$NH_3$) m/z: 396.0 (M+H)$^+$; $^1$H NMR (300 MHz, DMSO-D6) δ 0.91 (s, 9H), 3.12 (d, J=6.44 Hz, 2H), 3.59 (s, 2H), 7.64 (m, 1H), 7.88 (d, J=8.14 Hz, 1H), 8.06 (m, 1H), 8.37 (t, J=6.27 Hz, 1H).

EXAMPLE 27B

4-{6-[(neopentylamino)carbonyl]-1,4-dihydroindeno[1,2-c]pyrazol-3-yl}benzoic acid The desired product was prepared by replacing Example 1C with Example 27A in Example 1D. MS (DCI/$NH_3$) m/z: 390.1 (M+H)$^+$; $^1$H NMR (500 MHz, DMSO-D6) δ 0.93 (s, 9H), 3.14 (d, J=6.24 Hz, 2H), 3.99 (s, 2H), 7.73 (d, J=8.11 Hz, 1H), 7.91 (d, J=7.80 Hz, 1H), 7.96 (d, J=8.42 Hz, 2H), 8.04-8.10 (m, 3H), 8.37 (t, J=6.24 Hz, 1H).

EXAMPLE 28

3-[4-(aminocarbonyl)phenyl]-N-neopentyl-1,4-dihydroindeno[1,2-c]pyrazole-6-carboxamide The desired product was prepared replacing Example 1C and 4-carboxybenzene boronic acid with Example 27A and 4-(4,4,5,5-tetramethyl-[1,3,2]dioxaborolan-2-yl)-benzamide in Example 1D. MS (DCI/$NH_3$) m/z: 389.2 (M+H)$^+$; $^1$H NMR (300 MHz, DMSO-D6) δ 0.93 (s, 9H), 3.14 (d, J=6.10 Hz, 2H) 3.99 (s, 2H), 7.41 (s, 1H), 7.73 (d, J=8.14 Hz, 1H), 7.90 (d, J=8.48 Hz, 2H), 7.97-8.10 (m, 3H), 8.39 (t, J=6.27 Hz, 1H).

EXAMPLE 29

4'-(6-{[(cis-4-methylcyclohexyl)amino]methyl}-1,4-dihydroindeno[1,2-c]pyrazol-3-yl)-1,1'-biphenyl-4-ol

EXAMPLE 29A

4'-(4,4,5,5-Tetramethyl-[1,3,2]dioxaborolan-2-yl)-biphenyl-4-ol

A mixture of 4'-bromo-biphenyl-4-ol (0.300 g, 1.20 mmol), bis(pinacolato)-diboron (0.336 g, 1.32 mmol), $PdCl_2$(dppf).$CH_2Cl_2$ (0.0293 g, 3%), dppf (0.0199 g, 3%), and KOAc (0.353 g, 3.60 mmol) in 1,4-dioxane (6 mL) was heated at 90° C. overnight. The reaction mixture was concentrated and the residue was extracted with EtOAc, washed with brine, dried over $MgSO_4$, filtered, concentrated, and purified by flash chromatography eluted with hexane/EtOAc (1:1) to give 0.278 g (78%) of the desired product as white foam. MS (DCI/$NH_3$) m/z: 296.1 (M+H)$^+$; $^1$H NMR (300 MHz, CDCl$_3$) δ 1.36 (s, 12H), 6.90 (d, J=8.48 Hz, 2H), 7.53 (dd, J=12.72, 8.65 Hz, 4H), 7.85 (d, J=8.14 Hz, 2H).

EXAMPLE 29B

4'-(6-{[(cis-4-methylcyclohexyl)amino]methyl}-1,4-dihydroindeno[1,2-c]pyrazol-3-yl)-1,1'-biphenyl-4-ol The desired product was prepared by replacing Example 1C (trans) and 4-carboxybenzene boronic acid with Example 1C (cis) and Example 29A in Example 1D. MS (DCI/$NH_3$) m/z: 450.2 (M+H)$^+$; $^1$H NMR (300 MHz, CD$_3$OD) δ 1.04 (d, J=7.12 Hz, 3H), 1.47-2.01 (m, 9H), 3.28 (m, 1H), 3.96 (s, 2H), 4.31 (s, 2H), 6.89 (d, J=8.82 Hz, 2H), 7.46-7.59 (m, 3H), 7.67-7.76 (m, 3H), 7.78-7.89 (m, 3H).

EXAMPLE 30

4'-(6-{[(trans-4-hydroxycyclohexyl)amino]methyl}-1,4-dihydroindeno[1,2-c]pyrazol-3-yl) -3-methoxy-1,1'-biphenyl-4-ol

EXAMPLE 30A

4'-Bromo-3-methoxy-biphenyl-4-ol

A mixture of 2-methoxy-4-(4,4,5,5-tetramethyl-[1,3,2]dioxaborolan-2-yl)-phenol (0.250 g, 1.00 mmol), 1,4-dibromobenzene (0.259 g, 1.10 mmol), Pd(PPh$_3$)$_4$ (0.0580 g, 5%), and CsF (0.456 g, 3.00 mmol) in DME/MeOH (25 mL, 1:1) was heated at 70° C. overnight. The reaction mixture was concentrated and the residue was extracted with $CH_2Cl_2$, washed with water, dried over $MgSO_4$, filtered, concentrated, and purified by flash chromatography eluted with hexane/$CH_2Cl_2$ (1:9) to give 0.151 g (54%) of the desired product. MS (DCI/$NH_3$) m/z: 279.9 (M+H)$^+$; $^1$H NMR (300 MHz, CD$_3$OD) δ 3.91 (s, 3H), 6.86 (d, J=8.14 Hz, 1H), 7.06 (m, 1H), 7.14 (d, J=2.03 Hz, 1H), 7.44-7.58 (m, 3H).

EXAMPLE 30B

3-Methoxy-4'-(4,4,5,5-tetramethyl-[1,3,2]dioxaborolan-2-yl)-biphenyl-4-ol

The desired product was prepared by replacing 4'-bromo-biphenyl-4-ol with Example 30A in Example 29A. MS (DCI/$NH_3$) m/z: 326.1 (M+H)$^+$; $^1$H NMR (300 MHz, CD$_3$OD) δ 1.36 (s, 12H), 3.92 (s, 3H), 6.87 (d, J=8.14 Hz, 1H), 7.11 (d, J=8.14 Hz, 1H), 7.19 (d, J=2.37 Hz, 1H), 7.57 (d, J=8.14 Hz, 2H), 7.76 (d, J=8.48 Hz, 2H).

EXAMPLE 30C

4'-(6-{[(trans-4-hydroxycyclohexyl)amino]methyl}-1,4-dihydroindeno[1,2-c]pyrazol-3-yl) -3-methoxy-1,1'-biphenyl-4-ol The desired product was prepared by replacing Example 1C and 4-carboxybenzene boronic acid with Example 4A and Example 30B in Example 1D. MS (DCI/$NH_3$) m/z: 482.2 (M+H)$^+$; $^1$H NMR (500 MHz, CD$_3$OD) δ 1.31-1.43 (m, 2H), 1.46-1.59 (m, 2H), 2.01-2.14 (m, 2H), 2.19-2.32 (m, 2H), 3.15 (m, 1H), 3.59 (m, 1H), 3.93 (s, 5H), 4.28 (s, 2H), 6.89 (d, J=8.11 Hz, 1H), 7.14 (d, J=8.11 Hz, 1H), 7.22 (d, J=1.87 Hz, 1H), 7.50 (d, J=7.49 Hz, 1H), 7.66-7.75 (m, 3H), 7.79-7.88 (m, 3H).

EXAMPLE 31

4'-(6-{[(trans-4-hydroxycyclohexyl)amino]methyl}-1,4-dihydroindeno[1,2-c]pyrazol-3-yl) -3-(hydroxymethyl)-1,1'-biphenyl-4-ol

EXAMPLE 31A

4'-Bromo-3-hydroxymethyl-biphenyl-4-ol

The desired product was prepared by replacing 2-methoxy-4-(4,4,5,5-tetramethyl-[1,3,2]dioxaborolan-2-yl)-phenol with 2-hydroxymethyl-4-(4,4,5,5-tetramethyl-[1,3,2]dioxaborolan-2-yl)-phenol in Example 30A. MS (DCI/NH$_3$) m/z: 278.0, 279.8 (M, M+2). $^1$H NMR (500 MHz, CD$_3$OD) δ 4.61 (s, 2H), 6.75 (d, J=8.42 Hz, 1H), 7.26 (d, J=10.92 Hz, 1H), 7.37 (d, J=8.42 Hz, 2H), 7.40-7.49 (m, 3H).

EXAMPLE 31B

3-Hydroxymethyl-4'-(4,4,5,5-tetramethyl-[1,3,2]dioxaborolan-2-yl)-biphenyl-4-ol

The desired product was prepared by replacing 4'-bromo-biphenyl-4-ol with Example 31A in Example 29A. MS (DCI/NH$_3$) m/z: 326.1 (M+1)$^+$; $^1$H NMR (300 MHz, CD$_3$OD) δ 1.36 (s, 12H), 4.71 (s, 2H), 6.85 (d, J=8.48 Hz, 1H), 7.35-7.46 (m, 1H), 7.547.62 (m, 3H) 7.76 (d, J=8.14 Hz, 2H).

EXAMPLE 31C

4'-(6-{[(trans-4-hydroxycyclohexyl)amino]methyl}-1,4-dihydroindeno[1,2-c]pyrazol-3-yl) -3-(hydroxymethyl)-1,1'-biphenyl-4-ol The desired product was prepared by replacing Example 1C and 4-carboxybenzene boronic acid with Example 4A and Example 31B in Example 1D. MS (ESI) m/z: 482.0 (M+H)$^+$; $^1$H NMR (500 MHz, CD$_3$OD) δ 1.30-1.43 (m, 2H), 1.45-1.61 (m, 2H), 2.00-2.13 (m, 2H), 2.16-2.32 (m, 2H), 3.17 (m, 1H), 3.58 (m, 1H), 3.93 (s, 2H), 4.27 (s, 2H), 4.73 (s, 2H), 6.88 (d, J=8.42 Hz, 1H), 7.40-7.52 (m, 2H), 7.63 (s, 1H), 7.67-7.75 (m, 3H), 7.77-7.86 (m, 3H).

EXAMPLE 32

3-methoxy-4'-{6-[(neopentylamino)methyl]-1,4-dihydroindeno[1,2-c]pyrazol-3-yl}-1,1'-biphenyl-4-ol The desired product was prepared by replacing Example 1C and 4-carboxybenzene boronic acid with Example 15A and Example 30B in Example 1D. MS (DCI/NH$_3$) m/z: 454.2 (M+H)$^+$; $^1$H NMR (300 MHz, CD$_3$OD) δ 1.04 (s, 9H), 3.95 (s, 3H), 3.96 (s, 2H), 4.33 (s, 2H), 6.90 (d, J=8.14 Hz, 1H), 7.15 (dd, J=8.31, 2.20 Hz, 1H), 7.23 (d, J=2.03 Hz, 1H), 7.56 (m, 1H), 7.69-7.77 (m, 3H), 7.80-7.88 (m, 3H).

EXAMPLE 33

4'-(6-{[(3-hydroxy-2,2-dimethylpropyl)amino]methyl}-1,4-dihydroindeno[1,2-c]pyrazol-3-yl)-3-methoxy-1,1'-biphenyl-4-ol The desired product was prepared by replacing Example 1C and 4-carboxybenzene boronic acid with Example 17A and Example 30B in Example 1D. MS (DCI/NH$_3$) m/z: 470.2 (M+H)$^+$; $^1$H NMR (300 MHz, CD$_3$OD) δ 1.02 (s, 6H), 3.00 (s, 2H), 3.45 (s, 2H), 3.95 (s, 5H), 4.30 (s, 2H), 6.89 (d, J=8.14 Hz, 1H), 7.15 (dd, J=8.14, 2.03 Hz, 1H), 7.23 (d, J=2.03 Hz, 1H) , 7.50 (d, J=1.36 Hz, 1H), 7.68-7.76 (m, 3H) 7.78-7.91 (m, 3H).

EXAMPLE 34

3-(4'-hydroxy-1,1'-biphenyl-4-yl)-1,4-dihydroindeno[1,2-c]pyrazol-6-ol

EXAMPLE 34A 5-(allyloxy)-2-[(4-bromophenyl)(hydroxy)methylene]-1-indanone

The desired product was prepared by replacing terephthalic acid monomethyl ester with 4-bromo-benzoic acid in Example 22B. MS (DCI/NH$_3$) m/z: 371.4 (M+H)$^+$; $^1$H NMR (300 MHz, CDCl$_3$) δ 3.86 (s, 2H), 4.64 (d, J=5.43 Hz, 2H), 5.29-5.52 (m, 2H), 6.08 (m, 1H), 6.92-7.04 (m, 2H), 7.63 (d, J=8.82 Hz, 2H), 7.73-7.86 (m, 3H).

EXAMPLE 34B

6-Allyloxy-3-(4-bromo-phenyl)-1,4-dihydro-indeno[1,2-c]pyrazole

The desired product was prepared by replacing Example 22B with Example 34A in Example 22C. MS (DCI/NH$_3$) m/z: 367.0 (M+1)$^+$, 367.9 (M+1+2)$^+$; $^1$H NMR (400 MHz, CDCl$_3$) δ 3.71 (s, 2H), 4.59 (d, J=5.22 Hz, 2H), 5.24-5.53 (m, 2H), 6.07 (m, 1H), 6.90 (d, J=8.29 Hz, 1H), 7.09 (m, 1H), 7.46-7.61 (m, 6H).

EXAMPLE 34C 3-(4'-hydroxy-1,1'-biphenyl-4-yl)-1,4-dihydroindeno[1,2-c]pyrazol-6-ol The desired product was prepared by replacing Example 1C and 4-carboxybenzene boronic acid with Example 34B and 4-(4,4,5,5-tetramethyl-[1,3,2]dioxaborolan-2-yl)-phenol in Example 1D. MS (DCI/NH$_3$) m/z: 341.1 (M+H)$^+$; $^1$H NMR (500 MHz, DMSO-d$_6$) δ 3.80 (s, 2H), 6.77 (d, J=10.29 Hz, 1H), 6.87 (d, J=8.73 Hz, 2H), 6.99 (s, 1H), 7.45 (d, J=8.42 Hz, 1H), 7.56 (d, J=8.42 Hz, 2H), 7.70 (d, J=8.11 Hz, 2H), 7.82 (d, J=8.42 Hz, 2H), 9.45 (s, 1H), 9.57 (s, 1H).

EXAMPLE 35

3-(4'-hydroxy-3'-methoxy-1,1'-biphenyl-4-yl)-1,4-dihydroindeno[1,2-c]pyrazol-6-ol The desired product was prepared by replacing Example 1C and 4-carboxybenzene boronic acid with Example 34B and 2-methoxy-4-(4,4,5,5-tetramethyl-[1,3,2]dioxaborolan-2-yl)-phenol in Example 1D. MS (DCI/NH$_3$) m/z: 371.1

(M+H)+; 1H NMR (500 MHz, CD3OD) δ 3.88 (s, 2H), 3.95 (s, 3H), 6.78-6.98 (m, 2H), 7.02-7.29 (m, 3H), 7.55 (m, 1H), 7.69-7.89 (m, 4H).

EXAMPLE 36

4'-[6-(hydroxymethyl)-1,4-dihydroindeno[1,2-c]pyrazol-3-yl]-1,1'-biphenyl-4-ol

The desired product was prepared by replacing Example 1C and 4-carboxybenzene boronic acid with Example 19A and 4-(4,4,5,5-tetramethyl-[1,3,2]dioxaborolan-2-yl)-phenol in Example 1D. MS (DCI/NH3) m/z: 355.1 (M+H)+; 1H NMR (300 MHz, CD3OD) δ 3.89 (s, 2H), 4.68 (s, 2H), 6.88 (d, J=8.82 Hz, 2H), 7.37 (d, J=6.78 Hz, 1H), 7.53 (d, J=8.82 Hz, 2H), 7.60 (s, 1H), 7.65-7.74 (m, 3H), 7.83 (d, J=8.48 Hz, 2H).

EXAMPLE 37

4'-(1,4-dihydroindeno[1,2-c]pyrazol-3-yl)-1,1'-biphenyl-4-ol

EXAMPLE 37A

3-Iodo-1,4-dihydro-indeno[1,2-c]pyrazole

The desired product was prepared by replacing Example 1A with 1,4 dihydro-indeno[1,2-c]pyrazole, prepared according to procedure described in U.S. Pat. No. 6,297,238, in Example 1B. MS (DCI/NH3) m/z: 282.9 (M+H)+; 1H NMR (300 MHz, CD3OD) δ 3.54 (s, 2H), 7.23-7.42 (m, 2H), 7.54 (d, J=7.12 Hz, 1H), 7.62 (d, J=6.44 Hz, 1H).

EXAMPLE 37B

4'-(1,4-dihydroindeno[1,2-c]pyrazol-3-yl)-1,1'-biphenyl-4-ol

The desired product was prepared by replacing Example 1C and 4-carboxybenzene boronic acid with Example 37A and Example 29A in Example 1D. MS (DCI/NH3) m/z: 325.1 (M+H)+; 1H NMR (300 MHz, DMSO-d6) δ 3.90 (s, 2H), 6.87 (d, J=8.82 Hz, 2H), 7.23-7.45 (m, 2H), 7.53-7.63 (m, 3H), 7.65-7.79 (m, 3H), 7.85 (d, J=7.80 Hz, 2H), 9.60 (s, 1H), 13.22 (s, 1H).

EXAMPLE 38

4'-[6-(hydroxymethyl)-1,4-dihydroindeno[1,2-c]pyrazol-3-yl]-3-methoxy-1,1'-biphenyl -4-ol The desired product was prepared by replacing Example 1C and 4-carboxybenzene boronic acid with Example 19A and Example 30B in Example 1D. MS (DCI/NH3) m/z: 385.1 (M+H)+; 1H NMR (500 MHz, DMSO-d6) δ 3.88 (s, 5H), 4.58 (s, 2H), 6.88 (d, J=8.11 Hz, 1H), 7.16 (dd, J=8.27, 2.03 Hz, 1H), 7.27 (d, J=2.18 Hz, 1H, 7.32 (d, J=7.80 Hz, 1H), 7.55 (s, 1H), 7.62 (d, J=7.49 Hz, 1H), 7.76 (d, J=8.42 Hz, 2H), 7.86 (d, J=8.42 Hz, 2H).

EXAMPLE 39

3-(3'-fluoro-4'-hydroxy-1,1'-biphenyl-4-yl)-1,4-dihydroindeno[1,2-c]pyrazol-6-ol The desired product was prepared by replacing Example 1C and 4-carboxybenzene boronic acid with Example 34B and 2-fluoro-4-(4,4,5,5-tetramethyl-[1,3,2]dioxaborolan-2-yl)-phenol in Example 1D. MS (DCI/NH3) m/z: 359.0 (M+H)+; 1H NMR (400 MHz, CD3OD) δ 3.84 (s, 2H), 6.83 (dd, J=8.29, 2.45 Hz, 1H), 6.96-7.07 (m, 2H), 7.33 (m, 1H), 7.40 (dd, J=12.27, 2.15 Hz, 1H), 7.54 (d, J=8.29 Hz, 1H), 7.70 (d, J=8.59 Hz, 2H), 7.787.88 (m, 2H).

EXAMPLE 40

3-(3'-amino-4'-hydroxy-1,1'-biphenyl-4-yl)-1,4-dihydroindeno[1,2-c]pyrazol-6-ol

EXAMPLE 40A

2-Amino-4-(4,4,5,5-tetramethyl-[1,3,2]dioxaborolan-2-yl)-phenol

A mixture of Pd2(dba)3 (0.0765 g) and Cy-MAP (0.165 g) in degassed 1,4-dioxane (6 mL) was stirred at room temperature for 30 minutes. To the above mixture was added 2-amino -4-chloro-phenol (0.300 g, 2.09 mmol), bis(pinacolato) diboron (0.557 g, 2.19 mmol), and KOAc (0.308 g, 3.14 mmol). The reaction mixture was heated at 85° C. overnight, allowed to cool to room temperature, concentrated under reduced pressure and the residue was treated with EtOAc. The ethyl acetate layer was washed with brine, dried over MgSO4, filtered, and the filtrate was concentrated under reduced pressure. The residue was purified by flash chromatography eluting with hexanes/EtOAc (7:3 to 1:1) to give 0.273 g (69%) of the desired product as brown solid. MS (DCI/NH3) m/z: 235.8 (M+H)+; 1H NMR (300 MHz, DMSO-d6) δ 1.24 (s, 12H), 3.92 (s, 1H), 6.62 (d, J=7.80 Hz, 1H), 6.78 (dd, J=7.63, 1.53 Hz, 1H), 6.96 (d, J=1.36 Hz, 1H).

EXAMPLE 40B 3-(3'-amino-4'-hydroxy-1,1'-biphenyl-4-yl)-1,4-dihydroindeno[1,2-c]pyrazol-6-ol The desired product was prepared by replacing Example 1C and 4-carboxybenzene boronic acid with Example 34B and 40A in Example 1D. MS (DCI/NH3) m/z: 356.1 (M+H)+; 1H NMR (300 MHz, CD3OD) δ 3.84 (s, 2H), 6.83 (dd, J=8.31, 2.20 Hz, 1H), 7.05 (d, J=2.37 Hz, 1H), 7.12 (d, J=8.48 Hz, 1H,) 7.53 (d, J=8.14 Hz, 1H), 7.60 (d, J=2.37 Hz, 1H), 7.63-7.68 (m, 1H), 7.71 (d, J=8.48 Hz, 2H), 7.87 (d, J=8.48 Hz, 2H).

EXAMPLE 41

4-hydroxy-4'-[6-(hydroxymethyl)-1,4-dihydroindeno[1,2-c]pyrazol-3-yl]-5-methoxy-1,1'-biphenyl-2-carbaldehyde

EXAMPLE 41A

4'-Bromo-4-hydroxy-5-methoxy-biphenyl-2-carbaldehyde

A mixture of 2-bromo-5-hydroxy-4-methoxy-benzaldehyde (1.00 g, 4.32 mmol), 4-bromophenyl boronic acid (1.04 g, 5.18 mmol), Pd(PPh3)4 (0.250 g), and CsF (1.97 g, 12.6 mmol) in DME/MeOH (1:1, 65 mL) was heated at 70° C. overnight. The mixture was diluted with CH2Cl2 and washed with water. The organic layer was dried over MgSO4, filtered, and the filtrate concentrated under reduced pressure. The residue was purified by flash chromatography eluting with hexane/CH2Cl2 (1:9) to give 0.809 g (60%) of the desired product which was carried into the next step without further purification. MS (DCI/NH3) m/z: 307.4 (M+H)+.

EXAMPLE 41B

4-Hydroxy-5-methoxy-4'-(4,4,5,5-tetramethyl-[1,3,2]dioxaborolan-2-yl)-biphenyl-2-carbaldehyde The desired product was prepared by replacing 4'-bromobiphenyl-4-ol with Example 41A in Example 29A. The product was carried into the next step without further purification. MS (DCI/NH$_3$) m/z: 372.2 (M+NH$_4$)$^+$.

EXAMPLE 41C 4-hydroxy-4'-[6-(hydroxymethyl)-1,4-dihydroindeno[1,2-c]pyrazol-3-yl]-5-methoxy-1,1'-biphenyl-2-carbaldehyde The desired product was prepared by replacing Example 1C and 4-carboxybenzene boronic acid with Example 19A and 41B in Example 1D. MS (DCI/NH$_3$) m/z: 413.1 (M+H)$^+$; $^1$H NMR (500 MHz, DMSO-d$_6$) δ 3.90 (s, 2H), 3.94 (s, 3H), 4.58 (s, 2H), 7.03 (s, 1H), 7.33 (d, J=7.80 Hz, 1H), 7.36 (s, 1H), 7.55-7.58 (m, 3H), 7.62 (d, J=7.80 Hz, 1H), 7.92 (d, J=8.11 Hz, 2H), 9.76 (s, 1H).

EXAMPLE 42

3-(4'-hydroxy-1,1'-biphenyl-4-yl)-N-(trans-4-hydroxycyclohexyl)-1,4-dihydroindeno[1,2-c]pyrazole-6-carboxamide The desired product was prepared by replacing Example 1C and 4-carboxybenzene boronic acid with Example 26B and Example 29A in Example 1D. The microwave assisted reaction was run for 450 to 2000 seconds at 160 to 180° C. MS (DCI/NH$_3$) m/z: 466.2 (M+H)$^+$; $^1$H NMR (300 MHz, CD$_3$OD) δ 1.38-1.52 (m, 4H), 1.93-2.10 (m, 4H), 3.58 (m, 1H), 3.883 (m, 1H), 3.94 (s, 2H), 6.88 (d, J=8.81 Hz, 2H), 7.52 (d, J=8.48 Hz, 2H), 7.69 (d, J=8.48 Hz, 2H), 7.75-7.87 (m, 4H), 8.02 (s, 1H).

EXAMPLE 43

3-(4'-hydroxy-1,1'-biphenyl-4-yl)-N-neopentyl-1,4-dihydroindeno[1,2-c]pyrazole-6-carboxamide The desired product was prepared by replacing Example 1C and 4-carboxybenzene boronic acid with Example 27A and Example 29A in Example 1D. MS (DCI/NH$_3$) m/z: 438.2 (M+H)$^+$; $^1$H NMR (300 MHz, DMSO-d$_6$) δ 0.93 (s, 9H), 3.14 (d, J=6.10 Hz, 2H), 3.97 (s, 2H), 6.88 (d, J=8.48 Hz, 2H), 7.58 (d, J=8.82 Hz, 2H), 7.73 (d, J=8.48 Hz, 3H), 7.83-7.96 (m, 3H), 8.07 (s, 1H), 8.39 (t, J=6.44 Hz, 1H), 9.60 (s, 1H).

EXAMPLE 44

4-[7-(hydroxymethyl)-1,4-dihydroindeno[1,2-c]pyrazol-3-yl]benzoic acid

EXAMPLE 44A 1,4-dihydroindeno[1,2-c]pyrazole-7-carbaldehyde

The desired product was prepared by replacing 6 bromo-1,4-dihydro-indeno[1,2-c]pyrazole with 7-bromo-1,4-dihydro-indeno[1,2-c]pyrazole in Example 1A.

EXAMPLE 44B 3-iodo-1,4-dihydroindeno[1,2-c]pyrazole-7-carbaldehyde

The desired product was prepared by replacing Example 1A with Example 44A in Example 1B. MS (DCI/NH$_3$) m/z: 310.9 (M+H)$^+$; $^1$H NMR (300 MHz, DMSO-d$_6$) δ 3.64 (s, 0.8H), 3.69 (s, 1.2H), 7.78 (t, J=8.82 Hz, 1H), 7.88 (t, J=7.97 Hz, 1H), 8.02 (s, 0.4H), 8.11 (s, 0.6H), 10.08 (s, 1H).

EXAMPLE 44C (3-Iodo-1,4-dihydro-indeno[1,2-c]pyrazol-7-yl)-methanol

The desired product was prepared by replacing Example 1B with Example 44B in Example 19A. MS (DCI/NH$_3$) m/z: 312.9 (M+H)$^+$; $^1$H NMR (300 MHz, CD$_3$OD) δ 3.52 (s, 2H), 4.67 (s, 2H), 7.30 (d, J=9.49 Hz, 1H), 7.51 (d, J=7.80 Hz, 1H), 7.64 (s, 1H).

EXAMPLE 44D

4-[7-(hydroxymethyl)-1,4-dihydroindeno[1,2-c]pyrazol-3-yl]benzoic acid

The desired product was prepared by replacing Example 1C with Example 44C in Example 1D. MS (DCI/NH$_3$) m/z: 307.0 (M+H)$^+$; $^1$H NMR (300 MHz, CD$_3$OD) δ 3.89 (s, 2H), 4.70 (s, 2H), 7.33 (d, J=7.80 Hz, 1H), 7.56 (d, J=8.48 Hz, 1H), 7.74 (s, 1H), 7.91 (d, J=8.81 Hz, 2H), 8.09-8.18 (m, 3H).

EXAMPLE 45

4-[7-(hydroxymethyl)-1,4-dihydroindeno[1,2-c]pyrazol-3-yl]benzamide

The desired product was prepared by replacing Example 1C and 4-carboxybenzene boronic acid with Example 44C and 4-(4,4,5,5-tetramethyl-[1,3,2]dioxaborolan-2-yl)-benzamide in Example 1D. MS (DCI/NH$_3$) m/z: 306.0 (M+H)$^+$; $^1$H NMR (500 MHz, DMSO-d$_6$) δ 3.88 (s, 2H), 4.59 (s, 2H), 5.22 (s, 1H), 7.25 (d, J=7.80 Hz, 1H), 7.32-7.45 (m, 1H), 7.52 (d, J=7.80 Hz, 1H), 7.65 (s, 1H), 7.88 (s, 2H), 7.99 (d, J=7.80 Hz, 2H), 13.29 (s, 1H).

EXAMPLE 46

4'-[7-(hydroxymethyl)-1,4-dihydroindeno[1,2-c]pyrazol-3-yl]-3-methoxy-1,1'-biphenyl -4-ol The desired product was prepared by replacing Example 1C and 4-carboxybenzene boronic acid with Example 44C and Example 30B in Example 1D. MS (DCI/NH$_3$) m/z: 385.1 (M+H)$^+$; $^1$H NMR (300 MHz, DMSO-d$_6$) δ 3.87 (s, 2H), 3.88 (s, 3H), 4.59 (s, 2H), 6.88 (d, J=8.14 Hz, 1H), 7.16 (dd, J=8.14, 2.03 Hz, 1H), 7.21-7.29 (m, 2H), 7.54 (m, 1H), 7.65 (s, 1H), 7.76 (d, J=8.48 Hz, 2H), 7.86 (d, J=8.48 Hz, 2H), 9.14 (s, brd, 1H).

EXAMPLE 47

N-{3-[7-(hydroxymethyl)-1,4-dihydroindeno[1,2-c]pyrazol-3-yl]phenyl}acetamide

The desired product was prepared by replacing Example 1C and 4-carboxybenzene boronic acid with Example 44C and 3-acetamidobenzene boronic acid in Example 1D. MS (DCI/NH$_3$) m/z: 320.0 (M+H)$^+$; $^1$H NMR (300 MHz, CD$_3$OD) δ 2.18 (s, 3H), 3.86 (s, 2H), 4.69 (s, 2H), 7.34 (dd, J=7.80, 1.36 Hz, 1H), 7.42-7.47 (m, 2H, 7.52-7.58 (m, 2H), 7.73 (d, J=0.68 Hz, 1H), 8.15 (m, 1H).

EXAMPLE 48

4-[7-(4-morpholinylmethyl)-1,4-dihydroindeno[1,2-c]pyrazol-3-yl]benzoic acid

EXAMPLE 48A

3-Iodo-7-morpholin-4-ylmethyl-1,4-dihydro-indeno[1,2-c]pyrazole

The desired product was prepared by replacing Example 1B with Example 44B in Example 7A. MS (DCI/NH$_3$) m/z: 382.0 (M+H)$^+$; $^1$H NMR (300 MHz, CD$_3$OD) δ 2.39-2.55 (m, 4H), 3.52 (s, 2H), 3.59 (s, 2H), 3.66-3.74 (m, 4H), 7.29 (dd, J=7.80, 1.70 Hz, 1H), 7.50 (d, J=7.80 Hz, 1H), 7.63 (m, 1H).

EXAMPLE 48B

4-[7-(4-morpholinylmethyl)-1,4-dihydroindeno[1,2-c]pyrazol-3-yl]benzoic acid

The desired product was prepared by replacing Example 1C with Example 48A in Example 1D. MS (DCI/NH$_3$) m/z: 376.2 (M+H)$^+$; $^1$H NMR (400 MHz, CD$_3$OD) δ 3.33-3.52 (m, 4H), 3.65-3.86 (m, 2H), 3.97 (s, 2H), 3.99-4.14 (m, 2H), 4.46 (s, 2H), 7.47 (d, J=7.67 Hz, 1H), 7.73 (d, J=7.67 Hz, 1H), 7.82-7.96 (m, 3H), 8.14 (d, J=8.59 Hz, 2H).

EXAMPLE 49

4-[7-(4-morpholinylmethyl)-1,4-dihydroindeno[1,2-c]pyrazol-3-yl]benzamide

The desired product was prepared by replacing Example 1C and 4-carboxybenzene boronic acid with Example 48A and 4-(4,4,5,5-tetramethyl-[1,3,2]dioxaborolan-2-yl)-benzamide in Example 1D. MS (DCI/NH$_3$) m/z: 375.1 (M+H)$^+$; $^1$H NMR (400 MHz, CD$_3$OD) δ 3.21-3.33 (m, 2H), 3.38-3.49 (m, 2H), 3.67-3.81 (m, 2H), 3.95 (s, 2H), 4.01-4.12 (m, 2H), 4.46 (s, 2H), 7.47 (dd, J=7.67, 1.53 Hz, 1H), 7.72 (d, J=7.98 Hz, 1H), 7.84-7.91 (m, 3H), 8.00 (d, J=8.29 Hz, 2H).

EXAMPLE 50

4-(7-{[(2-hydroxyethyl)amino]methyl}-1,4-dihydroindeno[1,2-c]pyrazol-3-yl)benzoic acid

EXAMPLE 50A

2-[(3-Iodo-1,4-dihydro-indeno[1,2-c]pyrazol-7-ylmethyl)-amino]-ethanol

The desired product was prepared by replacing Example 1B and morpholine with Example 44B and 2-amino-ethanol in Example 7A. MS (DCI/NH$_3$) m/z: 356.0 (M+H)$^+$; $^1$H NMR (300 MHz, CD$_3$OD) δ 2.81 (t, J=5.77 Hz, 2H), 3.54 (s, 2H), 3.70 (t, J=5.77 Hz, 2H), 3.92 (s, 2H), 7.33 (dd, J=7.80, 1.70 Hz, 1H), 7.54 (d, J=7.80 Hz, 1H), 7.64 (s, 1H).

EXAMPLE 50B 4-(7-{[(2-hydroxyethyl)amino]methyl}-1,4-dihydroindeno[1,2-c]pyrazol-3-yl)benzoic acid The desired product was prepared by replacing Example 1C with Example 50A in Example 1D. MS (DCI/NH$_3$) m/z: 350.1 (M+H)$^+$; $^1$H NMR (400 MHz, CD$_3$OD) δ 3.09 (t, J=5.52 Hz, 2H), 3.74 (t, J=5.52 Hz, 2H), 3.87 (s, 2H), 4.25 (s, 2H), 7.36 (dd, J=7.67, 1.84 Hz, 1H), 7.60 (d, J=7.98 Hz, 1H), 7.76 (d, J=1.23 Hz, 1H), 7.80 (d, J=8.59 Hz, 2H), 8.05 (d, J=8.90 Hz, 2H).

EXAMPLE 51

4'-[7-(hydroxymethyl)-1,4-dihydroindeno[1,2-c]pyrazol-3-yl]-1,1'-biphenyl-4-ol

The desired product was prepared by replacing Example 1C and 4-carboxybenzene boronic acid with Example 44C and Example 29A in Example 1D. MS (DCI/NH$_3$) m/z: 355.1 (M+H)$^+$; $^1$H NMR (500 MHz, DMSO-d$_6$) δ 3.86 (s, 2H), 4.59 (s, 2H), 6.87 (d, J=8.42 Hz, 2H), 7.24 (d, J=7.80 Hz, 1H), 7.52 (d, J=7.80 Hz, 1H), 7.57 (d, J=8.42 Hz, 2H), 7.64 (s, 1H), 7.71 (d, J=8.42 Hz, 2H), 7.85 (d, J=8.42 Hz, 2H), 9.56 (s, 1H).

EXAMPLE 52

4-{7-[(neopentylamino)methyl]-1,4-dihydroindeno[1,2-c]pyrazol-3-yl}benzamide

EXAMPLE 52A (2,2-Dimethyl-propyl)-(3-iodo-1,4-dihydro-indeno[1,2-c]pyrazol-7-ylmethyl)-amine The desired product was prepared by replacing Example 1B and morpholine with Example 44B and neopentylamine in Example 7A. MS (DCI/NH$_3$) m/z: 382.0 (M+H)$^+$; $^1$H NMR (300 MHz, CD$_3$OD) δ 0.92 (s, 9H), 2.35 (s, 2H), 3.52 (s, 2H), 3.84 (s, 2H), 7.30 (dd, J=7.80, 1.70 Hz, 1H), 7.50 (d, J=7.80 Hz, 1H), 7.62 (s, 1H).

EXAMPLE 52B

4-{7-[(neopentylamino)methyl]-1,4-dihydroindeno[1,2-c]pyrazol-3-yl}benzamide

The desired product was prepared by replacing Example 1C and 4-carboxybenzene boronic acid with Example 52A and 4-(4,4,5,5-tetramethyl-[1,3,2]dioxaborolan-2-yl)-benzamide in Example 1D. MS (DCI/NH$_3$) m/z: 375.2 (M+H)$^+$; $^1$H NMR (300 MHz, DMSO-d$_6$) δ 0.95 (s, 9H), 2.74 (s, 2H), 3.97 (s, 2H), 4.28 (s, 2H), 7.37-7.50 (m, 2H), 7.66 (d, J=7.80 Hz, 1H), 7.84-7.94 (m, 3H), 7.98-8.06 (m, 3H), 8.60 (s, brd, 1H).

EXAMPLE 53

4'-{7-[(neopentylamino)methyl]-1,4-dihydroindeno[1,2-c]pyrazol-3-yl}-1,1'-biphenyl-4-ol The desired product was prepared by replacing Example 1C and 4-carboxybenzene boronic acid with Example 52A and Example 29A in Example 1D. MS (DCI/NH$_3$) m/z: 424.2 (M+H)$^+$; $^1$H NMR (300 MHz, DMSO-d$_6$) δ 0.97 (s, 9H), 2.67-2.81 (m, 2H), 3.95 (s, 2H), 4.20-4.38 (m, 2H), 6.88 (d, J=8.48 Hz, 2H), 7.46 (dd, J=7.97, 1.53 Hz, 1H), 7.57 (d, J=8.81 Hz, 2H), 7.66 (d, J=7.80 Hz, 1H), 7.73 (d, J=8.48 Hz, 2H), 7.82-7.88 (m, 2H), 7.91 (s, 1H), 8.57 (s, brd, 1H).

EXAMPLE 54

4-{7-[(methylamino)carbonyl]-1,4-dihydroindeno[1,2-c]pyrazol-3-yl}benzoic acid

EXAMPLE 54A

3-Iodo-1,4-dihydro-indeno[1,2-c]pyrazole-7-carboxylic acid

The desired product was prepared by replacing Example 2B with Example 44B in Example 26A. MS (DCI/NH$_3$) m/z: 326.9 (M+H)$^+$; $^1$H NMR (300 MHz, DMSO-d$_6$) δ 3.62 (s, 2H), 7.66 (d, J=7.80 Hz, 1H), 7.90 (dd, J=7.97, 1.53 Hz, 1H, 8.12 (d, J=1.36 Hz, 1H).

EXAMPLE 54B

3-Iodo-1,4-dihydro-indeno[1,2-c]pyrazole-7-carboxylic acid methylamide

The desired product was prepared by replacing Example 22D and NH$_4$Cl with Example 54A and methylamine in Example 23. MS (DCI/NH$_3$) m/z: 339.9 (M+H)$^+$; $^1$H NMR (300 MHz, DMSO-d$_6$) δ 2.79 (s, 1.2H), 2.81 (s, 1.8H), 3.55 (s, 0.8H), 3.60 (s, 1.2H), 7.60 (d, J=7.12 Hz, 1H), 7.77 (m, 1H), 8.08 (m, 1H), 8.52 (d, J=3.73 Hz, 1H), 13.21 (s, 0.6H), 13.54 (s, 0.4H).

EXAMPLE 54C

4-{7-[(methylamino)carbonyl]-1,4-dihydroindeno[1,2-c]pyrazol-3-yl}benzoic acid

The desired product was prepared by replacing Example 1C with Example 54B in Example 1D. The microwave-assisted reaction was run for 900 seconds instead of 450 seconds in Example 1D. MS (DCI/NH$_3$) m/z: 334.1 (M+H)$^+$; $^1$H NMR (500 MHz, DMSO-d$_6$) δ 2.82 (d, J=4.41 Hz, 3H), 3.98 (s, 2H), 7.66 (d, J=7.80 Hz, 1H), 7.81 (d, J=8.73 Hz, 1H), 7.94 (d, J=8.11 Hz, 2H), 8.06 (d, J=8.11 Hz, 2H), 8.16 (s, 1H), 8.53 (d, J=4.37 Hz, 1H), 12.99 (s, 0.4H), 13.49 (s, 0.6H).

EXAMPLE 55

3-[4-(aminocarbonyl)phenyl]-N-methyl-1,4-dihydroindeno[1,2-c]pyrazole-7-carboxamide The desired product was prepared by replacing Example 1C and 4-carboxybenzene boronic acid with Example 54B and 4-(4,4,5,5-tetramethyl-[1,3,2]dioxaborolan-2-yl)-benzamide in Example 1D. The microwave-assisted reaction was run for 900 seconds instead of 450 seconds in Example 1D. MS (DCI/NH$_3$) m/z: 333.6 (M+H)$^+$; $^1$H NMR (500 MHz, DMSO-d$_6$) δ 2.82 (d, J=4.41 Hz, 3H), 3.98 (s, 2H), 7.65 (d, J=7.80 Hz, 1H), 7.81 (dd, J=7.80, 1.56 Hz, 1H), 7.89 (d, J=8.42 Hz, 2H), 8.00 (d, J=8.42 Hz, 2H), 8.16 (s, 1H), 8.53 (d, J=4.68 Hz, 1H).

EXAMPLE 56

3-(4'-hydroxy-1,1'-biphenyl-4-yl)-N-methyl-1,4-dihydroindeno[1,2-c]pyrazole-7-carboxamide The desired product was prepared by replacing Example 1C and 4-carboxybenzene boronic acid with Example 54B and Example 29A in Example 1D. The microwave-assisted reaction was run for 900 seconds instead of 450 seconds in Example 1D. MS (DCI/NH$_3$) m/z: 382.1 (M+H)$^+$; $^1$H NMR (300 MHz, DMSO-d$_6$) δ 2.82 (d, J=4.41 Hz, 3H), 3.96 (s, 2H), 6.87 (d, J=8.48 Hz, 2H), 7.57 (d, J=8.48 Hz, 2H), 7.65 (d, J=7.80 Hz, 1H), 7.73 (d, J=8.48 Hz, 2H), 7.81 (dd, J=7.97, 1.53 Hz, 1H), 7.86 (d, J=8.48 Hz, 2H), 8.17 (s, 1H), 8.55 (d, J=4.75 Hz, 1H), 9.60 (s, brd, 1H).

EXAMPLE 57

4-{7-[(neopentylamino)carbonyl]-1,4-dihydroindeno[1,2-c]pyrazol-3-yl}benzoic acid

EXAMPLE 57A

3-Iodo-1,4-dihydro-indeno[1,2-c]pyrazole-7-carboxylic acid (2,2-dimethyl-propyl)-amide The desired product was prepared by replacing Example 22D and NH$_4$Cl with Example 54A and neopentylamine in Example 23. MS (DCI/NH$_3$) m/z: 396.0 (M+H)$^+$; $^1$H NMR (300 MHz, DMSO-d$_6$) δ 0.92 (s, 9H), 3.11 (s, 0.8H), 3.13 (s, 1.2H), 3.56 (s, 0.8H), 3.61 (s, 1.2H), 7.61 (d, J=7.80 Hz, 1H), 7.79 (d, J=7.80 Hz, 1H), 7.99 (s, 0.4H), 8.13 (s, 0.6H), 8.44 (s, brd, 1H), 13.22 (s, brd, 0.6H), 13.53 (s, brd, 0.4H).

EXAMPLE 57B

4-{7-[(neopentylamino)carbonyl]-1,4-dihydroindeno[1,2-c]pyrazol-3-yl}benzoic acid The desired product was prepared by replacing Example 1C with Example 57A in Example 1D. The microwave-assisted reaction was run for 900 seconds instead of 450 seconds in Example 1D. MS (DCI/NH$_3$) m/z: 390.1 (M+H)$^+$; $^1$H NMR (300 MHz, DMSO-d$_6$) δ 0.93 (s, 9H), 3.15 (d, J=6.44 Hz, 2H), 3.99 (s, 2H), 7.66 (d, J=8.14 Hz, 1H), 7.767.90 (m, 1H), 7.95 (d, J=8.14 Hz, 2H), 8.06 (d, J=8.14 Hz, 2H), 8.18 (s, 1H), 8.47 (t, J=6.44 Hz, 1H).

EXAMPLE 58

3-(4'-hydroxy-1,1'-biphenyl-4-yl)-N-neopentyl-1,4-dihydroindeno[1,2-c]pyrazole-7-carboxamide The desired product was prepared by replacing Example 1C and 4-carboxybenzene boronic acid with Example 57A and Example 29A in Example 1D. The microwave-assisted reaction was run for 900 seconds instead of 450 seconds in Example 1D. MS (DCI/NH$_3$) m/z: 438.2 (M+H)$^+$; $^1$H NMR (500 MHz, DMSO-d$_6$) δ 0.94 (s, 9H), 3.15 (d, J=6.24 Hz, 2H), 3.96 (s, 2H), 6.88 (d, J=8.42 Hz, 2H), 7.57 (d, J=8.74 Hz, 2H), 7.65 (d, J=8.11 Hz, 1H), 7.73 (d, J=8.11 Hz, 2H), 7.82 (d, J=9.36 Hz, 1H), 7.86 (d, J=8.42 Hz, 2H), 8.19 (s, 1H), 8.45 (t, J=6.24 Hz, 1H), 9.57 (s, brd, 1H).

EXAMPLE 59

4-(7-{[(trans-4-hydroxycyclohexyl)amino]carbonyl}-1,4-dihydroindeno[1,2-c]pyrazol-3-yl)benzoic acid

EXAMPLE 59A

3-Iodo-1,4-dihydro-indeno[1,2-c]pyrazole-7-carboxylic acid (trans-4-hydroxy-cyclohexyl)amide The desired product was prepared by replacing Example 22D and NH$_4$Cl with Example 54A and trans-4-aminocyclohexanol in Example 23. MS (DCI/NH$_3$) m/z: 424.0 (M+H)$^+$; $^1$H NMR (300 MHz, DMSO-d$_6$) δ 1.09-1.50 (m, 2H), 1.72-1.92 (m, 4H), 3.39 (m, 1H), 3.55 (s, 0.8H), 3.60 (s, 1.2H), 3.66-3.82 (m, 1H), 4.55 (d, J=4.41 Hz, 1H), 7.59 (m, 1H), 7.77 (t, J=7.46 Hz, 1H), 7.98 (s, 0.4H), 8.12 (s, 0.6H), 8.28 (d, J=8.14 Hz, 1H), 13.21 (s, 0.6H) 13.53 (s, 0.4H).

EXAMPLE 59B 4-(7-{[(trans-4-hydroxycyclohexyl)amino]carbonyl}-1,4-dihydroindeno[1,2-c]pyrazol-3-yl)benzoic acid The desired product was prepared by replacing Example 1C with Example 59A in Example 1D. The microwave-assisted reaction was run for 900 seconds instead of 450 seconds in Example 1D. MS (DCI/NH$_3$) m/z: 418.1 (M+H)$^+$; $^1$H NMR (500 MHz, DMSO-d$_6$) δ 1.20-1.32 (m, 2H), 1.35-1.47 (m, 2H), 1.79-1.90 (m, 4H), 3.36 (m, 1H), 3.76 (m, 1H), 3.97 (s, 2H), 7.64 (d, J=7.80 Hz, 1H), 7.81 (d, J=7.80 Hz, 1H), 7.94 (d, J=8.11 Hz, 2H), 8.05 (d, J=8.42 Hz, 2H), 8.17 (s, 1H), 8.29 (d, J=7.80 Hz, 1H).

EXAMPLE 60

6-[6-(allyloxy)-1,4-dihydroindeno[1,2-c]pyrazol-3-yl]nicotinic acid

EXAMPLE 60A methyl 6-[[5-(allyloxy)-1-oxo-1,3-dihydro-2H-inden-2-ylidene](hydroxy)methyl]nicotinate The desired product was prepared by replacing terephthalic acid monomethyl ester with 5-(methoxycarbonyl)-2-pyridinecarboxylic acid in Example 22B.

EXAMPLE 60B methyl 6-[6-(allyloxy)-1,4-dihydroindeno[1,2-c]pyrazol-3-yl]nicotinate The desired product was prepared by replacing Example 22B with Example 60A in Example 22C.

EXAMPLE 60C

6-[6-(allyloxy)-1,4-dihydroindeno[1,2-c]pyrazolC3-yl]nicotinic acid

The desired product was prepared by replacing Example 22C with Example 60B in Example 22D. MS (DCI/NH$_3$) m/z: 334.0 (M+H)$^+$; $^1$H NMR (500 MHz, DMSO-d$_6$) δ 3.88 (s, 2H), 4.63 (d, J=4.99 Hz, 2H), 5.28 (d, J=10.61 Hz, 1H), 5.43 (d, J=17.47 Hz, 1H), 6.08 (m, 1H), 6.97 (dd, J=8.27, 2.03 Hz, 1H), 7.22 (s, 1H), 7.56 (d, J=8.11 Hz, 1H), 7.94 (s, 1H), 8.36 (d, J=8.11 Hz, 1H), 9.12 (s, 1H), 13.40 (s, brd, 1H).

EXAMPLE 61

6-(6-hydroxy-1,4-dihydroindeno[1,2-c]pyrazol-3-yl)nicotinic acid

EXAMPLE 61A methyl 6-(6-hydroxy-1,4-dihydroindeno[1,2-c]pyrazol-3-yl)nicotinate The desired product was prepared by replacing Example 22C with Example 60B in Example 24.

EXAMPLE 61B 6-(6-hydroxy-1,4-dihydroindeno[1,2-c]pyrazol-3-yl)nicotinic acid The desired product was prepared by replacing Example 22C with Example 61A in Example 22D. MS (DCI/NH$_3$) m/z: 294.0 (M+H)$^+$; $^1$H NMR (300 MHz, DMSO-d$_6$) δ 3.83 (s, 2H), 6.78 (dd, J=8.14, 2.37 Hz, 1H), 7.00 (d, J=2.03 Hz, 1H), 7.45 (d, J=8.14 Hz, 1H), 7.92 (d, J=8.14 Hz, 1H), 8.36 (dd, J=8.14, 2.03 Hz, 1H), 9.11 (d, J=2.03 Hz, 1H), 9.50 (s, brd, 1H).

EXAMPLE 62

6-(allyloxy)-3-[4-(1H-tetraazol-5-yl)phenyl]-1,4-dihydroindeno[1,2-c]pyrazole

EXAMPLE 62A

4-[[5-(allyloxy)-1-oxo-1,3-dihydro-2H-inden-2-ylidene](hydroxy)methyl]benzonitrile The desired product was prepared by replacing terephthalic acid monomethyl ester with 4-cyanobenzoic acid in Example 22B.

EXAMPLE 62B 4-(6-Allyloxy-1,4-dihydro-indeno[1,2-c]pyrazol-3-yl)-benzonitrile The desired product was prepared by replacing Example 22B with Example 62A in Example 22C. MS (DCI/NH$_3$) m/z: 314.1 (M+H)$^+$; $^1$H NMR (300 MHz, DMSO-d$_6$) δ 3.85 (s, 0.8H), 3.90 (s, 1.2H), 4.46-4.68 (m, 2H), 5.28 (dd, J=10.51, 1.70 Hz, 1H), 5.43 (dd, J=17.29, 2.03 Hz, 1H), 6.09 (m, 1H), 6.97 (m, 1H), 7.167.28 (m, 1H), 7.46-7.65 (d, J=8.48 Hz, 1H), 7.87-8.08 (m, 4H), 13.31 (s, brd, 1H).

EXAMPLE 62C 6-(allyloxy)-3-[4-(1H-tetraazol-5-yl)phenyl]-1,4-dihydroindeno[1,2-c]pyrazole A mixture of Example 62B (61.5 mg, 0.196 mmol), NaN$_3$ (19.1 mg, 0.294 mmol), and Et$_3$N.HCl (40.5 mg, 0.294 mmol) in DMF (2 mL) was heated at 140° C. for 4 hours. To this mixture were added more NaN$_3$ (60.0 mg) and Et$_3$N.HCl (120 mg). The reaction mixture was stirred overnight, cooled, and concentrated. The crude material was purified using the HPLC condition in Example 8 to give 20.0 mg (29%) of the desired product as brown solid. MS (DCI/NH$_3$) m/z: 357.1 (M+H)$^+$; $^1$H NMR (300 MHz, DMSO-d$_6$) δ 3.90 (s, 2H), 4.53-4.71 (m, 2H), 5.29 (dd, J=10.51, 1.70 Hz, 1H), 5.44 (dd, J=17.29, 2.03 Hz, 1H), 6.07 (m, 1H), 6.98 (dd, J=8.31, 2.20 Hz, 1H), 7.22 (d, J=2.03 Hz, 1H), 7.57 (d, J=8.14 Hz, 1H), 8.02 (d, J=8.14 Hz, 2H), 8.16 (d, J=8.48 Hz, 2H), 13.22 (s, brd, 1H).

EXAMPLE 63

4-(6-{[(trans-4-methylcyclohexyl)amino]methyl}-1,4-dihydroindeno[1,2-c]pyrazol-3-yl)phenol The desired product was prepared by replacing 4-carboxybenzene boronic acid with 4-(4,4,5,5-tetramethyl-[1,3,2]dioxaborolan-2-yl)-phenol in Example 1D. MS (DCI/NH$_3$) m/z: 374.2 (M+H)$^+$; $^1$H NMR (300 MHz, CD$_3$OD) δ 0.95 (d, J=6.44 Hz, 3H), 1.00-1.18 (m, 2H), 1.35-1.56 (m, 3H), 1.81-1.95 (m, 2H), 2.15-2.30 (m, 2H), 3.12 (m, 1H), 3.88 (s, 2H), 4.28 (s, 2H), 6.91 (d, J=8.82 Hz, 2H), 7.49 (d, J=7.80 Hz, 1H), 7.63 (d, J=8.82 Hz, 2H), 7.69 (s, 1H), 7.79 (d, J=7.80 Hz, 1H).

EXAMPLE 64

4'-(6,7-dimethoxy-1,4-dihydroindeno[1,2-c]pyrazol-3-yl)-1,1'-biphenyl-4-ol

EXAMPLE 64A (4-Bromophenyl)-imidazol-1-yl-methanone

4-Bromobenzoic acid (10 g, 50 mmol) in 50 ml of DMF was treated with carbonyl-1,1'-diimidazole (18 g, 112.5 mmol). The mixture was stirred for 3 hours and poured into water. The mixture was filtered and the filter cake washed with water and dried to provide the title compound. MS (DCI/NH$_3$) m/z: 252.9 (M+H)$^+$. $^1$H NMR (300 MHz, DMSO-D$_6$) δ ppm 7.17 (dd, J=1.65, 0.81 Hz, 1H) 7.69 (t, J=1.48 Hz, 1H) 7.77 (m, 2H) 7.83 (m, 2H) 8.21 (dd, J=1.36, 0.85 Hz, 1H).

EXAMPLE 64B 2-(4-Bromobenzoyl)-5,6-dimethoxy-indan-1-one 5,6-Dimethoxy-indan-1-one (2 g, 10.4 mmol) in 25 ml of THF was treated with NaH (60%, 624 mg, 15.6 mmol) at 0° C. After the suspension was stirred at room temperature for 1 hour, the mixture was treated with Example 64A (2.61 g, 10.4 mmol) in 5 ml of THF dropwise. After stirring for 3 hours at room temperature, the mixture was poured into water and acidified with hydrochloric acid. The mixture was filtered and the filter cake was washed with water and recrystallized from ethanol to provide the title compound. MS (DCI/NH$_3$) m/z: 375.0 (M+H)$^+$.

EXAMPLE 64C 3-(4-Bromophenyl)-6,7-dimethoxy-1,4-dihydroindeno[1,2-c]pyrazole

Example 64B (820 mg, 2.18 mmol), hydrazine monohydrate (0.127 mL, 2.63 mmol), and acetic acid (0.15 ml, 2.63 mmol) were combined in 30 ml of ethanol and heated at 90° C. for 6 hours. The mixture was allowed to cool to room temperature and filtered. The filter cake was dried to provide the title compound. MS (DCI/NH$_3$) m/z: 373.0 (M+H)$^+$. $^1$H NMR (300 MHz, DMF-D$_7$) δ ppm 3.84 (s, 2H), 3.89 (s, 3H), 3.93 (s, 3H), 7.31 (s, 1H), 7.34 (s, 1H), 7.71 (d, J=8.48 Hz, 2H), 7.89 (d, J=8.48 Hz, 2H), 13.17 (s, 1H).

EXAMPLE 64D

4'-(6,7-dimethoxy-1,4-dihydroindeno[1,2-c]pyrazol-3-yl)-1,1'-biphenyl-4-ol

Example 64C (50 mg, 0.14 mmol)), 4-hydroxylphenyl boronic acid (23.3 mg, 0.17 mmol), Na$_2$CO$_3$ (1 M, 0.3 mL), and Pd(PPh$_3$)$_2$Cl$_2$ (9.9 mg, 0.014 mmol) were combined in DME:EtOH:H$_2$O (7:2:3, 1.5 mL) in a capped 2 mL vial and heated at 160° C. for 600 seconds in a Smith Synthesizer. The mixture was cooled using 40 psi pressurized air, the solvents were evaporated, and the residue was purified using preparative HPLC (for conditions, see Example 1D) to provide the title compound. MS (DCI/NH$_3$) m/z: 385.1 (M+H)$^+$. $^1$H NMR (500 MHz, DMSO-D$_6$) δ ppm 3.79 (s, 2H), 3.82 (s, 3H), 3.85 (s, 3H), 6.87 (d, J=8.66 Hz, 2H), 7.23 (s, 1H), 7.25 (s, 1H), 7.57 (d, J=8.66 Hz, 2H), 7.71 (d, J=8.34 Hz, 2H), 7.82 (d, J=8.42 Hz, 2H), 9.55 (s, 1H).

EXAMPLE 65

6,7-dimethoxy-3-[4-(1H-tetraazol-5-yl)phenyl]-1,4-dihydroindeno[1,2-c]pyrazole

Example 64C (50 mg, 0.14 mmol)), zinc cyanide (17.4 mg, 1.48 mmol), and Pd(PPh$_3$)$_4$ (15.6 mg, 0.014 mmol) were combined in DMF (3 mL) in a capped 5 mL vial and heard at 180° C. for 300 seconds in a Smith Synthesizer. The mixture was cooled using 40 psi and then treated with sodium azide (105.3 mg, 1.62 mmol) and NH$_4$Cl (87 mg, 1.62 mmol). The vial was recapped and heated at 220° C. for 15 minutes. After the reaction mixture was cooled using 40 psi pressurized air, the solvent was removed and the residue was purified using preparative HPLC (for conditions, see Example 1D) to provide the title compound. MS (DCI/NH$_3$) m/z: 361.0 (M+H)$^+$. $^1$H NMR (500 MHz, DMSO-D$_6$) δ ppm 3.83 (s, 2H), 3.84 (s, 3H), 3.85 (s, 3H), 7.24 (s, 1H), 7.26 (s, 1H), 8.01 (d, J=8.42 Hz, 2H), 8.15 (d, J=8.42 Hz, 2H).

EXAMPLE 66

4-(6,7-dimethoxy-1,4-dihydroindeno[1,2-c]pyrazol-3-yl)benzoic acid

Example 64C (78 mg, 0.21 mmol), PdCl$_2$(dppf)-CH$_2$Cl$_2$ (18 mg), triethyl amine (0.088 mL), were combined in THF (98 mL) and H$_2$O (1 mL) and stirred under a CO atmosphere (500 psi) at 120° C. for 16 hours. The mixture was allowed to cool to room temperature, concentrated under reduced pressure and the residue was purified by HPLC (for conditions, see Example 1D) to provide the title compound. MS (DCI/NH$_3$) m/z: 337.0 (M+H)$^+$. $^1$H NMR (500 MHz, DMSO-D$_6$) δ ppm 3.81 (s, 2H), 3.82 (s, 3H), 3.84 (s, 3H), 7.23 (s, 1H), 7.25 (s, 1H), 7.91 (d, J=8.30 Hz, 2H), 8.04 (d, J=8.30 Hz, 2H).

EXAMPLE 67

4-(4-hydroxy-1,4-dihydroindeno[1,2-c]pyrazol-3-yl)benzoic acid

EXAMPLE 67A 2-(4-bromobenzoyl)-1H-indene-1,3 (2H)-dione

Methanol (8.5 ml) was treated with sodium (4.8 g) in benzene (90 mL). The reaction mixture was refluxed overnight, allowed to cool to room temperature, and treated with phthalic acid dimethyl ester (38.84 g) and 1-(4-bromophenyl)ethanone (39.81 g) in benzene (50 mL). Distillation of the reaction mixture was performed at 80° C. overnight to remove methanol. The reaction mixture was poured into diluted HCl and filtered. The filter cake was collected and recrystallized from ethanol to provide the title compound.

EXAMPLE 67B 3-(4-bromophenyl)indeno[1,2-c]pyrazol-4(1H)-one

Example 67A (5.8 g) and hydrazine monohydrate (0.982 ml, 20.24 mmol) were combined in ethanol (300 mL) and refluxed at 90° C. overnight. The mixture was allowed to cool to room temperature and was filtered. The filter cake was dried to provide the title compound. MS (DCI/NH$_3$) m/z: 327.3 (M+H)$^+$.

EXAMPLE 67C butyl 4-(4-oxo-1,4-dihydroindeno[1,2-c]pyrazol-3-yl)benzoate

Pd(OAc)$_2$ (3.5 mg), Ph$_3$P (16 mg), DIEA (2.6 ml), and Example 67B (100 mg) were combined in butanol and treated with a stream of CO for 5 minutes. The mixture was stirred at 120° C. overnight under a CO atmosphere. The mixture was allowed to cool to room temperature, concentrated, and the residue was purified by silicon gel chromatography using a mixture of hexane and ethyl acetate as eluent to provide the title compound. MS (DCI/NH$_3$) m/z: 347.0 (M+H)$^+$.

EXAMPLE 67D 4-(4-hydroxy-1,4-dihydroindeno[1,2-c]pyrazol-3-yl) benzoic acid

Example 67C (51 mg) in 2 ml of THF/MeOH (1:1) was treated with NaBH (5.6 mg) at 0° C. The reaction mixture was allowed to warm to room temperature and stir for 1 hour. The mixture was concentrated and the residue was suspended in THF (1 mL), MeOH (2 mL), and aqueous NaOH (lN, 1 mL). After stirring at 60° C. for 2 hours, the mixture was concentrated and the residue was purified by HPLC to provide the title compound. MS (DCI/NH$_3$) m/z: 293.3 (M+H)$^+$. $^1$H NMR (400 MHz, DMSO-D$_6$) δ ppm 5.59 (d, J=8.67 Hz, 1H), 5.84 (d, J=8.67 Hz, 1H), 7.33 (m, 2H), 7.54 (d, J=7.13 Hz, 1H), 7.59 (d, J=7.29 Hz, 1H), 8.03 (d, J=8.44 Hz, 2H), 8.10 (d, J=8.44 Hz, 2H), 13.19 (s, 1H).

EXAMPLE 68

4'-[6-(morpholin-4-ylmethyl)-1,4-dihydroindeno[1,2-c]pyrazol-3-yl]-1,1'-biphenyl-4-ol

EXAMPLE 68A 1,4-dihydroindeno[1,2-c]pyrazole-6-carbaldehyde

To a solution of 6-bromo-1,4-dihydro-indeno[1,2-c]pyrazole (0.100 g, 0.425 mmol, see U.S. Pat. No. 6,297,238 for preparation) in THF (3 mL) at −78° C. was added PhLi in cyclohexane/ether (1.8 M, 0.71 mL, 1.28 mmol) followed by s-BuLi in cyclohexane (1.3 M, 0.98 mL, 1.28 mmol) 30 minutes later. The reaction mixture was stirred at −78° C. for 60 minutes and DMF (0.33 mL, 4.25 mmol) was added. The dry ice bath was removed after 30 minutes. After an additional 30 minutes, the reaction was quenched with water. The reaction mixture was extracted with EtOAc, washed with 50% brine, dried over MgSO$_4$, filtered, and concentrated. The concentrate was purified by flash chromatography eluted with EtOAc/hexane (7:3 to 8:2) to give 0.053 g (68%) of the desired product as brown solid. MS (DCI/NH$_3$) m/z: 185.0 (M+H)$^+$; $^1$H NMR (300 MHz, CD$_3$OD) δ ppm 3.76 (s, 2H), 7.63 (s, 1H), 7.62-7.97 (m, 2H), 8.04 (s, 1H), 10.00 (s, 1H).

EXAMPLE 68B 3-iodo-1,4-dihydroindeno[1,2-c]pyrazole-6-carbaldehyde

A suspension of Example 68A (7.90 g, 0.0429 mol) and N-iodosuccinimide (11.6 g, 0.0515 mol) in DMF (150 mL) was heated at 80° C. for 5.5 hours. The reaction was cooled and the solvent was evaporated. The concentrate was triturated with EtOAc and ether to give 7.20 g of brown solid as the desired product. The filtrate was concentrated and purified by flash chromatography eluted with EtOAc/hexane (7:3) to give 1.30 g of the desired product (combined yield: 64%). MS (DCI/NH$_3$) m/z: 310.9 (M+H)$^+$; $^1$H NMR (300 MHz, DMSO-D$_6$) δ ppm 3.63 (s, 0.8H), 3.68 (s, 1.2H), 7.72 (d, J=7.46 Hz, 0.5H), 7.83 (d, J=7.80 Hz, 0.5H), 7.96 (m, 1H), 8.07 (m, 1H), 10.03 (s, 1H), 13.45 (s, 0.6H), 13.72 (s, 0.4H).

EXAMPLE 68C 3-iodo-6-(morpholin-4-ylmethyl)-1,4-dihydroindeno[1,2-c]pyrazole A mixture of Example 68B (1.00 g, 3.22 mmol), morpholine (0.84 mL, 9.66 mmol), and TsOH.H$_2$O (61.2 mg, 0.322 mmol) in toluene (50 mL) was heated to refluxing overnight. The solvent was evaporated. To the resulting residue were added EtOH (40 mL), THF (10 mL), and NaBH$_4$ (0.182 g, 4.83 mmol) at room temperature. The mixture was stirred overnight and the solid was filtered. The filtrate was concentrated, treated with 1N HCl, and extracted with EtOAc. The aqueous layer was basified using 3N NaOH and extracted with EtOAc. The organic layer was dried over MgSO$_4$, filtered, and concentrated. The residue was purified by flash chromatography eluted with EtOAc/ MeOH (95:5) to give 0.387 g (32%) of the desired product as pale yellow solid. MS (DCI/NH$_3$) m/z: 382.0 (M+H)$^+$; $^1$H NMR (300 MHz, CD$_3$OD) δ ppm 2.44-2.51 (m, 4H), 3.53 (s, 2H), 3.57 (s, 2H), 3.66-3.72 (m, 4H), 7.34 (d, J=8.14 Hz, 1H), 7.54 (s, 1H), 7.58 (d, J=7.80 Hz, 1H).

EXAMPLE 68D

4'-(4,4,5,5-tetramethyl-1,3,2-dioxaborolan-2-yl)-1,1'-biphenyl-4-ol

A mixture of 4'-bromo-biphenyl-4-ol (0.300 g, 1.20 mmol), bis(pinacolato)diboron (0.336 g, 1.32 mmol), PdCl$_2$(dppf).CH$_2$Cl$_2$ (0.0293 g, 3%), dppf (0.0199 g, 3%), and KOAc (0.353 g, 3.60 mmol) in 1,4-dioxane (6 mL) was heated at 90° C. overnight. The reaction mixture was concentrated and the residue was extracted with EtOAc, washed with brine, dried over MgSO$_4$, filtered, concentrated, and purified by flash chromatography eluted with hexane/EtOAc (1:1) to give 0.278 g (78%) of the desired product as white foam. MS (DCI/NH$_3$) m/z: 296.1 (M+H)$^+$; $^1$H NMR (300 MHz, CDCl$_3$) δ ppm 1.27 (s, 4H), 1.36 (s, 8H), 6.90 (d, J=8.48 Hz, 2H), 7.53 (dd, J=12.72, 8.65 Hz, 4H), 7.85 (d, J=8.14 Hz, 2H).

EXAMPLE 68E

4'-(6-morpholin-4-ylmethyl-1,4-dihydro-indeno[1,2-c]pyrazol-3-yl)-biphenyl-4-ol

A mixture of Example 68C (60.0 mg, 0.157 mmol), Example 68D (51.2 mg, 0.173 mmol), Na$_2$CO$_3$ (1 M, 0.22 mL, 0.220 mmol), and Pd(PPh$_3$)$_2$Cl$_2$ (11.0 mg, 0.0157 mmol) in DME/EtOH/H$_2$O (7:2:3, 1.4 mL) in a capped 2 mL vial was heated to 160 to 170° C. for 450 to 600 seconds in a Smith Synthesizer (300W). The reaction was cooled using 40 psi pressurized air. Solvents were evaporated and the crude product was purified using preparative HPLC to give 22.9 mg (22%) of the desired product as TFA salt. The purification was processed on a Phenomenex® C. 18 column (250 mm×21.2 mm, 5 μm particle size) using a gradient of 0% to 70% acetonitrile : 0.1% aqueous TFA over 46 min at a flow rate of 25 mL/min.

Examples 69 to 83, represented by FIG. (I) and listed in Table 1, were synthesized in a similar fashion as that described in Example 68E.

TABLE 1

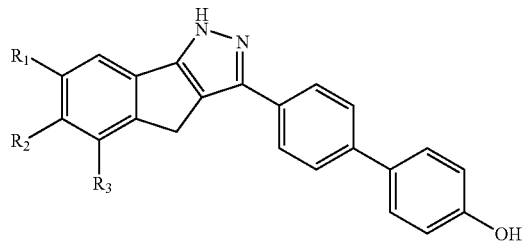

FIG. (I)

| Exmp. | R$_1$ | R$_2$ | R$_3$ | $^1$H NMR | MS m/z (M+H)$^+$ | Yield |
|---|---|---|---|---|---|---|
| 68E | H | ![morpholinylmethyl] | H | (500 MHz, DMSO-D$_6$) δ ppm 3.17 (s, brd, 2 H) 3.26-3.38 (m, 2 H) 3.55-3.75 (m, 2 H) 3.89-4.06 (m, 4 H) 4.43 (s, 2 H) 6.88 (d, J=8.42 Hz, 2 H) 7.52 (d, J=7.80 Hz, 1 H) 7.57 (d, J=8.42 Hz, 2 H) 7.69-7.81 (m, 4 H) 7.87 (d, J=8.42 Hz, 2 H) 10.09 (s, 1 H) | 424.2 (DCI/ NH$_3$) | 22.9 mg 22% |
| 69 | H | H | ![neopentylaminomethyl] | (400 MHz, CD$_3$OD) δ ppm 1.07 (s, 9 H) 3.00 (s, 2 H) 4.02 (s, 2 H) 4.46 (s, 2 H) 6.80 (d, J=8.59 Hz, 1 H) 6.89 (d, J=8.59 Hz, 2 H) 7.35 (d, J=8.59 Hz, 1 H) 7.50-7.55 (m, 3 H) 7.70 (d, J=8.29 Hz, 2 H) 7.84-7.86 (m, 2H) | 424.2 (DCI/ NH$_3$) | 12.5 mg 15% |
| 70 | H | ![neopentylaminomethyl] | H | (300 MHz, CD$_3$OD) δ ppm 1.06 (s, 9 H) 2.87 (s, 2 H) 3.96 (s, 2 H) 4.33 (s, 2 H) 6.80 (d, J=8.81 Hz, 0.5 H) 6.89 (d, J=8.81 Hz, 2 H) 7.35 (d, J=8.81 Hz, 0.5 H) 7.50-7.56 (m, 3 H) 7.68-7.75 (m, 3 H) 7.80-7.86 (m, 3 H) | 424.3 (DCI/ NH$_3$) | 17.4 mg 20% |

TABLE 1-continued

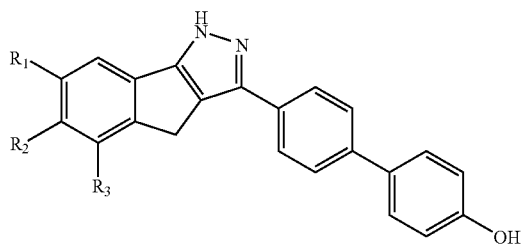

FIG. (I)

| Exmp. | $R_1$ | $R_2$ | $R_3$ | $^1$H NMR | MS m/z $(M+H)^+$ | Yield |
|---|---|---|---|---|---|---|
| 71 | H | H | ![HN-CH2CH2-OH group] | (400 MHz, CD$_3$OD) δ ppm 3.28-3.31 (m, 2 H) 3.88-3.91 (m, 2 H) 4.04 (s, 2 H) 4.45 (s, 2 H) 6.80 (d, J=8.59 Hz, H) 6.80 (d, J=8.59 Hz, 0.5 H) 6.89 (d, J=8.59 Hz, 2 H) 7.35 (d, J=8.90 Hz, 0.5 H) 7.47 (d, J=7.67 Hz, 1 H) 7.50-7.55 (m, 3 H) 7.70 (d, J=8.29 Hz, 2 H) 7.82-7.86 (m, 3 H) | 398.2 (DCI/ NH$_3$) | 13.7 mg 16% |
| 72 | H | ![HN-CH2CH2-OH group] | H | (300 MHz, DMSO-D$_6$) δ ppm 2.98-3.05 (m, 2 H) 3.68 (t, J=5.42 Hz, 2 H) 3.94 (s, 2 H) 4.17-4.31 (m, 2 H) 6.88 (d, J=8.81 Hz, 2 H) 7.51 (d, J=7.80 Hz, 1 H) 7.57 (d, J=8.81 Hz, 2 H) 7.69-7.77 (m, 4 H) 7.87 (d, J=9.00 Hz, 2 H) 8.85 (s, brd, 2 H) | 398.2 (DCI/ NH$_3$) | 61.2 mg 50% |
| 73 | ![HN-CH2CH2-OH group] | H | H | (400 MHz, DMSO-D$_6$) δ ppm 3.00-3.02 (m, 2 H) 3.68 (t, J=5.37 Hz, 2 H) 3.94 (s, 2 H) 4.28 (t, J=5.22 Hz, 2 H) 6.88 (d, J=8.59 Hz, 2 H) 7.43 (d, J=7.98 Hz, 1 H) 7.57 (d, J=8.59 Hz, 2 H) 7.65 (d, J=7.67 Hz, 1 H) 7.73 (d, J=8.59 Hz, 2 H) 7.84-7.88 (m, 3 H) 8.91 (s, 2 H) | 398.2 (DCI/ NH$_3$) | 31.5 mg 30% |
| 74 | H | ![HN-butyl group] | H | (300 MHz, CD$_3$OD) δ ppm 1.00 (t, J=7.29 Hz, 3 H) 1.39-1.52 (m, 2 H) 1.66-1.77 (m, 2 H) 3.06-3.11 (m, 2 H) 3.96 (s, 2 H) 4.28 (s, 2 H) 6.80 (d, J=8.81 Hz, 0.5 H) 6.89 (d, J=8.48 Hz, 2 H) 7.35 (d, J=8.48 Hz, 0.5 H) 7.49-7.54 (m, 3H) 7.69-7.72 (m, 3H) 7.80-7.85 (m, 3H) | 410.2 (DCI/ NH$_3$) | 18.5 mg 21% |

TABLE 1-continued

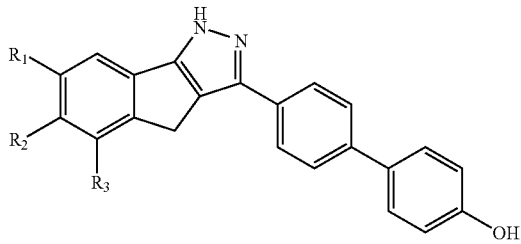

FIG. (I)

| Exmp. | $R_1$ | $R_2$ | $R_3$ | $^1$H NMR | MS m/z $(M+H)^+$ | Yield |
|---|---|---|---|---|---|---|
| 75 | H | ![piperidine-OH] | H | (300 MHz, DMSO-$D_6$) δ ppm 1.57 (m, 1 H) 1.71-1.90 (m, 2 H) 1.99 (m, 1 H) 3.00 (m, 1 H) 3.22 (s, brd, 2 H) 3.34-3.45 (m, 2 H) 3.96 (s, 2 H) 4.38 (dd, J=15.26, 4.75 Hz, 2 H) 6.88 (d, J=8.48 Hz, 2 H) 7.48-7.59 (m, 3 H) 7.70-7.78 (m, 4 H) 7.87 (d, J=8.48 Hz, 2 H) 9.35 (s, brd, 1 H) 9.61 (s, brd, 1 H) | 438.2 (DCI/ $NH_3$) | 45.3 38% |
| 76 | H | ![N-methylpiperazine] | H | (300 MHz, $CD_3OD$) δ ppm 2.88 (s, 3 H) 2.93-3.03 (m, brd, 4 H) 3.33-3.37 (m, 4 H) 3.91 (d, J=4.07 Hz, 4 H) 6.88 (d, J=8.81 Hz, 2 H) 7.42 (d, J=7.46 Hz, 1 H) 7.53 (d, J=8.81 Hz, 2 H) 7.63 (s, 1 H) 7.70 (d, J=8.48 Hz, 2 H) 7.74 (d, J=7.80 Hz, 1 H) 7.82 (d, J=8.99 Hz, 2 H) | 437.2 (DCI/ $NH_3$) | 45.0 mg 38% |
| 77 | H | ![aminomethylpyridine] | H | (500 MHz, DMSO-$D_6$) δ ppm 3.91 (s, 2 H) 4.63 (d, J=5.61 Hz, 2 H) 6.88 (d, J=8.42 Hz, 2 H) 6.97 (t, J=6.86 Hz, 2 H) 7.38 (d, J=7.80 Hz, 1 H) 7.49-7.60 (m, 4 H) 7.68 (d, J=7.49 Hz, 1 H) 7.72 (d, J32 8.42 Hz, 2 H) 7.85 (d,J=8.11 Hz, 2 H) 8.13 (d, J=5.61 Hz, 1 H) 9.09 (t, J=5.61 Hz, 1 H) 13.22 (s, brd, 1 H) | 431.2 (DCI/ $NH_3$) | 21.6 mg 21% |
| 78 | H | ![aminoalcohol] | H | (500 MHz, DMSO-$D_6$) δ ppm 0.90 (s, 6 H) 2.76-2.87 (m, 2 H) 3.24 (s, 2 H) 3.94 (s, 2 H) 4.24 (s, 2 H) 6.87 (d, J=8.42 Hz, 2 H) 7.52 (d, J=8.11 Hz, 1 H) 7.56 (d, J=8.42 Hz, 2 H) 7.68-7.77 (m, 4 H) 7.86 (d, J=8.42 Hz, 2 H) 8.53 (s, brd, 2 H) 9.60 (s, brd, 1 H) | 440.2 (DCI/ $NH_3$) | 23.4 mg 34% |

TABLE 1-continued

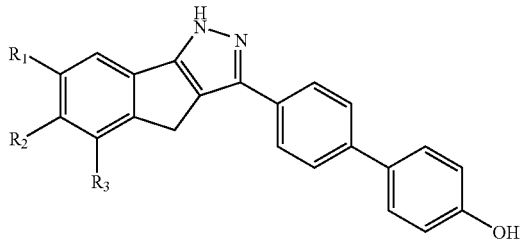

FIG. (I)

| Exmp. | R₁ | R₂ | R₃ | ¹H NMR | MS m/z (M+H)⁺ | Yield |
|---|---|---|---|---|---|---|
| 79 | H | (1-piperidinyl-4-carboxamide-methyl) | H |  | 465.2 (DCI/NH₃) | 33.0 mg 31% |
| 80 | H | ((5-methylpyrazin-2-yl)methylamino-methyl) | H | (300 MHz, CD₃OD) δ ppm 2.58 (s, 3 H) 3.94 (s, 2 H) 4.40 (s, 2 H) 4.46 (s, 2 H) 6.88 (d, J=8.81 Hz, 2 H) 7.52 (d, J=8.81 Hz, 3 H) 7.68-7.71(m, 3 H) 7.77-7.89 (m, 3 H) 8.55 (s, 1 H) 8.62 (s, 1 H) | 460.2 (DCI/NH₃) | 27.3 mg 24% |
| 81 | H | (pyridin-2-ylmethylamino-methyl) | H | (300 MHz, CD₃OD) δ ppm 3.97 (s, 2 H) 4.40 (s, 2 H) 4.42 (s, 2 H) 6.87-6.90 (m, 2 H) 7.42-7.46 (m, 2 H) 7.50-7.57 (m, 4 H) 7.69-7.76 (m, 3 H) 7.80-7.88 (m, 4 H) 8.68 (m, 1 H) | 445.2 (DCI/NH₃) | 14.5 mg 12% |
| 82 | (2-pyrrolidin-1-yl-ethylamino-ethyl) | H | H | (500 MHz, DMSO-D₆) δ ppm 1.91-2.02 (m, brd, 4 H) 3.09 (s, brd, 2 H) 3.39-3.41 (m, 2 H) 3.50-3.53 (m, 2 H) 3.65 (s, 2 H) 3.95 (s, 2 H) 4.34 (s, 2 H) 6.88 (d, J=8.73 Hz, 2 H) 7.43 (d, J=7.80 Hz, 1 H) 7.57 (d, J=8.73 Hz, 2 H) 7.66 (d, J=7.80 Hz, 1 H) 7.73 (d, J=8.42 Hz, 2 H) 7.86 (d, J=8.11 Hz, 3 H) 9.33 (s, brd, 2 H) 10.26 (s, brd, 1 H) | 451.2 (DCI/NH₃) | 40.9 mg 38% |

TABLE 1-continued

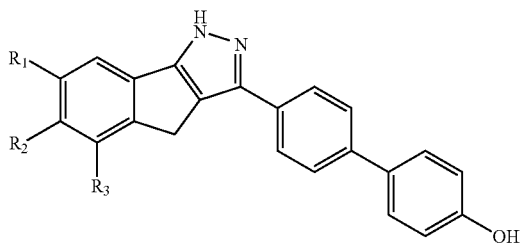

FIG. (I)

| Exmp. | R₁ | R₂ | R₃ | ¹H NMR | MS m/z (M+H)⁺ | Yield |
|---|---|---|---|---|---|---|
| 83 | H | (thiomorpholinylethyl group) | H | (300 MHz, DMSO-D₆) δ ppm 2.81-3.05 (m, 4 H) 3.13-3.71 (m, (m, 4 H) 3.13-3.71 (m, 4 H) 3.96 (s, 2 H) 4.44 (s, 2 H) 6.88 (d, J=8.48 Hz, 2 H) 7.51 (d, J=8.14 Hz, 1 H) 7.57 (d, J=8.48 Hz, 2 H) 7.69-7.80 (m, 4 H) 7.87 (d, J=8.48 Hz, 2 H) 9.62 (s, brd, 1 H) 9.77 (s, brd, 1 H) | 440.2 (DCI/ NH₃) | 22.5 mg 22% |

EXAMPLE 84

4'-[6-(morpholin-4-ylcarbonyl)-1,4-dihydroindeno[1,2-c]pyrazol-3-yl]-1,1'-biphenyl-4-ol

EXAMPLE 84A 3-iodo-1,4-dihydroindeno[1,2-c]pyrazole-6-carboxylic acid

A mixture of Example 68B (3.00 g, 9.67 mmol), KH₂PO₄ (5.26 g, 0.0387 mol), and H₂NSO₃H (1.41 g, 0.0145 mol) in 1,4 dioxane/H₂O (100/30 mL) was stirred at 0° C. for 15 minutes. To this mixture was added NaClO₂ (1.14 g, 0.0126 mol) in H₂O (15 mL) dropwise. The reaction mixture was stirred for 15 minutes at 0° C. followed by the addition of NaHSO₃ (1.11 g, 0.0106 mol). The resulting suspension was warmed to room temperature and stirred for 1 hour. The reaction mixture was treated with Na₂S₂O₃ solution and concentrated to remove most of the solvents. Water was added to the resulting slurry and the suspension was stirred for 1 hour. The solid material was filtered, rinsed with water, and dried in a vacuum oven to give 3.49 g of the desired product as yellow solid. This product was used in the following step without further purification. MS (DCI/NH₃) m/z: 327.0 (M+H)⁺; ¹H NMR (300 MHz, DMSO-D₆) δ ppm 3.57 (s, 2H), 7.67 (m, 1H), 7.98 (d, J=7.80 Hz, 1H), 8.10 (s, 1H).

EXAMPLE 84B 3-iodo-6-(morpholin-4-ylcarbonyl)-1,4-dihydroindeno[1,2-c]pyrazole A mixture of Example 84A (0.210 g, 0.644 mmol), PyBOP (0.503 g, 0.966 mmol), morpholine (0.084 mL, 0.966 mmol), and diisopropylethylamine (0.39 mL, 2.25 mmol) in DMF (5 mL) was stirred at room temperature overnight. The reaction mixture was diluted with EtOAc and washed with water and NaHCO₃. The organic layer was dried over MgSO₄, filtered, concentrated, and purified by flash chromatography eluted with EtOAc to give 0.122 g (48%) of the desired product as red solid. MS (DCI/NH₃) m/z: 396.0 (M+H)⁺; ¹H NMR (300 MHz, DMSO-D₆) δ ppm 3.46-3.67 (m, 10H) 7.41 (m, 1H) 7.59 (s, brd, 1.5H) 7.67 (d, J=7.46 Hz, 0.5H).

EXAMPLE 84C

4'-[6-(morpholin-4-ylcarbonyl)-1,4-dihydroindeno[1,2-c]pyrazol-3-yl]-1,1'-biphenyl-4-ol The desired product was prepared by substituting Example 68C with Example 84B in Example 68E. The reaction temperature and time were raised to 180° C. and 1000 seconds, respectively.

EXAMPLE 85

N-cyclohexyl-3-(4'-hydroxy-1,1'-biphenyl-4-yl)-1,4-dihydroindeno[1,2-c]pyrazole-6-carboxamide

EXAMPLE 85A

N-cyclohexyl-3-iodo-1,4-dihydroindeno[1,2-c]pyrazole-6-carboxamide

A mixture of Example 84A (0.359 g, 1.07 mmol), HOBt (0.218 g, 1.61 mmol), EDC (0.308, 1.61 mmol), cyclohexylamine (0.18 mL, 1.61 mmol), and Et₃N (0.22 mL 1.61 mmol) in DMF (8 mL) was stirred at room temperature overnight. The reaction mixture was diluted with EtOAc and washed with NaHCO₃ and brine. The organic layer was dried over MgSO₄ filtered, concentrated, and triturated with ether to give 0.216 g (50%) of the desired product as yellow solid. MS (DCI/NH₃) m/z: 408.0 (M+H)⁺; ¹H NMR (300 MHz, DMSO₄₆) δ ppm 1.09-1.44 (m, 5H) 1.58-1.91 (m, 5H) 3.48-3.67 (m, 2H) 3.77 (m, 1H) 7.61 (m, 1H) 7.86 (d, J=7.46 Hz, 1H) 8.02 (s, 1H) 8.23 (d, J=8.14 Hz, 1H) 13.27 (s, 0.5H) 13.58 (s, 0.5H).

EXAMPLE 85B

N-cyclohexyl-3-(4'-hydroxy-1,1'-biphenyl-4-yl)-1,4-dihydroindeno[1,2-c]pyrazole-6-carboxamide The desired product was prepared by substituting Example 68C with Example 85A in Example 68E. The reaction temperature and time were raised to 180° C. and 1000 seconds, respectively.

Examples 86 to 97, represented by FIG. (II) and listed in Table 2, were synthesized in a similar fashion as described in Example 84C or 85B.

TABLE 2

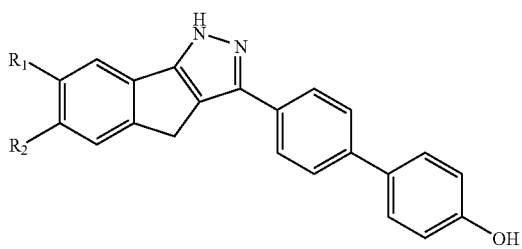

FIG. (II)

| Exmp. | $R_1$ | $R_2$ | $^1$H NMR | MS m/z $(M+H)^+$ | Yield |
|---|---|---|---|---|---|
| 84C | H | ![morpholine carbonyl] | (300 MHz, DMSO-$D_6$) δ ppm 3.43-3.73 (m, 8 H) 3.95 (s, 2 H) 6.87 (d, J=8.81 Hz, 2 H) 7.42 (d, J=7.80 Hz, 1 H) 7.57 (d, J=8.81 Hz, 2 H) 7.63 (s, 1 H) 7.72 (d, J=8.99 Hz, 3 H) 7.86 (d, J=6.00 Hz, 2 H) 9.60 (s, brd, 1 H) | 438.1 (DCI/ NH$_3$) | 21.5 mg 31% |
| 85B | H | ![cyclohexyl amide] | (300 MHz, DMSO-$D_6$) δ ppm 1.07-1.42 (m, 5 H) 1.56-1.92(m, 5 H) 3.80 (m, 1 H) 3.96 (s, 2 H) 6.87 (d, J=8.48 Hz, 2 H) 7.58 (d, J=8.48 Hz, 2 H) 7.74 (d, J=10.51 Hz, 2 H) 7.82-7.93 (m, 3 H) 8.05 (s, 1 H) 8.25 (d, J=7.80 Hz, 1 H) 9.60 (s, 1 H) 13.37 (s, 1 H) | 450.1 (DCI/ NH$_3$) | 28.1 mg 34% |
| 86 | ![morpholine carbonyl] | H | (400 MHz, CD$_3$OD) δ ppm 3.47-3.86 (m, 8 H) 3.95-3.96 (m, 2 H) 6.88 (d, J=8.90 Hz, 2 H) 7.39 (d, J=7.67 Hz, 1 H) 7.52 (d, J=8.59 Hz, 2 H) 7.69 (d, J=8.59 Hz, 3 H) 7.78 (s, 1 H) 7.82 (d, J=8.29 Hz, 2 H) | 438.1 (DCI/ NH$_3$) | 5.0 mg 7.1% |
| 87 | ![hydroxyethyl amide] | H | (500 MHz, DMSO-$D_6$) δ ppm 3.31-3.43 (m, 2 H) 3.56 (t, J=6.24 Hz, 2 H) 3.96 (s, 2 H) 6.88 (d, J=8.73 Hz, 2 H) 7.57 (d, J=8.42 Hz, 2 H) 7.65 (d, J=7.80 Hz, 1 H) 7.73 (d, J=8.11 Hz, 2 H) 7.80-7.90 (m, 3 H) 8.20 (s, 1 H) 8.52 (t, J=5.62 Hz, 1 H) 9.58 (s, 1 H) 13.30 (s, brd, 1 H) | 412.1 (DCI/ NH$_3$) | 5.0 mg 18% |

TABLE 2-continued

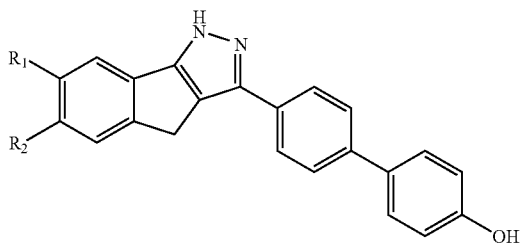

FIG. (II)

| Exmp. | R$_1$ | R$_2$ | $^1$H NMR | MS m/z (M+H)$^+$ | Yield |
|---|---|---|---|---|---|
| 88 | H | (4-hydroxypiperidin-1-yl)carbonyl | (300 MHz, CD$_3$OD) δ ppm 1.44-1.66(m, 2 H) 1.81-2.01 (m, 2 H) 3.32-3.42 (m, 2 H) 3.75 (m, 1 H) 3.90 (m, 1 H) 3.96 (s, 2 H) 4.22 (m, 1 H) 6.88 (d, J=8.81 Hz, 2 H) 7.45 (d, J=7.80 Hz, 1 H) 7.53 (d, J=8.81 Hz, 2 H) 7.65 (s, 1 H) 7.70 (d, J=8.48 Hz, 2 H) 7.78-7.85 (m, 3 H) | 452.1 (DCI/ NH$_3$) | 23.2 mg 33% |
| 89 | H | piperazin-1-ylcarbonyl | (500 MHz, CD$_3$OD) δ ppm 3.33 (s, brd, 4 H) 3.91 (s, brd, 4 H) 3.98 (s, 2 H) 6.89 (d, J=8.73 Hz, 2 H) 7.53 (d, J=8.73 Hz, 3 H) 7.70-7.72 (m, 3 H) 7.83-7.86 (m, 3 H) | 437.4 (DCI/ NH$_3$) | 6.9 mg 5.1% |
| 90 | H | (4-methylpiperazin-1-yl)carbonyl | (400 MHz, DMSO-D$_6$) δ ppm 2.85 (s, 3H) 3.01-3.20 (m, brd, 2 H) 3.22-3.58 (m, 4 H) 3.97 (s, 2 H) 4.24 (m, 2 H) 4.05-4.46 (m, 2 H) 6.88 (d, J=8.29 Hz, 2 H) 7.49 (d, J=7.98 Hz, 1 H) 7.57 (d, J=8.29 Hz, 2 H) 7.68 (s, 1 H) 7.74 (t, J=8.75 Hz, 3 H) 7.87 (d, J=8.29 Hz, 2 H) 9.99 (s, brd, 1 H) | 451.2 (DCI/ NH$_3$) | 17.2 mg 15% |
| 91 | H | N-(pyridin-4-ylmethyl)carbamoyl | (500 MHz, DMSO-D$_6$) δ ppm 3.99 (s, 2 H) 4.70 (d, J=5.61 Hz, 2 H) 6.88 (d, J=8.42 Hz, 2 H) 7.58 (d, J=8.73 Hz, 2 H) 7.74 (d, J=8.11 Hz, 2 H) 7.79 (d, J=6.86 Hz, 3 H) 7.88 (d, J=8.11 Hz, 2 H) 7.98 (d, J=7.80 Hz, 1 H) 8.14 (s, 1 H) 8.76 (d, J=5.61 Hz, 2 H) 9.32 (t, J=5.77 Hz, 1 H) 9.59 (s, brd, 1 H) | 459.2 (DCI/ NH$_3$) | 7.0 mg 37% |
| 92 | H | (4-carbamoylpiperidin-1-yl)carbonyl | (300 MHz, DMSO-D$_6$) δ ppm 1.46-1.59 (m, 2 H) 1.67-1.85 (m, 2 H) 2.34-2.53 (m, 2 H) 2.81-3.12 (m, 2 H) 3.95 (s, 2 H) 6.74-6.84 (m, 2 H) 6.87 (d, J=8.48 Hz, 2 H) 7.30 (s, 1 H) 7.37 (t, J=8.14 Hz, 2 H) 7.57 (d, J=8.82 Hz, 2 H) 7.73 (d, J=8.14 Hz, 2 H) 7.86 (d, J=8.48 Hz, 2 H) 9.36 (s, 0.5 H) 9.59 (s, 0.5 H) 13.34 (s, 1 H) | 479.2 (DCI/ NH$_3$) | 14.1 mg 17% |

TABLE 2-continued

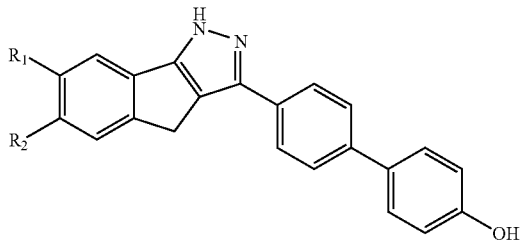

FIG. (II)

| Exmp. | R$_1$ | R$_2$ | $^1$H NMR | MS m/z (M+H)$^+$ | Yield |
|---|---|---|---|---|---|
| 93 | H | ![structure: -C(=O)-NH-CH2-pyrazine-5-methyl] | (300 MHz, DMSO-D$_6$) δ ppm 2.48 (s, 3 H) 3.98 (s, 2 H) 4.60 (d, J=5.76 Hz, 2 H) 6.87 (d, J=8.48 Hz, 2 H) 7.57 (d, J=8.81 Hz, 2 H) 7.72-7.80 (m, 3 H) 7.83-7.90 (m, 2 H) 7.95 (dd, J=7.97, 1.53 Hz, 1 H) 8.11 (s, 1 H) 8.50 (d, J=10.85 Hz, 2 H) 9.19 (t, J=5.59 Hz, 1 H) 9.59 (s, brd, 1 H) | 474.2 (DCI/ NH$_3$) | 9.1 mg 9.3% |
| 94 | H | ![structure: -C(=O)-NH-CH2-2-pyridyl] | (300 MHz, DMSO-D$_6$) δ ppm 3.99 (s, 2 H) 4.66 (d, J=5.76 Hz, 2 H) 6.88 (d, J=8.82 Hz, 2 H) 7.44 (m, 1 H) 7.52 (d, J=8.14 Hz, 1 H) 7.58 (d, J=8.48 Hz, 2 H) 7.70-7.80 (m, 3 H) 7.88 (d, J=8.48 Hz, 2 H) 7.92-8.02 (m, 2 H) 8.14 (s, 1 H) 8.61 (d, J=4.41 Hz, 1 H) 9.22 (t, J=5.76 Hz, 1 H) 9.61 (s, brd, 1 H) | 459.2 (DCI/ NH$_3$) | 23.7 mg 24% |
| 95 | H | ![structure: -C(=O)-NH-CH2-pyridyl-CF3] | (300 MHz, DMSO-D$_6$) δ ppm 3.98 (s, 2 H) 4.63 (d, J=5.43 Hz, 2 H) 6.88 (d, J=8.48 Hz, 2 H) 7.58 (d, J=8.82 Hz, 2 H) 7.75 (t, J 8.31 Hz, 3 H) 7.86-7.91 (m, 3 H) 7.95 (d, J=8.14 Hz, 1 H) 8.03 (d, J=9.49 Hz, 1 H) 8.11 (s, 1 H) 8.78 (s, 1 H) 9.24 (t, J=5.59 Hz, 1 H) 9.60 (s, brd, 1 H) | 527.2 (DCI/ NH$_3$) | 9.5 mg 8.1% |
| 96 | H | ![structure: -C(=O)-NH-CH2CH2-N(CH3)2] | (300 MHz, DMSO-D$_6$) δ ppm 2.87 (s, 3 H) 2.88 (s, 3 H) 3.27-3.330 (m, 2 H) 3.64 (q, J=5.76 Hz, 2 H) 3.99 (s, 2 H) 6.88 (d, J=8.82 Hz, 2 H) 7.58 (d, J=8.82 Hz, 2 H) 7.72-7.80 (m, 3 H) 7.86-7.94 (m, 3 H) 8.08 (s, 1 H) 8.73 (t, J=5.43 Hz, 1 H) 9.31 (s, 1 H) 9.61 (s, 1 H) | 439.2 (DCI/ NH$_3$) | 31.2 mg 53% |

TABLE 2-continued

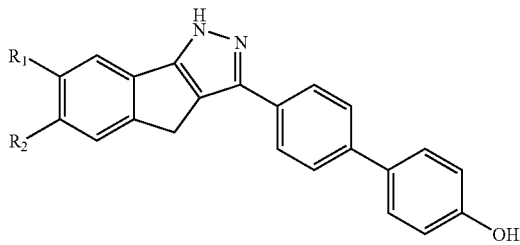

FIG. (II)

| Exmp. | R₁ | R₂ | ¹H NMR | MS m/z (M+H)⁺ | Yield |
|---|---|---|---|---|---|
| 97 | H | ![structure: O=C-NH-CH₂-pyridin-3-yl] | (300 MHz, DMSO-D₆) δ ppm 3.98 (s, 2 H) 4.63 (d, J=5.76 Hz, 2 H) 6.88 (d, J=8.48 Hz, 2 H) 7.57 (d, J=8.48 Hz, 2 H) 7.72-7.81 (m, 4 H) 7.87 (d, J=8.48 Hz, 2 H) 7.95 (d, J=7.80 Hz, 1 H) 8.11 (s, 1 H) 8.22 (d, J=7.80 Hz, 1 H) 8.69 (d, J=5.43 Hz, 1 H) 8.78 (s, 1 H) 9.24 (t, J=5.76 Hz, 1 H) 9.61 (s, 1 H) | 459.2 (DCI/ NH₃) | 21.0 mg 14% |

EXAMPLE 98

N-[3-(4'-hydroxy-1,1'-biphenyl-4-yl)-1,4-dihydroindeno[1,2-c]pyrazol-6-yl]-2-morpholin-4-ylacetamide

EXAMPLE 98A 6-bromo-1-{[2-(trimethylsilyl)ethoxy]methyl}-1,4-dihydroindeno[1,2-c]pyrazole and 6-bromo-2-{[2-(trimethylsilyl)ethoxy]methyl}-2,4-dihydroindeno[1,2-c]pyrazole To a solution of 6-bromo-1,4-dihydro-indeno[1,2-c]pyrazole (4.08 g, 0.0174 mol, see U.S. Pat. No. 6,297,238 for preparation) in DMF (100 mL) at 0° C. was added NaH (60%, 0.764 g, 0.0191 mol). After 20 minutes, SEMCl (3.4 mL, 0.0191 mol) was added to the above mixture and the ice bath was removed. The reaction was quenched with water 3.5 hours later. The reaction mixture was diluted with EtOAc and washed with brine. The organic layer was dried over MgSO₄, filtered, concentrated, and purified by flash chromatography eluted with EtOAc/hexane (2:8) to give 5.14 g (81%) of the desired products as brown oil. MS (DCI/NH₃) m/z: 365.0 (M+H)⁺; ¹H NMR (300 MHz, CDCl₃) δ ppm 0.00-0.02 (m, 9H) 0.89-0.98 (m, 2H) 3.59-3.68 (m, 4H) 5.52 (s, 1.3H) 5.68 (s, 0.7H) 7.51 (m, 2.4H) 7.67 (m, 1.6H).

EXAMPLE 98B

N-(1-{[2-(trimethylsilyl)ethoxy]methyl}-1,4-dihydroindeno[1,2-c]pyrazol-6-yl)acetamide To a solution of Example 98A (5.77 g, 0.0158 mol) in degassed 1,4-dioxane (50 mL) were added Pd(OAc)₂ (70.9 mg, 2 mol %), Xantphos (274 mg, 3 mol %), Cs₂CO₃ (7.72 g, 0.0237 mol), and acetamide (1.12 g, 0.0190 mol). The mixture was heated at 100° C. overnight and cooled. The solvent was evaporated and the residue was extracted with EtOAc, washed with water, brine, NaHCO₃, dried over MgSO₄, filtered, concentrated, and purified by flash chromatography eluted with EtOAc/hexane (6:4 to 8:2) to give 4.06 g (75%) of the desired product as yellow solid. MS (DCI/NH₃) m/z: 344.1 (M+H)⁺; ¹H NMR (300 MHz, CDCl₃) δ ppm 0.00-0.02 (m, 9H) 0.94 (dd, J=16.44, 8.31 Hz, 2H) 2.23 (s, 3H) 3.60-3.68 (m, 4H) 5.51 (s, 1.3H) 5.67 (s, 0.7H) 7.35 (m, 1H) 7.45 (d, J=7.46 Hz, 1H) 7.60 (d, J=8.14 Hz, 0.4H) 7.73 (d, J=8.14 Hz, 0.6H) 7.91 (d, J=12.21 Hz, 1H).

EXAMPLE 98C 1,4-dihydroindeno[1,2-c]pyrazol-6-amine

To a solution of Example 98B (1.96 g, 5.71 mmol) in EtOH (25 mL) was added conc. HCl (1.5 mL). The mixture was heated at 80° C. for 7 hours and cooled. The solvent was evaporated and the residue was dissolved in water and washed with EtOAc. The aqueous layer was basified with 3N NaOH until pH=9 and extracted with EtOAc (2×). The combined organic layers were dried and concentrated to give the desired product (0.920 g, quantitative yield) as yellow foam. MS (DCI/NH₃) m/z: 172.0 (M+H)⁺; ¹H NMR (300 MHz, DMSO-D₆) δ ppm 3.44 (s, 2H) 5.10 (s, 2H) 6.52 (dd, J=8.14, 2.03 Hz, 1H) 6.71 (s, 1H) 7.26 (d, J=8.14 Hz, 1H) 7.48 (s, 1H) 12.27 (s, 1H).

EXAMPLE 98D 2-chloro-N-1,4-dihydroindeno[1,2-c]pyrazol-6-ylacetamide

To a solution of Example 98C (0.250 g, 1.46 mmol) in acetone (10 mL) were added saturated NaHCO₃ solution (5 mL) and chloroacetyl chloride (0.13 mL, 1.61 mmol). The mixture was heated at 50° C. for 90 minutes and cooled. The solvent was partially evaporated and water was added to the suspension. The solid was filtered, washed with water, and dried to give the desired product (0.280 g, 78%) as off-white solid. A small amount of the product (30 mg) was further purified using reversed-phase HPLC to afford an analytical sample. MS (DCI/NH$_3$) m/z: 248.0 (M+H)$^+$; $^1$H NMR (500 MHz, DMSO-D$_6$) δ ppm 3.62 (s, 2H) 4.27 (s, 2H) 7.52 (d, J=8.42 Hz, 1H) 7.58 (m, 1H) 7.61 (s, 1H) 7.85 (s, 1H) 10.34 (s, 1H).

EXAMPLE 98E 2-chloro-N-(3-iodo-1,4-dihydroindeno[1,2-c]pyrazol-6-yl)acetamide To a solution of Example 98D (0.140 g, 0.565 mmol) in DMF (3 mL) was added NIS (0.153 g, 0.678 mmol) and the mixture was heated at 80° C. for 4 hours and cooled. The reaction mixture was diluted with water and extracted with EtOAc. The organic layer was washed water, brine, dried, filtered, and concentrated, and purified by flash chromatography eluted with EtOAc/hexane (7:3 to 9:1) to give 47 mg of the desired product as brown solid. MS (DCI/NH$_3$) m/z: 373.9 (M+H)$^+$; $^1$H NMR (300 MHz, DMSO-D$_6$) δ ppm 3.53 (s, 2H) 4.26 (s, 2H) 7.52 (s, brd, 2H) 7.87 (s, 1H) 10.38 (s, 1H).

EXAMPLE 98F

N-(3-iodo-1,4-dihydroindeno[1,2-c]pyrazol-6-yl)-2-morpholin-4-ylacetamide

To a solution of Example 98E (44.5 mg, 0.119 mmol) in EtOH (2 ML) was added morpholine (31.3 μL). The mixture was heated at 60° C. for 4 hours and cooled. The solvent was evaporated and the residue was purified by flash chromatography eluted with EtOAc to give 39.5 mg (78%) of the desired product as yellow foam. MS (DCI/NH$_3$) m/z: 425.0 (M+H)$^+$; $^1$H NMR (300 MHz, DMSO-D$_6$) δ ppm 2.51-2.53 (m, 4H) 3.14 (s, 2H) 3.51 (s, 2H) 3.64 (m, 4H) 7.50 (m, brd, 1H) 7.59 (m, 1H) 7.90 (s, 1H) 9.81 (s, 1H).

EXAMPLE 98G

N-[3-(4'-hydroxy-1,1'-biphenyl-4-yl)-1,4-dihydroindeno[1,2-c]pyrazol-6-yl]-2-morpholin-4-ylacetamide The desired product was prepared by substituting Example 68C with Example 98F in Example 68E.

Examples 99 to 103, represented by FIG. (III) and listed in Table 3, were synthesized in a similar fashion as described in Example 98G.

TABLE 3

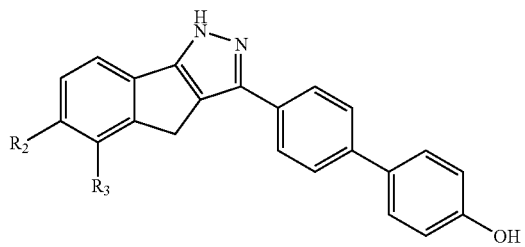

FIG. (III)

| Exmp. | R$_2$ | R$_3$ | $^1$H NMR | MS m/z (M+H)$^+$ | Yield |
|---|---|---|---|---|---|
| 98G | (morpholinyl-acetamide group) | H | (500 MHz, CD$_3$OD) δ ppm 3.47 (s, brd, 4 H) 3.90 (s, 2 H) 3.99 (s, brd, 4 H) 4.18 (s, 2 H) 6.89 (d, J=8.73 Hz, 2 H) 7.51-7.57 (m, 3 H) 7.68-7.71 (m, 3 H) 7.81 (d, J=8.42 Hz, 2 H) 7.94 (s, 1 H) | 467.2 (DCI/NH$_3$) | 26.6 mg 45% |
| 99 | H | (acetamide group) | (500 MHz, DMSO-D$_6$) δ ppm 2.16 (s, 3 H) 3.87 (s, 2 H) 6.88 (d, J=8.74 Hz, 2 H) 7.35 (t, J=7.64 Hz, 1 H) 7.46 (d, J=7.18 Hz, 1 H) 7.57 (d, J=8.42 Hz, 2 H) 7.67 (d, J=8.11 Hz, 1 H) 7.73 (d, J=8.42 Hz, 2 H) 7.86 (d, J=8.42 Hz, 2 H) 9.56 (s, 2 H) | 382.0 (DCI/NH$_3$) | 15.2 mg 21% |

TABLE 3-continued

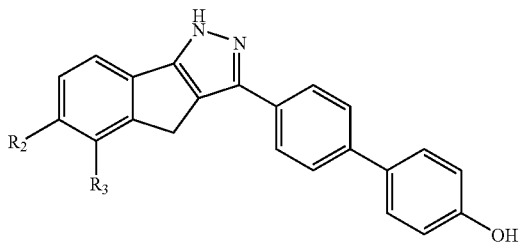

FIG. (III)

| Exmp. | R₂ | R₃ | ¹H NMR | MS m/z (M+H)⁺ | Yield |
|---|---|---|---|---|---|
| 100 | ![HN-CH2-C(=O)-NH-CH2-(4-pyridyl)] | H | (300 MHz, CD₃OD) δ ppm 3.91 (s, 2 H) 4.08 (s, 2 H) 4.45 (s, 2 H) 6.89 (d, J=8.82 Hz, 2 H) 7.51-7.56 (m, 3 H) 7.70 (d, J=8.14 Hz, 5 H) 7.81-7.84 (m, 2 H) 7.94 (s, 1 H) 8.74 (d, J=5.43 Hz, 2 H) | 488.2 (DCI/ NH₃) | 26.3 mg 20% |
| 101 | ![HN-CH2-C(=O)-NH-trans-4-hydroxycyclohexyl] | H | (500 MHz, CD₃OD) δ ppm 1.22-1.35(m, 2 H) 1.38-1.50 (m, 2 H) 1.99 (d, J=10.07 Hz, 2 H) 2.08 (d, J=12.51 Hz, 2 H) 3.08 (m, J=23.19 Hz, 1 H) 3.49 (m, 1 H) 3.81 (s, 2 H) 3.91 (s, 2 H) 6.79 (d, J=8.85 Hz, 2 H) 7.44 (m, 3 H) 7.60 (d, J=10.07 Hz, 3 H) 7.72 (d, J=8.24 Hz, 2 H) 7.85 (s, 1 H) | 495.2 (DCI/ NH₃) | 46.8 mg 41% |
| 102 | ![HN-CH2-C(=O)-NH-n-butyl] | H | (400 MHz, CD₃OD) δ ppm 1.02 (t, J=7.36 Hz, 3 H) 1.43-1.52 (m, 2 H) 1.70-1.78 (m, 2 H) 3.12 (t, J=8.00 Hz, 2 H) 3.89 (s, 2 H) 4.00 (s, 2 H) 6.89 (d, J=8.59 Hz, 2 H) 7.51-7.55 (m, 3 H) 7.69 (d, J=8.59 Hz, 3 H) 7.81 (d, J=8.59 Hz, 2 H) 7.93 (s, 1 H) | 453.2 (DCI/ NH₃) | 8.9 mg 12% |

TABLE 3-continued

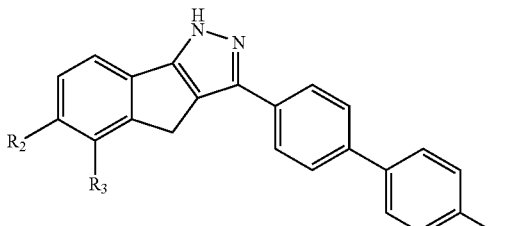

FIG. (III)

| Exmp. | R₂ | R₃ | ¹H NMR | MS m/z (M+H)⁺ | Yield |
|---|---|---|---|---|---|
| 103 | (HN-CH₂-C(=O)-NH-CH₂-CH₂-OH) | H | (400 MHz, CD₃OD) δ ppm 3.27 (t, J=4.00 Hz, 2 H) 3.87 (t, J=4.00 Hz, 2 H) 3.90 (s, 2 H) 4.05 (s, 2 H) 6.89 (d, J=8.29 Hz, 2 H) 7.51-7.56 (m, 4 H) 7.69 (d, J=8.29 Hz, 2 H) 7.80-7.86 (m, 2 H) 7.94 (s, 1 H) | 441.2 (DCI/ NH₃) | 16.5 mg 27% |

EXAMPLE 104

3-(4'-hydroxy-1,1'-biphenyl-4-yl)-7-methoxy-N-(pyridin-4-ylmethyl)-1,4-dihydroindeno[1,2-c]pyrazole-6-carboxamide

EXAMPLE 104A 2-(hydroxymethylene)-6-methoxyindan-1-one

To a mixture of ethyl formate (15.75 mL, 0.195 mol) and NaH (60%, 7.80 g, 0.195 mol) in benzene (550 mL) was added a suspension of 6-methoxy-indan-1-one (15.81 g, 0.0974 mol) in benzene (150 mL) dropwise at 0° C. The reaction mixture was stirred at room temperature overnight and treated with water. The solid was filtered, washed with water, and oven dried to give the desired product (16.86 g, 91%). The product may exist in sodium salt form, however, it was carried into the next reaction without further characterization. MS (DCI/NH₃) m/z: 191.1 (M+H)⁺; ¹H NMR (300 MHz, DMSO-D₆) δ ppm 3.50 (s, 2H) 3.80 (s, 3H) 7.13-7.20 (m, 2H) 7.47 (d, J=8.14 Hz, 1H) 7.74 (s, brd, 1H).

EXAMPLE 104B 7-methoxy-1,4-dihydroindeno[1,2-c]pyrazole

A mixture of Example 104A (16.86 g, 0.0886 mol), hydrazine monohydrate (5.2 mL, 0.106 mol), and AcOH (6.1 mL, 0.106 mol) in EtOH (375 mL) was heated at 90° C. for 2 hours. The solvent was evaporated and the residue was triturated with water and filtered. The filtering cake was triturated again with NaHCO₃ solution, filtered, washed with water, and oven dried to give the desired product (13.9 g, 84%). MS (DCI/NH₃) m/z: 187.0 (M+H)⁺; ¹H NMR (300 MHz, DMSO-D₆) δ ppm 3.52 (s, 2H) 3.81 (s, 3H) 6.81 (dd, J=8.31, 2.54 Hz, 1H) 7.17 (s, 1H) 7.40 (d, J=8.14 Hz, 1H) 7.62 (s, 1H) 12.71 (s, 1H).

EXAMPLE 104C 6-bromo-7-methoxy-1,4-dihydroindeno[1,2-c]pyrazole

To a solution of Example 104B (8.91 g, 0.0478 mol) in AcOH (150 mL) was added Br₂ (3.43 mL, 0.0669). The reaction mixture was concentrated after 5 minutes and the residue was triturated into EtOAc and hexane, and then filtered. The solid was stirred in NaHCO₃ solution and filtered, washed with water, and oven dried to give the desired product (11.99 g, 95%). The material with slight impurity was used in the next step without further purification. MS (DCI/NH₃) m/z: 265.0 (M+H)⁺; ²⁶⁶·⁹ (M+H+2)⁺.

EXAMPLE 104D 7-methoxy-1,4-dihydroindeno[1,2-c]pyrazole-6-carbaldehyde

To a suspension of Example 104C (5.49 g, 0.0207 mol) in THF (300 mL) was added PhLi (1.9 M, 21.8 mL, 0.0414 mol) at −78° C. s-BuLi (1.4 M, 29.6 mL, 0.0414 mol) and DMF (12.8 mL, 0.166 mol) were added to the reaction mixture after 30 and 60 minutes, respectively. The mixture was stirred at −78° C. for 1 hour and the cold bath was removed. The reaction was quenched with saturated NH₄Cl solution after 1 hour at room temperature. The mixture was extracted with EtOAc, washed with water, brine, dried over MgSO₄, filtered, concentrated, and triturated with ether to give 3.62 g (81%) of the desired product. MS (DCI/NH₃) m/z: 215.1 (M+H)⁺; ¹H NMR (300 MHz, DMSO-D₆) δ ppm 3.62 (s, 2H) 4.01 (s, 3H) 7.45 (s, 1H), 7.73 (s, 1H) 7.80 (s, 1H) 10.37 (s, 1H) 13.07 (s, 1H).

EXAMPLE 104E 3-iodo-7-methoxy-1,4-dihydroindeno[1,2-c]pyrazole-6-carbaldehyde The desired product was prepared by substituting Example 68A with Example 104D in Example 68B. After the reaction, the solvent was evaporated and the residue was triturated with ether to give the crude product, which was used in the next step without further purification. MS (DCI/NH$_3$) m/z: 340.9 (M+H)$^+$.

EXAMPLE 104F 3-iodo-7-methoxy-1,4-dihydroindeno[1,2-c]pyrazole-6-carboxylic acid The desired product was prepared by substituting Example 68B with Example 104E in Example 84A. The crude product was used in the next step without further purification. MS (DCI/NH$_3$) m/z: 374.0 (M+NH$_4$)$^+$.

EXAMPLE 104G

The desired product was prepared by substituting Example 84A and cyclohexylamine with Example 104F and 4-(aminomethyl)pyridine in Example 85A. The slightly impure product was used in the next step without further purification. MS (DCI/NH$_3$) m/z: 447.0 (M+H)$^+$. The formation of tertiary amides in this step towards corresponding final compounds listed in Table 4 was done following the protocol in Example 84B.

EXAMPLE 104H 3-(4'-hydroxy-1,1'-biphenyl-4-yl)-7-methoxy-N-(pyridin-4-ylmethyl)-1,4-dihydroindeno[1,2-c]pyrazole-6-carboxamide The desired product was prepared by substituting Example 68C with Example 104G in Example 68E.

EXAMPLE 105

4'-(6-{[(2-hydroxyethyl)amino]methyl}-7-methoxy-1,4-dihydroindeno[1,2-c]pyrazol-3-yl)-1,1'-biphenyl-4-ol

EXAMPLE 105A

2-[(3-Iodo-7-methoxy-1,4-dihydro-indeno[1,2-c]pyrazol-6-ylmethyl)-amino]-ethanol The desired product was prepared by substituting Example 68B and morpholine with Example 104D and 2-aminoethanol in Example 68C. The slightly impure product was used in the next step without further purification. MS (DCI/NH$_3$) m/z: 386.0 (M+H)$^+$.

EXAMPLE 105B

4'-(6-{[(2-hydroxyethyl)amino]methyl}-7-methoxy-1,4-dihydroindeno[1,2-c]pyrazol-3-yl)-1,1'-biphenyl-4-ol The desired product was prepared by substituting Example 68C with Example 105A in Example 68E.

Examples 106 to 116, represented by FIG. (IV) and listed in Table 4, were synthesized in a similar fashion as described in Example 104H or Example 105B.

TABLE 4

FIG. (IV)

| Exmp. | R$_2$ | $^1$H NMR | MS m/z (M+H)$^+$ | Yield |
|---|---|---|---|---|
| 104H | 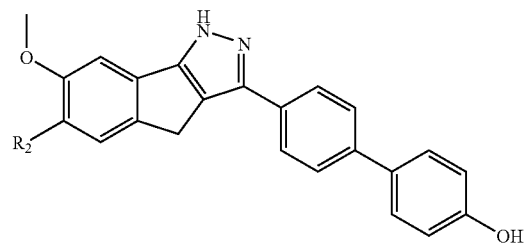 | (400 MHz, DMSO-D$_6$) δ ppm 3.89 (s, 2 H) 4.06 (s, 3 H) 4.75 (d, J=6.14 Hz, 2 H) 6.88 (d, J=8.59 Hz, 2 H) 7.47 (s, 1 H) 7.57 (d, J=8.90 Hz, 2 H) 7.73 (d, J=8.59 Hz, 2 H) 7.86 (d, J=8.59 Hz, 4 H) 7.98 (s, 1 H) 8.83 (s, brd, 2 H) 9.04 (t, J=5.98 Hz, 1 H) | 489.1 (DCI/ NH$_3$) | 13.3 mg 18% |

TABLE 4-continued

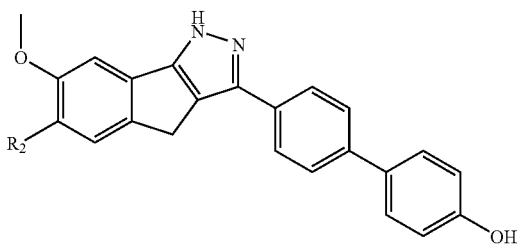

FIG. (IV)

| Exmp. | R₂ | ¹H NMR | MS m/z (M+H)⁺ | Yield |
|---|---|---|---|---|
| 105B | (CH₂NH-CH₂CH₂OH group) | (300 MHz, CD₃OD) δ ppm 3.14-3.18(m, 2 H) 3.78-3.88(m, 4 H) 4.04 (s, 3 H) 4.32 (s, 2 H) 6.89 (d, J=8.48 Hz, 2 H) 7.47-7.57 (m, 4 H) 7.70 (d, J=8.14 Hz, 2 H) 7.81-7.84 (m, 2 H) | 428.2 (DCI/NH₃) | 11.7 mg 16% |
| 106 | (4-methylpiperazin-1-yl carbonyl) | (500 MHz, DMSO-D₆) δ ppm 2.85-3.11 (m, 4 H) 3.28-3.57(m, 4 H) 3.84-3.93 (m, 8 H) 6.88 (d, J=8.42 Hz, 2 H) 7.42 (m, 2 H) 7.57 (d, J=8.73 Hz, 2 H) 7.72 (d, J=8.42 Hz, 2 H) 7.85 (d, J=8.42 Hz, 2 H) 10.03 (s, brd, 1 H) | 481.2 (DCI/NH₃) | 6.4 mg 17% |
| 107 | (trans-4-hydroxycyclohexylaminocarbonyl) | (400 MHz, DMSO-D₆) δ ppm 1.31-1.39 (m, 4 H) 1.82-1.90 (m, 4 H) 3.43 (m, 1 H) 3.74 (m, 1 H) 3.85 (s, 2 H) 3.97 (s, 3 H) 6.86 (d, J=8.90 Hz, 2 H) 7.38 (s, 1 H) 7.56 (d, J=8.90 Hz, 2 H) 7.71 (d, J=8.59 Hz, 2 H) 7.84 (d, J=8.59 Hz, 2 H) 7.91 (s, 1 H) 7.94 (d, J=7.98 Hz, 1 H) 9.58 (s, brd, 1 H) | 496.2 (DCI/NH₃) | 15.6 mg 18% |
| 108 | (morpholin-4-ylcarbonyl) | (500 MHz, DMSO-D₆) δ ppm 3.20-3.53 (m, 8 H) 3.65 (s, 2 H) 3.85-3.91 (m, 3 H) 6.87 (d, J=8.42 Hz, 2 H) 7.37 (d, J=12.79 Hz, 2 H) 7.57 (d, J=8.73 Hz, 2 H) 7.72 (d, J=8.11 Hz, 2 H) 7.84 (d, J=8.42 Hz, 2 H) 9.59 (s, 1 H) | 468.2 (DCI/NH₃) | 5.1 mg 6.8% |
| 109 | (4-carbamoylpiperidin-1-ylcarbonyl) | (500 MHz, DMSO-D₆) δ ppm 1.19-1.51 (m, 2 H) 1.69 (m, 1 H) 1.85 (m, 1 H) 2.82-3.03 (m, 2 H) 3.30-3.33 (m, 2 H) 3.78 (s, 2 H) 3.82 (s, 3 H) 4.32 (m, 1 H) 6.80 (d, J=8.73 Hz, 2 H) 7.26-7.31 (m, 2 H) 7.50 (d, J32 8.73 Hz, 2 H) 7.65 (d, J=8.11 Hz, 2 H) 7.77 (d, J=8.42 Hz, 2 H) 9.52 (s, brd, 1 H) | 510.1 (DCI/NH₃) | 4.7 mg 6.1% |

TABLE 4-continued

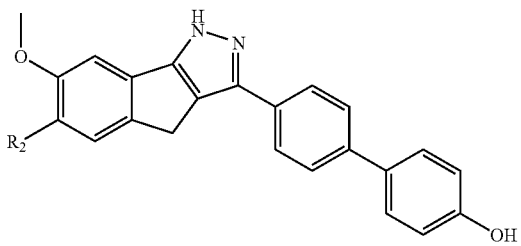

FIG. (IV)

| Exmp. | R₂ | ¹H NMR | MS m/z (M+H)⁺ | Yield |
|---|---|---|---|---|
| 110 | (piperidin-1-yl-carbonyl with 4-OH) | | 482.1 (DCI/NH₃) | 2.9 mg 3.6% |
| 111 | (4-methylpiperazin-1-yl-methyl) | (500 MHz, DMSO-D₆) δ ppm 2.85 (s, 3 H) 2.95-3.70 (m, brd, 8 H) 3.86 (s, 2 H) 3.95 (s, 3 H) 4.26 (s, brd, 2 H) 6.88 (d, J=8.54 Hz, 2 H) 7.42 (s, 1 H) 7.57 (d, J=8.54 Hz, 2 H) 7.62 (s, 1 H) 7.73 (d, J=8.54 Hz, 2 H) 7.86 (d, J=8.54 Hz, 2 H) | 467.3 (DCI/NH₃) | 37.3 mg 36% |
| 112 | (3-(pyrrolidin-1-yl)propylaminomethyl) | (300 MHz, CD₃OD) δ ppm 2.11-2.15(m, 4 H) 3.37-3.64 (m, 8 H) 3.87 (s, 2 H) 4.04 (s, 3 H) 4.38 (s, 2 H) 6.89 (d, J=8.48 Hz, 2 H) 7.50 (d, J=6.44 Hz, 2 H) 7.54 (s, 1 H) 7.62 (s, 1 H) 7.70 (d, J=8.48 Hz, 2 H) 7.82 (d, J=9.00 Hz, 2 H) | 481.2 (DCI/NH₃) | 26.2 mg 22% |
| 113 | (trans-4-hydroxycyclohexylaminomethyl) | (500 MHz, DMSO-D₆) δ ppm 1.17-1.24 (m, 2 H) 1.40-1.48 (m, 2 H) 1.91 (d, J=10.60 Hz, 2 H) 2.11 (d, J=11.54 Hz, 2 H) 3.04 (m, 1 H) 3.39 (m, 1 H) 3.86 (s, 2 H) 3.96 (s, 3 H) 4.17 (s, 2 H) 6.88 (d, J=8.73 Hz, 2 H) 7.40 (s, 1 H) 7.56-7.60 (m, 3 H) 7.73 (d, J=8.42 Hz, 2 H) 7.86 (d, J=8.42 Hz, 2 H) 8.50 (s, 2 H) 9.59 (s, brd, 1 H) | 482.2 (DCI/NH₃) | 30.0 mg 34% |
| 114 | (pyridin-4-ylaminomethyl) | (400 MHz, DMSO-D₆) δ ppm 3.76 (s, 2 H) 3.93 (s, 3 H) 4.30 (d, J=5.83 Hz, 2 H) 6.51 (d, J=5.83 Hz, 2 H) 6.85 (d, J=8.59 Hz, 2 H) 6.92 (t, J=5.98 Hz, 1 H) 7.36 (m, 2 H) 7.55 (d, J=8.59 Hz, 2 H) 7.69 (d, J=7.67 Hz, 2 H) 7.81 (d, J=8.29 Hz, 2 H) 8.00 (d, J=5.83 Hz, 2 H) | 461.1 (DCI/NH₃) | 9.3 mg 19% |

TABLE 4-continued

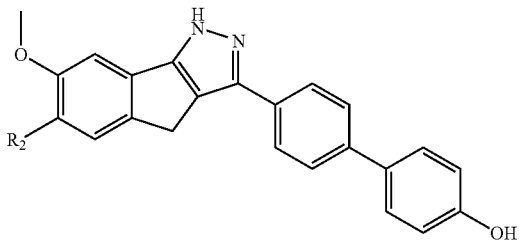

FIG. (IV)

| Exmp. | R₂ | ¹H NMR | MS m/z (M+H)⁺ | Yield |
|---|---|---|---|---|
| 115 | ![piperidine-CH2CH2-N, 4-carboxamide] | (500 MHz, CD₃OD) δ ppm 1.79-1.88 (m, 2 H) 1.97-2.01 (m, 2 H) 2.45 (m, 1 H) 2.98-3.03 (m, 2 H) 3.51-3.52 (m, 2 H) 3.79 (s, 2 H) 3.94 (s, 3 H) 4.29 (s, 2 H) 6.79 (d, J=8.42 Hz, 2 H) 7.41-7.44 (m, 3 H) 7.52 (s, 1 H) 7.61 (d, J=8.42 Hz, 2 H) 7.72 (d, J=8.11 Hz, 2 H) | 495.2 (DCI/ NH₃) | 2.3 mg 7.2% |
| 116 | ![piperidine-CH2CH2-N, 4-OH] | (500 MHz, DMSO-D₆) δ ppm 1.60 (m, 1 H) 1.76 (d, J=13.41 Hz, 1 H) 1.87 (m, 1 H) 1.97 (d, J=11.23 Hz, 1 H) 3.04 (m, 1 H) 3.19-3.23 (m, 2 H) 3.39 (d, J=11.54 Hz, 1 H) 3.67 (m, 1 H) 3.87 (s, 2 H) 3.94-3.96 (m, 3 H) 4.31 (dd, J=17.78, 4.68 Hz, 2 H) 6.88 (d, J=8.73 Hz, 2 H) 7.43 (d, J=2.81 Hz, 1 H) 7.57 (d, J=8.73 Hz, 2 H) 7.65 (d, J=13.10 Hz, 1 H) 7.73 (d, J=8.42 Hz, 2 H) 7.86 (d, J=8.42 Hz, 2 H) 9.19 (s, 1 H) 9.60 (s, brd, 1 H) | 468.2 (DCI/ NH₃) | 12.0 mg 15% |

EXAMPLE 117

3-fluoro-4'-[6-(hydroxymethyl)-1,4-dihydroindeno[1,2-c]pyrazol-3-yl]-1,1'-biphenyl-4-ol

EXAMPLE 117A (3-iodo-1,4-dihydroindeno[1,2-c]pyrazol-6-yl)methanol

To a suspension of Example 68B (0.500 g, 1.61 mmol) in a mixture of MeOH (9 mL) and THF (3 mL) was added NaBH₄ (73.0 mg, 1.93 mmol) at room temperature. The mixture was stirred for 2 hours and the solvent was evaporated. The desired product (0.324 g, 65%) was recrystallized from hot CH₂Cl₂ with a small amount of MeOH. MS (DCI/NH₃) m/z: 312.9 (M+H)⁺; ¹H NMR (300 MHz, CD₃OD) δ ppm 3.54 (s, 2H), 4.66 (s, 2H), 7.35 (d, J=7.80 Hz, 1H), 7.55 (s, 1H), 7.59 (d, J=7.80 Hz, 1H).

EXAMPLE 117B 3-fluoro-4'-[6-(hydroxymethyl)-1,4-dihydroindeno[1,2-c]pyrazol-3-yl]-1,1'-biphenyl-4-ol The desired product was prepared by substituting Example 68C and Example 68D with Example 117A and 2-fluoro-4-(4,4,5,5-tetramethyl-[1,3,2]dioxaborolan-2-yl)-phenol respectively in Example 68E. MS (DCI/NH₃) m/z: 373.1 (M+H)⁺; ¹H NMR (400 MHz, DMSO-D₆) δ ppm 3.89 (s, 2H) 4.57 (s, 2H) 7.05 (t, J=8.00 Hz, 1H) 7.32 (d, J=7.36 Hz, 1H) 7.41 (d, J=8.29 Hz, 1H) 7.54-7.59 (m, 2H) 7.61 (d, J=7.67 Hz, 1H) 7.76 (d, J=8.29 Hz, 2H) 7.86 (d, J=12.0 Hz, 2H) 10.00 (s, brd, 1H).

The intermediates leading to the compounds represented by FIG. V and shown in Table 5 were prepared in the similar fashion as the examples shown in Table 1, Table 2, or Table 4. The final Suzuki coupling reaction was done similar to the procedure described in Example 117B.

TABLE 5

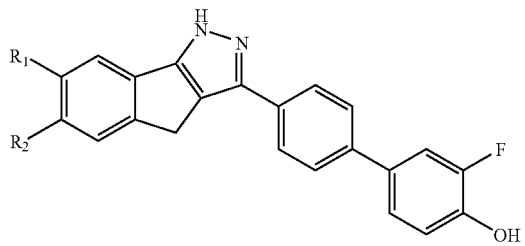

FIG. (V)

| Exmp. | R1 | R2 | ¹H NMR | MS m/z (M+H)⁺ | Yield |
|---|---|---|---|---|---|
| 118 | OMe | ![pyrrolidinylethylaminomethyl] | (500 MHz, CD$_3$OD) δ ppm 2.12 (s, brd, 4 H) 3.34-3.51 (m, 4 H) 3.51-3.57 (m, 2 H) 3.59-3.65 (m, 2 H) 3.85 (s, 2 H) 4.03 (s, 3 H) 4.37 (s, 2 H) 7.01 (t, J=8.73 Hz, 1 H) 7.34 (d, J=8.42 Hz, 1 H) 7.40 (dd, J=12.48, 2.18 Hz, 1 H) 7.48 (s, 1 H) 7.61 (s, 1 H) 7.70 (d, J=8.42 Hz, 2 H) 7.82 (d, J=8.42 Hz, 2 H) | 499.2 DCI/ NH$_3$ | 6.4 mg 14% |
| 119 | H | ![N-methylpiperazinylmethyl] | (300 MHz, CD$_3$OD) δ ppm 2.86 (s, 3 H) 2.80-2.90 (m, 4 H) 3.22-3.31 (m, 4 H) 3.83 (s, 1 H) 3.91 (s, 2 H) 7.01 (t, J=9.00 Hz, 1 H) 7.33-7.47 (m, 3 H) 7.70-7.76 (s, 1 H) 7.72 (m, 3 H) 7.84 (d, J=8.48 Hz, 2 H) | 455.2 DCI/ NH$_3$ | 37.0 mg 26% |
| 120 | H | ![pyridin-2-ylmethylaminocarbonylmethyl] | (500 MHz, DMSO-D$_6$) δ ppm 3.99 (s, 2 H) 4.66 (s, 2 H) 7.06 (t, J=8.73 Hz, 1 H) 7.35-7.45 (m, 2 H) 7.48 (d, J=7.80 Hz, 1 H) 7.57 (d, J=12.16 Hz, 1 H) 7.72-7.81 m 3 H) 7.84-7.95 (m, 3 H) 7.98 (d, J=7.80 Hz, 1 H) 8.14 (s, 1 H) 8.59 (d, J=4.37 Hz, 1 H) 9.20 (t, J=5.46 Hz, 1 H) 10.03 (s, brd, 1 H) | 477.2 DCI/ NH$_3$ | 40.0 mg 30% |

TABLE 5-continued

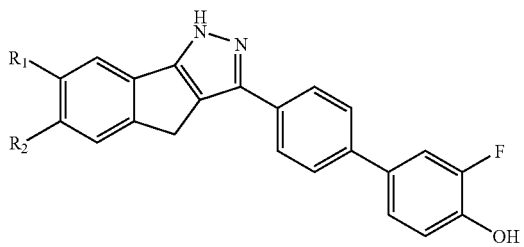

FIG. (V)

| Exmp. | R1 | R2 | ¹H NMR | MS m/z (M+H)⁺ | Yield |
|---|---|---|---|---|---|
| 121 | H | [pyrrolidinyl-ethyl-NH-CH₂- group] | (400 MHz, DMSO-D₆) δ ppm 1.83-2.11 (m, 4 H) 3.01-3.17 (m, 2 H) 3.32-3.75 (m, 6 H) 3.95 (s, 2 H) 4.33 (s, 2 H) 7.06 (t, J=8.00 Hz, 1 H) 7.42 (d, J=7.67 Hz, 2 H) 7.57 (dd, J=12.89, 2.15 Hz, 1 H) 7.67 (d, J=7.98 Hz, 1 H) 7.78 (d, J=8.29 Hz, 2 H) 7.83=7.90 (m, 3 H) 9.24 (s, brd, 1 H) 10.06 (s, brd, 1 H) | 469.2 DCI/ NH₃ | 25.5 mg 26% |
| 122 | OMe | [morpholinyl-carbonyl-CH₂- group] | (400 MHz, DMSO-D₆) δ ppm 3.15-3.25 (m, 2 H) 3.48-3.57 (m, 2 H) 3.65 (s, brd, 4 H) 3.85 (s, 2 H) 3.91 (s, 3 H) 7.05 (t, J=8.90 Hz, 1 H) 7.31-7.45 (m, 3 H) 7.56 (dd, J=12.89, 2.15 Hz, 1 H) 7.76 (d, J=8.59 Hz, 2 H) 7.84-7.87 (m, 2 H) 10.00 (s, brd, 1 H) | 486.2 DCI/ NH₃ | 9.0 mg 14% |

EXAMPLE 123

5-{6-[(4-methylpiperazin-1-yl)methyl]-1,4-dihydroindeno[1,2-c]pyrazol-3-yl}pyridine-2-carbonitrile

EXAMPLE 123A 3-iodo-1-{[2-(trimethylsilyl)ethoxy]methyl}-1,4-dihydroindeno[1,2-c]pyrazole-6-carbaldehyde To a mixture of Example 68A (1.00 g, 3.22 mmol) and NaH (60%, 0.142 g, 3.55 mmol) in DMF (20 mL) was added SEMCl (0.63 mL, 3.55 mmol). After 4 hours, the reaction was quenched with water and extracted with EtOAc. The organic layer was washed with NaHCO₃, dried over MgSO₄, filtered, concentrated, and purified by flash chromatography eluted with hexane/EtOAc (8:2 to 1:1) to give 0.887 g (63%) of the desired product as yellow solid. MS (DCI/NH₃) m/z: 440.9 (M+H)⁺; ¹H NMR (300 MHz, CDCl₃) δ ppm −0.01 (m, 9H) 0.75-1.10 (m, 2H) 3.46-3.76 (m, 2H) 5.61 (s, 1H) 5.68 (s, 1H) 7.80 (d, J=7.80 Hz, 0.5H) 7.87-7.97 (m, 1.5H) 8.03 (d, J=5.76 Hz, 1H) 10.06 (s, 1H).

EXAMPLE 123B 3-iodo-6-[(4-methylpiperazin-1-yl)methyl]-1-{[2-(trimethylsilyl)ethoxy]methyl}-1,4-dihydroindeno[1,2-c]pyrazole The desired product was prepared by substituting Example 68B and morpholine with Example 123A and 1-methylpiperazine respectively in Example 68C. MS (ESI) m/z: 525.1 (M+H)⁺.

EXAMPLE 123C

6-fluoropyridin-3-ylboronic acid

To a mixture of 5-bromo-2-fluoro-pyridine (1.71 g, 6.20 mmol) in dry ether (100 mL) was added n-BuLi (1.6 M in hexane, 41.4 mL, 0.0663 mol) at −78° C. After 30 minutes, trimethyl borate (8.2 mL, 0.0722 mol) was added to the above mixture and the reaction was warmed to room temperature and stirred overnight. The reaction was quenched with water and brine and acidified with 10% HCl until pH=8. The mixture was extracted with EtOAc, washed with 50% brine, dried over $MgSO_4$, filtered, concentrated to give 5.1 g (60%) of the desired product. The crude product was used in the next step without further purification.

EXAMPLE 123D

3-(6-fluoropyridin-3-yl)-6-[(4-methylpiperazin-1-yl)methyl]-1-{[2-(trimethylsilyl)ethoxy]methyl}-1,4-dihydroindeno[1,2-c]pyrazole The desired product was prepared by substituting Example 68C and Example 68D with Example 123B and Example 123C in Example 68E. The product was purified by flash chromatography instead of reversed-phase HPLC. MS (ESI) m/z: 494.3 $(M+H)^+$.

EXAMPLE 123E

5-{6-[(4-methylpiperazin-1-yl)methyl]-1,4-dihydroindeno[1,2-c]pyrazol-3-yl}pyridine-2-carbonitrile A mixture of Example 123D (70.6 mg, 0.142 mmol) and NaCN (9.7 mg, 0.199 mmol) in DMF (1.2 mL) in a capped vial was heated to 210° C. for 1200 seconds in a Smith Synthesizer (300W). The reaction was cooled using 40 psi pressurized air. The mixture was extracted with EtOAc and the organic layer was washed with 50% brine, $NaHCO_3$, dried over $MgSO_4$, filtered, concentrated. The crude product was treated with HCl (conc., 2 drops) and EtOH (3 mL) and the mixture was heated at 75° C. for 2.5 hours. The solvent was evaporated and the residue was purified using reversed-phase HPLC to give 7.5 mg of the desired product as TFA salt.

EXAMPLE 124

3-(6-cyanopyridin-3-yl)-N-(pyridin-2-ylmethyl)-1,4-dihydroindeno[1,2-c]pyrazole-6-carboxamide

EXAMPLE 124A

3-iodo-N-(pyridin-2-ylmethyl)-1,4-dihydroindeno[1,2-c]pyrazole-6-carboxamide The desired product was prepared by substituting cyclohexylamine with 2-(aminomethyl)pyridine in Example 85A. $CH_2Cl_2$ was used for trituration. MS ($DCI/NH_3$) m/z: 417.0 $(M+H)^+$; $^1H$ NMR (300 MHz, DMSO-$D_6$) δ ppm 3.58 (s, 1H) 3.63 (s, 1H) 4.58 (d, J=5.76 Hz, 2H) 7.26 (m, 1H) 7.33 (d, J=7.80 Hz, 1H) 7.60 (d, J=8.14 Hz, 0.5H) 7.74 (m, 1.5H) 7.95 (t, J=7.97 Hz, 1H) 8.10 (d, J=5.42 Hz, 1H) 8.50 (m, 1H) 9.14 (t, J=5.93 Hz, 1H) 13.29 (s, 0.4H) 13.61 (s, 0.6H).

EXAMPLE 124B

1-[bis(4-methoxyphenyl)methyl]-3-iodo-N-(pyridin-2-ylmethyl)-1,4-dihydroindeno[1,2-c]pyrazole-6-carboxamide A mixture of Example 124A (0.176 g, 0.423 mmol), bis-(4-methoxy-phenyl)-methyl chloride (0.122 g, 0.465 mmol), and $Et_3N$ (71 μL, 0.507 mmol) in DMF (2.0 mL) was stirred at room temperature for 4 hours. The reaction mixture was diluted with 50% brine and extracted with EtOAc. The organic layer was washed with brine, dried over $MgSO_4$, filtered, concentrated, and purified by flash chromatography eluted with EtOAc to give 0.166 g (61%) of the desired as pale yellow solid. MS (ESI) m/z: 643.1 $(M+H)^+$.

EXAMPLE 124C

1-[bis(4-methoxyphenyl)methyl]-3-(6-fluoropyridin-3-yl)-N-(pyridin-2-ylmethyl)-1,4-dihydroindeno[1,2-c]pyrazole-6-carboxamide The desired product was prepared by substituting Example 68C and Example 68D with Example 124B and Example 123C in Example 67E. The product was purified by flash chromatography instead of reversed-phase HPLC. MS (ESI) m/z: 612.2 $(M+H)^+$.

EXAMPLE 124D

3-(6-cyanopyridin-3-yl)-N-(pyridin-2-ylmethyl)-1,4-dihydroindeno[1,2-c]pyrazole-6-carboxamide The desired product was prepared by substituting Example 123D with Example 124C in Example 123E. Acidic deprotection was done in EtOH and 1,4-dioxane at 40° C. overnight.

Examples 125 to 129, represented by FIG. (VI) and shown in Table 6, were synthesized in the similar fashion as described in Example 123E or Example 124D. The pyrazole nitrogen of the intermediates could also be protected by SEM group.

TABLE 6

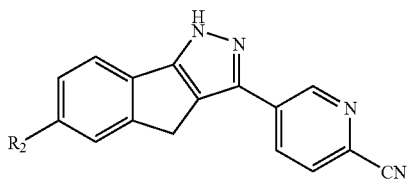

FIG. (VI)

| Exmp. | R2 | ¹H NMR | MS m/z (M+H)⁺ | Yield |
|---|---|---|---|---|
| 123E | *N-methylpiperazinylmethyl* | (300 MHz, CD₃OD) δ ppm 2.80-2.92 (m, 7 H) 3.20-3.31 (m, 4 H) 3.81 (s, 2 H) 3.94 (s, 2 H) 7.41 (d, J=8.14 Hz, 1 H) 7.63 (s, 1 H) 7.69 (d, J=7.80 Hz, 1 H) 7.97 (d, J=8.81 Hz, 1 H) 8.37 (dd, J=8.14, 2.37 Hz, 1 H) 9.16 (dd, J=2.20, 0.85 Hz, 1 H) | 371.1 (ESI) | 7.2 mg 7.1% |
| 124D | *(pyridin-2-ylmethyl)carbamoyl* | (300 MHz, CD₃OD) δ ppm 4.02 (s, 2 H) 4.86 (s, 2 H) 7.62-7.91(m, 3 H) 7.98 (d, J=8.14 Hz, 2 H) 8.15 (s, 1 H) 8.26-8.44 (m, 2 H) 8.69 (d, J=6.44 Hz, 1 H) 9.19 (m, 1 H) | 393.1 (ESI) | 12.3 mg 12% |
| 125 | *(4-hydroxypiperidin-1-yl)methyl* | (500 MHz, CD₃OD) δ ppm 1.69 (m, 1 H) 1.96-1.97 (m, 2 H) 2.15 (d, J=12.48 Hz, 1 H) 3.09 (m, 1 H) 3.33-3.42 (m, 2 H) 3.55 (d, J=13.10 Hz, 1 H) 3.99 (s, 2 H) 4.09 (m, 1 H) 4.39 (d, J=9.04 Hz, 2 H) 7.54 (t, J=8.73 Hz, 1 H) 7.74 (d, J=9.98 Hz, 1 H) 7.80 (d, J=7.80 Hz, 1 H) 7.96 (d, J=8.11 Hz, 1 H) 8.36 (dd, J=8.11, 2.18 Hz, 1 H) 9.15 (d, J=1.56 Hz, H) | 372.1 (ESI) | 2.2 mg 10% |
| 126 | *((pyridin-2-ylmethyl)amino)methyl* | (500 MHz, CD₃OD) δ ppm 3.98 (s, 2 H) 4.40 (s, 2 H) 4.41 (s, 2 H) 7.39-7.46 (m, 2 H) 7.55 (d, J=7.80 Hz, 1 H) 7.75 (s, 1 H) 7.79 (d, J=7.80 Hz, 1 H) 7.86 (t, J=6.86 Hz, 1 H) 7.96 (d, J=8.11 Hz, 1 H) 8.36 (dd, J=8.11, 2.18 Hz, 1 H) 8.66 (d, J=5.93 Hz, 1 H) 9.16 (d, J=2.18 Hz, 1 H) | 379.1 (ESI) | 5.4 mg 13% |
| 127 | *trans-((4-hydroxycyclohexyl)amino)methyl* | (500 MHz, CD₃OD) δ ppm 1.20-1.49 (m, 4 H) 2.00 (d, J=11.85 Hz, 2 H) 2.16 (d, J=12.16 Hz, 2 H) 3.09 (m, 1 H) 3.48 (m, 1 H) 3.90 (m, 1 H) 4.22 (s, 2 H) 7.44 (d, J=7.80 Hz, 1 H) 7.65 (s, 1 H) 7.70 (d, J=7.80 Hz, 1 H) 7.88 (d, J=8.11 Hz, 1 H) 8.28 (d, J=10.29 Hz, 1 H) 9.07 (d, J=1.56 Hz, 1 H) | 386.1 (ESI) | 2.0 mg 1.4% |

TABLE 6-continued

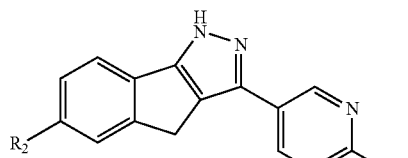

FIG. (VI)

| Exmp. | R2 | ¹H NMR | MS m/z (M+H)⁺ | Yield |
|---|---|---|---|---|
| 128 | (trans-4-hydroxycyclohexyl)amide | (500 MHz, DMSO-D₆) δ ppm 1.18-1.31(m, 2 H) 1.33-1.44 (m, 2 H) 1.78-1.90 (m, 4 H) 3.40 (m, 1 H) 3.74 (m, 1 H) 3.98 (s, 1 H) 4.03 (s, 1 H) 4.52 (s, 1 H) 7.64 (d, J=7.80 Hz, 0.5 H) 7.75 (d, J=8.11 Hz, 0.5 H) 7.89 (t, J=8.89 Hz, 1 H) 8.04 (d, J=5.30 Hz, 1 H) 8.11 (d, J=8.11 Hz, 0.5 H) 8.20 (d, J=7.80 Hz, 1.5 H) 8.39 (t, J=8.89 Hz, 1 H) | 400.1 (ESI) | 5.6 mg 10% |
| 129 | [(6-trifluoromethyl-pyridin-3-yl)methyl]amide | (500 MHz, DMSO-D₆) δ ppm 4.05 (s, 2 H) 4.63 (d, J=5.93 Hz, 2 H) 7.76 (m, 1 H) 7.87-8.19 (m, 4 H) 8.41 (d, J=8.11 Hz, 1 H) 8.76 (m, 1 H) 9.17-9.26 (m, 2 H) | 461.4 (ESI) | 5.3 mg 6.5% |

EXAMPLE 130

5-[6-(hydroxymethyl)-1,4-dihydroindeno[1,2-c]pyrazol-3-yl]pyridine-2-carbonitrile

EXAMPLE 130A (3-iodo-1-{[2-(trimethylsilyl)ethoxy]methyl}-1,4-dihydroindeno[1,2-c]pyrazol-6-yl)methanol To a solution of Example 123A (1.500 g, 3.41 mmol) in MeOH (18 mL) and THF (14 mL) was added NaBH₄ (64.5 mg, 1.70 mmol) at 0° C. The reaction mixture was stirred at room temperature for 90 minutes and quenched with water. The solvents were evaporated and the residue was extracted with EtOAc, washed with NaHCO₃, dried over MgSO₄, filtered, concentrated, and purified by flash chromatography eluted with EtOAc/hexane (1:1) to give 1.195 g (79%) of the desired product as off white solid. MS (ESI) m/z: 443.0 (M+H)⁺.

EXAMPLE 130B (3-(6-fluoropyridin-3-yl)-1-{[2-(trimethylsilyl)ethoxy]methyl}-1,4-dihydroindeno[1,2-c]pyrazol-6-yl)methanol The desired product was prepared by substituting Example 68C and Example 68D with Example 130A and Example 123C in Example 68E. The product was purified by flash chromatography instead of reversed-phase HPLC. MS (ESI) m/z: 412.1 (M+H)⁺.

EXAMPLE 130C

5-[6-(hydroxymethyl)-1,4-dihydroindeno[1,2-c]pyrazol-3-yl]pyridine-2-carbonitrile The desired product was prepared by substituting Example 123D with Example 130B in Example 123E. MS (ESI) m/z: 289.0 (M+H)⁺. ¹H NMR (300 MHz, DMSO-D₆) δ ppm 3.95 (s, 2H) 4.57 (s, 2H) 7.34 (d, J=7.80 Hz, 1H) 7.56 (s, 1H) 7.62 (m, 1H) 8.17 (m, 1H) 8.39 (dd, J=8.14, 2.37 Hz, 1H) 9.18 (s, 1H).

EXAMPLE 131

5-{6-[(pyridin-3-yloxy)methyl]-1,4-dihydroindeno[1,2-c]pyrazol-3-yl}pyridine-2-carbonitrile

EXAMPLE 131A 5-(6-(hydroxymethyl)-1-{[2-(trimethylsilyl)ethoxy]methyl}-1,4-dihydroindeno[1,2-c]pyrazol-3-yl)pyridine-2-carbonitrile The desired product was prepared by substituting Example 123D with Example 130B in Example 123E except that the final removal of SEM protecting group using HCl was not performed. MS (ESI) m/z: 419.1 (M+H)+.

EXAMPLE 131B

5-{6-[(pyridin-3-yloxy)methyl]-1,4-dihydroindeno[1,2-c]pyrazol-3-yl}pyridine-2-carbonitrile A mixture of Example 131A (60.0 mg, 0.143 mmol), di-t-butyl azodicarboxylate (39.6 mg, 0.172 mmol), Ph$_3$P on solid support (3 mmol/g, 57.3 mg, 0.172 mmol), and 3-hydroxypyridine (16.4 mg, 0.172 mmol) in THF (2 mL) was stirred at room temperature overnight. The solid was filtered and the solvent was evaporated. The crude product was treated with HCl (concentrated, 4 drops) and EtOH (4 mL). The mixture was heated in a capped vial at 75° C. for 2 hours. The solvent was evaporated and the residue was purified using reversed-phase HPLC to give the desired product (12.4 mg) as TFA salt. MS (ESI) m/z: 366.0 (M+H)+. $^1$H NMR (300 MHz, DMSO-D$_6$) δ ppm 4.01 (s, 2H) 5.83 (s, 2H) 7.58 (d, J=7.80 Hz, 1H) 7.74 (m, 1H) 7.80 (s, 1H) 7.93-8.05 (m, 2H) 8.18 (d, J=8.14 Hz, 1H) 8.40 (dd, J=8.14, 2.37 Hz, 1H) 8.62-8.84 (m, 2H) 9.19 (s, 1H) 12.14 (s, 1H).

EXAMPLE 132

5-{6-[(pyridin-4-yloxy)methyl]-1,4-dihydroindeno[1,2-c]pyrazol-3-yl}pyridine-2-carbonitrile The desired product was prepared by substituting 3-hydroxypyridine with 4-hydroxypyridine in Example 131B. MS (ESI) m/z: 366.0 (M+H)+. $^1$H NMR (300 MHz, DMSO-D$_6$) δ ppm 3.99 (s, 2H) 5.56 (s, 2H) 7.10 (d, J=7.46 Hz, 2H) 7.46 (d, J=7.80 Hz, 1H) 7.677.83 (m, 2H) 8.17 (d, J=8.14 Hz, 1H) 8.39 (dd, J=8.14, 2.03 Hz, 1H) 8.62 (d, J=7.12 Hz, 2H) 9.18 (d, J=2.03 Hz, 1H).

EXAMPLE 133

3-(6-fluoropyridin-3-yl)-7-methoxy-4,4-dimethyl-1,4-dihydroindeno[1,2-c]pyrazol-6-ol

EXAMPLE 133A 6-methoxy-3,3-dimethyl-5-{[2-(trimethylsilyl)ethoxy]methoxy}indan-1-one To a solution of 5-hydroxy-6-methoxy-3,3-dimethyl-indan-1-one (40.0 g, 0.194 mol, see preparation in J. Chem. Soc. Perkin Trans. I 1982, p2013-2017) in CH$_2$Cl$_2$ (400 mL) were added diisopropylethylamine (35.5 mL, 0.204 mol) and SEMCl (34.9 mL, 0.198 mol). The reaction mixture was stirred at room temperature for 3 hours and concentrated. The residue was purified by flash chromatography eluted with EtOAc/hexane (2:8) to give 60.5 g (93%) of the desired product as brown oil. MS (DCI/NH$_3$) m/z: 337.1 (M+H)+; $^1$H NMR (300 MHz, CDCl$_3$) δ ppm 0.00 (s, 9H) 0.96 (t, J=8.10 Hz, 2H) 1.39 (s, 6H) 2.56 (s, 2H) 3.83 (t, J=8.10 Hz, 2H) 3.90 (s, 3H) 5.39 (s, 2H) 7.15 (s, 1H) 7.20 (s, 1H).

EXAMPLE 133B 2-(hydroxymethylene)-6-methoxy-3,3-dimethyl-5-{[2-(trimethylsilyl)ethoxy]methoxy}indan-1-one To a solution of Example 133A (2.41 g, 7.15 mmol) in THF (15 mL) was added NaH (60%, 0.343 g, 8.58 mmol) at 0° C. After 1 hour, ethyl formate (0.73 mL, 8.58 mmol) was added. The reaction mixture was heated at 50° C. for 2 hour, cooled, quenched with water, and extracted with EtOAc. The organic layer was washed with 5% citric acid, brine, dried over MgSO$_4$, filtered, concentrated, and purified by flash chromatography eluted with EtOAc/hexane (1:1) to give 1.17 g of the desired product as purple gel. MS (DCI/NH$_3$) m/z: 365.2 (M+H)+. $^1$H NMR (300 MHz, CDCl$_3$) δ ppm 0.00 (s, 9H) 0.96 (t, J=8.10 Hz, 2H) 1.43 (s, 6H) 3.83 t, t, J=8.10 Hz, 2H) 3.93 (s, 3H), 7.18 (s, 1H) 7.27 (d, J=2.37 Hz, 2H).

EXAMPLE 133C 7-methoxy-4,4-dimethyl-6-{[2-(trimethylsilyl)ethoxy]methoxy}-1,4-dihydroindeno[1,2-c]pyrazole A mixture of Example 133B (0.886 g, 2.43 mol), hydrazine monohydrate (0.14 mL, 2.92 mol), and AcOH (38 µL, 0.729 mmol) in EtOH (20 mL) was heated at 85° C. for 1.5 hours. The solvent was evaporated and the residue was purified by flash chromatography eluted with EtOAc/hexane (1:1) to give 0.865 g of the desired product as yellow solid. MS (DCI/NH$_3$) m/z: 362.1 (M+H)+; $^1$H NMR (300 MHz, DMSO-D$_6$) δ ppm 0.00 (s, 9H) 0.91 (t, J=8.10 Hz, 2H) 1.40 (s, 6H) 3.78 (t, J=8.10 Hz, 2H) 3.84 (s, 3H) 5.22 (s, 2H) 7.17 (s, 1H) 7.20 (s, 1H) 7.53 (s, 1H).

EXAMPLE 133D 3-iodo-7-methoxy-4,4-dimethyl-6-{[2-(trimethylsilyl)ethoxy]methoxy}-1,4-dihydroindeno[1,2-c]pyrazole A suspension of Example 133C (10.4 g, 0.0290 mol) and N-iodosuccinimide (7.82 g, 0.0348 mol) in 1,4-dioxane (300 mL) was heated at 90° C. for 7.5 hours. The reaction was cooled and the solvent was evaporated. The concertrate was purified by flash chromatography eluted with EtOAc/hexane (1:1) to give 8.79 g of the desired product. MS (DCI/NH$_3$) m/z: 487.1 (M+H)+; $^1$H NMR (300 MHz, CDCl$_3$) δ ppm 0.00 (s, 9H) 0.97 (t, J=8.10 Hz, 2H) 1.48 (s, 6H) 3.85 (t, J=8.10 Hz, 2H) 3.92 (s, 3H) 5.32 (s, 2H) 7.21 (s, 1H) 7.22 (s, 1H).

EXAMPLE 133E 3-(6-fluoropyridin-3-yl)-7-methoxy-4,4-dimethyl-1,4-dihydroindeno[1,2-c]pyrazol-6-ol The desired product was prepared by substituting Example 68C and Example 68D with Example 133D and Example 123C in Example 68E. The product was purified by flash chromatography instead of reversed-phase HPLC. This intermediate was treated with HCl (concentrated, 3 drops) and EtOH (2 mL). The mixture was stirred at room temperature for 2 hours. The solvent was evaporated and the residue was purified using reversed-phase HPLC to give the desired product (13.0 mg) as TFA salt. MS (ESI) m/z: 326.0 (M+H)+. $^1$H NMR (300 MHz, CD$_3$OD) δ ppm 1.52 (s, 6H) 3.93 (s, 3H) 6.93 (s, 1H) 7.147.31 (m, 2H) 8.16 (m, 1H) 8.56 (d, J=1.70 Hz, 1H).

EXAMPLE 134

5-(6-hydroxy-7-methoxy-4,4-dimethyl-1,4-dihydroindeno[1,2-c]pyrazol-3-yl)pyridine-2-carbonitrile

EXAMPLE 134A 3-iodo-7-methoxy-4,4-dimethyl-6-{[2-(trimethylsilyl)ethoxy]methoxy}-1-{[2-(trimethylsilyl)ethoxy]methyl}-1,4-dihydroindeno[1,2-c]pyrazole To a mixture of Example 133D (0.475 g, 0.977 mmol) and NaH (60%, 0.043 g, 1.07 mmol) in THF (10 mL) was added SEMCl (0.19 mL, 1.07 mmol). After 2 hours, the reaction was quenched with water and extracted with EtOAc. The organic layer was washed with NaHCO$_3$, dried over MgSO$_4$, filtered, concentrated, and purified by flash chromatography eluted with hexane/EtOAc (8:2) to give 0.455 g (75%) of the desired product as yellow gel. MS (DCI/NH$_3$) m/z: 617.2 (M+H)$^+$.

EXAMPLE 134B 3-iodo-7-methoxy-4,4-dimethyl-1-{[2-(trimethylsilyl)ethoxy]methyl}-1,4-dihydroindeno[1,2-c]pyrazol-6-ol A mixture of Example 134A (0.450 g, 0.730 mmol) and HCl (concentrated, 0.4 mL) in EtOH (10 mL) was stirred at room temperature for 3 hours. The solvent was evaporated at room temperature and the residue was purified by flash chromatography eluted with hexane/EtOAc/CH$_2$Cl$_2$ (7:3:1 to 1:1:0) to give 0.321 g (90%) of the desired product as pale yellow gel. MS (DCI/NH$_3$) m/z: 487.1 (M+H)$^+$.

EXAMPLE 134C 3-(6-fluoropyridin-3-yl)-7-methoxy-4,4-dimethyl-1-{[2-(trimethylsilyl)ethoxy]methyl}-1,4-dihydroindeno[1,2-c]pyrazol-6-ol The desired product was prepared by substituting Example 68C and Example 68D with Example 134B and Example 123C in Example 68E. The product was purified by flash chromatography instead of reversed-phase HPLC. MS (ESI) m/z: 456.1 (M+H)$^+$.

EXAMPLE 134D 5-(6-hydroxy-7-methoxy-4,4-dimethyl-1-{[2-(trimethylsilyl)ethoxy]methyl}-1,4-dihydroindeno[1,2-c]pyrazol-3-yl)pyridine-2-carbonitrile The desired product was prepared by substituting Example 123D with Example 134C in Example 123E. The product was purified by flash chromatography instead of reversed-phase HPLC. MS (ESI) m/z: 463.1 (M+H)$^+$.

EXAMPLE 134E 5-(6-hydroxy-7-methoxy-4,4-dimethyl-1,4-dihydroindeno[1,2-c]pyrazol-3-yl)pyridine-2-carbonitrile A mixture of Example 134D (23.0 mg, 0.0497 mmol) and HCl (concentrated, 2 drops) in EtOH (2 mL) was stirred at 75° C. for 1.5 hours. The solvent was evaporated and the residue was purified using reversed-phase HPLC to give the desired product (4.0 mg) as TFA salt. MS (ESI) m/z: 333.0 (M+H)$^+$; $^1$H NMR (300 MHz, CD$_3$OD) δ ppm 1.56 (s, 6H) 3.93 (s, 3H) 6.94 (s, 1H) 7.20 (s, 1H) 7.99 (d, J=8.14 Hz, 1H) 8.32 (dd, J=8.14, 2.37 Hz, 1H) 9.11 (d, J=2.37 Hz, 1H).

EXAMPLE 135

5-[7-methoxy-4,4-dimethyl-6-(pyridin-3-ylmethoxy)-1,4-dihydroindeno[1,2-c]pyrazol-3-yl]pyridine-2-carbonitrile

EXAMPLE 135A 3-iodo-7-methoxy-4,4-dimethyl-6-(pyridin-3-ylmethoxy)-1-[[2-(trimethylsilyl)ethoxy]methyl]-1,4-dihydroindeno[1,2-c]pyrazole A mixture of Example 134B (200.0 mg, 0.411 mmol), di-t-butyl azodicarboxylate (0.189 g, 0.822 mmol), Ph$_3$P on solid support (3 mmol/g, 0.274 g, 0.822 mmol), and 3-pyridylcarbinol (80 μL, 0.822 mmol) in THF (3 mL) was stirred at room temperature overnight. The solid was filtered and the solvent was evaporated. The crude product was purified by flash chromatography eluted with EtOAc to give 0.242 g (100%) of the desired product as yellow gel. MS (DCI/NH$_3$) m/z: 578.1 (M+H)$^+$.

EXAMPLE 135B 3-(6-fluoropyridin-3-yl)-7-methoxy-4,4-dimethyl-6-(pyridin-3-ylmethoxy)-1-{[2-(trimethylsilyl)ethoxy]methyl}-1,4-dihydroindeno[1,2-c]pyrazole The desired product was prepared by substituting Example 68C and Example 68D with Example 135A and Example 123C in Example 68E. The product was purified by flash chromatography instead of reversed-phase HPLC. MS (ESI) m/z: 547.2 (M+H)$^+$.

EXAMPLE 135C

5-[7-methoxy-4,4-dimethyl-6-(pyridin-3-ylmethoxy)-1,4-dihydroindeno[1,2-c]pyrazol-3-yl]pyridine-2-carbonitrile The desired product was prepared by substituting Example 123D with Example 135B in Example 123E.

Examples 136 to 142, represented by FIG. (VII) and shown in Table 7, were synthesized in a similar fashion as Example 135C.

TABLE 7

FIG. (VII)

| Exmp. | R₂ | ¹H NMR | MS m/z (M + H)⁺ | Yield |
|---|---|---|---|---|
| 135C | (3-pyridylmethyl) | (300 MHz, DMSO-D₆) δ ppm 1.55 (s, 6H) 3.85 (s, 3H) 5.26 (s, 2H) 7.21 (s, 1H) 7.40 (s, 1H) 7.66 (dd, J=7.97, 5.26 Hz, 1H) 8.08-8.22 (m, 2H) 8.35 (m, 1H) 8.68 (dd, J=5.09, 1.36 Hz, 1H) 8.81 (s, 1H) 9.14 (s, 1H) | 424.1 (ESI) | 14.1 mg |
| 136 | (3-morpholinopropyl) | (300 MHz, DMSO-D₆) δ ppm 1.55 (s, 6H) 2.07-2.27 (m, 2H) 3.02-3.20 (m, 2H) 3.25-3.36 (m, 4H) 3.76 (t, J=11.53 Hz, 2H) 3.85 (s, 3H) 4.00 (d, J=12.21 Hz, 2H) 4.15 (t, J=5.76 Hz, 2H) 7.20 (s, 1H) 7.28 (s, 1H) 8.17 (d, J=8.14 Hz, 1H) 8.34 (dd, J=8.14, 2.03 Hz, 1H) 9.14 (d, J=2.03 Hz, 1H) 10.30 (s, brd, 1H) | 460.5 (ESI) | 17.1 mg |
| 137 | (tetrahydrofuran-3-yl) | (300 MHz, DMSO-D₆) δ ppm 1.55 (s, 6H) 1.99 (m, 1H) 2.21 (m, 1H) 3.83 (s, 3H) 3.68-4.04 (m, 4H) 5.05 (m, 1H) 7.18 (s, 1H) 7.22 (s, 1H) 8.16 (d, J=8.14 Hz, 1H) 8.33 (dd, J=8.14, 2.37 Hz, 1H) 9.14 (s, 1H) | 403.1 (ESI) | 15.2 mg |
| 138 | (2,3-dihydroxypropyl) | (500 MHz, CD₃OD) δ ppm 1.59 (s, 6H) 3.71 (m, 2H) 3.93 (s, 3H) 3.99-4.09 (m, 2H) 4.15 (m, 1H) 7.17 (s, 1H) 7.26 (s, 1H) 7.99 (d, J=7.17 Hz, 1H) 8.32 (dd, J=8.11, 2.18 Hz, 1H) 9.11 (m, 1H) | 407.2 (ESI) | 12.0 mg |
| 139 | (2-pyridylmethyl) | (300 MHz, CD₃OD) δ ppm 1.58 (s, 6H) 3.93 (s, 3H) 5.42 (s, 2H) 7.28 (s, 1H) 7.32 (s, 1H) 7.78 (m, 1H) 7.99 (t, J=7.46 Hz, 2H) 8.28-8.37 (m, 2H) 8.74 (d, J=6.44 Hz, 1H) 9.11 (d, J=2.37 Hz, 1H) | 424.1 (ESI) | 11.6 mg |
| 140 | (3-morpholinoethyl) | (300 MHz, CD₃OD) δ ppm 1.60 (s, 6H) 3.33-3.42 (m, 2H) 3.62-3.75 (m, 4H) 3.78-3.91 (m, 2H) 3.97 (s, 3H) 4.04-4.19 (m, 2H) 4.36-4.50 (m, 2H) 7.26 (s, 1H) 7.33 (s, 1H) 8.00 (d, J=7.46 Hz, 1H) 8.32 (dd, J=8.14, 2.37 Hz, 1H) 9.11 (d, J=2.03 Hz, 1H) | 446.2 (ESI) | 23.3 mg |

TABLE 7-continued

FIG. (VII)

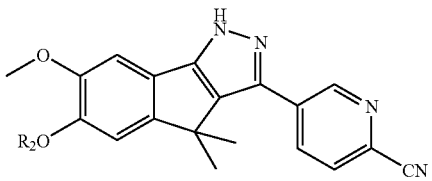

| Exmp. | R$_2$ | $^1$H NMR | MS m/z (M + H)$^+$ | Yield |
|---|---|---|---|---|
| 141 | (piperidinylpropyl) | (300 MHz, CD$_3$OD) δ ppm 1.59 (s, 6H) 1.74-1.92 (m, 4H) 1.95-2.09 (m, 2H) 2.25-2.37 (m, 2H) 2.77-3.14 (m, 2H) 3.40 (t, J=7.29 Hz, 2H) 3.69 (d, J=11.87 Hz, 2H) 3.94 (s, 3H) 4.23 (t, J=5.42 Hz, 2H) 7.17 (s, 1H) 7.29 (s, 1H) 8.00 (d, J=8.14 Hz, 1H) 8.32 (dd, J=8.14, 2.37 Hz, 1H) 9.11 (d, J=2.03 Hz, 1H) | 458.2 (ESI) | 20.4 mg |
| 142 | Me | (300 MHz, CD$_3$OD) δ ppm 1.60 (s, 6H) 3.91 (s, 6H) 7.14 (s, 1H) 7.24 (s, 1H) 7.99 (d, J=8.14 Hz, 1H) 8.33 (dd, J=8.14, 2.37 Hz, 1H) 9.12 (d, J=3.05 Hz, 1H) | 347.0 (ESI) | 15.2 mg |

EXAMPLE 143

5-[7-methoxy-6-(pyridin-2-ylmethoxy)-1,4-dihydroindeno[1,2-c]pyrazol-3-yl]pyridine-2-carbonitrile

EXAMPLE 143A 6-methoxy-5-{[2-(trimethylsilyl)ethoxy]methoxy}indan-1-one

To a solution of 5-hydroxy-6-methoxy-indan-1-one (21.1 g, 0.118 mol, see preparation in J. Org. Chem. 57, 1992, 589-594) and N,N-diisopropylethylamine (21.6 mL, 0.124 mol) in CH$_2$Cl$_2$ (200 mL) was added SEMCl (21.3 mL, 0.121 mol). The mixture was stirred at room temperature for 2 hours and diluted with NaHCO$_3$ solution. After separation, the organic layer was dried over MgSO$_4$, filtered, concentrated, and purified by flash chromatography eluted with EtOAc/hexane (3:7 to 1:1) to give 26.3 g (72%) of the desired product as brown oil. MS (ESI) m/z: 309.0 (M+H)$^+$; $^1$H NMR (300 MHz, CDCl$_3$) δ ppm −0.01 (s, 9H) 0.96 (t, J=8.25 Hz, 2H) 2.66 (t, J=5.70 Hz, 2H) 3.03 (t, J=5.70 Hz, 2H) 3.80 (t, J=8.25 Hz, 2H) 3.90 (s, 3H) 5.36 (s, 2H) H) 7.20 (s, 1H) 7.22 (s, 1H).

EXAMPLE 143B phenyl 6-chloronicotinate

A mixture of 6-chloronicotinic acid (68.0 g, 0.431 mol), phenol (40.6 g, 0.431 mol), DCC (93.6 g, 0.453 mol), and DMAP (1.60 g, 0.0129 mol) in ether (1 L) was stirred at room temperature overnight. The solvent was evaporated and the residue was stirred in CH$_2$Cl$_2$. The solid was filtered and the filtrate was purified by flash chromatography eluted with CH$_2$Cl$_2$ to give 88.0 g (88%) of the desired product. MS (DCI/NH$_3$) m/z: 234.0 (M+H)$^+$; $^1$H NMR (300 MHz, CDCl$_3$) δ ppm 7.22 (d, J=8.14 Hz, 2H) 7.31 (t, J=7.29 Hz, 1H) 7.47 (dd, J=17.12, 7.97 Hz, 3H) 8.40 (m, 1H) 9.17 (d, J=1.70 Hz, 1H).

EXAMPLE 143C 3-(6-chloropyridin-3-yl)-7-methoxy-6-{[2-(trimethylsilyl)ethoxy]methoxy}-1,4-dihydroindeno[1,2-c]pyrazole To a solution of Example 143A (24.1 g, 0.0781 mol) in THF (400 mL) was added NaH (60%, 9.37 g, 0.234 mol) in 2 portions at room temperature. After 20 minutes, Example 143B (21.0 g, 0.0898 mol) was added. The reaction mixture was stirred for 3 hours, treated with EtOH, and concentrated. To the resulting residue were added EtOH (400 mL), glacial acetic acid (22.4 mL, 0.391 mol), and hydrazine monohydrate (11.4 mL, 0.234 mol). The mixture was heated at 90° C. for 2 hours, cooled, and concentrated. The residue was extracted with EtOAc and washed with NaHCO$_3$. The organic layer was dried over MgSO$_4$, filtered, concentrated, and triturated with ether to give 23.8 g (69%) of the desired product as off-white solid. MS (ESI) m/z: 444.1 (M+H)$^+$; $^1$H NMR (300 MHz, DMSO-D$_6$) δ ppm 0.00 (s, 9H) 0.92 (t, J=8.09 Hz, 2H) 3.77 (m, J=7.94 Hz, 2H) 3.86 (s, 3H) 5.24 (s, 2H) 6.70 (m, 1H) 7.30 (d, J=10.51 Hz, 2H) 7.66 (d, J=8.14 Hz, 1H) 8.23 (dd, J=8.31, 2.54 Hz, 1H) 8.83 (d, J=3.05 Hz, 1H).

3-(6-chloropyridin-3-yl)-7-methoxy-6-{[2-(trimethylsilyl)ethoxy]methoxy}-1-{[2-(trimethylsilyl)ethoxy]methyl}-1,4-dihydroindeno[1,2-c]pyrazole

EXAMPLE 143D

The desired product was prepared by substituting Example 68A with Example 143C in Example 123A. MS (ESI) m/z: 574.2 (M+H)$^+$.

EXAMPLE 143E 5-(7-methoxy-6-{[2-(trimethylsilyl)ethoxy]methoxy}-1-{[2-(trimethylsilyl)ethoxy]methyl}-1,4-dihydroindeno[1,2-c]pyrazol-3-yl)pyridine-2-carbonitrile A mixture of Example 143D (1.500 g, 2.61 mmol), $Pd_2(dba)_3$ (71.7 mg, 3 mol %), dppf (86.8 mg, 6 mol %), Zn (20.5 mg, 12 mol %), and $Zn(CN)_2$ (0.460 g, 3.92 mmol) in N,N-dimethylacetamide (40 mL) was degassed and heated at 120° C. overnight. The mixture was cooled and filtered through celite. The filtrate was diluted with 50% brine and extracted with EtOAc twice. The combined organic layers were washed with $NaHCO_3$ and brine, dried over $MgSO_4$, filtered, concentrated, and purified by flash chromatography eluted with EtOAc/hexane (4:6) to give 1.17 g (80%) of the desired product as pale yellow solid. MS (ESI) m/z: 565.2 $(M+H)^+$.

EXAMPLE 143F 5-(6-hydroxy-7-methoxy-1-{[2-(trimethylsilyl)ethoxy]methyl}-1,4-dihydroindeno[1,2-c]pyrazol-3-yl)pyridine-2-carbonitrile A mixture of Example 143E (9.96 g, 0.0176 mmol) and HCl (concentrated, 4.0 mL) in MeOH (200 mL) and $CH_2Cl_2$ (100 mL) was stirred at room temperature for 1.5 hours. Most of the solvents were evaporated at room temperature. The residue was extracted with EtOAc, washed with $NaHCO_3$, dried over $MgSO_4$, filtered, concentrated to give 7.63 g (quantitative yield) of the desired product as pale yellow solid. MS (ESI) m/z: 435.2 $(M+H)^+$.

EXAMPLE 143G

5-[7-methoxy-6-(pyridin-2-ylmethoxy)-1,4-dihydroindeno[1,2-c]pyrazol-3-yl]pyridine-2-carbonitrile The desired product was prepared by first substituting Example 134B and 3-pyridylcarbinol with Example 143F and 2-pyridylcarbinol in Example 135A. The intermediate was treated with HCl and EtOH at about 75° C. for about 2 hours. The suspension was cooled and the solid was filtered, washed with ether, and dried to give the desired product as HCl salt. Alternatively, the intermediate after acidic treatment was purified using reversed-phase HPLC to give the desired product as TFA salt.

EXAMPLE 144

5-{7-[(6-chloropyridin-3-yl)methoxy]-6-methoxy-1,4-dihydroindeno[1,2-c]pyrazol-3-yl}pyridine-2-carbonitrile

EXAMPLE 144A 5,6-dihydroxyindan-1-one

To a solution of 5,6-dimethoxy-indan-1-one (40.0 g, 0.208 mol) in $CH_2Cl_2$ (800 mL) at −78° C. was added $BBr_3$ (59.0 mL, 0.624 mol) dropwise. The dry ice bath was removed after the addition. The mixture was stirred at room temperature for 1 hour and poured into a large amount of ice/water and stirred vigorously. The pink solid was filtered, washed with water, and vacuum oven dried to give 33.3 g (98%) of the desired product. MS $(DCI/NH_3)$ m/z: 165.0 $(M+H)^+$; $^1H$ NMR (300 MHz, $CD_3OD$) δ ppm 2.58-2.61 (m, 2H) 2.98 (t, J=5.55 Hz, 2H) 6.85 (s, 1H) 7.04 (s, 1H).

EXAMPLE 144B 6-hydroxy-5-methoxyindan-1-one

A mixture of Example 144A (28.5 g, 0.173 mol), MeI (27.0 mL, 0.433 mol), and $Li_2CO_3$ (32.0 g, 0.519 mol) in DMF (800 mL) was heated at 55° C. overnight. DMF was evaporated and the residue was treated with water (1 L) and HCl (concentrated, 60 mL). The solid was filtered, washed with water until the filtrate became neutral, and dried to give 21.0 g (68%) of the desired product. MS $(DCI/NH_3)$ m/z: 179.0 $(M+H)^+$; $^1H$ NMR (300 MHz, $CD_3OD$) δ ppm 2.58-2.67 (m, 2H) 3.05 (t, J=5.55 Hz, 2H) 3.96 (s, 3H) 7.04 (s, 2H).

EXAMPLE 144C

5-{7-[(6-chloropyridin-3-yl)methoxy]-6-methoxy-1,4-dihydroindeno[1,2-c]pyrazol-3-yl}pyridine-2-carbonitrile The desired product was prepared by substituting 6-hydroxy-5-methoxyindan-1-one with Example 144B in Example 143A followed by the similar procedures in Examples 143C, 143D, 143E, 143F, and 143G.

Examples 145 to 163 represented by FIG. (VIII) and shown in Table 8 were synthesized in a similar fashion as described in Example 143G or 144C.

TABLE 8

FIG. (VIII)

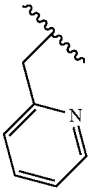

| Exmp. | R1 | R2 | ¹H NMR | MS m/z (M + H)⁺ | Yield |
|---|---|---|---|---|---|
| 143G | Me | 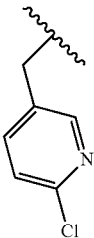 | (300 MHz, DMSO-D₆) δppm 3.84 (s, 2H) 3.89 (s, 3H) 5.26 (s, 2H) 7.33 (d, J=8.48 Hz, 2H) 7.44 (m, 1H) 7.64 (d, J=7.80 Hz, 1H) 7.87 (m, 1H) 7.95 (t, J=7.80 Hz, 1H) 8.15 (d, J=8.14 Hz, 1H) 8.36 (dd, J=8.14, 2.03 Hz, 1H) 8.63 (d, J=5.76 Hz, 1H) 8.82 (d, J=6.44 Hz, 1H) 9.14 (s, 1H) | 396.0 (ESI) | 18. mg |
| 144C | 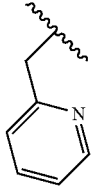 | Me | (500 MHz, DMSO-D₆) δppm 3.83 (s, 3H) 3.85 (s, 2H) 5.22 (s, 2H) 7.28 (s, 1H) 7.35 (s, 1H) 7.56 (d, J=8.42 Hz, 1H) 7.95 (dd, J=8.11, 2.50 Hz, 1H) 8.13 (d, J=8.11 Hz, 1H) 8.35 (m, 1H) 8.52 (d, J=2.50 Hz, 1H) 9.14 (d, J=1.56 Hz, 1H) | 430.1 (ESI) | 38.5 mg |
| 145 | 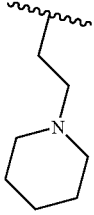 | Me | (500 MHz, CD₃OD) δ ppm 3.86 (s, 2H) 3.92 (s, 3H) 5.40 (s, 2H) 7.34 (s, 1H) 7.39 (s, 1H) 7.71 (m, 1H) 7.94 (t, J=8.89 Hz, 2H) 8.26 (t, J=7.64 Hz, 1H) 8.32 (d, J=8.11 Hz, 1H) 8.70 (d, J=4.68 Hz, 1H) 9.12 (s, 1H) | 396.2 (ESI) | 6.1 mg |
| 146 | 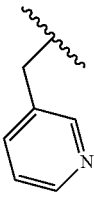 | Me | (500 MHz, CD₃OD) δ ppm 1.16-1.32 (m, 2H) 1.68-1.85 (m, 2H) 1.88-1.98 (m, 2H) 2.97-3.09 (m, 2H) 3.47-3.56 (m, 2H) 3.67 (d, J=12.16 Hz, 2H) 3.77 (s, 2H) 3.87 (s, 3H) 4.28-4.36 (m, 2H) 7.26 (s, 1H) 7.30 (s, 1H) 7.86 (d, J=7.80 Hz, 1H) 8.22 (dd, J=8.26, 2.34 Hz, 1H) 9.02 (s, 1H) | 416.1 (ESI) | 2.6 mg |
| 147 | 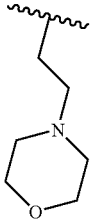 | Me | (500 MHz, DMSO-D₆) δ ppm 3.87 (s, 3H) 3.88 (s, 2H) 5.40 (s, 2H) 7.32 (s, 1H) 7.43 (s, 1H) 8.07 (dd, J=7.96, 5.77 Hz, 1H) 8.15 (d, J=8.42 Hz, 1H) 8.38 (dd, J=8.11, 2.18 Hz, 1H) 8.62 (d, J=8.11 Hz, 1H) 8.89 (d, J=5.30 Hz, 1H) 9.01 (s, 1H) 9.16 (s, 1H) | 396.0 (ESI) | 47.0 mg |
| 148 |  | Me | (400 MHz, DMSO-D₆) δ ppm 3.20-3.77 (m, brd, 8H) 3.85 (s, 3H) 3.88 (s, 2H) 3.95-4.07 (m, 2H) 4.37-4.44 (m, 2H) 7.32 (s, 1H) 7.39 (s, 1H) 8.15 (d, J=7.98 Hz, 1H) 8.35 (d, J=8.29 Hz, 1H) 9.14 (s, 1H) | 418.1 (ESI) | 18.9 mg |

TABLE 8-continued

FIG. (VIII)

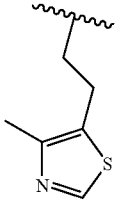

| Exmp. | R1 | R2 | ¹H NMR | MS m/z (M + H)⁺ | Yield |
|---|---|---|---|---|---|
| 149 | 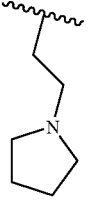 | Me | (500 MHz, DMSO-D₆) δ ppm 2.39 (s, 3H) 3.26 (t, J=6.24 Hz, 2H) 3.82 (s, 3H) 3.85 (s, 2H) 4.21 (t, J=6.24 Hz, 2H) 7.25 (d, J=5.62 Hz, 2H) 8.14 (d, J=8.42 Hz, 1H) 8.35 (m, 1H) 8.88 (s, 1H) 9.14 (s, 1H) | 430.0 (ESI) | 14.0 mg |
| 150 | 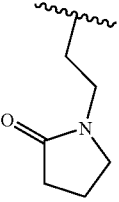 | Me | (400 MHz, DMSO-D₆) δ ppm 1.77-1.95 (m, 2H) 1.97-2.11 (m, 2H) 3.01-3.24 (m, 2H) 3.50-3.69 (m, 4H) 3.77-3.94 (m, 5H) 4.42 (t, J=4.91 Hz, 2H) 7.29 (s, 1H) 7.36 (s, 1H) 8.14 (d, J=7.98 Hz, 1H) 8.37 (d, J=10.43 Hz, 1H) 9.15 (s, 1H) 10.99 (s, brd, 1H) | 402.1 (ESI) | 34.0 mg |
| 151 |  | Me | (500 MHz, DMSO-D₆) δ ppm 1.88-2.00 (m, 2H) 2.23 (t, J=8.11 Hz, 2H) 3.50-3.55 (m, 2H) 3.58 (t, J=5.46 Hz, 2H) 3.84 (s, 3H) 3.86 (s, 2H) 4.14 (t, J=5.46 Hz, 2H) 7.27 (d, J=3.74 Hz, 2H) 8.15 (d, J=8.11 Hz, 1H) 8.35 (d, J=8.11 Hz, 1H) 9.15 (s, 1H) | 416.1 (ESI) | 16.2 mg |
| 152 | 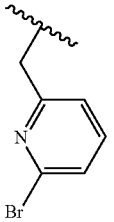 | Me | (500 MHz, DMSO-D₆) δ ppm 3.75 (t, J=5.15 Hz, 2H) 3.82 (s, 3H) 3.84 (s, 2H) 4.04 (t, J=5.15 Hz, 2H) 7.24 (d, J=8.73 Hz, 2H) 8.13 (d, J=8.11 Hz, 1H) 8.34 (d, J=10.29 Hz, 1H) 9.14 (s, 1H) | 349.0 (ESI) | 21.2 mg |
| 153 | 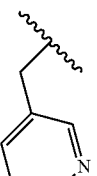 | Me | (500 MHz, DMSO-D₆) δ ppm 3.84 (s, 2H) 3.86 (s, 3H) 5.22 (s, 2H) 7.30 (d, J=10.61 Hz, 2H) 7.59 (dd, J=12.79, 7.80 Hz, 2H) 7.81 (t, J=7.80 Hz, 1H) 8.13 (d, J=8.11 Hz, 1H) 8.35 (dd, J=8.11, 2.18 Hz, 1H) 9.13 (s, 1H) | 474.0 (ESI) | 51.7 mg |
| 154 | Me |  | (300 MHz, DMSO-D₆) δ ppm 3.87 (s, 5H) 5.26 (s, 2H) 7.31 (s, 1H) 7.38 (s, 1H) 7.67 (dd, J=7.63, 5.26 Hz, 1H) 8.15 (m, 2H) 8.36 (dd, J=8.14, 2.03 Hz, 1H) 8.68 (d, J=5.09 Hz, 1H) 8.80 (s, 1H) 9.16 (d, J=2.37 Hz, 1H) | 396.0 (ESI) | 13.5 mg |

TABLE 8-continued

FIG. (VIII)

| Exmp. | R1 | R2 | ¹H NMR | MS m/z (M + H)⁺ | Yield |
|---|---|---|---|---|---|
| 155 | Me | (3-morpholinopropyl) | (300 MHz, CD₃OD) δ ppm 2.26-2.40 (m, 2H) 3.17-3.28 (m, 2H) 3.48 (t, J=7.29 Hz, 2H) 3.67 (d, J=12.88 Hz, 2H) 3.76-3.88 (m, 4H) 3.95 (s, 3H) 4.13 (dd, J=13.05, 3.22 Hz, 2H) 4.24 (t, J=5.59 Hz, 2H) 7.29 (s, 1H) 7.34 (s, 1H) 7.96 (d, J=8.14 Hz, 1H) 8.32 (dd, J=8.31, 2.20 Hz, 1H) 9.11 (s, 1H) | 432.1 (ESI) | 33.6 mg |
| 156 | Me | (tetrahydrofuran-3-yl)methyl | (300 MHz, DMSO-D₆) δ ppm 2.02 (m, 1H) 2.20 (m, 1H) 3.66-4.01 (m, 9H) 5.05 (s, brd, 1H) 7.21 (m, 1.5H) 7.31 (s, 0.5H) 8.11 (d, J=8.14 Hz, 0.5H) 8.19 (d, J=8.14 Hz, 0.5H) 8.36 (m, 1H) 9.15 (d, J=11.53 Hz, 1H) 13.41 (s, 0.5H) 13.46 (s, 0.5H) | 375.0 (ESI) | 18.4 mg |
| 157 | Me | 3-(dimethylamino)propyl | (300 MHz, CD₃OD) δ ppm 2.21-2.39 (m, 2H) 3.02 (s, 6H) 3.45 (t, J=6.95 Hz, 2H) 3.81 (s, 2H) 3.97 (s, 3H) 4.25 (t, J=5.43 Hz, 2H) 7.28 (s, 1H) 7.34 (s, 1H) 7.95 (d, J=8.14 Hz, 1H) 8.30 (dd, J=8.14, 2.37 Hz, 1H) 9.10 (d, J=2.37 Hz, 1H) | 390.0 (ESI) | 14.0 mg |
| 158 | Me | 2-(4-methylthiazol-5-yl)ethyl | (300 MHz, CD₃OD) δ ppm 2.62 (s, 3H) 3.46 (t, J=5.43 Hz, 2H) 3.83 (s, 2H) 3.93 (s, 3H) 4.33 (t, J=5.59 Hz, 2H) 7.28 (s, 1H) 7.32 (s, 1H) 7.97 (d, J=8.14 Hz, 1H) 8.32 (dd, J=8.14, 2.37 Hz, 1H) 9.11 (d, J=2.03 Hz, 1H) 9.91 (s, 1H) | 430.0 (ESI) | 62.1 mg |
| 159 | Me | 2-hydroxyethyl | (300 MHz, DMSO-D₆) δ ppm 3.74 (t, J=5.09 Hz, 2H) 3.85 (s, 5H) 4.04 (t, J=5.26 Hz, 2H) 7.25 (s, 2H) 8.15 (d, J=8.48 Hz, 1H) 8.35 (dd, J=8.31, 2.20 Hz, 1H) 9.15 (s, 1H) | 349.0 (ESI) | 25.5 mg |
| 160 | Me | (6-bromopyridin-2-yl)methyl | (500 MHz, DMSO-D₆) δ ppm 3.84 (s, 2H) 3.89 (s, 3H) 5.21 (s, 2H) 7.33 (s, 2H) 7.58-7.65 (m, 2H) 7.83 (m, J=7.80, 7.80 Hz, 1H) 8.14 (s, 1H) 8.35 (dd, J=8.11, 2.18 Hz, 1H) 9.14 (s, 1H) 13.44 (s, brd, 1H) | 474.0 (ESI) | 5.2 mg |

TABLE 8-continued

FIG. (VIII)

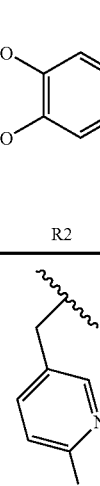

| Exmp. | R1 | R2 | ¹H NMR | MS m/z (M + H)⁺ | Yield |
|---|---|---|---|---|---|
| 161 | Me | 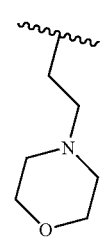 | (300 MHz, DMSO-D₆) δ ppm 3.87 (s, 5H) 5.21 (s, 2H) 7.22-7.40 (m, brd, 2H) 7.58 (d, J=8.14 Hz, 1H) 7.97 (dd, J=8.14, 2.37 Hz, 1H) 8.17 (s, 1H) 8.36 (dd, J=8.14, 2.03 Hz, 1H) 8.53 (d, J=2.37 Hz, 1H) 9.15 (s, 1H) | 430.0 (ESI) | 11.4 mg |
| 162 | Me | | (300 MHz, DMSO-D₆) δ ppm 3.18-3.33 (m, 2H) 3.54-3.66 (m, 4H) 3.79 (t, J=11.53 Hz, 2H) 3.88 (s,5H) 4.01 (d, J=12.55 Hz, 2H) 4.44 (t, J=5.09 Hz, 2H) 7.35 (d, J=6.78 Hz, 2H) 8.17 (d, J=7.80 Hz, 1H) 8.38 (dd, J=8.14, 2.03 Hz, 1H) 9.16 (s, 1H) 10.69 (s, brd, 1H) | 418.0 (ESI) | 92.5 mg |
| 163 | Me | 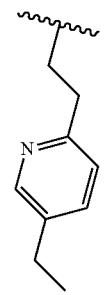 | (300 MHz, CD₃OD) δ ppm 1.35 (t, J=7.63 Hz, 3H) 2.90 (q, J=7.46 Hz, 2H) 3.54 (t, J=5.59 Hz, 2H) 3.82 (s, 2H) 3.84 (s, 3H) 4.47 (t, J=5.76 Hz, 2H) 7.28 (d, J=3.05 Hz, 2H) 7.96 (d, J=8.82 Hz, 1H) 8.08 (d, J=8.14 Hz, 1H) 8.32 (dd, J=8.14, 2.03 Hz, 1H) 8.48 (dd, J=8.48, 2.03 Hz, 1H) 8.68 (d, J=2.03 Hz, 1H) 9.11 (d, J=2.03 Hz, 1H) | 438.0 (ESI) | 98.6 mg |

EXAMPLE 164

4'-(6,7-dimethoxy-1,4-dihydroindeno[1,2-c]pyrazol-3-yl)-3-methoxy-1,1'-biphenyl-4-ol Example 64C (50 mg, 0.14 mmol), 2-methoxy-4-(4,4,5,5-tetramethyl[1,3,2]dioxaborolan-2-yl)-phenol (42.3 mg, 0.17 mmol), Na₂CO₃ (1 M, 0.3 mL), and Pd(PPh₃)₂Cl₂ (9.9 mg, 0.014 mmol) were combined in DME/EtOH/H₂O (7:2:3, 1.5 mL) in a capped 2 mL vial and heated to 160° C. for 600 seconds in a Smith Synthesizer. The reaction was cooled using 40 psi pressurized air, the solvents were evaporated, and the residue was purified using preparative HPLC. MS (DCI/NH₃) m/z: 415.06 (M+H)⁺. ¹H NMR (500 MHz, DMSO-D₆) δ ppm 3.79 (s, 2H) 3.82 (s, 3H) 3.85 (s, 3H) 3.88 (s, 3H) 6.87 (d, J=8.11 Hz, 1H) 7.16 (dd, J=8.11, 2.18 Hz, 1H) 7.23 (s, 1H) 7.25 (s, 1H) 7.27 (d, J=1.87 Hz, 1H) 7.75 (d, J=8.42 Hz, 2H) 7.83 (d, J=8.42 Hz, 2H).

EXAMPLE 165

4-(6,7-dimethoxy-1,4-dihydroindeno[1,2-c]pyrazol-3-yl)phenol

EXAMPLE 165A

4-Benzyloxybenzoic acid (2 g, 8.76 mmol) and 1,1'-carbonyldiimidazole (2.3 g, 14 mmol) were combined in DMF. The reaction mixture was stirred overnight and poured into ice-water. The resulting precipitate was collected by filtration, washed with water, and dried. The title product (2.4 g) was obtained at 99% yield. MS (DCI/NH₃) m/z: 279.08 (M+H)⁺.

EXAMPLE 165B

2-[4-(benzyloxy)benzoyl]-5,6-dimethoxyindan-1-one 5,6-Dimethoxyindanone (1 g, 5.2 mmol) in 45 mL of THF was treated with NaH (60%, 312 mg, 7.8 mmol). After the addition of Example 165A (1.45 g, 5.2 mmol), the reaction mixture was stirred overnight and poured into ice water. The resulting mixture was acidified with concentrated HCl.

Yellow solid was collected by filtration, washed with water and hot ethanol. The title product (1.2 g) was obtained at 57% yield. MS (DCI/NH$_3$) m/z: 403.11 (M+H)$^+$.

EXAMPLE 165C

3-[4-(benzyloxy)phenyl]-6,7-dimethoxy-1,4-dihydroindeno[1,2-c]pyrazole

Example 165B (500 mg, 1.24 mmol), hydrazine monohydrate (72 μL), and acetic acid (85 μL) were combined in 20 mL of ethanol, heated at 90° C. overnight and cooled. The precipitates were collected by filtration to give the title compound. MS (DCI/NH$_3$) m/z: 399.11 (M+H)$^+$. $^1$H NMR (500 MHz, DMSO-D$_6$) δ ppm 3.73 (s, 2H) 3.81 (s, 3H) 3.84 (s, 3H) 5.17 (s, 2H) 7.14 (d, J=7.49 Hz, 2H) 7.21 (d, J=8.11 Hz, 2H) 7.34 (t, J=7.18 Hz, 1H) 7.41 (t, J=7.49 Hz, 2H) 7.48 (d, J=7.18 Hz, 2H) 7.71 (d, J=8.11 Hz, 2H) 12.85 (s, 1H).

EXAMPLE 165D 4-(6,7-dimethoxy-1,4-dihydroindeno[1,2-c]pyrazol-3-yl)phenol

Example 165C (57 mg, 0.14 mmol) and Pd/C (10%, 15.2 mg) were combined in THF (20 mL) and stirred under hydrogen atmosphere for 24 hours. Pd/C was removed by filtration and the filtrate was concentrated. The residue was purified by HPLC to give the title compound. MS (DCI/NH$_3$) m/z: 309.03 (M+H)$^+$. $^1$H NMR (400 MHz, DMSO-D$_6$) δ ppm 3.71 (s, 2H) 3.81 (s, 3H) 3.83 (s, 3H) 6.87 (d, J=8.59 Hz, 2H) 7.20 (s, 1H) 7.22 (s, 1H) 7.60 (d, J=8.59 Hz, 2H).

EXAMPLE 166

3-(4'-hydroxy-1,1'-biphenyl-4-yl)-1,4-dihydroindeno[1,2-c]pyrazole-6,7-diol

EXAMPLE 166A 3-(4-bromophenyl)-1,4-dihydroindeno[1,2-c]pyrazole-6,7-diol

Example 64C (142 mg, 0.38 mmol) in 1,2-dichloroethane (50 mL) was treated with BBr$_3$.SMe$_2$ (597 mg, 1.91 mmol), heated at 80° C. for 30 hours and cooled. Reaction was quenched with water (20 mL), and the resulting mixture was treated with ether (100 mL). The precipitate was collected by filtration and further purified by HPLC. MS (DCI/NH$_3$) m/z: 344.94 (M+H)$^+$.

EXAMPLE 166B 3-(4'-hydroxy-1,1'-biphenyl-4-yl)-1,4-dihydroindeno[1,2-c]pyrazole-6,7-diol Example 166A (35 mg, 0.10 mmol), 4-hydroxylphenyl boronic acid (18 mg), Na$_2$CO$_3$ (1 M, 0.25 mL), and Pd(PPh$_3$)$_2$Cl$_2$ (9.9 mg, 0.014 mmol) were combined in DME/EtOH/H$_2$O (7:2:3, 1.5 mL) in a capped 2 mL vial and heated to 160° C. for 600 seconds in a Smith Synthesizer. The reaction was cooled using 40 psi pressurized air, the solvents were evaporated, and the residue was purified using preparative HPLC to give the title compound. MS (DCI/NH$_3$) m/z: 357.04 (M+H)$^+$. $^1$H NMR (500 MHz, DMSO-D$_6$) δ ppm 3.69 (s, 2H) 6.87 (d, J=8.54 Hz, 2H) 6.96 (s, 1H) 7.04 (s, 1H) 7.56 (d, J=8.54 Hz, 2H) 7.70 (d, J=8.54 Hz, 2H) 7.81 (d, J=8.54 Hz, 2H).

EXAMPLE 167

4-(6,7-dimethoxy-1,4-dihydroindeno[1,2-c]pyrazol-3-yl)benzonitrile

A mixture of Example 64C (50 mg, 0.14 mmol), zinc cyanide (17.4 mg, 1.48 mmol), Pd(PPh$_3$)$_4$ (15.6 mg, 0.014 mmol) in DMF (3 mL) in a capped 5 mL vial was heated to 180° C. for 300 seconds in a Smith Synthesizer. The reaction was cooled using 40 psi pressurized air, and the solvent was evaporated. The residue was purified by preparative HPLC to give the title product. MS (DCI/NH$_3$) m/z: 318.04 (M+H)$^+$. $^1$H NMR (500 MHz, DMSO-D$_6$) δ ppm 3.81 (s, 2H) 3.82 (s, 3H) 3.84 (s, 3H) 7.23 (s, 1H) 7.25 (s, 1H) 7.96 (s, 4H).

EXAMPLE 168

3-(6-hydroxy-2-naphthyl)-1,4-dihydroindeno[1,2-c]pyrazol-6-ol

EXAMPLE 168A 1-(6-methoxy-2-naphthoyl)-1H-imidazole

6-Methoxynanphthalene-2-carboxylic acid (2 g, 9.9 mmol) and 1'1'-carbonyldimidazole (2.4 g, 14.8 mmol) were combined in DMF (10 mL) and stirred overnight. The white solid was collected by filtration, washed with water and dried to give the title compound.

EXAMPLE 168B 5-(benzyloxy)-2-(6-methoxy-2-naphthoyl)indan-1-one

5-Benzyloxyindanone (1.5 g, 6.29 mmol) was treated with NaH (60%, 377 mg) in THF (50 mL), and then Example 168A (1.59 g) was added. The reaction was stirred for 6 hours at room temperature. The precipitates were collected by filtration and dissolved in water, acidified with concentrated HCl, and the resulting precipitates were collected, washed with water and dried to give the title compound.

EXAMPLE 168C 6-(benzyloxy)-3-(6-methoxy-2-naphthyl)-1,4-dihydroindeno[1,2-c]pyrazole The desired product was prepared using the procedure in Example 165C replacing Example 165B with Example 168B. MS (DCI/NH$_3$) m/z: 419.14 (M+H)$^+$.

EXAMPLE 168D 3-(6-hydroxy-2-naphthyl)-1,4-dihydroindeno[1,2-c]pyrazol-6-ol

The desired product was prepared using the procudure in Example 166A replacing Example 64C with Example 168C. MS (DCI/NH$_3$) m/z: 315.04 (M+H)$^+$. $^1$H NMR (500 MHz, DMSO-D$_6$) δ ppm 3.89 (s, 2H) 6.84 (dd, J=8.24, 2.14 Hz, 1H) 7.07 (d, J=1.53 Hz, 1H) 7.13-7.14 (m, 2H) 7.54 (d, J=8.24 Hz, 1H) 7.75-7.79 (m, 2H) 7.82 (d, J=9.76 Hz, 1H) 8.14 (s, 1H).

EXAMPLE 169

6,7-dimethoxy-3-[4-(1H-pyrrol-2-yl)phenyl]-1,4-dihydroindeno[1,2-c]pyrazole

The desired product was prepared using the procedure in Example 164 replacing 2-methoxy-4-(4,4,5,5-tertramethyyl[1,3,2]dioxaborolan-2-yl)-phenol with 1-tert-Bocpyrrolyl-2-boronic acid. MS (DCI/NH$_3$) m/z: 358.12 (M+H)$^+$. $^1$H NMR (400 MHz, DMSO-D$_6$) δ ppm 3.79 (s, 2H) 3.82 (s, 3H) 3.84 (s, 3H) 6.14 (q, J=2.35 Hz, 1H) 6.59 (s, 1H) 6.88 (s, 1H) 7.23 (d, J=9.21 Hz, 2H) 7.72-7.77 (m, 4H) 11.32 (s, 1H).

EXAMPLE 170

6,7-dimethoxy-3-[4-(1H-pyrazol-4-yl)phenyl]-1,4-dihydroindeno[1,2-c]pyrazole

EXAMPLE 170A

1-[chloro(4-methoxyphenyl)methyl]-4-methoxybenzene

Bis(4-methoxyphenyl)methanol (30 g) was treated with thionyl chloride (40 mL). The resulting mixture was refluxed for 2.5 hours and concentrated to give the desired product.

EXAMPLE 170B

1-[bis(4-methoxyphenyl)methyl]-4-iodo-1H-pyrazole

4-Iodo-1H-pyrazole (1 g, 5.15 mmol), Example 170A (1.49 g, 5.67 mmol), and triethylamine (0.79 mL) were combined in THF (20 mL), and refluxed for 1.5 hour. The inorganic salts were removed by filtration, and the filtrate was concentrated. The residue was recrystalized from a mixture of ethyl acetate and hexane to give 1.56 g of product at 72% yield. MS (DCI/NH$_3$) m/z: 420.0 (M+H)$^+$. $^1$H NMR (400 MHz, DMSO-D$_6$) δ ppm 3.72 (s, 6H) 6.78 (s, 1H) 6.90 (d, J=8.59 Hz, 4H) 7.06 (d, J=8.59 Hz, 4H) 7.58 (s, 1H) 7.81 (s, 1H).

EXAMPLE 170C

1-[bis(4-methoxyphenyl)methyl]-3-(4-bromophenyl)-6,7-dimethoxy-1,4-dihydroindeno[1,2-c]pyrazole The desired product was prepared using the procedure in Example 170B replacing 4 iodo-1H-pyrazole with Example 64C. The title product (2.0 g) was obtained at 83% yield. MS (DCI/NH$_3$) m/z: 597.12 (M+H)$^+$. $^1$H NMR (400 MHz, DMSO-D$_6$) δ ppm 3.60 (s, 3H) 3.73 (s, 6H) 3.75 (s, 2H) 3.78 (s, 3H) 6.61 (s, 1H) 6.94 (d, J=8.59 Hz, 4H) 7.14 (s, 1H) 7.20 (s, 1H) 7.25 (d, J=8.59 Hz, 4H) 7.62 (d, J=8.59 Hz, 2H) 7.72 (d, J=8.59 Hz, 2H).

EXAMPLE 170D

1-[bis(4-methoxyphenyl)methyl]-6,7-dimethoxy-3-[4-(4,4,5,5-tetramethyl-1,3,2-dioxaborolan-2-yl)phenyl]-1,4-dihydroindeno[1,2-c]pyrazole Example 170C (1 g, 1.67 mmol), bis(pinacolato)diborane (467 mg, 1.84 mmol), PdCl$_2$(dppf).CH$_2$Cl$_2$ (41 mg, 0.05 mmol), dppf (28 mg), and K2OAc were combined in 1,4-dioxane (35 mL) and purged with a stream of nitrogen. The reaction was heated at 90° C. overnight and concentrated. The residue was purified by flash chromatography eluting with hexane:ethyl acetate (2:1). The desired product (950 mg) was obtained at 88% yield. $^1$H NMR (500 MHz, DMSO-D$_6$) δ ppm 1.31 (s, 12H) 3.58 (s, 3H) 3.73 (s, 6H) 3.77 (s, 2H) 3.78 (s, 3H) 6.54 (s, 1H) 6.95 (d, J=8.73 Hz, 4H) 7.14 (s, 1H) 7.22 (s, 1H) 7.24 (d, J=8.73 Hz, 4H) 7.74 (d, J=8.11 Hz, 2H) 7.80 (d, J=8.11 Hz, 2H).

EXAMPLE 170E

1-[bis(4-methoxyphenyl)methyl]-3-(4-{1-[bis(4-methoxyphenyl)methyl]-1H-pyrazol-4-yl}phenyl)-6,7-dimethoxy-1,4-dihydroindeno[1,2-c]pyrazole Example 170B (67 mg, 0.159 mmol), Example 170D (84 mg, 0.13 mmol), Na$_2$CO$_3$ (1 M, 0.3 mL), and Pd(PPh$_3$)$_2$Cl$_2$ (9.9 mg, 0.014 mmol) were combined in DME/EtOH/H$_2$O (7:2:3, 1.5 mL) in a capped 2 mL vial and heated to 160° C. for 1000 seconds in a Smith Synthesizer. The reaction was cooled using 40 psi pressurized air, the solvents were evaporated, and the residue was purified using flash chromatography eluting with hexane:ethyl acetate (1:1). The title product (84 mg) was obtained at 65% yield. MS (DCI/NH$_3$) m/z: 811.37 (M+H)$^+$. $^1$H NMR (400 MHz, DMSO-D$_6$) δ ppm 3.57 (s, 3H) 3.73 (s, 6H) 3.75 (s, 6H) 3.76 (s, 2H) 3.78 (s, 3H) 6.51 (s, 1H) 6.79 (s, 1H) 6.92-6.96 (m, 8H) 7.12 (s, 1H) 7.14 (d, J=8.90 Hz, 4H) 7.21 (s, 1H) 7.25 (d, J=8.59 Hz, 4H) 7.64 (d, J=8.29 Hz, 2H) 7.75 (d, J=8.59 Hz, 2H) 7.99 (s, 1H) 8.14 (s, 1H).

EXAMPLE 170F 6,7-dimethoxy-3-[4-(1H-pyrazol-4-yl)phenyl]-1,4-dihydroindeno[1,2-c]pyrazole Example 170E (60 mg, 0.078 mmol) was treated with 4 M HCl in dioxane (5 mL). The reaction was stirred overnight and concentrated. The residue was washed with a mixture of hexane and ethyl acetate to give light yellow product. MS (DCI/NH$_3$) m/z: 359.07 (M+H)$^+$. $^1$H NMR (400 MHz, DMSO-D$_6$) δ ppm 3.82 (s, 2H) 3.83 (s, 3H) 3.85 (s, 3H) 7.25 (s, 1H) 7.27 (s, 1H) 7.76 (d, J=8.29 Hz, 2H) 7.81 (d, J=8.29 Hz, 2H) 8.16 (s, 2H).

EXAMPLE 171

4'-(6,7-dimethoxy-1,4-dihydroindeno[1,2-c]pyrazol-3-yl)-1,1'-biphenyl-4-yl 1,4'-bipiperidine-1'-carboxylate

EXAMPLE 171A

4'-{1-[bis(4-methoxyphenyl)methyl]-6,7-dimethoxy-1,4-dihydroindeno[1,2-c]pyrazol-3-yl}-1,1'-biphenyl-4-ol The desired product was prepared using the procedure in Example 166B replacing Example 166A with Example 170C. However, the product was purified by flash chromatography instead of HPLC. The title product (168 mg) was obtained at 82% yield. MS (DCI/NH$_3$) m/z: 611.24 (M+H)$^+$.

EXAMPLE 171B

4'-{1-[bis(4-methoxyphenyl)methyl]-6,7-dimethoxy-1,4-dihydroindeno[1,2-c]pyrazol-3-yl}-1,1'-biphenyl-4-yl 1,4'-bipiperidine-1'-carboxylate Example 171A (150 mg, 0.25 mmol) in pyridine (4 mL) was treated with [1,4']bipiperidinyl-1'-carbonyl chloride (190 mg, 3 mmol) and stirred for 3 days. Reaction mixture was poured into water and extracted with dichloromethane and ethyl acetate. The organic layer was dried over MgSO$_4$, and evaporated. The residue was purified by flash chromatography eluting with ethyl acetate:MeOH:NH$_4$OH (100:5:0.5). The title compound (160 mg) was obtained at 81% yield.

EXAMPLE 171C

4'-(6,7-dimethoxy-1,4-dihydroindeno[1,2-c]pyrazol-3-yl)-1,1'-biphenyl-4-yl 1,4'-bipiperidine-1'-carboxylate Example 171B (90 mg, 0.11 mmol) in dichloromethane was treated with TFA (4.5 mL), and the reaction was stirred overnight and concentrated. The residue was purified by preparative HPLC. The title product (50 mg) was obtained at 56% yield. MS (DCI/NH$_3$) m/z: 579.30 (M+H)$^+$. $^1$H NMR (500 MHz, DMSO-D$_6$) δ ppm 1.65-1.73 (m, 6H) 1.86-1.89 (m, 2H) 2.08-2.10 (m, 2H) 2.93-3.02 (m, 4H) 3.09 (m, 1H) 3.43-3.49 (m, 4H) 3.81 (s, 2H) 3.83 (s, 3H) 3.85 (s, 3H) 7.23-7.26 (m, 4H) 7.77 (d, J=8.54 Hz, 2H) 7.81 (d, J=8.54 Hz, 2H) 7.89 (J=8.86 Hz, 2H) 9.11 (s, 1H).

EXAMPLE 172

3-(4-bromophenyl)-7-methoxy-1,4-dihydroindeno[1,2-c]pyrazol-6-ol

EXAMPLE 172A 5-hydroxy-6-methoxyindan-1-one 5,6-Dimethoxy-1-indanone (1 g, 5.20 mmol) and NaCN (2.55 g, 52 mmol) were combined in DMSO (10 mL). The reaction was stirred at 100° C. for two days, cooled, diluted with water and extracted with dichloromethane. The aqueous solution was acidified with concentrated HCl, and extracted with dichloromethane. The organic layer was dried over MgSO$_4$ and evaporated to give the title compound (500 mg). MS (DCI/NH$_3$) m/z: 178.99 (M+H)$^+$. $^1$H NMR (500 MHz, CD$_2$Cl$_2$) δ ppm 2.59 (t, J=5.62 Hz, 2H) 3.01 (t, J=5.62 Hz, 2H) 3.93 (s, 3H) 6.33 (s, 1H) 6.95 (s, 1H) 7.17 (s, 1H).

EXAMPLE 172B 6-methoxy-5-[(4-methoxybenzyl)oxy]indan-1-one

Example 172A (1.4 g, 7.86 mmol), 4-methoxybenzyl chloride (2.13 g, 15.72 mmol), Na$_2$CO$_3$ (1.67 g, 15.72) and sodium iodide (1.18 g, 7.86) were combined in acetone (50 mL). The reaction was stirred for 3 days, and then the solvent was removed. The residue was mixed with water (300 mL) and ethyl acetate (100 mL). The precipitate was collected by filtration, washed with a mixture of hexane and ethyl acetate (2:1) and dried to give the title product (1.4 g). MS (DCI/NH$_3$) m/z: 299.14 (M+H)$^+$.

EXAMPLE 172C 2-(4-bromobenzoyl)-6-methoxy-5-[(4-methoxybenzyl)oxy]indan-1-one Example 172B (1.2 g, 4.0 mmol) in 40 mL of THF was treated with NaH (60%, 240 mg, 6.0 mmol). After the addition of Example 64A (1.31 g), the reaction mixture was stirred overnight and poured into ice water. The resulting mixture was acidified with concentrated HCl. The precipitate was collected by filtration and recrystallized from ethanol. The title product (1.7 g) was obtained at 88% yield. MS (DCI/NH$_3$) m/z: 481.04 (M+H)$^+$.

EXAMPLE 172D 3-(4-bromophenyl)-7-methoxy-6-[(4-methoxybenzyl)oxy]-1,4-dihydroindeno[1,2-c]pyrazole The desired product was prepared using the procedure in Example 165C replacing Example 165B with Example 172C. The title compound (1.45 g) was obtained at 92% yield. MS (DCI/NH$_3$) m/z: 479.05 (M+H)$^+$.

EXAMPLE 172E 3-(4-bromophenyl)-7-methoxy-1,4-dihydroindeno[1,2-c]pyrazol-6-ol Example 172D (280 mg, 0.59 mmol) in HOAc (35 mL) was heated at 90° C. for 24 hours, and the solvent was evaporated. The residue was triturated with a mixture of hexane and ethyl acetate to give the title product (220 mg) at 90% yield. MS (DCI/NH$_3$) m/z: 357.98 (M+H)$^+$. $^1$H NMR (500 MHz, DMSO-D$_6$) δ ppm 3.69 (s, 2H) 3.85 (s, 3H) 7.01 (s, 1H) 7.20 (s, 1H) 7.67 (d, J=8.42 Hz, 2H) 7.73 (d, J=8.42 Hz, 2H).

EXAMPLE 173

3-(4'-hydroxy-1,1'-biphenyl-4-yl)-7-methoxy-1,4-dihydroindeno[1,2-c]pyrazol-6-ol The desired product was prepared using the procedure in Example 166B replacing Example 166A with Example 172E. MS (DCI/NH$_3$) m/z: 371.14 (M+H)$^+$. $^1$H NMR (400 MHz, DMSO-D$_6$) δ ppm 3.72 (s, 2H) 3.84 (s, 3H) 6.86 (d, J=8.59 Hz, 2H) 7.00 (s, 1H) 7.20 (s, 1H) 7.55 (d, J=8.59 Hz, 1H) 7.69 (d, J=8.59 Hz, 2H) 7.80 (d, J=8.59 Hz, 2H) 8.96 (s, 1H) 9.53 (s, 1H).

EXAMPLE 174

3-(4'-hydroxy-3'-methoxy-1,1'-biphenyl-4-yl)-7-methoxy-1,4-dihydroindeno[1,2-c]pyrazol-6-ol The desired product was prepared using the procedure in Example 164 replacing Example 64C with Example 172E. MS (DCI/NH$_3$) m/z: 400.14 (M+H)$^+$. $^1$H NMR (500 MHz, DMSO-D$_6$) δ ppm 3.73 (s, 2H) 3.86 (s, 3H) 3.88 (s, 3H) 6.87 (d, J=8.11 Hz, 1H) 7.02 (s, 1H) 7.15 (dd, J=8.11, 2.18 Hz, 1H) 7.21 (s, 1H) 7.26 (d, J=1.87 Hz, 1H) 7.74 (d, J=8.42 Hz, 2H) 7.81 (d, J=8.42 Hz, 2H) 9.00 (s, 1H) 9.12 (s, 1H).

EXAMPLE 175

4'-[7-methoxy-6-(pyridin-2-ylmethoxy)-1,4-dihydroindeno[1,2-c]pyrazol-3-yl]-1,1'-biphenyl-4-ol

EXAMPLE 175A 5-(benzyloxy)-6-methoxyindan-1-one

Example 172A (15 g, 84.3 mmol), benzyl bromide (15 mL, 126.3 mmol), and $K_2CO_3$ (23.25 g, 168.5 mmol) were combined in acetone (50 mL). The reaction was stirred for 2 days, and the inorganic salt was removed by filtration. The filtrate was concentrated, and the residue was recrystallized from a mixture of hexane and ethyl acetate to give the title product (17.1 g) at 76% yield. MS (DCI/$NH_3$) m/z: 269.11 $(M+H)^+$.

EXAMPLE 175B 5-(benzyloxy)-2-(4-bromobenzoyl)-6-methoxyindan-1-one

The desired product was prepared using the procedure in Example 172C replacing Example 172B with Example 175A. MS (DCI/$NH_3$) m/z: 450.98 $(M+H)^+$.

EXAMPLE 175C 6-(benzyloxy)-3-(4-bromophenyl)-7-methoxy-1,4-dihydroindeno[1,2-c]pyrazole The desired product was prepared using the procedure in Example 165C replacing Example 165B with Example 175B. MS (DCI/$NH_3$) m/z: 449.08 $(M+H)^+$.

EXAMPLE 175D 6-(benzyloxy)-3-(4-bromophenyl)-7-methoxy-1-{[2-(trimethylsilyl)ethoxy]methyl}-1,4-dihydroindeno[1,2-c]pyrazole To a suspension of NaH (60%, 1.21 g, 30.25 mmol) in DMF (150 mL) was added Example 175C (12.3 g, 27.50 mmol). The mixture was stirred for 30 min and then SEMCl (5.35 mL, 30.25 mmol) was added dropwise. The reaction was stirred for 2 hours and poured into ice-water. The precipitate was collected by filtration and dried to give the title product (15.0 g) at 94% yield.

EXAMPLE 175E

4'-(6-(benzyloxy)-7-methoxy-1-{[2-(trimethylsilyl)ethoxy]methyl}-1,4-dihydroindeno[1,2-c]pyrazol-3-yl)-1,1'-biphenyl-4-ol The desired product was prepared using the procedure in Example 166B replacing Example 166A with Example 175D. MS (DCI/$NH_3$) m/z: 591.27 $(M+H)^+$.

EXAMPLE 175F 6-(benzyloxy)-7-methoxy-3-(4'-{[2-(trimethylsilyl)ethoxy]methyl}-1,1'-biphenyl-4-yl)-1-{[2-(trimethylsilyl)ethoxy]methyl}-1,4-dihydroindeno[1,2-c]pyrazole Example 175E (2.97 g, 5.03 mmol) was treated with NaH (60%, 221 mg, 5.53 mmol) in DMF for 1 hour, and then SEMCl (0.98 mL, 5.53 mmol) was added dropwise. The reaction was stirred at room temperature for 1 hour, poured into ice water, and extracted with ethyl acetate. The organic layer was dried over $MgSO_4$, and concentrated. The residue was purified by flash chromatography eluting with hexane:ethyl acetate (4:1). The title product (3.02 g) was obtained at 88% yield. MS (DCI/$NH_3$) m/z: 721.35 $(M+H)^+$.

EXAMPLE 175G 7-methoxy-3-(4'-{[2-(trimethylsilyl)ethoxy]methoxy}-1,1'-biphenyl-4-yl)-1-{[2-(trimethylsilyl)ethoxy]methyl}-1,4-dihydroindeno[1,2-c]pyrazol-6-ol Example 175F (3.0 g, 4.16 mmol) and Pd/C (10%, 443 mg, 0.416 mmol) were combined in THF (350 mL) and stirred under hydrogen atmosphere for 4 days. The solid was removed by filtration through Celite. The filtrate was concentrated, and the residue was purified by flash chromatography eluting with hexane:ethyl acetate (2:1). The title product (2.3 g) was obtained at 88% yield. MS (DCI/$NH_3$) m/z: 631.24 $(M+H)^+$.

EXAMPLE 175H

4'-[7-methoxy-6-(pyridin-2-ylmethoxy)-1,4-dihydroindeno[1,2-c]pyrazol-3-yl]-1,1'-biphenyl-4-ol Example 175G (50 mg, 0.0792 mmol), $Cs_2CO_3$ (103 mg, 0.317 mmol) and 2-chloromethylpyridine.HCl (14.3 mg, 0.087 mmol) were combined in DMF (2 mL). The reaction mixture was purged with a stream of nitrogen, stirred at 50° C. under nitrogen atmosphere overnight and concentrated. The residue was suspended in methanol (2 mL), treated with 4N HCl in dioxane (2 mL) and heated at 50° C. for 5 hours. Solvent was removed, and the residue was purified by preparative HPLC to give the title compound (11.6 mg, 2TFA salt) at 22.3% yield.

Examples 176 to 188 represented by FIG. (IX) and shown in Table 9 were synthesized in a similar fashion as described in Example 175H, except substituting the appropriate organic chloride or bromide for 2-chloromethylpyridine.HCl.

TABLE 9

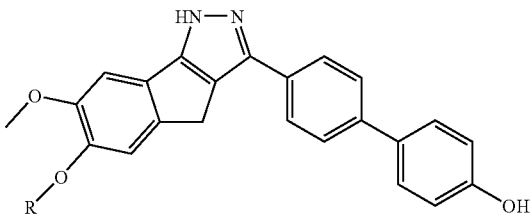

FIG. (IX)

| Example | R | ¹H NMR | MS | Yield |
|---|---|---|---|---|
| 175H | 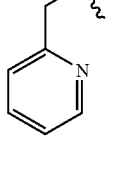 | ¹H NMR (500 MHz, DMSO-D₆) δ ppm 3.91 (s, 2H) 3.98 (s, 3H) 5.50 (s, 2H) 6.97 (d, J=8.42 Hz, 2H) 7.45 (s, 1H) 7.46 (s, 1H) 7.66 (d, J=8.42 Hz, 2H) 7.81 (d, J=8.42 Hz, 2H) 7.85 (t, J=7.64 Hz, 1H) 7.94 (d, J=8.42 Hz, 2H) 8.02 (d, J=7.80 Hz, 1H) 8.40 (t, J=7.64 Hz, 1H) 8.89 (d, J=4.99 Hz, 1H) | (DCI/NH₃) 462.16 (M + H)⁺ | 11.6 mg 27.3% |
| 176 | 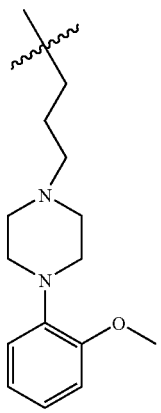 | ¹H NMR (500 MHz, DMSO-D₆) δ ppm 3.77 (s, 2H) 3.90 (s, 3H) 5.36 (s, 2H) 6.86 (d, J=8.42 Hz, 2H) 7.30 (s, 1H) 7.33 (s, 1H) 7.55 (d, J=8.42 Hz, 2H) 7.70 (d, J=8.42 Hz, 2H) 7.78 (d, J=5.61 Hz, 2H) 7.81 (d, J=8.42 Hz, 2H) 8.75 (d, J=6.24 Hz, 2H) | (DCI/NH₃) 462.15 (M + H)⁺ | 10.5 mg 20.2% |
| 177 | 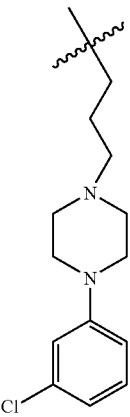 | ¹H NMR (500 MHz, DMSO-D₆) δ ppm 2.19-2.24 (m, 2H) 2.95 (t, J=11.54 Hz, 2H) 3.23-3.29 (m, 2H) 3.35-3.42 (m, 2H) 3.55-3.58 (m, 2H) 3.66-3.68 (m, 2H) 3.80 (s, 2H) 3.81 (s, 3H) 3.88 (s, 3H) 4.14 (t, J=5.77 Hz, 2H) 6.87 (d, J=8.42 Hz, 2H) 6.92-7.04 (m, 4H) 7.27 (s, 1H) 7.30 (s, 1H) 7.57 (d, J=8.73 Hz, 2H) 7.72 (d, J=8.42 Hz, 2H) 7.83 (d, J=8.42 Hz, 2H) | (DCI/NH₃) 603.15 (M + H)⁺ | 15.4 mg 21.7% |
| 178 | | ¹H NMR (500 MHz, DMSO-D₆) δ ppm 2.18-2.24 (m, 2H) 3.00-3.10 (m, 2H) 3.20 (s, br, 2H) 3.33-3.43 (m, 2H) 3.62-3.71 (m, 2H) 3.80 (s, 2H) 3.88 (s, 3H) 3.91-4.00 (m, 2H) 4.14 (t, J=5.77 Hz, 2H) 6.87-6.90 (m, 4H) 6.99 (dd, J=8.42, 1.87 Hz, 2H) 7.24 (d, J=1.87 Hz, 1H) 7.26 (s, 1H) 7.30 (s, 1H) 7.57 (d, J=8.42 Hz, 2H) 7.72 (d, J=8.42 Hz, 2H) 7.83 (d, J=8.42 Hz, 2H) | (DCI/NH₃) 607.25 (M + H)⁺ | 9.7 mg 13.7% |

TABLE 9-continued

FIG. (IX)

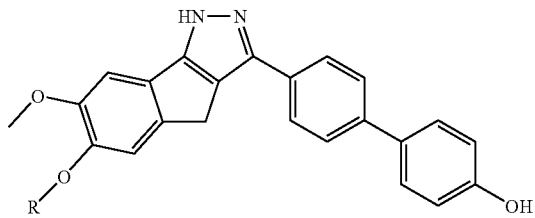

| Example | R | ¹H NMR | MS | Yield |
|---|---|---|---|---|
| 179 | (CH₂CH₂N(CH₃)₂ group) | ¹H NMR (500 MHz, DMSO-D₆) δ ppm 2.93 (s, 3H) 2.94 (s, 3H) 3.51-3.57 (m, 2H) 3.81 (s, 2H) 3.89 (s, 3H) 4.36 (t, J=4.68 Hz, 2H) 6.87 (d, J=8.42 Hz, 2H) 7.33 (s, 1H) 7.34 (s, 1H) 7.57 (d, J=8.42 Hz, 2H) 7.72 (d, J=8.42 Hz, 2H) 7.83 (d, J=8.42 Hz, 2H) | (DCI/NH₃) 442.20 (M + H)⁺ | 16.5 mg 32.7% |
| 180 | (CH₂CH₂-piperidinyl group) | ¹H NMR (500 MHz, DMSO-D₆) δ ppm 1.37-1.45 (m, 1H) 1.68-1.76 (m, 3H) 1.85-1.88 (m, 2H) 3.04-3.11 (m, 2H) 3.52 (m, 2H) 3.61-3.63 (m, 2H) 3.81 (s, 2H) 3.89 (s, 3H) 4.37 (t, J=4.68 Hz, 2H) 6.87 (d, J=8.73 Hz, 2H) 7.33 (s, 1H) 7.34 (s, 1H) 7.57 (d, J=8.42 Hz, 2H) 7.72 (d, J=8.11 Hz, 2H) 7.83 (d, J=8.42 Hz, 2H). | (DCI/NH₃) 482.24 (M + H)⁺ | 11.3 mg 21.1% |
| 181 | (CH₂CH₂CH₂-piperidinyl group) | ¹H NMR (500 MHz, DMSO-D₆) δ ppm 1.37-1.45 (m, 1H) 1.62-1.73 (m, 3H) 1.84-1.87 (m, 2H) 2.14-2.19 (m, 2H) 2.90-2.97 (m, 2H) 3.20-3.29 (m, 2H) 3.51-3.53 (m, J=11.54 Hz, 2H) 3.79 (s, 2H) 3.87 (s, 3H) 4.11 (t, J=5.77 Hz, 2H) 6.87 (d, J=8.42 Hz, 2H) 7.25 (s, 1H) 7.29 (s, 1H) 7.56 (d, J=8.73 Hz, 2H) 7.71 (d, J=8.42 Hz, 2H) 7.83 (d, J=8.11 Hz, 2H). | (DCI/NH₃) 496.25 (M + H)⁺ | 12.6 mg 18.3% |
| 182 | (isobutyl N(CH₃)₂ group) | ¹H NMR (500 MHz, DMSO-D₆) δ ppm 1.21 (d, J=6.24 Hz, 2H) 1.36 (d, J=6.86 Hz, 1H) 2.87-2.96 (m, 6H) 3.82 (s, 2H) 3.91 (s, 3H) 4.26 (m, 1H) 6.87 (d, J=8.42 Hz, 2H) 7.32-7.37 (m, 2H) 7.57 (d, J=8.73 Hz, 2H) 7.72 (d, J=8.42 Hz, 2H) 7.83 (d, J=8.73 Hz, 2H) | (DCI/NH₃) 456.24 (M + H)⁺ | 11.9 mg 23.1% |
| 183 | (CH₂CH₂-(N-methylpyrrolidinyl) group) | ¹H NMR (500 MHz, DMSO-D₆) δ ppm 1.91-2.03 (m, 3H) 2.12 (m, 1H) 2.82~2.86 (m, 3H) 3.04-3.20 (m, 2H) 3.35-3.56 (m, 4H) 3.86 (s, 2H) 3.87 (s, 3H) 4.64 (m, 1H) 6.87 (d, J=8.73 Hz, 2H) 7.25 (d, J=3.12 Hz, 1H) 7.30 (s, 1H) 7.56 (d, J=8.73 Hz, 2H) 7.71 (d, J=8.73 Hz, 2H) 7.82 (d, J=8.42 Hz, 2H) | (DCI/NH₃) 482.21 (M + H)⁺ | 12.3 mg 23.0% |

TABLE 9-continued

FIG. (IX)

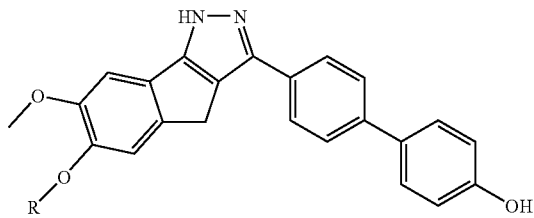

| Example | R | ¹H NMR | MS | Yield |
|---|---|---|---|---|
| 184 | (CH₂CH₂-imidazol-1-yl) | ¹H NMR (500 MHz, DMSO-D₆) δ ppm 3.78 (s, 2H) 3.83 (s, 3H) 4.42 (t, J=4.83 Hz, 2H) 4.63 (t, J=4.83 Hz, 2H) 6.87 (d, J=8.42 Hz, 2H) 7.24 (s, 1H) 7.28 (s, 1H) 7.56 (d, J=8.42 Hz, 2H) 7.70-7.72 (m, 3H) 7.82 (d, J=8.42 Hz, 2H) 7.84 (m, 1H) 9.16 (s, 1H). | (DCI/NH₃) 465.08 (M + H)⁺ | 9.8 mg 22.0% |
| 185 | (CH₂CH₂-morpholin-4-yl) | ¹H NMR (500 MHz, DMSO-D₆) δ ppm 3.60 (s, br, 2H) 3.73 (s, br, 2H) 3.80 (s, 2H) 3.88 (s, 3H) 3.95 (s, 2H) 4.01 (s, br, 2H) 4.37-4.38 (m, 2H) 6.86 (d, J=8.73 Hz, 2H) 7.33 (s, 2H) 7.56 (d, J=8.42 Hz, 2H) 7.71 (d, J=8.42 Hz, 2H) 7.82 (d, J=8.42 Hz, 2H). | (DCI/NH₃) 484.23 (M + H)⁺ | 11 mg 24% |
| 186 | (CH₂CH₂CH₂-N(CH₃)₂) | ¹H NMR (500 MHz, DMSO-D₆) δ ppm 2.10-2.16 (m, 2H) 2.84 (s, 3H) 2.85 (s, 3H) 3.24-3.28 (m, 2H) 3.78 (s, 2H) 3.87 (s, 3H) 4.09-4.11 (m, 2H) 6.86 (d, J=8.42 Hz, 2H) 7.24 (s, 1H) 7.28 (s, 1H) 7.55 (d, J=8.42 Hz, 2H) 7.70 (d, J=8.42 Hz, 2H) 7.82 (d, J=8.11 Hz, 2H) | (DCI/NH₃) 456.23 (M + H)⁺ | 16 mg 31% |
| 187 | (CH₂CH₂-pyrrolidin-1-yl) | ¹H NMR (500 MHz, DMSO-D₆) δ ppm 1.90-1.91 (m, 2H) 2.03-2.05 (m, 2H) 3.12-3.21 (m, J=6.86 Hz, 2H) 3.61 (d, J=4.05 Hz, 2H) 3.67-3.69 (m, 2H) 3.80 (s, 2H) 3.89 (s, 3H) 4.31-4.33 (m, 2H) 6.86 (d, J=8.73 Hz, 2H) 7.32 (s, 1H) 7.33 (s, 1H) 7.56 (d, J=8.73 Hz, 2H) 7.71 (d, J=8.11 Hz, 2H) 7.82 (d, J=8.11 Hz, 2H). | (DCI/NH₃) 468.24 (M + H)⁺ | 8.1 mg 15.5% |
| 188 | (CH₂CH₂-N(Et)₂) | ¹H NMR (500 MHz, DMSO-D₆) δ ppm 1.22-1.28 (m, 6H) 3.25-3.31 (m, 4H) 3.53-3.56 (m, 2H) 3.80 (s, 2H) 3.88 (s, 3H) 4.33-4.35 (m, 2H) 6.86 (d, J=8.73 Hz, 2H) 7.31 (s, 1H) 7.32 (s, 1H) 7.56 (d, J=8.42 Hz, 2H) 7.71 (d, J=8.42 Hz, 2H) 7.82 (d, J=8.42 Hz, 2H). | (DCI/NH₃) 470.27 (M + H)⁺ | 11.6 mg 22.0% |

EXAMPLE 189

4'-[7-methoxy-6-(pyridin-3-ylmethoxy)-1,4-dihydroindeno[1,2-c]pyrazol-3-yl]-1,1'-biphenyl-4-ol Example 175G (50 mg, 0.0792 mmol), di-tert-butyl azodicarboxylate (44 mg, 0.19 mmol), polymer-supported $Ph_3P$ (3 mmol/g, 63 mg, 0.19 mmol) and pyridin-3-yl-methanol (22 mg, 0.20 mmol) were combined in THF (3 mL). The reaction was stirred at room temperature for 3 days, and the insoluble material was removed by filtration and washed with THF thoroughly. The filtrate was concentrated, and the residue was suspended in methanol (2 mL), treated with 4N HCl in dioxane (2 mL) and heated at 50° C. for 5 hours. The precipitate was collected by filtration to give the title compound. The filtrate was concentrated, and the residue was purified by HPLC to give another portion of the title compound.

Examples 190 to 204 represented by FIG. (X) and shown in Table 10 were synthesized in a similar fashion as described in Example 189, except substituting the appropriate alcohol for pyridin-3-yl-methanol.

TABLE 10

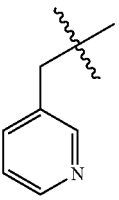

FIG. (X)

| Example | R | $^1$H NMR | MS | Yield |
|---|---|---|---|---|
| 189 | 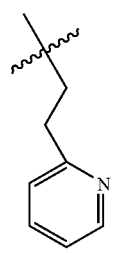 | $^1$H NMR (400 MHz, DMSO-D$_6$) δ ppm 3.92 (s, 2H) 3.98 (s, 3H) 5.47 (s, 2H) 6.98 (d, J=8.59 Hz, 2H) 7.45 (s, 1H) 7.48 (s, 1H) 7.66 (d, J=8.59 Hz, 2H) 7.82 (d, J=8.59 Hz, 2H) 7.94 (d, J=8.59 Hz, 2H) 8.18 (dd, J=7.98, 5.52 Hz, 1H) 8.72 (d, J=8.29 Hz, 1H) 9.00 (d, J=4.91 Hz, 1H) 9.10 (d, J=1.53 Hz, 1H). | (DCI/NH$_3$) 462.14 (M + H)$^+$ | 18.6 mg 43.9% |
| 190 | 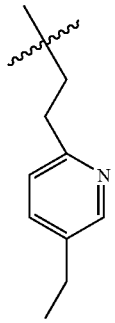 | $^1$H NMR (400 MHz, DMSO-D$_6$) δ ppm 3.40 (t, J=6.29 Hz, 2H) 3.78 (s, 2H) 3.79 (s, 3H) 4.43 (t, J=6.44 Hz, 2H) 6.87 (d, J=8.59 Hz, 2H) 7.25 (s, 2H) 7.56 (d, J=8.59 Hz, 2H) 7.68 (d, J=6.44 Hz, 1H) 7.71 (d, J=8.29 Hz, 2H) 7.82 (d, J=8.29 Hz, 2H) 7.85 (d, J=9.21 Hz, 1H) 8.25 (t, J=7.98 Hz, 1H) 8.75 (d, J=5.52 Hz, 1H) | (DCI/NH$_3$) 476.20 (M + H)$^+$ | 20.1 mg 38.3% |
| 191 | 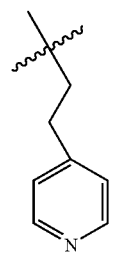 | $^1$H NMR (400 MHz, DMSO-D$_6$) δ ppm 1.25 (t, J=7.52 Hz, 3H) 2.80 (q, J=7.36 Hz, 2H) 3.48 (t, J=6.14 Hz, 2H) 3.78 (s, 5H) 4.45 (t, J=6.14 3.78 (s, 5H) 4.45 (t, J=6.14 Hz, 2H) 6.88 (d, J=8.59 Hz, 2H) 7.25 (s, 1H) 7.26 (s, 1H) 7.56 (d, J=8.59 Hz, 2H) 7.71 (d, J=8.59 Hz, 2H) 7.83 (d, J=8.59 Hz, 2H) 8.02 (d, J=8.59 Hz, 1H) 8.44 (d, J=6.75 Hz, 1H) 8.76 (d, J=1.84 Hz, 1H) | (DCI/NH$_3$) 504.2 (M + H)$^+$ | 19.7 mg 43.1% |
| 192 | | $^1$H NMR (400 MHz, DMSO-D$_6$) δ ppm 3.40 (t, J=6.14 Hz, 2H) 3.79 (s, 2H) 3.82 (s, 3H) 4.42 (t, J=6.14 Hz, 2H) 6.88 (d, J=8.90 Hz, 2H) 7.27 (s, 2H) 7.57 (d, J=8.90 Hz, 2H) 7.72 (d, J=8.59 Hz, 2H) 7.83 (d, J=8.59 Hz, 2H) 8.11 (d, J=6.44 Hz, 2H) 8.88 (d, J=6.75 Hz, 2H). | (DCI/NH$_3$) 476.13 (M + H)$^+$ | 15.3 mg 35.2% |

TABLE 10-continued

FIG. (X)

| Example | R | ¹H NMR | MS | Yield |
|---|---|---|---|---|
| 193 | (CH with two CH₂OH groups) | ¹H NMR (500 MHz, CD₃OD) δ ppm 3.81-3.83 m, 6H) 3.95 (s, 3H) 4.32 (m, 1H) 6.89 (d, J=8.73 Hz, 2H) 7.38 (s, 1H) 7.39 (s, 1H) 7.53 (d, J=8.73 Hz, 2H) 7.70 (d, J=8.73 Hz, 2H) 7.82 (d, J=8.42 Hz, 2H) | (DCI/NH₃) 445.1 (M + H)⁺ | 9.6 mg 22.4% |
| 194 | (CH₂-CH(OH)-CH₂OH, stereochem.) | ¹H NMR (500 MHz, CD₃OD) δ ppm 3.69 (dd, J=11.38, 5.46 Hz, 1H) 3.74 (m, 1H) 3.83 (s, 2H) 3.94 (s, 3H) 4.02-4.08 (m, 2H) 4.15 (dd, J=9.36, 4.37 Hz, 1H) 6.89 (d, J=8.42 Hz, 2H) 7.29 (s, 1H) 7.35 (s, 1H) 7.53 (d, J=8.73 Hz, 2H) 7.70 (d, J=8.42 Hz, 2H) 7.82 (d, J=8.42 Hz, 2H) | (DCI/NH₃) 445.2 (M + H)⁺ | 7.3 mg 17.0% |
| 195 | (CH₂-CH(OH)-CH₂OH, other stereochem.) | ¹H NMR (500 MHz, CD₃OD) δ ppm 3.70-3.73 (m, 2H) 3.86 (s, 2H) 3.95 (s, 3H) 4.02-4.08 (m, 2H) 4.16 (m, 1H) 6.89 (s, br, 2H) 7.30 (s, 1H) 7.36 (s, 1H) 7.53 (s, br, 2H) 7.71 (s, 2H) 7.82 (s, br, 2H) | (DCI/NH₃) 445.14 (M + H)⁺ | 8.2 mg 19.1% |
| 196 | (propyl-O-propyl-6-methylpyridin-2-yl) | ¹H NMR (400 MHz, DMSO-D₆) δ ppm 1.97-2.04 (m, 2H) 2.67 (s, 3H) 3.02-3.06 (m, 2H) 3.56 (t, J=5.98 Hz, 2H) 3.73-3.75 (m, 2H) 3.79 (s, 2H) 3.84 (s, 3H) 4.10-4.13 (m, 2H) 6.87 (d, J=8.59 Hz, 2H) 7.22 (s, 1H) 7.27 (s, 1H) 7.57 (d, J=8.59 Hz, 2H) 7.70 (d, J=6.14 Hz, 1H) 7.72 (d, J=8.29 Hz, 4H) 7.77 (d, J=7.98 Hz, 1H) 7.82-7.84 (m, 2H) 8.33 (t, J=7.98 Hz, 1H) | (DCI/NH₃) 548.1 (M + H)⁺ | 19.3 mg 32.8% |
| 197 | (CH₂-C(CH₃)(CH₂OH)(CH₂Cl)) | ¹H NMR (500 MHz, DMSO-D₆) δ ppm 1.06 (s, 3H) 3.46 (s, 2H) 3.72 (d, J=8.11 Hz, 2H) 3.78 (s, 2H) 3.86 (s, 3H) 3.89 (s, 2H) 6.87 (d, J=8.73 Hz, 2H) 7.23 (s, 1H) 7.26 (s, 1H) 7.56 (d, J=8.73 Hz, 2H) 7.71 (d, J=8.42 Hz, 2H) 7.82 (d, J=8.42 Hz, 2H). | HRFABMS: 490.1645 (Calc. 490.1659) | 7.7 mg 16.6% |

TABLE 10-continued

FIG. (X)

*[Structure: pyrazole-fused indene core with methoxy and OR substituents on one aromatic ring, and a biphenyl-4-ol substituent]*

| Example | R | ¹H NMR | MS | Yield |
|---|---|---|---|---|
| 198 | *[CH₂-C(=O)-N(CH₂CH₃)₂ group]* | ¹H NMR (500 MHz, DMSO-D₆) δ ppm 1.15 (t, J=7.02 Hz, 3H) 1.27 (t, J=7.02 Hz, 3H) 3.40 (dd, J=14.03, 7.17 Hz, 2H) 3.47 (dd, J=14.35, 7.17 Hz, 2H) 3.88 (s, 2H) 3.96 (s, 3H) 4.89 (s, 2H) 6.97 (d, J=8.73 Hz, 2H) 7.24 (s, 1H) 7.38 (s, 1H) 7.66 (d, J=8.73 Hz, 2H) 7.80 (d, J=8.42 Hz, 2H) 7.93 (d, J=8.42 Hz, 2H) | (DCI/NH₃) 484.20 (M + H)⁺ | 13.6 mg 29.6% |
| 199 | *[CH₂-(tetrahydrofuran-3-yl) group]* | ¹H NMR (500 MHz, DMSO-D₆) δ ppm 1.64 (m, 1H) 1.98 (m, 1H) 2.64 (m, 1H) 3.53 (dd, J=8.73, 5.30 Hz, 2H) 3.62 (dd, J=14.97, 7.80 Hz, 1H) 3.71~3.77 (s, 2H) 3.73 (s, 2H) 3.80 (s, 3H) 3.87 (m, 1H) 3.93 (m, 1H) 6.82 (d, J=8.73 Hz, 2H) 7.20 (s, 1H) 7.21 (s, 1H) 7.51 (d, J=8.73 Hz, 2H) 7.66 (d, J=8.42 Hz, 2H) 7.78 (d, J=8.42 Hz, 2H) | (DCI/NH₃) 455.20 (M + H)⁺ | 10.3 mg 23.6% |
| 200 | *[CH₂-(tetrahydropyran-4-yl) group]* | ¹H NMR (500 MHz, DMSO-D₆) δ ppm 1.55-1.62 (m, 2H) 1.90-1.92 (m, 2H) 3.39-3.43 (m, 2H) 3.73 (s, 2H) 3.81 (s, 3H) 3.82-3.84 (m, 2H) 4.44 (m, 1H) 6.82 (d, J=8.73 Hz, 2H) 7.23 (s, 2H) 7.52 (d, J=8.42 Hz, 2H) 7.66 (d, J=8.42 Hz, 2H) 7.77 (d, J=8.42 Hz, 2H) | (DCI/NH₃) 455.19 (M + H)⁺ | 9.5 mg 21.8% |
| 201 | *[CH₂CH₂-(pyridin-3-yl) group]* | ¹H NMR (500 MHz, DMSO-D₆) δ ppm 3.41 (t, J=6.24 Hz, 2H) 3.88 (s, 2H) 3.93 (s, 3H) 4.44 (t, J=6.24 Hz, 2H) 6.97 (d, J=8.42 Hz, 2H) 7.35 (s, 1H) 7.36 (s, 1H) 7.66 (d, J=8.73 Hz, 2H) 7.81 (d, J=8.73 Hz, 2H) 7.92 (d, J=8.42 Hz, 2H) 8.13 (dd, J=7.95, 5.77 Hz, 1H) 8.69 (d, J=8.11 Hz, 1H) 8.92 (d, J=5.30 Hz, 1H) 9.04 (s, 1H) | (DCI/NH₃) 476.18 (M + H)⁺ | 16.2 mg 37.3% |
| 202 | *[(tetrahydrofuran-3-yl) group]* | ¹H NMR (500 MHz, DMSO-D₆) δ ppm 2.03 (m, 1H) 2.18 D₆) δ ppm 2.03 (m, 1H) 2.18 (m, 1H) 3.75-3.80 (s, 3H) 3.84-3.91 (s, 6H) 5.03 (dd, J=5.93, 4.37 Hz, 1H) 6.87 (d, J=8.73 Hz, 2H) 7.20 (s, 1H) 7.27 (s, 1H) 7.57 (d, J=8.42 Hz, 2H) 7.71 (d, J=8.11 Hz, 2H) 7.82 (d, J=8.11 Hz, 2H) 9.56 (s, 1H) 13.04 (s, 1H) | (DCI/NH₃) 441.15 (M + H)⁺ | 7.8 mg 18.3% |
| 203 | *[CH₂-(cyclohex-3-enyl) group]* | ¹H NMR (500 MHz, DMSO-D₆) δ ppm 1.35-1.41 (m, 1H) 1.83-1.89 (m, 2H) 2.05-2.06 (m, 2H) 2.18 (dd, J=15.91, 4.05 Hz, 1H) 3.79 (s, 2H) 3.84 (s, 3H) 3.91 (m, 1H) 5.66-5.71 (m, 2H) 6.87 (d, J=8.73 Hz, 2H) 7.24 (s, 1H) 7.26 (s, 1H) 7.56 (d, J=8.73 Hz, 2H) 7.71 (d, J=8.42 Hz, 2H) 7.83 (d, J=8.42 Hz, 2H) | (DCI/NH₃) 465.22 (M + H)⁺ | 12.6 mg 28.3% |

TABLE 10-continued

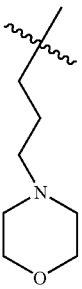

FIG. (X)

| Example | R | ¹H NMR | MS | Yield |
|---|---|---|---|---|
| 204 | (morpholinobutyl group) | ¹H NMR (400 MHz, DMSO-D$_6$) δ ppm 2.31-2.37 (m, 2H) 3.16-3.23 (m, 2H) 3.35-3.39 (m, 2H) 3.57 (d, J=11.97 Hz, 2H) 3.92 (s, 2H) 3.94-3.97 (m, 2H) 3.96 (s, 3H) 4.07 (d, J=9.82 Hz, 2H) 4.22 (t, J=5.98 Hz, 2H) 6.98 (d, J=8.59 Hz, 2H) 7.37 (s, 1H) 7.41 (s, 1H) 7.66 (d, J=8.59 Hz, 2H) 7.82 (d, J=8.29 Hz, 2H) 7.95 (d, J=8.29 Hz, 2H) 11.23 (s, 1H). | (DCI/NH$_3$) 498.13 (M + H)$^+$ | 41.6 mg 92% |

EXAMPLE 205

4-(6-hydroxy-7-methoxy-1,4-dihydroindeno[1,2-c]pyrazol-3-yl)benzonitrile

EXAMPLE 205A 6-methoxy-5-{[2-(trimethylsilyl)ethoxy]methoxy}indan-1-one

Example 172A (1 g, 5.62 mmol) and N,N-diisopropylethylamine (2.94 mL, 16.86 mmol) were combined in dichloromethane and treated with SEMCl (1.49 mL, 8.43 mmol). The reaction mixture was stirred for 1 hour, diluted with dichloromethane, washed with cold water and saturated NaHCO$_3$. The organic layer was dried over MgSO$_4$ and concentrated. The residue was purified by flash chromatography eluting with hexane:ethyl acetate (2:1). The title product (1.3 g) was obtained at 75% yield. MS (DCI/NH$_3$) m/z: 309.1 (M+H)$^+$.

EXAMPLE 205B 4-(1H-imidazol-1-ylcarbonyl)benzonitrile

The desired product was prepared using the procedure in Example 165A replacing 4-benzyloxybenzoic acid with 4-cyanobenzoic acid.

EXAMPLE 205C

4-[(6-methoxy-1-oxo-5-{[2-(trimethylsilyl)ethoxy]methoxy}-2,3-dihydro-1H-inden-2-yl)carbonyl]benzonitrile Example 205A (5.4 g, 17.51 mmol) in 250 mL of THF was treated with NaH (60%, 1.06 g, 26.37 mmol). After the addition of Example 205B (5.2 g, 26.37 mmol), the reaction mixture was stirred overnight and poured into ice water. The resulting mixture was acidified with concentrated HCl. Yellow solid was collected, washed with water and dried. MS (DCI/NH$_3$) m/z: 438.17 (M+H)$^+$.

EXAMPLE 205D 4-(7-methoxy-6-{[2-(trimethylsilyl)ethoxy]methoxy}-1,4-dihydroindeno[1,2-c]pyrazol-3-yl)benzonitrile The desired product was prepared using the procedure in Example 165C replacing Example 165B with Example 205C. The title compound (6.5 g) was obtained at 88% yield. MS (DCI/NH$_3$) m/z: 434.19 (M+H)$^+$. ¹H NMR (500 MHz, DMSO-D$_6$) δ ppm 0.00 (s, 9H) 0.92 (t, J=8.11 Hz, 2H) 3.77 (t, J=8.11 Hz, 2H) 3.81 (s, 2H) 3.86 (s, 3H) 5.24 (s, 2H) 7.32 (s, 2H) 7.96 (s, 4H) 13.32 (s, 1H).

EXAMPLE 205E 4-(7-methoxy-6-{[2-(trimethylsilyl)ethoxy]methoxy}-1-{[2-(trimethylsilyl)ethoxy]methyl}-1,4-dihydroindeno[1,2-c]pyrazol-3-yl)benzonitrile The desired product was prepared using the procedure in Example 175D replacing Example 175C with Example 205D. The title compound (6.5 g) was obtained at 83% yield. MS (DCI/NH$_3$) m/z: 564.28 (M+H)$^+$.

EXAMPLE 205F 4-(6-hydroxy-7-methoxy-1,4-dihydroindeno[1,2-c]pyrazol-3-yl)benzonitrile Example 205E (50 mg, 0.089 mmol) in ethanol (2 mL) was treated with 4N HCl in dioxane (2 mL) and heated at 50° C. for 5 hours. The precipitate was collected by filtration to give the title compound (22 mg) at 82% yield. MS (DCI/NH$_3$) m/z: 304.06 (M+H)$^+$. ¹H NMR (400 MHz, DMSO-D$_6$) δ ppm 3.74 (s, 2H) 3.84 (s, 3H) 7.01 (s, 1H) 7.20 (s, 1H) 7.93 (s, 4H).

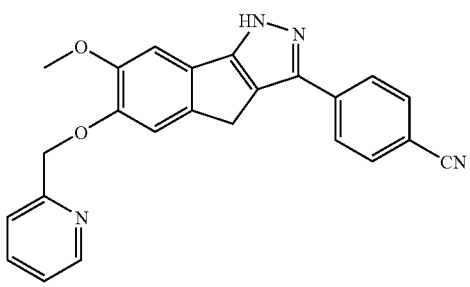

EXAMPLE 206

4-[7-methoxy-6-(pyridin-2-ylmethoxy)-1,4-dihydroindeno[1,2-c]pyrazol-3-yl]benzonitrile

EXAMPLE 206A 4-(6-hydroxy-7-methoxy-1-{[2-(trimethylsilyl)ethoxy]methyl}-1,4-dihydroindeno[1,2-c]pyrazol-3-yl)benzonitrile Example 205E (1.5 g, 2.66 mmol) in ethanol (40 mL) was treated with 4N HCl in dioxane (1 mL). The reaction was stirred at room temperature for 30 min. The precipitate was collected by filtration to give the title compound (0.98 g) at 85% yield. MS (DCI/NH$_3$) m/z: 434.21 (M+H)$^+$.

EXAMPLE 206B

4-[7-methoxy-6-(pyridin-2-ylmethoxy)-1,4-dihydroindeno[1,2-c]pyrazol-3-yl]benzonitrile Example 206A (50 mg, 0.115 mmol), di-tert-butyl azodicarboxylate (53.1 mg, 0.23 mmol), polymer-supported Ph$_3$P (3 mmol/g, 77 mg, 0.23 mmol) and pyridin-2-yl-methanol (25.2 mg, 0.23 mmol) were combined in THF (3 mL). The reaction was stirred at room temperature overnight, and the insoluble material was removed by filtration and washed with THF thoroughly. The filtrate was concentrated, and the residue was suspended in methanol (2 mL), treated with 4N HCl in dioxane (2 mL) and heated at 50° C. for 5 hours. The reaction mixture was concentrated, and the residue was purified by preparative HPLC to give the title compound (32.4 mg) at 71% yield.

Examples 207 to 219 represented by FIG. (XI) and shown in Table 11 were synthesized in a similar fashion as described in Example 206B, except substituting the appropriate alcohol for pyridin-3-yl-methanol.

TABLE 11

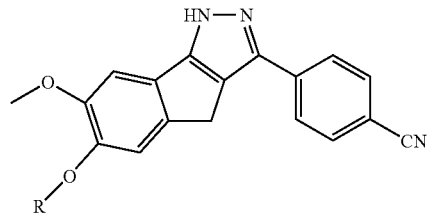

FIG. (XI)

| Example | R | $^1$H NMR | MS | Yield |
|---|---|---|---|---|
| 206B | ![pyridin-2-ylmethyl] | $^1$H NMR (500 MHz, DMSO-D$_6$) δ ppm 3.80 (s, 2 H) 3.89 (s, 3 H) 5.26 (s, 2 H) 7.31 (s, 1 H) 7.33 (s, 1 H) 7.47 (dd, J=7.02, 5.49 Hz, 1 H) 7.67 (d, J=7.93 Hz, 1 H) 7.96 (s, 3 H) 7.96 (m, 1 H) 7.99 (m, 1 H) 8.65 (d, J=4.27 Hz, 1 H) | (ESI) 395.7 (M + H)$^+$ | 32.4 mg 48% |
| 207 | ![pyridin-3-ylmethyl] | $^1$H NMR (400 MHz, DMSO-D$_6$) δ ppm 3.81 (s, 2 H) 3.86 (s, 3 H) 5.26 (s, 2 H) 7.30 (s, 1 H) 7.35 (s, 1 H) 7.71 (dd, J=7.67, 5.22 Hz, 1 H) 7.95 (s, 4 H) 8.20 (d, J=7.98 Hz, 1 H) 8.70 (dd, J=5.06, 1.38 Hz, 1 H) 8.82 (d, J=1.23 Hz, 1 H). | (DCI/NH$_3$) 395.13 (M + H)$^+$ | 29 mg 43% |

TABLE 11-continued

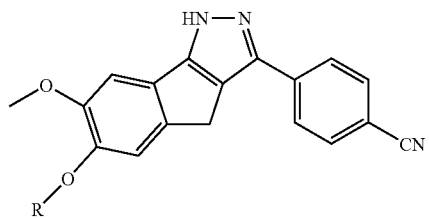

FIG. (XI)

| Example | R | ¹H NMR | MS | Yield |
|---|---|---|---|---|
| 208 | ![structure: CH2-C(CH3)2 linked to 4-pyridyl] | ¹H NMR (500 MHz, DMSO-D₆) δ ppm 3.81 (s, 2 H) 3.91 (s, 3 H) 5.40 (s, 2 H) 7.32 (s, 1 H) 7.34 (s, 1 H) 7.85 (d, J=5.80 Hz, 2 H) 7.96 (s, 4 H) 8.81 (d, J=6.10 Hz, 2 H) | (DCI/NH₃) 395.07 (M + H)⁺ | 35.1 mg 52% |
| 209 | ![structure: tetrahydropyran-4-yl] | ¹H NMR (400 MHz, DMSO-D₆) δ ppm 1.57-1.66 (m, 2 H) 1.93-1.97 (m, 2 H) 3.43-3.49 (m, 2 H) 3.79 (s, 2 H) 3.84 (s, 3 H) 3.86-3.91 (m, 2 H) 4.46-4.51 (m, 1 H) 7.27 (s, 1 H) 7.27 (s, 1 H) 7.94 (s, 4 H) | (DCI/NH₃) 388.12 (M + H)⁺ | 18 mg 32% |
| 210 | ![structure: propyl-morpholine] | ¹H NMR (500 MHz, DMSO-D₆) δ ppm 2.31-2.37 (m, 2 H) 3.17-3.23 (m, 2 H) 3.36-3.40 (m, 2 H) 3.56-3.59 (m 2 H) 3.92 (s, 2 H) 3.95-3.97 (m, 2 H) 3.96 (s, 3 H) 4.06-4.09 (m, 2 H) 4.22 (t, J=5.93 Hz, 2 H) 7.37 (s, 1 H) 7.40 (s, 1 H) 8.05 (d, J=8.42 Hz, 2 H) 8.08 (d, J=8.42 Hz, 2 H) | (DCI/NH₃) 431.07 (M + H)⁺ | 105 mg 90% |
| 211 | ![structure: CH2-CH(OH)-CH2OH] | ¹H NMR (500 MHz, DMSO-D₆) δ ppm 3.45-3.51 (m, 2 H) 3.80 (s, 2 H) 3.83 (m, 1 H) 3.85 (s, 3 H) 3.92 (dd, J=9.98, 5.93 Hz, 1 H) 4.03 (dd, J=9.82, 4.52 Hz, 1 H) 7.23 (s, 1 H) 7.25 (s, 1 H) 7.96 (s, 4 H) | (DCI/NH₃) 378.05 (M + H)⁺ | 20 mg 37% |
| 212 | ![structure: CH2-CH(CH2OH)2] | ¹H NMR (500 MHz, DMSO-D₆) δ ppm 3.55-3.66 (m, 4H), 3.81 (s, 2 H) 3.85 (s, 3 H) 4.22 (m, 1 H) 7.26 (s, 1 H) 7.32 (s, 1 H) 7.96 (s, 4 H). | (DCI/NH₃) 378.09 (M + H)⁺ | 25 mg 46% |

TABLE 11-continued

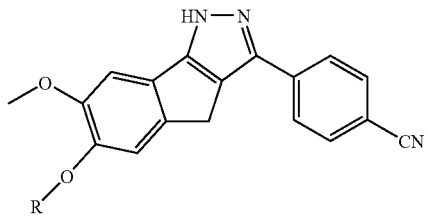

FIG. (XI)

| Example | R | ¹H NMR | MS | Yield |
|---|---|---|---|---|
| 213 | (pyridine-ethyl group) | ¹H NMR (500 MHz, DMSO-D₆) δ ppm 1.23 (t, J=7.48 Hz, 3 H) 2.75 (q, J=7.53 Hz, 2H) 3.38 (t, J=6.41 Hz, 2 H) 3.78 (s, 3 H) 3.80 (s, 2 H) 4.42 (t, J=6.41 Hz, 2 H) 7.25 (s, 1 H) 7.26 (s, 1 H) 7.84 (d, J=7.63 Hz, 1 H) 7.98 (s, 4 H) 8.22 (s, 1H) 8.67 (s, 1 H) | (ESI) 437.04 (M + H)⁺ | 45 mg 62% |
| 214 | (5-methylthiazol-4-yl-ethyl) | ¹H NMR (500 MHz, DMSO-D₆) δ ppm 2.39 (s, 3 H) 3.26 (t, J=6.10 Hz, 2 H) 3.79 (s, 2 H) 3.84 (s, 3 H) 4.19 (t, J=6.26 Hz, 2 H) 7.22 (s, 1 H) 7.26 (s, 1 H) 7.96 (s, 4H) 8.92 (s, 1 H) | (ESI) 427.0 (M − H)⁻ | 38 mg 63% |
| 215 | (dimethylaminopropyl) | ¹H NMR (500 MHz, DMSO-D₆) δ ppm 2.16-2.21 (m, 2 H) 2.79 (s, 3 H) 2.79 (s, 3 H) 3.21-3.25 (m, 2 H) 3.82 (s, 2 H) 3.87 (s, 3 H) 4.12 (t, J=6.08 Hz, 2 H) 7.27 (s, 1 H) 7.30 (s, 1 H) 7.95 (d, J=8.73 Hz, 2 H) 7.98 (d, J=8.73 Hz, 2 H) 10.65 (s, 1 H) | (DCI/NH₃) 389.43 (M + H)⁺ | 26 mg 49% |
| 216 | (tetrahydrofuran-3-yl-methyl) | ¹H NMR (500 MHz, DMSO-D₆) δ ppm 1.66-1.72 (m, 1 H) 2.00-2.06 (m, 1 H) 2.65-2.71 (m, 1 H) 3.57-3.59 (m, 1 H) 3.64-3.69 (m, 1 H) 3.75-3.79 (m, 2 H) 3.80 (s, 2 H) 3.85 (s, 3 H) 3.91-3.94 (m, 1 H) 3.97-4.00 (m, 1 H) 7.25 (s, 1 H) 7.28 (s, 1 H) 7.95 (d, J=8.73 Hz, 2 H) 7.98 (d, J=8.73 Hz, 2 H) | (DCI/NH₃) 388.2 (M + H)⁺ | 19 mg 39% |
| 217 | (tetrahydrofuran-3-yl) | ¹H NMR (500 MHz, DMSO-D₆) δ ppm 2.02 (m, 1 H) 2.19 (m, 1 H) 3.75-3.90 (m, 4 H) 3.81 (s, 2 H) 3.85 (s, 3 H) 5.04 (dd, J=6.08, 4.52 Hz, 1 H) 7.20 (s, 1 H) 7.29 (s, 1 H) 7.96 (s, 4 H) 13.30 (s, 1 H) | (DCI/NH₃) 374.10 (M + H)⁺ | 16 mg 34% |

TABLE 11-continued

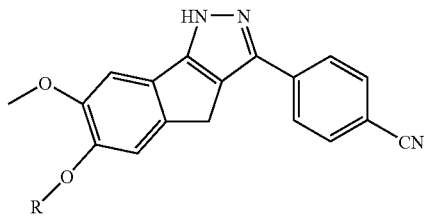

FIG. (XI)

| Example | R | $^1$H NMR | MS | Yield |
|---|---|---|---|---|
| 218 | (succinimide-ethyl group) | $^1$H NMR (500 MHz, DMSO-D$_6$) δ ppm 2.66 (s, 4 H) 3.76 (t, J=6.24 Hz, 2 H) 3.80 (s, 2 H) 3.83 (s, 3 H) 4.13 (t, J=6.24 Hz, 2 H) 7.22 (s, 1 H) 7.27 (s, 1 H) 7.95 (d, J=8.73 Hz, 2 H) 7.97 (d, J=8.73 Hz, 2 H) | (DCI/NH$_3$) 429.11 (M + H)$^+$ | 22 mg 41% |
| 219 | (3,5-dimethylpyrazole-ethyl group) | $^1$H NMR (500 MHz, DMSO-D$_6$) δ ppm 2.23 (s, 3 H) 2.41 (s, 3 H) 3.79 (s, 2 H) 3.81 (s, 3 H) 4.36 (t, J=5.15 Hz, 2 H) 4.54 (t, J=4.99 Hz, 2 H) 6.12 (s, 1 H) 7.18 (s, 1 H) 7.27 (s, 1 H) 7.95 (d, J=8.42 Hz, 2 H) 7.98 (d, J=8.42 Hz, 2 H) | (DCI/NH$_3$) 426.06 (M + H)$^+$ | 28 mg 53% |

EXAMPLE 220

3-(4-cyanophenyl)-N-(4-hydroxycyclohexyl)-7-methoxy-1,4-dihydroindeno[1,2-c]pyrazole-6-carboxamide

EXAMPLE 220A 6-methoxy-1-oxo-2,3-dihydro-1H-inden-5-yl trifluoromethanesulfonate Example 172A (6 g, 33.67 mmol), 2,6-lutidine (5.88 mL, 50.52 mmol), and 4-dimethylaminopyridine (822 mg, 6.72 mmol) were combined at ±35° C.~−30° C. and then dropwise treated with triflic anhydride (8.52 mL, 50.64 mmol). The reaction mixture was slowly warmed to room temperature with stirring and concentrated. The residue was purified by flash chromatography eluting with hexane:ethyl acetate (2:1). The title product (9.8 g) was obtained at 94% yield. MS (DCI/NH$_3$) m/z: 328.01 (M+NH$_4$)$^+$.

EXAMPLE 220B methyl 6-methoxy-1-oxoindane-5-carboxylate

Example 220A (5.7 g, 18.37 mmol), PdC$_2$(dppf).CH$_2$Cl$_2$ (1.5 g) and triethylamine (7.7 mL) were combined in methanol (50 mL) and stirred for 16 hours at 110° C. under carbon monoxide atmosphere (500 psi). The solvent was removed, and the residue was purified by flash chromatography eluting with hexane:ethyl acetate (2:1). The title product (3.1 g) was obtained at 77% yield. MS (DCI/NH$_3$) m/z: 221.02 (M+H)$^+$.

EXAMPLE 220C methyl 2-(4-cyanobenzoyl)-6-methoxy-1-oxoindane-5-carboxylate

The desired product was prepared using the procedure in Example 205C replacing Example 205A with Example 220B. MS (DCI/NH$_3$) m/z: 350.07 (M+H)$^+$.

EXAMPLE 220D methyl 3-(4-cyanophenyl)-7-methoxy-1,4-dihydroindeno[1,2-c]pyrazole-6-carboxylate The desired product was prepared using the procedure in Example 165C replacing Example 165B with Example 220C. The title compound (3.7 g) was obtained at 81% yield. MS (DCI/NH$_3$) m/z: 346.08 (M+H)$^+$. $^1$H NMR (400 MHz, DMSO-D$_6$) δ ppm 3.80 (s, 3H) 3.90 (s, 2H) 3.91 (s, 3H) 7.44 (s, 1H) 7.83 (s, 1H) 7.95 (d, J=8.59 Hz, 2H) 7.99 (d, J=8.59 Hz, 2H) 13.69 (s, 1H).

EXAMPLE 220E

3-(4-cyanophenyl)-7-methoxy-1,4-dihydroindeno[1,2-c]pyrazole-6-carboxylic acid Example 220D (1 g, 2.90 mmol), 2N NaOH (10 mL), THF(20 mL) and ethanol (20 mL) were combined and stirred overnight. The reaction mixture was concentrated, diluted with water and acidified with HCl. The precipitate was collected by filtration to give the title product (905 mg) at 85% yield. MS (DCI/NH$_3$) m/z: 349.06 (M+NH$_4$)$^+$. $^1$H NMR (500 MHz, DMSO-D$_6$) δ ppm 3.89 (s, 2H) 3.92 (s, 3H) 7.39 (s, 1H) 7.85 (s, 1H) 7.98 (s, 4H).

EXAMPLE 220F

3-(4-cyanophenyl)-N-(4-hydroxycyclohexyl)-7-methoxy-1,4-dihydroindeno[1,2-c]pyrazole-6-carboxamide Example 220E (50 mg, 0.15 mmol), 4-aminocyclohexanol (52 mg, 0.45 mmol), BOP Reagent (100 mg, 0.23 mmol) and triethylamine (0.063 mL) were combined in DMF (2.5 mL) and stirred overnight. The precipitate was collected by filtration to give the title compound (44 mg) at 68% yield. MS (DCI/NH$_3$) m/z: 429.2 (M+H)$^+$.

Examples 221 to 227 represented by FIG. (XII) and shown in Table 12 were synthesized in a similar fashion as described in Example 220F, except substituting the appropriate amine for 4-aminocyclohexanol.

TABLE 12

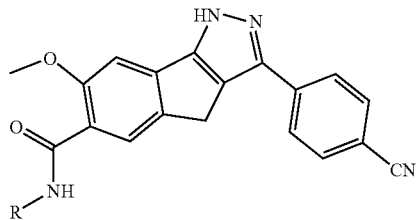

FIG. (XII)

| Example | R | $^1$H NMR | MS | Yield |
|---|---|---|---|---|
| 220F | cyclohexyl-OH | $^1$H NMR (500 MHz, DMSO-D$_6$) δ ppm 1.32-1.38 (m, 4H) 1.83-1.90 (m, 4 H) 3.42-3.46 (m, 1 H) 3.72-3.75 (m, 1 H) 3.89 (s, 2 H) 3.98 (s, 3 H) 4.53 (d, J=4.05 Hz, 1 H) 7.39 (s, 1 H) 7.90 (s, 1 H) 7.94 (d, J=7.80 Hz, 1 H) 7.98 (s, 4 H) 13.60 (s, 1 H) | (DCI/NH$_3$) 429.2 (M + H)$^+$ | 44 mg 68% |
| 221 | 2-pyridyl-CH$_2$- | $^1$H NMR (500 MHz, DMSO-D$_6$) δ ppm 3.92 (s, 2 H) 4.06 (s, 3 H) 4.65 (d, J=5.61 Hz, 2 H) 7.28 (dd, J=6.86, 4.99 Hz, 1 H) 7.39 (d, J=7.80 Hz, 1 H) 7.46 (s, br, 1 H) 7.79 (m, 1 H) 7.99 (s, 4 H) 8.05 (s, 1 H) 8.55 (d, J=4.05 Hz, 1 H) 9.04 (t, J=5.61 Hz, 1 H) 13.64 (s, 1 H) | (DCI/NH$_3$) 422.14 (M + H)$^+$ | 55 mg 86% |
| 222 | 3-pyridyl-CH$_2$- | $^1$H NMR (500 MHz, DMSO-D$_6$) δ ppm 3.90 (s, 2 H) 4.00 (s, 3 H) 4.55 (d, J=5.93 Hz, 2 H) 7.37 (dd, J=7.80, 4.99 Hz, 1 H) 7.43 (s, 1 H) 7.75 (d, J=7.80 Hz, 1 H) 7.96 (s, 1 H) 7.98 (s, 4 H) 8.46 (dd, J=4.99, 1.56 Hz, 1 H) 8.58 (d, J=1.87 Hz, 1 H) 8.83 (t, J=6.08 Hz, 1 H) 13.62 (s, 1 H) | (DCI/NH$_3$) 422.17 (M + H)$^+$ | 34 mg 53% |
| 223 | 4-pyridyl-CH$_2$- | $^1$H NMR (500 MHz, DMSO-D$_6$) δ ppm 3.91 (s, 2 H) 4.03 (s, 3 H) 4.55 (d, J=6.24 Hz, 2 H) 7.33 (d, J=5.93 Hz, 2 H) 7.44 (s, br, 1 H) 7.98 (d, J=7.49 Hz, 4 H) 8.51 (d, J=5.93 Hz, 2 H) 8.85 (t, J=6.08 Hz, 1 H) 13.62 (s, 1 H) | (DCI/NH$_3$) 422.13 (M + H)$^+$ | 55 mg 86% |

TABLE 12-continued

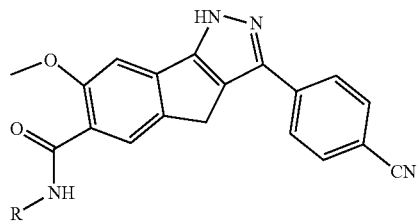

FIG. (XII)

| Example | R | $^1$H NMR | MS | Yield |
|---|---|---|---|---|
| 224 | (4-morpholinophenyl) | $^1$H NMR (500 MHz, DMSO-D$_6$) δ ppm 3.05-3.07 (m, 4 H) 3.73-3.75 (m, 4 H) 3.91 (s, 2 H) 4.02 (s, 3 H) 6.93 (d, J=9.04 Hz, 2 H) 7.44 (s, 1 H) 7.61 (d, J=9.04 Hz, 2 H) 7.89 (s, 1 H) 7.98 (s, 4 H) 9.94 (s, 1 H) 13.62 (s, 1 H) | (DCI/NH$_3$) 492.17 (M + H)$^+$ | 69 mg 93% |
| 225 | (3-pyrrolidin-1-yl-propyl) | $^1$H NMR (500 MHz, DMSO-D$_6$) δ ppm 1.84-1.91 (m, 2 H) 2.01-2.07 (m, 2 H) 3.08 (dd, J=10.92, 7.49 Hz, 2 H) 3.36 (q, J=5.82 Hz, 2 H) 3.65-3.69 (m, 4 H) 3.91 (s, 2 H) 4.02 (s, 3 H) 7.45 (s, 1 H) 7.98 (s, 4 H) 8.03 (s, 1 H) 8.53 (t, J=5.77 Hz, 1 H) 9.56 (s, 1 H) | (DCI/NH$_3$) 428.15 (M + H)$^+$ | 38 mg 48% |
| 226 | (3-piperidin-1-yl-propyl) | $^1$H NMR (500 MHz, DMSO-D$_6$) δ ppm 1.37-1.45 (m, 1 H) 1.62-1.69 (m, 3 H) 1.84 (d, J=14.66 Hz, 2 H) 2.93-2.99 (m, 2 H) 3.26 (q, J=5.93 Hz, 2 H) 3.67-3.71 (m, 4 H) 3.91 (s, 2 H) 4.01 (s, 3 H) 7.45 (s, 1 H) 7.98 (s, 4 H) 8.02 (s, 2 H) 8.54 (t, J=5.77 Hz, 1 H) 9.16 (s, 1 H) | (DCI/NH$_3$) 442.22 (M + H)$^+$ | 35 mg 43% |
| 227 | (3-morpholin-4-yl-propyl) | $^1$H NMR (500 MHz, DMSO-D$_6$) δ ppm 3.35 (t, J=5.93 Hz, 2 H) 3.69-3.72 (m, 10 H) 3.92 (s, 2 H) 4.02 (s, 3 H) 7.45 (s, 1 H) 7.99 (s, 4 H) 8.03 (s, 1 H) 8.55 (t, J=5.93 Hz, 1 H) 9.74 (s, 1 H) | (DCI/NH$_3$) 444.14 (M + H)$^+$ | 28 mg 34% |

EXAMPLE 228A (trans) 4-{[(3-iodo-7-methoxy-1,4-dihydroindeno[1,2-c]pyrazol-6-yl)methyl]amino}cyclohexanol Example 104E (150 mg, 0.44 mmol), trans4-aminocyclohexanol hydrochloride (100 mg, 0.66 mmol) and $K_2CO_3$ (91 mg, 0.66 mmol) were combined in ethanol (20 mL) and heated at 100° C. for 3 hours and cooled. After addition of $NaBH_4$ (16.6 mg, 0.44 mmol), the reaction was stirred at room temperature overnight and concentrated. The residue was purified by flash chromatography eluting with $CH_2Cl_2$: $CH_3OH:NH_4OH$ (100:10:1). The title compound (110 mg) was obtained at 57% yield. MS (ESI) m/z: 439.98 $(M+H)^+$.

EXAMPLE 228B 4-(6-{[trans(4-hydroxycyclohexyl)amino]methyl}-7-methoxy-1,4-dihydroindeno[1,2-c]pyrazol-3-yl)benzonitrile Example 228A (40 mg, 0.091 mmol), 4-cyanophenylboronic acid (16 mg, 0.11 mmol), $Na_2CO_3$ (1 M, 0.25 mL), and $Pd(PPh_3)_2Cl_2$ (6.4 mg, 0.009 mmol) were combined in $DME/EtOH/H_2O$ (7:2:3, 1.5 mL) in a capped 2 mL vial and heated to 160° C. for 600 seconds in a Smith Synthesizer. The reaction was cooled using 40 psi pressurized air, the solvents were evaporated, and the residue was purified using preparative HPLC. The title compound (20 mg) was obtained at 36% yield (based on 2TFA salt). MS ($DCI/NH_3$) m/z: 415.19 $(M+H)^+$. $^1H$ NMR (500 MHz, DMSO-$D_6$) δ ppm 1.14-1.23 (m, 2H) 1.38-1.45 (m, 2H) 1.89-1.91 (m, 2H) 2.07-2.10 (m, 2H) 3.00-3.05 (m, 2H) 3.88 (s, 2H) 3.94 (s, 3H) 4.14-4.17 (m, 2H) 7.39 (s, 1H) 7.60 (s, 1H) 7.96 (d, J=8.42 Hz, 2H) 7.99 (d, J=8.42 Hz, 2H) 8.45 (s, 2H).

EXAMPLE 229

4-[6-(1H-imidazol-1-ylmethyl)-7-methoxy-1,4-dihydroindeno[1,2-c]pyrazol-3-yl]benzonitrile

EXAMPLE 229A methyl 3-(4-cyanophenyl)-7-methoxy-1-{[2-(trimethylsilyl)ethoxy]methyl}-1,4-dihydroindeno[1,2-c]pyrazole-6-carboxylate The desired product was prepared using the procedure in Example 175D replacing Example 175C with Example 220D. The title compound (1.5 g) was obtained at 91% yield. MS ($DCI/NH_3$) m/z: 476.20 $(M+H)^+$.

EXAMPLE 229B 4-(6-(hydroxymethyl)-7-methoxy-1-{[2-(trimethylsilyl)ethoxy]methyl}-1,4-dihydroindeno[1,2-c]pyrazol-3-yl)benzonitrile Example 229A (200 mg, 0.42 mmol) and $NaBH_4$ (160 mg, 4.2 mmol) were combined in THF-MeOH (1:1), heated at 50° C. overnight, and concentrated. The residue was purified by flash chromatography eluting with a mixture of ethyl acetate and hexane. MS ($DCI/NH_3$) m/z: 448.19 $(M+H)^+$.

EXAMPLE 229C

4-[6-(1H-imidazol-1-ylmethyl)-7-methoxy-1,4-dihydroindeno[1,2-c]pyrazol-3-yl]benzonitrile Example 229B (20 mg, 0.045 mmol) and 1,1'-carbonyldiimidazole (30 mg, 0.18 mmol) were combined in acetonitrile (3 mL), heated at 80° C. for 24 hours and concentrated. The residue was treated with ethanol (2 mL) and 4N HCl in dioxane (2 mL), and the reaction mixture was stirred overnight. White precipitates was collected by filtration and dried to give the title compound (14.4 mg, HCl salt) at 80% yield. MS ($DCI/NH_3$) m/z: 368.14 $(M+H)^+$. $^1H$ NMR (400 MHz, DMSO-$D_6$) δ ppm 3.86 (s, 2H) 3.93 (s, 3H) 5.43 (s, 2H) 7.33 (s, 1H) 7.39 (s, 1H) 7.61 (s, 1H) 7.67 (s, 1H) 7.73 (s, 1H) 7.95-8.00 (m, 4H) 9.23 (s, 1H).

EXAMPLE 230

3-(6-chloropyridin-3-yl)-6,7-dimethoxy-1,4-dihydroindeno[1,2-c]pyrazole

EXAMPLE 230A 2-chloro-5-(1H-imidazol-1-ylcarbonyl)pyridine

The desired product was prepared using the procedure in Example 165A replacing 4-benzyloxybenzoic acid with 6-chloronicotinic acid.

EXAMPLE 230B

2-[(6-chloropyridin-3-yl)carbonyl]-5,6-dimethoxyindan-1-one

The desired product was prepared using the procedure in Example 165B replacing Example 165A with Example 230A. MS ($DCI/NH_3$) m/z: 331.98 $(M+H)^+$.

EXAMPLE 230C 3-(6-chloropyridin-3-yl)-6,7-dimethoxy-1,4-dihydroindeno[1,2-c]pyrazole The desired product was prepared using the procedure in Example 165C replacing Example 165B with Example 230B. The title product (937 mg) was obtained at 95% yield. MS ($DCI/NH_3$) m/z: 328.01 $(M+H)^+$. $^1H$ NMR (400 MHz, DMSO-$D_6$) δ ppm 3.80 (s, 2H) 3.82 (s, 3H) 3.84 (s, 3H) 7.23 (s, 2H) 7.65 (s, 1H) 8.21 (d, J=7.37 Hz, 1H) 8.82 (d, J=2.45 Hz, 1H) 13.22 (s, 1H).

EXAMPLE 231

4-[5-(6,7-dimethoxy-1,4-dihydroindeno[1,2-c]pyrazol-3-yl)pyridin-2-yl]phenol

The desired product was prepared using the procedure in Example 166B replacing Example 166A with Example 230C. MS ($DCI/NH_3$) m/z: 386.09 $(M+H)^+$. $^1H$ NMR (500 MHz, DMSO-$D_6$) δ ppm 3.82 (s, 3H) 3.83 (s, 2H) 3.84 (s, 3H) 6.89 (d, J=8.73 Hz, 2H) 7.24 (d, J=7.80 Hz, 2H) 7.98-8.01 (m, 3H) 8.23 (dd, J=8.42, 2.18 Hz, 1H) 8.99 (d, J=1.56 Hz, 1H).

EXAMPLE 232

4-[5-(6,7-dimethoxy-1,4-dihydroindeno[1,2-c]pyrazol-3-yl)pyridin-2-yl]-2-methoxyphenol The title product was prepared using the procedure in Example 164 replacing Example 64C with Example 230C at 83% yield. MS (ESI) m/z: 416.08 $(M+H)^+$. $^1H$ NMR (500 MHz, DMSO-$D_6$) δ ppm 3.82 (s, 3H) 3.83 (s, 2H) 3.84 (s, 3H) 3.88 (s, 3H) 6.89 (d, J=8.42 Hz, 1H) 7.24 (s, 1H) 7.25 (s, 1H) 7.59 (dd, J=8.26, 2.03 Hz, 1H) 7.74 (d, J=1.87 Hz, 1H) 8.04 (d, J=8.42 Hz, 1H) 8.21 (dd, J=8.42, 2.18 Hz, 1H) 9.00 (d, J=1.87 Hz, 1H).

EXAMPLE 233

4-[5-(6,7-dimethoxy-1,4-dihydroindeno[1,2-c]pyrazol-3-yl)pyridin-2-yl]-2-fluorophenol The title product was prepared using the similar procedure in Example 232 replacing 2-methoxy-4-(4,4,5,5-tetramethyl [1,3,2]dioxaborolan-2-yl)-phenol with 2-fluoro-4-(4,4,5,5-tetramethyl[1,3,2]dioxaborolan-2-yl)-phenol. MS (ESI) m/z: 404.07 (M+H)$^+$. $^1$H NMR (500 MHz, DMSO-D$_6$) δ ppm 3.83 (s, 3H) 3.84 (s, 2H) 3.85 (s, 3H) 7.07 (t, J=8.89 Hz, 1H) 7.24 (s, 1H) 7.26 (s, 1H) 7.84 (dd, J=8.42, 1.87 Hz, 1H) 7.94 (dd, J=12.79, 2.18 Hz, 1H) 8.04 (d, J=8.42 Hz, 1H) 8.21 (dd, J=8.42, 2.18 Hz, 1H) 9.02 (d, J=2.18 Hz, 1H).

EXAMPLE 234

5-(6,7-dimethoxy-1,4-dihydroindeno[1,2-c]pyrazol-3-yl)pyridine-2-carbonitrile

The title product was prepared using the procedure in Example 167 replacing Example 64C with Example 230C. MS (DCI/MH$_3$) m/z: 319.06 (M+H)$^+$. $^1$H NMR (500 MHz, DMSO-D$_6$) δ ppm 3.81 (s, 3H) 3.83 (s, 5H) 7.23 (s, 1H) 7.24 (s, 1H) 8.13 (d, J=8.11 Hz, 1H) 8.34 (dd, J=8.42, 2.18 Hz, 2H) 9.14 (d, J=1.56 Hz, 1H).

EXAMPLE 235

6-(6,7-dimethoxy-1,4-dihydroindeno[1,2-c]pyrazol-3-yl)nicotinonitrile

EXAMPLE 235A methyl 5-bromopyridine-2-carboxylate 2,5-Dibromopyridine (9.5 g, 40. 10mmol), PdCl$_2$(PPh$_3$)$_2$ (844 mg), triethylamine (8.36 mL), methanol (38 mL), and acetonitrile (114 mL) were combined, heated under carbon monoxide atmosphere (75 psi) at 60° C. for 16 hours and concentrated. The residue was purified by flash chromatography eluting with 25% ethyl acetate in hexane. The title compound (5.02 g) was obtained at 58% yield. MS (DCI/MH$_3$) m/z: 215.95 (M+H)$^+$. $^1$H NMR (500 MHz, DMSO-D$_6$) δ ppm 3.91 (s, 3H) 8.00 (d, J=8.11 Hz, 1H) 8.27 (dd, J=8.42, 2.49 Hz, 1H) 8.86 (d, J=1.56 Hz, 1H).

EXAMPLE 235B

2-[(5-bromopyridin-2-yl)carbonyl]-5,6-dimethoxyindan-1-one

The desired product was prepared using the procedure in Example 165B replacing Example 165A with Example 235A. The title compound (1.65 g) was obtained at 95% yield. MS (DCI/NH$_3$) m/z: 375.98 (M+H)$^+$.

EXAMPLE 235C 3-(5-bromopyridin-2-yl)-6,7-dimethoxy-1,4-dihydroindeno[1,2-c]pyrazole The desired product was prepared using the procedure in Example 165C replacing Example 165B with Example 235B. The title compound (1.35 g) was obtained at 85% yield. MS (DCI/NH$_3$) m/z: 373.94 (M+H)$^+$. $^1$H NMR (500 MHz, DMSO-D$_6$) δ ppm 3.76 (s, 2H) 3.80 (s, 3H) 3.83 (s, 3H) 7.20 (s, 1H) 7.25 (s, 1H) 7.72 (d, J=8.42 Hz, 1H) 8.17 (d, J=6.86 Hz, 1H) 8.76 (s, 1H) 13.25 (s, 1H).

EXAMPLE 235D 6-(6,7-dimethoxy-1,4-dihydroindeno[1,2-c]pyrazol-3-yl)nicotinonitrile The title product was prepared using the procedure in Example 167 replacing Example 64C with Example 235C at 70% yield. MS (DCI/MH$_3$) m/z: 319.06 (M+H)$^+$. $^1$H NMR (500 MHz, DMSO-D$_6$) δ ppm 3.81 (s, 2H) 3.82 (s, 3H) 3.84 (s, 3H) 7.21 (s, 1H) 7.26 (s, 1H) 7.98 (s, 1H) 8.39 (d, J=7.49 Hz, 1H) 9.08 (d, J=1.25 Hz, 1H).

EXAMPLE 236

4'-[6-(1-hydroxy-1-methylethyl)-1,4-dihydroindeno[1,2-c]pyrazol-3-yl]-1,1'-biphenyl-4-ol

EXAMPLE 236A methyl 1,4-dihydroindeno[1,2-c]pyrazole-6-carboxylate

The desired product was prepared using the procedure in Example 220B replacing Example 220A with 6-bromo-1,4-dihydro-indeno[1,2-c]pyrazole (for preparation, see U.S. Pat. No. 6,297,238). MS (DCI/NH$_3$) m/z: 215.05 (M+H)$^+$.

EXAMPLE 236B methyl 3-iodo-1,4-dihydroindeno[1,2-c]pyrazole-6-carboxylate

The desired product was prepared using the procedure in Example 68B replacing Example 68A with 236A. MS (DCI/NH$_3$) m/z: 340.92 (M+H)$^+$.

EXAMPLE 236C 2-(3-iodo-1,4-dihydroindeno[1,2-c]pyrazol-6-yl) propan-2-ol

To a solution of Example 236B (1 g, 2.94 mmol) in THF (145 mL) was dropwise added 1.4 M MeMgBr in THF-toluene (8.4 mL, 11.76 mmol). The reaction mixture was slowly warmed to room temperature, stirred for 24 hours, quenched with aqueous NH$_4$Cl, and extracted with ethyl acetate. The organic layer was dried over MgSO$_4$ and concentrated. The residue was purified by flash chromatography eluting with 50% ethyl acetate in hexane. The title compound (700 mg) was obtained at 70% yield. MS (DCI/NH$_3$) m/z: 340.95 (M+H)$^+$. $^1$H NMR (500 MHz, DMSO-D$_6$) δ ppm 1.44 (s, 6H) 3.48 (s, 2H) 5.02 (s, 1H) 7.44 (dd, J=7.80, 1.25 Hz, 1H) 7.48 (m, 1H) 7.65 (s, 1H).

EXAMPLE 236D

4'-[6-(1-hydroxy-1-methylethyl)-1,4-dihydroindeno[1,2-c]pyrazol-3-yl]-1,1'-biphenyl-4-ol Example 236C (45 mg, 0.13 mmol), Example 68D (47 mg, 0.16 mmol), Na$_2$CO$_3$ (1 M, 0.3 mL), and Pd(PPh$_3$)$_2$Cl$_2$ (9.9 mg, 0.014 mmol) were combined in DME/EtOH/H$_2$O (7:2:3, 1.5 mL) in a capped 2 mL vial and heated to 160° C. for 600 seconds in a Smith Synthesizer. The reaction was cooled using 40 psi pressurized air, the solvents were evaporated, and the residue was purified using preparative HPLC. The title compound (26.7 mg, TFA salt) was obtained at 42% yield. MS (DCI/NH$_3$) m/z: 383.1 (M+H)$^+$. $^1$H NMR (500 MHz, DMSO-D$_6$) δ ppm 1.47 (s, 6H) 3.86 (s, 2H) 6.86 (d, J=8.73 Hz, 2H) 7.45 (d, J=8.11 Hz, 1H) 7.557.58 (m, 3H) 7.69-7.72 (m, 3H) 7.84 (d, J=8.42 Hz, 2H).

EXAMPLE 237

4-[6-(1-hydroxy-1-methylethyl)-1,4-dihydroindeno[1,2-c]pyrazol-3-yl]benzonitrile The desired product was prepared using the procedure in Example 236D replacing Example 68D with 4-cyanophenyl boronic acid. The title compound (27.8 g) was obtained at 51% yield. MS (DCI/NH$_3$) m/z: 316.09 (M+H)$^+$. $^1$H NMR (500 MHz, DMSO-D$_6$) δ ppm 1.47 (s, 6H) 3.89 (s, 2H) 7.47 (dd, J=7.95, 1.40 Hz, 1H) 7.57 (d, J=8.11 Hz, 1H) 7.69 (s, 1H) 7.95 (d, J=8.42 Hz, 2H) 7.98 (d, J=8.42 Hz, 2H).

EXAMPLE 238

2-[3-(6-chloropyridin-3-yl)-1,4-dihydroindeno[1,2-c]pyrazol-6-yl]propan-2-ol

EXAMPLE 238A methyl 1-oxoindane-5-carboxylate

The desired product was prepared using the procedure in Example 220B replacing Example 220A with 5-bromoindanone. The title product was obtained at 85% yield. MS (DCI/NH$_3$) m/z: 208.06 (M+NH$_4$)$^+$. $^1$H NMR (400 MHz, DMSO-D$_6$) δ ppm 2.69-2.72 (m, 2H) 3.16-3.19 (m, 2H) 3.90 (s, 3H) 7.75 (d, J=7.98 Hz, 1H) 7.96 (dd, J=7.98, 1.53 Hz, 1H) 8.15 (s, 1H).

EXAMPLE 238B methyl 2-[(6-chloropyridin-3-yl)carbonyl]-1-oxoindane-5-carboxylate Example 238A (2.7 g, 14.2 mmol) in 45 mL of THF was treated with NaH (60%, 1.14 g, 28.4 mmol). After the addition of Example 230A (7.4 g, 35.5 mmol), the reaction mixture was stirred overnight and poured into ice water. The resulting mixture was acidified with concentrated HCl. Yellow solid was collected by filtration, washed with water and hot ethanol. The title product (4.3 g) was obtained at 92% yield. MS (DCI/NH$_3$) m/z: 330.01 (M+H)$^+$.

EXAMPLE 238C methyl 3-(6-chloropyridin-3-yl)-1,4-dihydroindeno[1,2-c]pyrazole-6-carboxylate The desired product was prepared using the procedure in Example 165C replacing Example 165B with Example 238B. The title compound (600 mg) was obtained at 74% yield. MS (DCI/NH$_3$) m/z: 325.98 (M+H)$^+$. $^1$H NMR (400 MHz, DMSO-D$_6$) δ ppm 3.88 (s, 3H) 3.98 (s, 1H) 4.01 (s, 1H) 7.60-7.83 (m, 2H) 8.00 (d, J=8.29 Hz, 1H) 8.14 (s, 1H) 8.25 (t, J=9.97 Hz, 1H) 8.85 (s, 1H) 13.66 (s, 1H).

EXAMPLE 238D

2-[3-(6-chloropyridin-3-yl)-1,4-dihydroindeno[1,2-c]pyrazol-6-yl]propan-2-ol

The desired product was prepared using the procedure in Example 236C replacing Example 236B with Example 238C. The title compound (250 mg) was obtained at 83% yield. MS (ESI) m/z: 326.02 (M+H)$^+$. $^1$H NMR (300 MHz, DMSO-D$_6$) δ ppm 1.47 (s, 6H) 3.89 (s, 2H) 5.06 (s, 1H) 7.48 (d, J=8.48 Hz, 1H) 7.58 (d, J=7.80 Hz, 1H) 7.66 (d, J=7.80 Hz, 1H) 7.70 (s, 1H) 8.24 (dd, J=8.48, 2.37 Hz, 1H) 8.85 (d, J=2.03 Hz, 1H) 13.37 (s, 1H).

EXAMPLE 239

4-{5-[6-(1-hydroxy-1-methylethyl)-1,4-dihydroindeno[1,2-c]pyrazol-3-yl]pyridin-2-yl}phenol The desired product was prepared using the procedure in Example 166B replacing Example 166A with Example 238D. The title compound (25.1 mg) was obtained at 28% yield. MS (DCI/NH$_3$) m/z: 384.2 (M+H)$^+$. $^1$H NMR (500 MHz, DMSO-D$_6$) δ ppm 1.49 (s, 6H) 3.93 (s, 2H) 6.92 (d, J=8.73 Hz, 2H) 7.49 (dd, J=8.11, 1.56 Hz, 1H) 7.60 (d, J=8.11 Hz, 1H) 7.72 (s, 1H) 8.00 (d, J=9.04 Hz, 2H) 8.04 (d, J=8.42 Hz, 1H) 8.29 (dd, J=8.42, 2.18 Hz, 1H) 9.03 (d, J=1.56 Hz, 1H).

EXAMPLE 240

3-(5,6-dichloropyridin-3-yl)-6,7-dimethoxy-1,4-dihydroindeno[1,2-c]pyrazole

EXAMPLE 240A 2,3-dichloro-5-(1H-imidazol-1-ylcarbonyl)pyridine

The desired product was prepared using the procedure in Example 165A replacing 4-benzyloxybenzoic acid with 5,6-chloronicotinic acid.

EXAMPLE 240B

2-[(5,6-dichloropyridin-3-yl)carbonyl]-5,6-dimethoxyindan-1-one

The desired product was prepared using the procedure in Example 165B replacing Example 165A with Example 240A.

EXAMPLE 240C 3-(5,6-dichloropyridin-3-yl)-6,7-dimethoxy-1,4-dihydroindeno[1,2-c]pyrazole The desired product was prepared using the procedure in Example 165C replacing Example 165B with Example 240B. MS (DCI/NH$_3$) m/z: 361.98 (M+H)$^+$. $^1$H NMR (400 MHz, DMSO-D$_6$) δ ppm 3.82 (s, 3H) 3.83 (s, 2H) 3.84 (s, 3H) 7.23 (s, 1H) 7.24 (s, 1H) 8.42 (d, J=2.15 Hz, 1H) 8.78 (d, J=2.15 Hz, 1H).

EXAMPLE 241

2-[3-(6-fluoropyridin-3-yl)-1,4-dihydroindeno[1,2-c]pyrazol-6-yl]propan-2-ol

The desired product was prepared using the procedure in Example 236D replacing Example 68D with 6-fluoronicotinic boronic acid. The title compound (350 g) was obtained at 96% yield. MS (DCI/NH$_3$) m/z: 310.08 (M+H)$^+$. $^1$H NMR (500 MHz, DMSO-D$_6$) δ ppm 1.48 (s, 6H) 3.88 (s, 2H) 5.07 (s, 1H) 7.35 (d, J=6.71 Hz, 1H) 7.48 (d, J=7.93 Hz, 1H) 7.58 (d, J=6.71 Hz, 1H) 7.70 (s, 1H) 8.38 (m, 1H) 8.67 (d, J=2.14 Hz, 1H) 13.31 (s, 1H).

EXAMPLE 242

6,7-dimethoxy-3-pyrazin-2-yl-1,4-dihydroindeno[1,2-c]pyrazole

EXAMPLE 242A 5,6-dimethoxy-2-(pyrazin-2-ylcarbonyl)indan-1-one

The desired product was prepared using the procedure in Example 165B replacing Example 165A with methyl pyrazine-2-carboxylate. MS (DCI/NH$_3$) m/z: 299.06 (M+H)$^+$.

EXAMPLE 242B 6,7-dimethoxy-3-pyrazin-2-yl-1,4-dihydroindeno[1,2-c]pyrazole

The desired product was prepared using the procedure in Example 165C replacing Example 165B with Example 242A. MS (DCI/NH$_3$) m/z: 295.05 (M+H)$^+$. $^1$H NMR (500 MHz, DMSO-D$_6$) δ ppm 3.82 (s, 3H) 3.85 (s, 5H) 7.23 (s, 1H) 7.28 (s, 1H) 8.59 (s, 1H) 8.72 (s, 1H) 9.05 (s, 1H) 13.41 (s, 1H).

EXAMPLE 243

6,7-dimethoxy-3-pyridin-3-yl-1,4-dihydroindeno[1,2-c]pyrazole

EXAMPLE 243A 6,7-dimethoxy-1,4-dihydroindeno[1,2-c]pyrazole

A mixture of 5,6-dimethoxyindanone (6.0 g, 31 mmol), formic acid ethyl ester (5.04 mL, 62 mmol), 95% NaH (2.35 g, 93 mmol) and benzene (100 mL) was stirred at room temperature overnight. The solvent was removed. To the residue was added slowly ethanol (200 mL), acetic acid (20 mL) and hydrazine monohydrate (20 mL). The mixture was heated to reflux for 3 hours and cooled. The solvents were removed. The residue was suspended in water (100 mL), and the solid was collected by filtration, washed with water (100 ML) and CCl$_4$ (100 mL), and dried to give the desired product as light yellow solid powder (5.80 g, 87%). MS (ESI) m/z 217 (M+H)$^+$. $^1$H NMR (300 MHz, DMSO-D$_6$) δ ppm 3.51 (s, 2H) 3.79 (s, 3H) 3.82 (s, 3H) 7.17 (s, 1H) 7.20 (s, 1H) 7.56 (s, 1H) 12.51 (s, 1H).

EXAMPLE 243B 3-iodo-6,7-dimethoxy-1,4-dihydroindeno[1,2-c]pyrazole

Example 243A (5.80 g, 26.8 mmol), N-iodosuccinimide (7.84 g, 34.9 mmol), and anhydrous DMF (100 mL) were mixed, stirred at 80° C. for 4 hours and concentrated. The residue was dissolved in dichloromethane (200 mL), washed with water (200 mL×3), dried over MgSO$_4$ and concentrated. The residue was purified by flash chromatography to give the title product as brown solid (5.84 g, 64%). MS (ESI) m/z 343 (M+H)$^+$. $^1$H NMR (300 MHz, DMSO-D$_6$) δ ppm 3.42 (s, 2H) 3.79 (s, 3H) 3.81 (s, 3H) 7.15 (s, 1H) 7.19 (s, 1H).

EXAMPLE 243C 6,7-dimethoxy-3-pyridin-3-yl-1,4-dihydroindeno[1,2-c]pyrazole

Example 243B (100 mg, 0.29 mmol), pyridyl-3-boronic acid (43 mg, 0.35 mmol), Na$_2$CO$_3$ (1 M, 0.35 mL), and Pd(PPh$_3$)$_2$Cl$_2$ (20 mg, 0.014 mmol) were combined in DME/EtOH/H$_2$O (7:2:3, 4 mL) in a capped 5 mL vial and heated to 160° C. for 600 seconds in a Smith Synthesizer. The reaction was cooled using 40 psi pressurized air, the solvents were evaporated, and the residue was purified using preparative HPLC. MS (DCI/NH$_3$) m/z: 294.1 (M+H)$^+$. $^1$H NMR (500 MHz, DMSO-D$_6$) δ ppm 3.83 (s, 5H) 3.85 (s, 3H) 7.24 (s, 1H) 7.25 (s, 1H) 7.73 (dd, J=7.95, 5.15 Hz, 1H) 8.39 (d, J=8.11 Hz, 1H) 8.65 (dd, J=4.99, 1.25 Hz, 1H) 9.07 (d, J=1.56 Hz, 1H).

EXAMPLE 244

6,7-dimethoxy-3-pyrimidin-5-yl-1,4-dihydroindeno[1,2-c]pyrazole

The desired product was prepared using the procedure in Example 243C replacing pyridyl-3-boronic acid with pyrimidyl-5-boronic acid. MS (DCI/NH$_3$) m/z: 295.06 (M+H)$^+$. $^1$H NMR (500 MHz, DMSO-D$_6$) δ ppm 3.82 (s, 3H) 3.85 (s, 5H) 7.24 (s, 1H) 7.25 (s, 1H) 9.16 (s, 1H) 9.20 (s, 2H).

EXAMPLE 245

3-(6-chloropyridin-3-yl)-7-ethyl-6-methoxy-1,4-dihydroindeno[1,2-c]pyrazole

EXAMPLE 245A 6-methoxy-3-oxo-2,3-dihydro-1H-inden-5-yl trifluoromethanesulfonate Example 144B (3.5 g, 19.64 mmol) and NaH (60%, 496 mg, 19.64 mmol) were combined and stirred at 40° C. until no bubble came out from the reaction mixture. After addition of N-phenyltrifluoromethanesulfonimide (8.41 g, 23.57 mmol), the reaction mixture was further stirred at 40° C. for 30 min and concentrated. The residue was purified by flash chromatography eluting with 50% ethyl acetate in hexane. The title compound (5.5 g) was obtained at 90% yield. MS (DCI/NH$_3$) m/z: 327.99 (M+NH$_4$)$^+$. $^1$H NMR (400 MHz, DMSO-D$_6$) δ ppm 2.65-2.68 (m, 2H) 3.11-3.14 (m, 2H) 4.01 (s, 3H) 7.52 (s, 1H) 7.62 (s, 1H).

EXAMPLE 245B 5-methoxy-6-vinylindan-1-one

Example 245A (4.5 g, 14.5 mmol), tributylvinyltin (5.54 g, 17.4 mmol), Pd(PPh$_3$)$_2$Cl$_2$ (1.02 g, 1.45 mmol) and lithium chloride (4.9 g, 116 mmol) were combined in DMF (60 mL) and heated at 80° C. for 2 hours, cooled. After addition of saturated potassium fluoride (100 mL), the resulting mixture was stirred for 30 min, and diluted with ethyl acetate (800 mL). Precipitates were removed by filtration, and the filtrate was washed with water extensively, then with 10% HCl. The organic layer was dried over MgSO$_4$ and concentrated. The residue was purified by flash chromatography eluting with 30% ethyl acetate in hexane. The title compound (1.65 g) was obtained at 60% yield. MS (DCI/NH$_3$) m/z: 189.04 (M+H)$^+$. $^1$H NMR (500 MHz, DMSO-D$_6$) δ ppm 2.47-2.49 (m, 2H) 2.94-2.96 (m, 2H) 3.81 (s, 3H) 5.19 (dd, J=11.23, 1.25 Hz, 1H) 5.74 (dd, J=17.78, 1.25 Hz, 1H) 6.83 (dd, J=17.78, 11.23 Hz, 1H) 7.06 (s, 1H) 7.60 (s, 1H).

EXAMPLE 245C 6-ethyl-5-methoxyindan-1-one

Example 245B (1.59 g, 8.46 mmol) and Pd—C (10%, 159 mg) were combined in THF (70 mL) and stirred under hydrogen atmosphere for 6 hours. Insoluble material was removed by filtration through Celite, the filtrate was evaporated to give the title product at quantitative yield.

EXAMPLE 245D

2-[(6-chloropyridin-3-yl)carbonyl]-6-ethyl-5-methoxyindan-1-one

The desired product was prepared using the procedure in Example 238B replacing Example 238A with Example 245C. The title compound (325 mg) was obtained at 71% yield.

EXAMPLE 245E 3-(6-chloropyridin-3-yl)-7-ethyl-6-methoxy-1,4-dihydroindeno[1,2-c]pyrazole The desired product was prepared using the procedure in Example 165C replacing Example 165B with Example 245D. MS (DCI/NH$_3$) m/z: 326.04 (M+H)$^+$. $^1$H NMR (500 MHz, DMSO-D$_6$) δ ppm 1.04 (t, J=7.49 Hz, 3H) 2.50 (q, J=7.49 Hz, 2H) 3.69 (s, 2H) 3.71 (s, 3H) 7.06 (s, 1H) 7.27 (d, J=8.42 Hz, 1H) 7.48 (d, J=8.42 Hz, 1H) 8.07 (s, 1H) 8.67 (d, J=2.18 Hz, 1H) 13.04 (s, 1H).

EXAMPLE 246

5-(7-ethyl-6-methoxy-1,4-dihydroindeno[1,2-c]pyrazol-3-yl)pyridine-2-carbonitrile The title product was prepared using the procedure in Example 167 replacing Example 64C with Example 245E at 65% yield. MS (DCI/MH$_3$) m/z: 317.04 (M+H)$^+$. $^1$H NMR (500 MHz, DMSO-D$_6$) δ ppm 1.18 (t, J=7.48 Hz, 3H) 2.64 (q, J=7.63 Hz, 2H) 3.86 (s, 3H) 3.89 (s, 2H) 7.23 (s, 1H) 7.43 (s, 1H) 8.15 (d, J=8.24 Hz, 1H) 8.35 (dd, J=8.24, 2.14 Hz, 1H) 9.15 (d, J=1.83 Hz, 1H).

EXAMPLE 247

3-(6-chloropyridin-3-yl)-7-ethyl-6-(tetrahydro-2H-pyran-4-yloxy)-1,4-dihydroindeno[1,2-c]pyrazole

EXAMPLE 247A 6-ethyl-5-hydroxyindan-1-one

Example 245C (1 g, 5.31 mmol) in dichloromethane (25 mL) at −78° C. was treated with BBr$_3$ (2 mL, 21.24 mmol). The reaction mixture was warmed to room temperature and stirred for 24 hours. The reaction was quenched with water and extracted with ethyl acetate. Organic layer was dried over MgSO$_4$ and concentrated. The residue was purified by flash chromatography eluting with 50% ethyl acetate in hexane. The title compound (0.8 g) was obtained at 85% yield.

EXAMPLE 247B 6-ethyl-5-(tetrahydro-2H-pyran-4-yloxy)indan-1-one

Example 247A (150 mg, 0.85 mmol), polymer supported Ph$_3$P (3 mmol/g, 0.57 g, 1.7 mmol), di-tert-butyl azodicarboxylate (392 mg, 1.70 mmol) and tetrahydropyran-4-ol (174 mg, 1.70 mmol) were combined in THF (4 mL) and stirred overnight. Insoluble material was removed by filtration, and the filtrate was concentrated. The residue was purified by flash chromatography eluting with a mixture of ethyl acetate and hexane. The title compound was obtained at quantitative yield. MS (DCI/MH$_3$) m/z: 261.1 (M+H)$^+$.

EXAMPLE 247C

2-[(6-chloropyridin-3-yl)carbonyl]-6-ethyl-5-(tetrahydro-2H-pyran-4-yloxy)indan-1-one The desired product was prepared using the procedure in Example 238B replacing Example 238A with Example 247B.

EXAMPLE 247D 3-(6-chloropyridin-3-yl)-7-ethyl-6-(tetrahydro-2H-pyran-4-yloxy)-1,4-dihydroindeno[1,2-c]pyrazole The desired product was prepared using the procedure in Example 165C replacing Example 165B with Example 247C. MS (DCI/NH$_3$) m/z: 396.1 (M+H)$^+$. $^1$H NMR (500 MHz, DMSO-D$_6$) δ ppm 1.19 (t, J=7.49 Hz, 3H) 1.61-1.68 (m, 2H) 1.98-2.01 (m, 2H) 2.66 (q, J=7.49 Hz, 2H) 3.51-3.55 (m, 2H) 3.81 (s, 2H) 3.84-3.87 (m, 2H) 4.63-4.68 (m, 1H) 7.26 (s, 2H) 7.42 (s, 1H) 7.63 (d, J=8.11 Hz, 1H) 8.20 (dd, J=8.11, 2.49 Hz, 1H) 8.80 (d, J=2.18 Hz 1H) 13.17 (s, 1H).

EXAMPLE 248

4-{5-[7-ethyl-6-(tetrahydro-2H-pyran-4-yloxy)-1,4-dihydroindeno[1,2-c]pyrazol-3-yl]pyridin-2-yl}phenol The desired product was prepared using the procedure in Example 166B replacing Example 166A with Example 247D. The title compound (35.2 mg) was obtained at 43% yield. MS (DCI/NH$_3$) m/z: 454.17 (M+H)$^+$. $^1$H NMR (500 MHz, DMSO-D$_6$) δ ppm 1.21 (t, J=7.49 Hz, 3H) 1.63-1.70 (m, 2H) 2.00-2.03 (m, 2H) 2.68 (q, J=7.49 Hz, 2H) 3.52-3.57 (m, 2H) 3.86 (s, 3H) 3.84-3.89 (m, 2H) 4.65-4.69 (m, 1H) 6.90 (d, J=8.73 Hz, 2H) 7.28 (s, 1H) 7.45 (s, 1H) 8.00 (d, J=8.73 Hz, 3H) 8.22 (dd, J=8.26, 2.03 Hz, 1H) 9.00 (d, J=2.18 Hz, 1H).

EXAMPLE 249

5-[7-ethyl-6-(3-morpholin-4-ylpropoxy)-1,4-dihydroindeno[1,2-c]pyrazol-3-yl]pyridine-2-carbonitrile

EXAMPLE 249A

6-ethyl-5-{[2-(trimethylsilyl)ethoxy]methoxy}indan-1-one

The desired product was prepared using the procedure in Example 205A replacing Example 172A with Example 247A.

EXAMPLE 249B

2-[(6-chloropyridin-3-yl)carbonyl]-6-ethyl-5-{[2-(trimethylsilyl)ethoxy]methoxy}indan-1-one The desired product was prepared using the procedure in Example 238B replacing Example 238A with Example 249A.

EXAMPLE 249C

3-(6-chloropyridin-3-yl)-7-ethyl-6-{[2-(trimethylsilyl)ethoxy]methoxy}-1,4-dihydroindeno[1,2-c]pyrazole The desired product was prepared using the procedure in Example 165C replacing Example 165B with Example 249B. The title compound (1.35 g) was obtained at 69% yield (for 3 steps).

EXAMPLE 249D

3-(6-chloropyridin-3-yl)-7-ethyl-6-{[2-(trimethylsilyl)ethoxy]methoxy}-1-{[2-(trimethylsilyl)ethoxy]methyl}-1,4-dihydroindeno[1,2-c]pyrazole The desired product was prepared using the procedure in Example 175D replacing Example 175C with Example 249C. The title compound (1.05 g) was obtained at 81% yield.

EXAMPLE 249E

5-(7-ethyl-6-{[2-(trimethylsilyl)ethoxy]methoxy}-1-{[2-(trimethylsilyl)ethoxy]methyl}-1,4-dihydroindeno[1,2-c]pyrazol-3-yl)pyridine-2-carbonitrile Example 249D (900 mg, 1.57 mmol), Pd$_2$(dba)$_3$ (36 mg, 0.039 mmol), dppf (43.5 mg, 0.078 mmol), zinc (204 mg, 0.39 mmol) and Zn(CN)$_2$ were combined in DMA (75 mL), heated at 130° C. for 3 hours and concentrated. The residue was purified by flash chromatography eluting with 20% ethyl acetate in hexane. The title product (872 mg) was obtained at 98.5% yield. MS (DCI/NH$_3$) m/z: 563.26 (M+H)$^+$.

EXAMPLE 249F

5-(7-ethyl-6-hydroxy-1-{[2-(trimethylsilyl)ethoxy]methyl}-1,4-dihydroindeno[1,2-c]pyrazol-3-yl)pyridine-2-carbonitrile The desired product was prepared using the procedure in Example 206A replacing Example 205E with Example 249E. The title compound (250 mg) was obtained at 81% yield. MS (DCI/NH$_3$) m/z: 433.19 (M+H)$^+$.

EXAMPLE 249G

5-[7-ethyl-6-(3-morpholin-4-ylpropoxy)-1,4-dihydroindeno[1,2-c]pyrazol-3-yl]pyridine-2-carbonitrile Example 249F (40 mg, 0.092 mmol), polymer supported Ph$_3$P (3 mmol/g, 46 mg, 0.139 mmol), di-tert-butyl azodicarboxylate (32 mg, 0.139 mmol) and 3-morpholin-4-ylpropan-1-ol (27 mg, 0.184 mmol) were combined in THF (3 mL) and stirred overnight. Insoluble material was removed by filtration, and the filtrate was concentrated. The residue was dissolved in a mixture of EtOH (5 mL) and CH$_2$Cl$_2$ (2 mL), treated with 4N HCl in dioxane (0.5 mL), stirred at 50° C. overnight and concentrated. The residue was purified by preparative HPLC. The title compound (33 mg) was obtained at 50% yield. MS (DCI/MH$_3$) m/z: 430.2 (M+H)$^+$.

Examples 250 to 254 represented by FIG. (XIII) and shown in Table 13 were synthesized in a similar fashion as described in Example 249G, except substituting the appropriate alcohol for 3-morpholin-4-ylpropan-1-ol.

TABLE 13

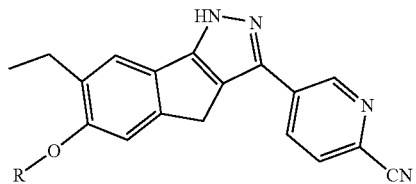

FIG. (XIII)

| Example | R | $^1$H NMR | MS | Yield |
|---|---|---|---|---|
| 249G | (propyl-morpholine group) | $^1$H NMR (400 MHz, DMSO-D$_6$) δ ppm 1.21 (t, J=7.52 Hz, 3 H) 2.16-2.23 (m, 2 H) 2.68 (q, J=7.57 Hz, 2 H) 3.10-3.17 (m, 2 H) 3.31-3.35 (m, 2 H) 3.63-3.70 (m, 4 H) 3.90 (s, 2 H) 4.02 (d, J=11.35 Hz, 2 H) 4.14 (t, J=5.98 Hz, 2 H) 7.23 (s, 1 H) 7.46 (s, 1 H) 8.15 (d, J=7.98 Hz, 1 H) 8.37 (dd, J=8.29, 2.15 Hz, 1 H) 9.16 (d, J=1.23 Hz, 1 H) 9.68 (s, 1 H) | (DCI/NH$_3$) 430.2 (M + H)$^+$ | 33 mg 50% |
| 250 | (tetrahydrofuran-3-ylmethyl) | $^1$H NMR (400 MHz, DMSO-D$_6$) δ ppm 1.19 (t, J=7.36 Hz, 3 H) 1.69-1.77 (m, 1 H) 2.01-2.10 (m, 1 H) 2.62-2.74 (m, 3 H) 3.59 (dd, J=8.59, 5.83 Hz, 1 H) 3.67-3.72 (m, 1 H) 3.76-3.84 (m, 2 H) 3.88 (s, 2 H) 3.95-4.06 (m, 2 H) 7.23 (s, 1 H) 7.43 (s, 1 H) 8.14 (d, J=8.28 Hz, 1 H) 8.35 (dd, J=7.98, 2.15 Hz, 1 H) 9.15 (d, J=1.53 Hz, 1 H) | (DCI/NH$_3$) 387.14 (M + H)$^+$ | 19 mg 35% |
| 251 | (tetrahydrofuran-3-yl) | $^1$H NMR (400 MHz, DMSO-D$_6$) δ ppm 1.18 (t, J=7.52 Hz, 3 H) 1.99-2.07 (m, 1 H) 2.20-2.29 (m, 1 H) 2.63 (q, J=7.67 Hz, 2 H) 3.79-3.96 (m, 6 H) 5.12-5.15 (m, 1 H) 7.21 (s, 1 H) 7.45 (d, br, 2 H) 8.15 (d, br, 1 H) 8.36 (s, 1 H) 9.15 (s, 1 H) 13.41 (s, 1 H) | (DCI/NH$_3$) 373.11 (M + H)$^+$ | 16 mg 31% |
| 252 | (4-hydroxycyclohexyl) | $^1$H NMR (400 MHz, DMSO-D$_6$) δ ppm 1.20 (t, J=7.52 Hz, 3 H) 1.36 (m, 1 H) 1.49 (m, 1 H) 1.62-1.65 (m, 2 H) 1.83-1.91 (m, 2 H) 2.02 (m, 1 H) 2.60-2.72 (m, 3 H) 3.59 (m, 1 H) 3.88 (s, 2 H) 4.39 (m, 1 H) 7.22 (s, 1 H) 7.25 (s, 1 H) 7.42 (s, 1 H) 8.14 (d, J=8.13 Hz, 1 H) 8.35 (dd, J=8.13, 2.30 Hz, 1 H) 9.15 (d, J=1.84 Hz, 1 H) | (DCI/NH$_3$) 401.14 (M + H)$^+$ | 5 mg 9% |
| 253 | (tetrahydropyran-4-yl) | $^1$H NMR (500 MHz, DMSO-D$_6$) δ ppm 1.30 (t, J=7.49 Hz, 3 H) 1.73-1.79 (m, 2 H) 2.09-2.12 (m, 2 H) 2.77 (q, J=7.49 Hz, 2 H) 3.62-3.66 (m, 2 H) 3.93-3.96 (m, 2 H) 3.97 (s, 2 H) 4.75-4.79 (m, 1 H) 7.38 (s, 1 H) 7.54 (s, 1 H) 8.24 (d, J=8.11 Hz, 1 H) 8.45 (dd, J=8.11, 2.18 Hz, 1 H) 9.24 (d, J=1.56 Hz, 1 H) | (DCI/NH$_3$) 387.18 (M + H)$^+$ | 90 mg 72% |

TABLE 13-continued

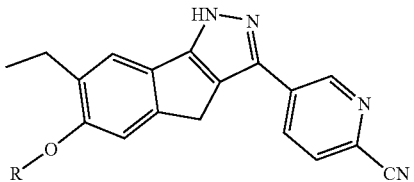

FIG. (XIII)

| Example | R | $^1$H NMR | MS | Yield |
|---|---|---|---|---|
| 254 | ![structure] (CH2-pyridin-2-yl) | $^1$H NMR (400 MHz, DMSO-D$_6$) δ ppm 1.24 (t, J=7.52 Hz, 6 H) 2.75 (q, J=7.47 Hz, 2 H) 3.89 (s, 2 H) 5.28 (s, 2 H) 7.32 (s, 1 H) 7.40 (dd, J=7.36, 5.52 Hz, 1 H) 7.49 (s, 1 H) 7.60 (d, J=7.98 Hz, 1 H) 7.92 (m, 1 H) 8.14 (d, J=8.28 Hz, 1 H) 8.36 (dd, J=8.13, 1.99 Hz, 1 H) 8.63 (d, J=4.60 Hz, 1 H) 9.15 (d, J=1.23 Hz, 1 H) | (DCI/NH$_3$) 394.15 (M + H)$^+$ | 45 mg 71% |

EXAMPLE 255

5-(6,7-diethyl-1,4-dihydroindeno[1,2-c]pyrazol-3-yl)pyridine-2-carbonitrile

EXAMPLE 255A 6-ethyl-1-oxo-2,3-dihydro-1H-inden-5-yl trifluoromethanesulfonate The desired product was prepared using the procedure in Example 245A replacing Example 144B with Example 247A. The title compound (8.5 g) was obtained at 72% yield. MS (DCI/NH$_3$) m/z: 325.99 (M+NH$_4$)$^+$. $^1$H NMR (500 MHz, DMSO-D$_6$) δ ppm 1.22 (t, J=7.49 Hz, 3H) 2.68-2.70 (m, 2H) 2.74 (q, J=7.49 Hz, 2H) 3.13-3.15 (m, 2H) 7.64 (s, 1H) 7.74 (s, 1H).

EXAMPLE 255B 6-ethyl-5-vinylindan-1-one

The desired product was prepared using the procedure in Example 245B replacing Example 245A with Example 255A. The title compound (430 mg) was obtained at 52% yield. MS (DCI/NH$_3$) m/z: 187.05 (M+H)$^+$. $^1$H NMR (500 MHz, DMSO-D$_6$) δ ppm 1.13 (t, J=7.63 Hz, 3H) 2.60-2.63 (m, 2H) 2.74 (q, J=7.43 Hz, 2H) 3.05-3.08 (m, 2H) 5.49 (dd, J=11.14, 1.07 Hz, 1H) 5.90 (dd, J=17.39, 1.22 Hz, 1H) 7.07 (dd, J=17.39, 10.98 Hz, 1H) 7.44 (s, 1H) 7.71 (s, 1H).

EXAMPLE 255C

2-[(6-chloropyridin-3-yl)carbonyl]-6-ethyl-5-vinylindan-1-one

The desired product was prepared using the procedure in Example 238B replacing Example 238A with Example 255B. The title compound was directly used for the preparation of Example 255D.

EXAMPLE 255D 3-(6-chloropyridin-3-yl)-7-ethyl-6-vinyl-1,4-dihydroindeno[1,2-c]pyrazole The desired product was prepared using the procedure in Example 165C replacing Example 165B with Example 255C. The title compound (250 mg) was obtained at 46% yield (for 2 steps). MS (DCI/NH$_3$) m/z: 322.04 (M+H)$^+$. $^1$H NMR (500 MHz, DMSO-D$_6$) δ ppm 1.19 (t, J=7.64 Hz, 3H) 2.77 (q, J=7.49 Hz, 2H) 3.88 (s, 2H) 5.34 (d, J=12.17 Hz, 1H) 5.79 (d, J=17.16 Hz, 1H) 7.07 (dd, J=17.31, 11.07 Hz, 1H) 7.48 (s, 1H) 7.65 (d, J=7.80 Hz, 1H) 7.74 (s, 1H) 8.24 (dd, J=8.42, 2.50 Hz, 2H) 8.84 (d, J=2.50 Hz, 1H) 13.41 (s, 1H).

EXAMPLE 255E

1-[bis(4-methoxyphenyl)methyl]-3-(6-chloropyridin-3-yl)-7-ethyl-6-vinyl-1,4-dihydroindeno[1,2-c]pyrazole The desired product was prepared using the procedure in Example 170B replacing 4-iodo-1H-pyrazole with Example 255D. The title product (220 mg) was obtained at 79% yield.

EXAMPLE 255F

1-[bis(4-methoxyphenyl)methyl]-3-(6-chloropyridin-3-yl)-6,7-diethyl-1,4-dihydroindeno[1,2-c]pyrazole Example 255E (130 mg) and Pt/C (5%, 13 mg) were combined in THF and stirred for 4 hours under hydrogen atmosphere. The insoluble material was removed by filtration, and the filtrate was evaporated. The title compound was obtained at quantitative yield.

EXAMPLE 255G

5-{1-[bis(4-methoxyphenyl)methyl]-6,7-diethyl-1,4-dihydroindeno[1,2-c]pyrazol-3-yl}pyridine-2-carbonitrile The title product was prepared using the procedure in Example 167 replacing Example 64C with Example 255F. The title product (62 mg) was obtained at 67% yield.

EXAMPLE 255H 5-(6,7-diethyl-1,4-dihydroindeno[1,2-c]pyrazol-3-yl)pyridine-2-carbonitrile Example 255G (60 mg, 0.11 mmol) in a mixture of ethanol (10 mL) and THF (5 mL) was treated with 4N HCl in dioxane (1 mL). The reaction was stirred for 4 hour, and the precipitate was collected, dried. The title product (30 mg) was obtained at 86% yield. MS (DCI/NH$_3$) m/z: 315.11 (M+H)$^+$. $^1$H NMR (500 MHz, DMSO-D$_6$) δ ppm 1.20-1.25 (m, 6H) 2.66-2.73 (m, 4H) 3.87 (s, 2H) 7.38 (s, 1H) 7.46 (s, 1H) 8.14 (d, J=8.11 Hz, 1H) 8.37 (dd, J=8.11, 2.18 Hz, 1H) 9.16 (d, J=1.56 Hz, 1H).

EXAMPLE 256

3-(6-chloropyridin-3-yl)-6,7-bis(2-methoxyethoxy)-1,4-dihydroindeno[1,2-c]pyrazole

EXAMPLE 256A 5,6-bis(2-methoxyethoxy)indan-1-one

Example 144A (800 mg, 4.88 mmol), 2-bromoethyl methyl ether (8 mL, 85.1 mmol), Cs$_2$CO$_3$ (9 g, 27.6 mmol) were combined in DMF and heated at 100° C. for 2 hours. Inorganic salts were removed by filtration, and the filtrate was concentrated. The residue was purified by flash chromatography eluting with 50% ethyl acetate in hexane. The title product (600 mg) was obtained at 44% yield. MS (DCI/NH$_3$) m/z: 281.00 (M+H)$^+$.

EXAMPLE 256B

2-[(6-chloropyridin-3-yl)carbonyl]-5,6-bis(2-methoxyethoxy)indan-1-one

The desired product was prepared using the procedure in Example 238B replacing
Example 238A with Example 256A.

EXAMPLE 256C 3-(6-chloropyridin-3-yl)-6,7-bis(2-methoxyethoxy)-1,4-dihydroindeno[1,2-c]pyrazole The desired product was prepared using the procedure in Example 165C replacing
Example 165B with Example 256B. The title compound (617 mg) was obtained at 82% yield (for 2 steps). MS (DCI/NH$_3$) m/z: 416.1 (M+H)$^+$. $^1$H NMR (500 MHz, DMSO-D$_6$) δ ppm 3.34 (s, 3H) 3.35 (s, 3H) 3.68-3.71 (m, 4H) 3.78 (s, 2H) 4.144.18 (m, 4H) 7.24 (s, 1H) 7.26 (s, 1H) 7.64 (d, J=7.80 Hz, 1H) 8.20 (dd, J=8.42, 2.50 Hz, 1H) 8.81 (d, J=2.18 Hz, 1H) 13.22 (s, 1H).

EXAMPLE 257

5-[6,7-bis(2-methoxyethoxy)-1,4-dihydroindeno[1,2-c]pyrazol-3-yl]pyridine-2-carbonitrile The title product was prepared using the procedure in Example 167 replacing Example 64C with Example 256C. The title product was obtained at 85% yield. MS (DCI/NH$_3$) m/z: 424.16 (M+NH$_4$)$^+$. $^1$H NMR (400 MHz, DMSO-D$_6$) δ ppm 3.34 (s, 3H) 3.35 (s, 3H) 3.68-3.71 (m, 4H) 3.85 (s, 2H) 4.15-4.19 (m, 4H) 7.26 (s, 1H) 7.27 (s, 1H) 8.14 (d, J=8.29 Hz, 1H) 8.35 (dd, J=8.29, 2.15 Hz, 1H) 9.15 (d, J=1.53 Hz, 1H).

EXAMPLE 258

6-hydroxy-3-(4'-hydroxy-1,1'-biphenyl-4-yl)-7-methoxyindeno[1,2-c]pyrazol-4(1H)-one

EXAMPLE 258A 6-hydroxy-7-methoxy-3-(4'-{[2-(trimethylsilyl)ethoxy]methoxy}-1,1'-biphenyl-4-yl)-1-{[2-(trimethylsilyl)ethoxy]methyl}indeno[1,2-c]pyrazol-4(1H)-one Example 175G (310 mg, 0.49 mmol) and Cs$_2$CO$_3$ (640 mg, 1.96 mmol) were combined in DMF and heated under air at 90° C. for 24 hours. Inorganic salt was removed by filtration, and the filtrate was concentrated. The residue was purified by flash chromatography eluting with 33% ethyl acetate in hexane. The title product (282 mg) was obtained at 89% yield. MS (DCI/NH$_3$) m/z: 645.29 (M+NH$_4$)$^+$.

EXAMPLE 258B 6-hydroxy-3-(4'-hydroxy-1,1'-biphenyl-4-yl)-7-methoxyindeno[1,2-c]pyrazol-4(1H)-one Example 258A (30 mg, 0.46 mmol) in ethanol (2 mL) was treated with 4N HCl in dioxane (2 mL). The reaction mixture was heated at 50° C. overnight and concentarted. The residue was purified by preparative HPLC. The title compound (19 mg) was obtained at 85% yield. MS (DCI/NH$_3$) m/z: 385.09 (M+NH$_4$)$^+$. $^1$H NMR (500 MHz, DMSO-D$_6$) δ ppm 3.92 (s, 3H) 6.88 (d, J=8.73 Hz, 2H) 7.01 (s, 1H) 7.14 (s, 1H) 7.62 (d, J=8.73 Hz, 2H) 7.78 (d, J=8.42 Hz, 2H) 8.22 (d, J=8.42 Hz, 2H) 9.53 (s, 1H) 9.63 (s, 1H) 13.46 (s, 1H).

EXAMPLE 259

3-(4'-hydroxy-1,1'-biphenyl-4-yl)-7-methoxy-6-(2-piperidin-1-ylethoxy)indeno[1,2-c]pyrazol-4(1H)-one Example 258A (40 mg, 0.0465 mmol), di-tert-butyl azodicarboxylate (21.4 mg, 0.093 mmol), polymer-supported Ph$_3$P (3 mmol/g, 31 mg, 0.093 mmol) and 2-piperidin-1-ylethanol (15 mg, 0.116 mmol) were combined in THF (3 mL). The reaction was stirred at room temperature for 2 days, and the insoluble material was removed by filtration and washed with THF thoroughly. The filtrate was concentrated, and the residue was treated with 4N HCl in dioxane (2 mL) and methanol (2 mL), and heated at 50° C. for 3 hours and concentrated. The residue was purified by HPLC to give title compound (14.4 mg) at 45% yield. MS (DCI/NH$_3$) m/z: 496.2 (M+H)$^+$.

Examples 260 and 261 represented by FIG. (XIV) and shown in Table 14 were synthesized in a similar fashion as described in Example 259, except substituting the appropriate alcohol for 2-piperidin-1-ylethanol.

TABLE 14

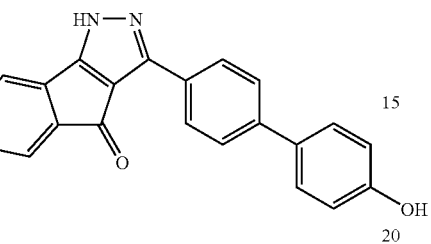

FIG. (XIV)

| Example | R | ¹H NMR | MS | Yield |
|---|---|---|---|---|
| 259 | (piperidin-1-yl)ethyl | ¹H NMR (500 MHz, DMSO-D$_6$) δ ppm 1.36-1.44 (m, 1 H) 1.66-1.76 (m, 3 H) 1.84-1.87 (m, 2 H) 3.02-3.08 (m, 2 H) 3.39 (m, 1 H) 3.43 (m, 1 H) 3.51-3.53 (m, 2 H) 3.96 (s, 3 H) 4.42 (t, J=4.99 Hz, 2 H) 6.88 (d, J=8.73 Hz, 2 H) 7.28 (s, 1 H) 7.33 (s, 1 H) 7.62 (d, J=8.73 Hz, 2 H) 7.80 (d, J=8.42 Hz, 2 H) 8.23 (d, J=8.42 Hz, 2 H) 9.34 9.34 (s, 1 H) 9.66 (s, 1 H) 13.57 (s, 1 H) | (DCI/NH$_3$) m/z: 496.2 (M + H)⁺ | 14.4 mg 45% |
| 260 | (1-methylpiperidin-3-yl)methyl | ¹H NMR (500 MHz, DMSO-D$_6$) δ ppm 1.23-1.31 (m, 1 H) 1.65-1.76 (m, 1 H) 1.84-1.98 (m, 2 H) 2.22-2.29 (m, 1 H) 2.79-2.88 (m, 5 H) 3.51-3.56 (m, 2 H) 3.94 (s, 3 H) 3.93-3.96 (m, 1H) 4.03-4.06 (m, 1 H) 6.88 (d, J=8.42 Hz, 2 H) 7.22 (s, 1 H) 7.23 (s, 1 H) 7.62 (d, J=8.73 Hz, 2 H) 7.80 (d, J=8.73 Hz, 2 H) 8.23 (d, J=8.73 Hz, 2 H) 9.35 (s, 1 H) 9.66 (s, 1 H) 13.57 (s, 1 H) | (DCI/NH$_3$) m/z: 496.21 (M + H)⁺ | 11.3 mg 41% |
| 261 | 3-[4-(3-chlorophenyl)piperazin-1-yl]propyl | ¹H NMR (500 MHz, DMSO-D$_6$) δ ppm 2.18-2.22 (m, 2 H) 3.03 (t, J=13.26 Hz, 2 H) 3.15-3.23 (m, 4 H) 3.66 (d, J=11.54 Hz, 2 H) 3.92-3.95 (m, 5 H) 4.18 (t, J=5.93 Hz, 2 H) 6.88 (m, 3 H) 6.99 (dd, J=8.42, 1.87 Hz, 1 H) 7.08 (s, 1 H) 7.24 (s, 1 H) 7.25 (d, J=8.11 Hz, 1 H) 7.29 (m, 1 H) 7.62 (d, J=8.42 Hz, 2 H) 7.80 (d, J=8.11 Hz, 2 H) 8.23 (d, J=8.42 Hz, 2 H) 9.38 (s, 1 H) 9.65 (s, 1 H) 13.57 (s, 1H) | (DCI/NH$_3$) m/z: 621.2 (M + H)⁺ | 15 mg 35% |

EXAMPLE 262

4-{6-[3-(dimethylamino)propoxy]-7-methoxy-4-oxo-1,4-dihydroindeno[1,2-c]pyrazol-3-yl}benzonitrile

EXAMPLE 262A 4-(7-methoxy-4-oxo-6-{[2-(trimethylsilyl)ethoxy]methoxy}-1-{[2-(trimethylsilyl)ethoxy]methyl}-1,4-dihydroindeno[1,2-c]pyrazol-3-yl)benzonitrile Example 205E (1.8 g, 3.19 mmol) and $Cs_2CO_3$ (4.16 g, 12.76 mmol) were combined in DMF (50 mL) and heated under air at 50° C. overnight. Inorganic salt was removed by filtration, and the filtrate was concentrated. The residue was purified by flash chromatography eluting with 25% ethyl acetate in hexane. The title product (1.82 g) was obtained at 99% yield. MS (DCI/NH$_3$) m/z: 578.25 (M+H)$^+$.

EXAMPLE 262B 4-(6-hydroxy-7-methoxy-4-oxo-1-{[2-(trimethylsilyl)ethoxy]methyl}-1,4-dihydroindeno[1,2-c]pyrazol-3-yl)benzonitrile The desired product was prepared using the procedure in Example 206A replacing Example 205E with Example 262A. The title compound was obtained at quantitative yield.

EXAMPLE 262C

4-{6-[3-(dimethylamino)propoxy]-7-methoxy-4-oxo-1,4-dihydroindeno[1,2-c]pyrazol-3-yl}benzonitrile Example 262B (40 mg, 0.089 mmol), di-tert-butyl azodicarboxylate (42 mg, 0.18 mmol), polymer-supported Ph$_3$P (3 mmol/g, 60 mg, 0.18 mmol) and 3-dimethylaminopropanol (18.6 mg, 0.18 mmol) were combined in THF (3 mL). The reaction was stirred at room temperature overnight, and the insoluble material was removed by filtration and washed with THF thoroughly. The filtrate was concentrated, and the residue was treated with 4N HCl in dioxane (2 mL) and methanol (2 mL), and heated at 50° C. for 5 hours. The reaction mixture was concentrated, and the residue was purified by HPLC to give the title compound (41 mg) at 77% yield. MS (DCI/NH$_3$) m/z: 403.14 (M+H)$^+$.

EXAMPLE 263

4-(6-hydroxy-7-methoxy-4-oxo-1,4-dihydroindeno[1,2-c]pyrazol-3-yl)benzonitrile

The desired product was prepared using the procedure in Example 205F replacing
Example 205E with Example 262A. The title compound was obtained at quantitative yield. MS (ESI) m/z: 315.99 (M−H)$^-$.

Examples 264 and 265 represented by FIG. (XV) and shown in Table 15 were synthesized in a similar fashion as described in Example 262C, except substituting the appropriate alcohol for 3-dimethylaminopropanol.

TABLE 15

FIG. (XV)

| Example | R | $^1$H NMR | MS | Yield |
|---|---|---|---|---|
| 262C | 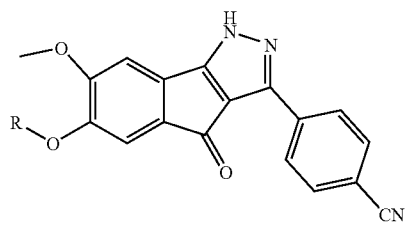 | $^1$H NMR (500 MHz, DMSO-D$_6$) δ ppm 2.10-2.16 (m, 2 H) 2.84 (s, 3 H) 2.85 (s, 3 H) 3.24 (s, br, 2 H) 3.94 (s, 3 H) 4.14 (t, J=6.08 Hz, 2 H) 7.21 (s, 1 H) 7.23 (s, 1 H) 8.06 (d, J=8.42 Hz, 2 H) 8.32 (d, J=8.42 Hz, 3 H) 9.40 (s, 1 H) 13.84 (s, 1 H) | (DCI/NH$_3$) m/z: 403.14 (M + H)$^+$ | 41 mg 77% |
| 263 | H | $^1$H NMR (400 MHz, DMSO-D$_6$) δ ppm 3.91 (s, 3 H) 7.01 (s, 1 H) 7.14 (s, 1 H) 8.05 (d, J=8.29 Hz, 2 H) 8.32 (d, J=8.29 Hz, 2 H) 9.60 (s, 1 H) 13.74 (s, 1 H) | (ESI) m/z: m/z: 315.99 (M − H)$^-$ | 30 mg 95% |

TABLE 15-continued

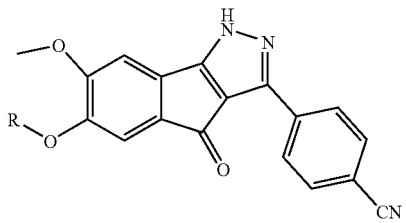

FIG. (XV)

| Example | R | ¹H NMR | MS | Yield |
|---|---|---|---|---|
| 264 | ![tetrahydrofuran-yl-methyl] | ¹H NMR (500 MHz, DMSO-D$_6$) δ ppm 1.96-2.00 (m, 1 H) 2.17-2.24 (m, 1 H) 3.74-3.78 (m, 1 H) 3.81-3.89 (m, 3 H) 3.92 (s, 3 H) 5.12 (dd, J=5.77, 4.52 Hz, 1 H) 7.15 (s, 1 H) 7.20 (s, 1 H) 8.05 (d, J=8.42 Hz, 2 H) 8.32 (d, J=8.42 Hz, 2 H) | (DCI/NH$_3$) m/z: 405.08 (M + H)$^+$ | 24 mg 56% |
| 265 | ![morpholinopropyl] | ¹H NMR (500 MHz, DMSO-D$_6$) δ ppm 2.18-2.23 (m, 2 H) 3.06-3.13 (m, 2 H) 3.25-3.29 (m, 2 H) 3.49 (d, J=12.16 Hz, 2 H) 3.77 (t, J=11.54 Hz, 2 H) 3.94 (s, 3 H) 3.98-4.00 (m, 2 H) 4.16 (t, J=6.08 Hz, 2 H) 7.22 (s, 1 H) 7.23 (s, 1 H) 8.06 (d, J=8.42 Hz, 2 H) 8.34 (d, J=8.73 Hz, 2 H) 10.48 (s, 1 H) 13.87 (s, 1 H) | (ESI) m/z: 445.06 (M + H)$^+$ | 99 mg 86% |

EXAMPLE 266

3-(6-chloropyridin-3-yl)-6,7-dimethoxy-4-methyl-1,4-dihydroindeno[1,2-c]pyrazol-4-ol

EXAMPLE 266A 3-(6-chloropyridin-3-yl)-6,7-dimethoxyindeno[1,2-c]pyrazol-4(1H)-one Example 230C (300 mg, 0.91 mmol) and Cs$_2$CO$_3$ (1.5 g, 4.6 mmol) were combined in DMF (30 mL), heated under air at 90° C. for 3 hours and concentrated. The residue was suspended in water, and the orange solid were collected by filtration and dried. The title product (287 mg) was obtained at 92% yield. MS (DCI/NH$_3$) m/z: 342.20 (M+H)$^+$. ¹H NMR (400 MHz, DMSO-D$_6$) δ ppm 3.82 (s, 3H) 3.90 (s, 3H) 7.15 (s, 1H) 7.16 (s, 1H) 7.75 (d, J=8.59 Hz, 1H) 8.48 (dd, J=8.44, 2.30 Hz, 1H) 9.14 (d, J=2.15 Hz, 1H).

EXAMPLE 266B 3-(6-chloropyridin-3-yl)-6,7-dimethoxy-4-methyl-1,4-dihydroindeno[1,2-c]pyrazol-4-ol To a suspension of 266A (100 mg, 0.29 mmol) in THF (15 mL) at 0° C. was added 1.4 M CH$_3$MgCl in toluene:THF (1:1, 1.3 mL). The reaction was warmed to room temperature, stirred for 1 day, quenched with water and concentrated. The residue was purified by preparative HPLC. MS (DCI/NH$_3$) m/z: 358.03 (M+H)$^+$. ¹H NMR (500 MHz, DMSO-D$_6$) δ ppm 1.57 (s, 3H) 3.83 (s, 6H) 3.86 (d, J=2.81 Hz, 1H) 7.10 (s, 1H) 7.17 (d, J=3.74 Hz, 1H) 7.69 (d, J=8.42 Hz, 1H) 8.37 (dd, J=8.42, 2.50 Hz, 1H) 9.01 (d, J=2.50 Hz, 1H).

EXAMPLE 267

4'-[6-methoxy-7-(2-pyrrolidin-1-ylethoxy)-1,4-dihydroindeno[1,2-c]pyrazol-3-yl]-1,1'-biphenyl-4-ol

EXAMPLE 267A 1-(4-bromobenzoyl)-1H-imidazole

To a solution of 4-bromo-benzoic acid (19.55 g, 97.3 mmol) in DMF (100 mL) was added 1,1'-carbonyldiimidazole (39.42 g, 243.2 mmol) slowly at room-temperature under N$_2$. After 2 hours, the reaction was completed and poured into ice water (1 L). The precipitate was filtered, washed with water (2 L), and dried in vacuo to give the desired product (16.7 g, 68%). MS (DCI/NH$_3$) m/z 252 (M+H)$^+$; ¹H NMR (300 MHz, DMSO-D$_6$) δ ppm 7.02 (s, 1H) 7.17 (s, 1H) 7.63-7.90 (m, 4H) 8.21 (s, 1H).

EXAMPLE 267B 6-(benzyloxy)-5-methoxyindan-1-one

Example 144B (8.65 g, 48.5 mmol), benzyl bromide (12 mL, 97.1 mmol), K$_2$CO$_3$ (20.2 g, 146.2 mmol) and anhydrous acetone (500 mL) were mixed and refluxed overnight. Acetone was removed, and the concentrate was treated with water (300 mL). The precipitate was filtered, washed with water (300 mL×2), and dried to give the desired product (11.80 g, 91%). MS (DCI/NH$_3$) m/z 269 (M+H)$^+$; $^1$H NMR (300 MHz, CD$_3$OD) δ ppm 2.61-2.67 (m, 2H) 3.04-3.10 (m, 2H) 3.95 (s, 3H) 5.12 (s, 2H) 7.10 (s, 1H) 7.21 (s, 1H) 7.28-7.39 (m, 3H) 7.41-7.47 (m, 2H).

EXAMPLE 267C 6-(benzyloxy)-2-(4-bromobenzoyl)-5-methoxyindan-1-one

To a solution of Example 267B (11.50 g, 42.9 mmol) in anhydrous THF (200 mL) was added 95% NaH (3.25 g, 128.7 mmol). The mixture was stirred at room temperature for 0.5 hour. Example 267A (16.2 g, 64.35 mmol) in THF (50 mL) was added dropwise to the above mixture. The reaction was run overnight, and poured into water (1.5 L). Concentrated hydrochloric acid (30 mL) was added dropwise to neutralize the mixture. The precipitate was filtered, recrystallized in ethanol (100 mL), and dried in vacuo to give the desired product (14.08 g, 73%). MS (APCI) m/z 451 (M+H)$^+$; $^1$H NMR (300 MHz, CDCl$_3$) δ ppm 3.82 (s, 2H) 3.98 (s, 3H) 5.21 (s, 2H) 6.99 (s, 1H) 7.30-7.42 (m, 5H) 7.44-7.50 (m, 2H) 7.59-7.65 (m, 2H) 7.74-7.81 (m, 2H).

EXAMPLE 267D 7-(benzyloxy)-3-(4-bromophenyl)-6-methoxy-1,4-dihydroindeno[1,2-c]pyrazole Example 267C (14.08 g, 31.2 mmol), hydrazine monohydrate (3.03 mL, 62.4 mmol), absolute ethanol (300 mL), and glacial acetic acid (3.57 mL, 62.4 mmol) were mixed and refluxed for 24 hours. The reaction was cooled. The precipitate was filtered, washed with water (30 mL×2) and ethanol (30 mL×2), and dried in vacuo overnight to give the desired product (11.66 g, 84%). MS (ESI) m/z 448 (M+H)$^+$.

EXAMPLE 267E 7-(benzyloxy)-3-(4-bromophenyl)-6-methoxy-1-{[2-(trimethylsilyl)ethoxy]methyl}-1,4-dihydroindeno[1,2-c]pyrazole To a mixture of Example 267D (11.66 g, 26.1 mmol) and DMF (500 mL) in ice bath was added 95% NaH (0.69 g, 27.41 mmol). The mixture was stirred at room temperature for 0.5 hour and then cooled at 0° C. 2-(trimethylsilyl) ethoxymethyl chloride (4.85 mL, 27.41 mmol) was added to the mixture. After 0.5 hour, the ice bath was removed. The reaction was run at room temperature for another hour, and then poured into water. Ethyl acetate (200 mL×3) was used to extract the product. The organic solution was dried with MgSO$_4$, concentrated, and purified by flash chromatography to give the desired product (10.84 g 72%). MS (DCI/NH$_3$) m/z 577 (M+H)$^+$.

EXAMPLE 267F

4'-(7-(benzyloxy)-6-methoxy-1-{[2-(trimethylsilyl)ethoxy]methyl}-1,4-dihydroindeno[1,2-c]pyrazol-3-yl)-1,1'-biphenyl-4-ol Example 267E (518 mg, 0.896 mmol), dichlorobis(triphenylphosphine)palladium(II) (63 mg, 0.090 mmol), 4-(hydroxyphenyl)boronic acid (147.3 mg, 1.07 mmol), 1M Na$_2$CO$_3$ solution (1 mL), DME/EtOH/H$_2$O (7:2:3, 3 mL) and a stirrer bar were mixed together in a capped tube. The mixture was heated to 160° C. for 5 minutes in a Smith Synthesizer. The reaction was repeated 19 times. The solution was combined, and concentrated. The residue was purified by flash chromatography to give the desired product (4.69 g, 47%). MS (DCI/NH$_3$) m/z 591 (M+H)$^+$.

EXAMPLE 267G 7-(benzyloxy)-6-methoxy-3-(4'-{[2-(trimethylsilyl)ethoxy]methoxy}-1,1'-biphenyl-4-yl)-1-{[2-(trimethylsilyl)ethoxy]methyl}-1,4-dihydroindeno[1,2-c]pyrazole To the solution of Example 267F (4.66 g, 7.9 mmol) in DMF (200 mL) was added 95% NaH (0.21 g, 8.28 mmol). The mixture was stirred at room temperature for 0.5 hour. 2-(trimethylsilyl)ethoxymethyl chloride (1.49 mL, 8.28 mmol) was added dropwise. The reaction was stirred for 1 hour. DMF was removed. The residue was treated with water (200 mL) and extracted with ethyl acetate (200 mL). The organic phase was dried with MgSO$_4$, and purified by flash chromatography to give the desired product (4.31 g, 76%). MS (DCI/NH$_3$) m/z 722 (M+H)$^+$.

EXAMPLE 267H 6-methoxy-3-(4'-{[2-(trimethylsilyl)ethoxy]methoxy}-1,1'-biphenyl-4-yl)-1-{[2-(trimethylsilyl)ethoxy]methyl}-1,4-dihydroindeno[1,2-c]pyrazol-7-ol Example 267G (4.20 g, 5.82 mmol), 10% Pd/C (2.1 g, 2 mmol), and THF (100 mL) were mixed. The reaction was shaken under H$_2$ (60 psi) at room temperature for 3 days. Flash chromatography was used to purify the desired product (2.67 g 71%). MS (DCI/NH$_3$) m/z 631 (M+H)$^+$.

EXAMPLE 267I

4'-[6-methoxy-7-(2-pyrrolidin-1-ylethoxy)-1,4-dihydroindeno[1,2-c]pyrazol-3-yl]-1,1'-biphenyl-4-ol Example 267H (50 mg, 0.079 mmol), 1-(2-chloroethyl) pyrrolidine hydrochloride (20 mg, 0.118 mmol), Cs$_2$CO$_3$ (77 mg, 0.238 mmol), and DMF (2 mL) were mixed in a vial and stirred at 60° C. overnight. LC-MS indicated the reaction was completed. The mixture was filtered and concentrated. To the residue was added ethanol (2 mL) and concentrated hydrochloric acid (2 mL). The reaction was heated at 50° C. for 5 hours. The mixture was concentrated, and purified with HPLC to give the desired product.

Examples 268 and 284 represented by FIG. (XVI) and shown in Table 16 were synthesized in a similar fashion as described in Example 267.

TABLE 16

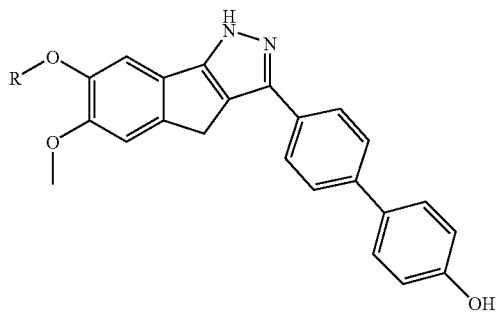

FIG. (XVI)

| Example # | —R | ¹H-NMR | MS m/z | Weight & Yield (%) |
|---|---|---|---|---|
| 2671 | pyrrolidin-1-yl-propyl (N-CH₂CH₂CH₂—) | ¹H NMR (500 MHz, DMSO-D₆) δ ppm 1.85-1.95 (m, 2 H) 2.00-2.10 (m, 2 H) 3.11-3.23 (m, 2 H) 3.59-3.71 (m, 4 H) 3.87 (s, 3 H) 3.89 (s, 2 H) 4.34-4.38 (m, 2 H) 6.87 (d, J=8.42 Hz, 2 H) 7.31 (s, 1 H) 7.40 (s, 1 H) 7.57 (d, J=8.73 Hz, 2 H) 7.72 (d, J=8.42 Hz, 2 H) 7.83 (d, J=8.73 Hz, 2 H) 9.60 (s, 1 H) 9.77 (s, 1 H) | MS (ESI) m/z 468 (M + H)⁺ | 31 mg, 56% |
| 268 | morpholin-4-yl-propyl | ¹H NMR (500 MHz, DMSO-D₆) δ ppm 3.20-3.32 (m, 2 H) 3.55-3.66 (m, 4 H) 3.70-3.78 (m, 2 H) 3.83 (s, 2 H) 3.86 (s, 3 H) 3.99-4.06 (m, 2 H) 4.40-4.44 (m, 2 H) 6.87 (d, J=8.42 Hz, 2 H) 7.31 (s, 1 H) 7.42 (s, 1 H) 7.57 (d, J=8.73 Hz, 2 H) 7.72 (d, J=8.42 Hz, 2 H) 7.80-7.83 (m, 2 H) 9.62 (s, 1 H) 10.00 (s, 1 H) | MS (ESI) m/z 484 (M + H)⁺ | 18 mg, 44% |
| 269 | N,N-diethylaminopropyl | ¹H NMR (500 MHz, DMSO-D₆) δ ppm 1.24 (t, J=7.02 Hz, 6 H) 3.16-3.28 (m, 2 H) 3.51-3.61 (m, 4 H) 3.87 (s, 2 H) 3.89 (s, 3 H) 4.48-4.54 (m, 2 H) 6.88 (d, J=8.73 Hz, 2 H) 7.27 (s, 1 H) 7.34 (s, 1 H) 7.57 (d, J=8.73 Hz, 2 H) 7.81 (d, J=8.42 Hz, 2 H) 8.23 (d, J=8.42 Hz, 2 H) 9.60 (s, 1 H) 9.92 (s, 1 H) | MS (ESI) m/z 470 (M + H)⁺ | 22 mg, 47% |
| 270 | pyridin-3-ylmethyl | ¹H NMR (500 MHz, DMSO-D₆) δ ppm 3.84 (s, 2 H) 3.87 (s, 3 H) 5.41 (s, 2 H) 6.88 (d, J=8.54 Hz, 2 H) 7.32 (s, 1 H) 7.43 (s, 1 H) 7.57 (d, J=8.54 Hz, 2 H) 7.73 (d, J=8.24 Hz, 2 H) 7.84 (d, J=8.54 Hz, 2 H) 8.05 (dd, J=7.93, 5.80 Hz, 1 H) 8.59 (d, J=7.93 Hz, 1 H) 8.89 (d, J=5.49 Hz, 1 H) 9.00 (s, 1 H) | MS (ESI) m/z 462 (M + H)⁺ | 12 mg, 26% |
| 271 | pyridin-2-ylmethyl | ¹H NMR (500 MHz, DMSO-D₆) δ ppm 3.81 (s, 2 H) 3.87 (s, 3 H) 5.31 (s, 2 H) 6.87 (d, J=8.85 Hz, 2 H) 7.29 (s, 1 H) 7.32 (s, 1 H) 7.48 (m, 1 H) 7.57 (d, J=8.54 Hz, 2 H) 7.67 (d, J=7.93 Hz, 1 H) 7.72 (d, J=8.54 Hz, 2 H) 7.82 (d, J=8.54 Hz, 2 H) 7.99 (m, 1 H) 8.66 (d, J=4.58 Hz, 1 H) | MS (ESI) m/z 462 (M + H)⁺ | 14 mg, 30% |

TABLE 16-continued

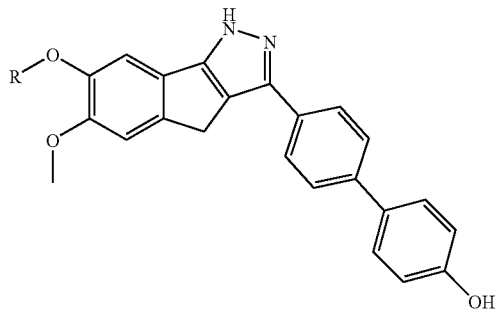

FIG. (XVI)

| Example # | —R | ¹H-NMR | MS m/z | Weight & Yield (%) |
|---|---|---|---|---|
| 272 | 3-chlorophenyl-piperazinyl-propyl | ¹H NMR (500 MHz, DMSO-D₆) δ ppm 2.23-2.31 (M, 2 H) 3.12-3.24 (m, 6 H) 3.30-3.41 (m, 2 H) 3.54-3.68 (m, 2 H) 3.85 (s, 3 H) 3.87 (s, 2 H) 4.11-4.21 (m, 2 H) 6.88 (d, J=8.73 Hz, 2 H) 6.99 (d, J=8.42, 1 H) 7.08 (s, 1 H) 7.27 (s, 1 H) 7.32 (s, 1 H) 7.57 (d, J=8.42 Hz, 2 H) 7.72 (d, J=8.42 Hz, 2 H) 7.80 (d, J=8.42 Hz, 1 H) 7.83 (d, J=8.42 Hz, 2 H) 8.24 (d, J=8.42 Hz, 1 H) 9.64 (s, 1 H) 10.44 (s, 1 H) | MS (ESI) m/z 608 (M + H)⁺ | 9 mg, 15% |
| 273 | pyridin-4-ylmethyl | ¹H NMR (500 MHz, DMSO-D₆) δ ppm 3.83 (s, 2 H) 3.91 (s, 3 H) 5.56 (s, 2 H) 6.88 (d, J=8.73 Hz, 2 H) 7.34 (s, 1 H) 7.37 (s, 1 H) 7.57 (d, J=8.73 Hz, 2 H) 7.72 (d, J=8.42 Hz, 2 H) 7.83 (d, J=8.42 Hz, 2 H) 8.06 (d, J=6.24 Hz, 2 H) 8.92 (d, J=6.24 Hz, 2 H) | MS (ESI) m/z 462 (M + H)⁺ | 5 mg, 11% |
| 274 | 2-(dimethylamino)ethyl | ¹H NMR (500 MHz, CD₃OD) δ ppm 3.07 (s, 6 H) 3.64-3.68 (m, 2 H) 4.01 (s, 3 H) 4.06 (s, 2 H) 4.44-4.47 (m, 2 H) 6.90 (d, J=8.54 Hz, 2 H) 7.48 (s, 1 H) 7.50 (s, 1 H) 7.56 (d, J=8.85 Hz, 2 H) 7.81 (d, J=8.54 Hz, 2 H) 7.90 (d, J=8.54 Hz, 2 H) | MS (ESI) m/z 442 (M + H)⁺ | 33 mg, 75% |
| 275 | 2-(piperidin-1-yl)ethyl | ¹H NMR (400 MHz, DMSO-D₆) δ ppm 1.44 (m, 1 H) 1.66-1.78 (m, 3 H) 1.82-1.91 (m, 2 H) 3.00-3.13 (m, 2 H) 3.52-3.58 (m, 4 H) 3.83 (s, 2 H) 3.87 (s, 3 H) 4.38-4.43 (m, 2 H) 6.84-6.90 (m, 2 H) 7.31 (s, 1 H) 7.40 (s, 1 H) 7.54-7.59 (m, 2 H) 7.70-7.75 (m, 2 H) 7.80-7.85 (m, 2 H) 9.32 (s, 1 H) 9.58 (s, 1 H) | MS (ESI) m/z 482 (M + H)⁺ | 26 mg, 54% |
| 276 | 3-(dimethylamino)propyl | ¹H NMR (400 MHz, DMSO-D₆) δ ppm 2.09-2.21 (m, 2 H) 2.85 (s, 3 H) 2.87 (s, 3 H) 3.20-3.34 (m, 2 H) 3.81 (s, 2 H) 3.85 (s, 3 H) 4.14 (t, J=5.98 Hz, 2 H) 6.87 (d, J=8.59 Hz, 2 H) 7.27 (s, 1 H) 7.30 (s, 1 H) 7.57 (d, J=8.59 Hz, 2 H) 7.72 (d, J=8.29 Hz, 2 H) 7.82 (d, J=8.33 Hz, 2 H) 9.33 (s, 1 H) | MS (ESI) m/z 456 (M + H)⁺ | 40 mg, 88% |

TABLE 16-continued

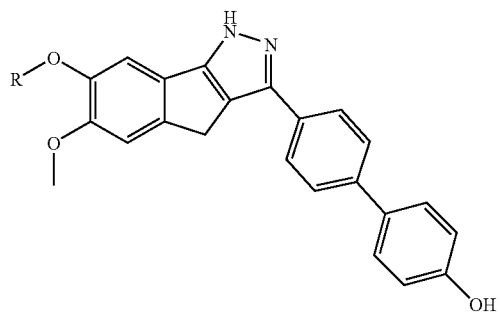

FIG. (XVI)

| Example # | —R | $^{1}$H-NMR | MS m/z | Weight & Yield (%) |
|---|---|---|---|---|
| 277 | (1-propylpiperidin-yl) | $^{1}$H NMR (400 MHz, DMSO-D$_6$) δ ppm 1.43 (m, 1 H) 1.56-1.75 (m, 3 H) 1.80-1.90 (m, 2 H) 2.12-2.24 (m, 2 H) 2.86-3.00 (m, 2 H) 3.19-3.30 (m, 2 H) 3.47-3.52 (m, 2 H) 3.85 (s, 3 H) 3.87 (s, 2 H) 4.15 (t, J=5.98 Hz, 2 H) 6.87 (d, J=8.59 Hz, 2 H) 7.23 (s, 1 H) 7.30 (s, 1 H) 7.57 (d, J=8.90 Hz, 2 H) 7.72 (d, J=8.59 Hz, 2 H) 7.82 (d, J=8.64 Hz, 2 H) 8.92 (s, 1 H) 9.61 (s, 1 H) | MS (ESI) m/z 496 (M + H)$^+$ | 30 mg, 60% |
| 278 | (dimethylamino-methyl-propyl) | $^{1}$H NMR (400 MHz, DMSO-D$_6$) δ ppm 1.37 (d, J=7.06 Hz, 3 H) 2.88 ppm 1.37 (d, J=7.06 Hz, 3 H) 2.88 (s, 3 H) 2.91 (s, 3 H) 3.33-3.53 (m, 2 H) 3.83 (s, 2 H) 3.87 (s, 3 H) 4.29 (m, 1 H) 6.87 (d, J=8.59 Hz, 2 H) 7.32 (s, 1 H) 7.42 (s, 1 H) 7.57 (d, J=8.59 Hz, 2 H) 7.72 (d, J=8.59 Hz, 2 H) 7.83 (d, J=8.62 Hz, 2 H) 9.57 (s, 1 H) | MS (ESI)m/z 456 (M + H)$^+$ | 21 mg, 46% |
| 279 | (bis(diethylaminomethyl)propyl) | $^{1}$H NMR (400 MHz, DMSO-D$_6$) δ ppm 1.09-1.31 (m, 12 H) 3.13-3.35 (m, 8 H) 3.84-3.89 (m, 4 H) 3.90 (s, 2 H) 3.92 (s, 3 H) 4.44 (m, 1 H) 6.88 (d, J=8.90 Hz, 2 H) 7.57 (d, J=8.59 Hz, 2 H) 7.62 (s, 1 H) 7.64 (s, 1 H) 7.82 (d, J=8.59 Hz, 2 H) 8.24 (d, J=8.59 Hz, 2 H) 9.44 (s, 1 H) | MS (ESI) m/z 555 (M + H)$^+$ | 10 mg, 18% |
| 280 | (1-ethylpiperidin-3-yl) | $^{1}$H NMR (400 MHz, DMSO-D$_6$) δ ppm 1.32 (t, J=5.98 Hz, 3 H) 1.62-1.71 (m, 2 H) 2.04-2.10 (m, 2 H) 3.12-3.27 (m, 4 H) 3.36-3.65 (m, 2 H) 3.87 (s, 3 H) 3.89 (s, 2 H) 4.47 (m, 1 H) 6.87 (d, J=8.59 Hz, 2 H) 7.31 (s, 1 H) 7.37 (s, 1 H) 7.57 (d, J=8.59 Hz, 2 H) 7.72 (d, J=8.29 Hz, 2 H) 7.81 (d, J=7.98 Hz, 2 H) 9.47 (s, 1 H) | MS (ESI) m/z 482 (M + H)$^+$ | 7 mg, 15% |
| 281 | (dimethylamino-methylbutyl) | $^{1}$H NMR (400 MHz, DMSO-D$_6$) δ ppm 1.08 (d, J=6.75 Hz, 3 H) 1.43 (m, 1 H) 2.86 (s, 3 H) 2.93 (s, 3 H) 3.12 (m, 1 H) 3.27 (m, 1 H) 3.87 (s, 3.12 (m, 1 H) 3.27 (m, 1 H) 3.87 (s, 3 H) 3.89 (s, 2 H) 3.95 (m, 1 H) 4.10 (m, 1 H) 6.87 (d, J=8.59 Hz, 2 H) 7.28 (s, 1 H) 7.31 (s, 1 H) 7.57 (d, J=8.59 Hz, 2 H) 7.72 (d, J=8.59 Hz, 2 H) 7.81 (d, J=8.59 Hz, 2 H) 8.90 (s, 1 H) | MS (ESI) m/z 470 (M + H)$^+$ | 6 mg, 13% |

TABLE 16-continued

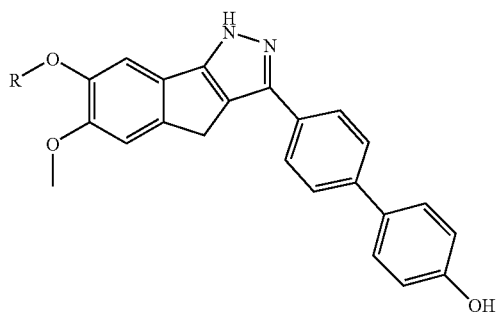

FIG. (XVI)

| Example # | —R | ¹H-NMR | MS m/z | Weight & Yield (%) |
|---|---|---|---|---|
| 282 | (N-methylpyrrolidin-2-yl)ethyl | ¹H NMR (400 MHz, DMSO-D₆) δ ppm 1.84-2.05 (m, 4 H) 2.10-2.19 (m, 2 H) 2.84 (s, 3 H) 3.07-3.21 (m, 2 H) 3.45 (m, 1 H) 3.80 (s, 2 H) 3.83 (s, 3 H) 4.61-4.71 (m, 2 H) 6.86 (d, J=8.59 Hz, 2 H) 7.27 (s, 1 H) 7.30 (s, 1 H) 7.56 (d, J=8.59 Hz, 2 H) 7.71 (d, J=8.29 Hz, 2 H) 7.78-7.84 (m, 2 H) 9.47 (s, 1 H) | MS (ESI) m/z 482 (M + H)⁺ | 19 mg, 39% |
| 283 | imidazol-1-ylethyl | ¹H NMR (400 MHz, DMSO-D₆) δ ppm 3.80 (s, 3 H) 3.84 (s, 2 H) 4.47 (t, J=5.59 Hz, 2 H) 4.64 (t, J=5.67 Hz, 2 H) 6.87 (d, J=8.90 Hz, 2 H) 7.26 (s, 1 H) 7.30 (s, 1 H) 7.56 (d, J=8.59 Hz, 2 H) 7.62 (d, J=8.90 Hz, 1 H) 7.72 (d, J=8.91 Hz, 2 H) 7.82 (d, J=8.83 Hz, 2 H) 8.23 (d, J=8.59 Hz, 1 H) 9.18 (s, 1 H) | MS (ESI) m/z 465 (M + H)⁺ | 25 mg, 54% |
| 284 | 3-(4-methylpiperazin-1-yl)propyl | ¹H NMR (300 MHz, DMSO-D₆) δ ppm 2.00-2.13 (m, 2 H) 2.71-2.74 (m, 2H) 2.79 (s, 3 H) 2.90-3.15 (m, 4 H) 3.31-3.54 (m, 4 H) 3.80 (s, 2 H) 3.84 (s, 3 H) 4.09-4.17 (m, 2 H) 6.87 (d, J=8.48 Hz, 2 H) 7.26 (s, 1 H) 7.28 (s, 1 H) 7.57 (d, J=8.82 Hz, 2 H) 7.72 (d, J=8.48 Hz, 2 H) 7.79-7.83 (m, 2 H) 9.59 (s, 1 H) | MS (ESI) m/z 511 (M + H)⁺ | 14 mg, 27% |

EXAMPLE 285

3-(4'-hydroxy-1,1'-biphenyl-4-yl)-6-methoxy-1,4-dihydroindeno[1,2-c]pyrazol-7-ol To Example 267H (33.3 mg, 0.053 mmol) were added ethanol (2 mL) and corcentrated hydrochloric acid (2 mL). The reaction was shaken at 50° C. for 5 hours. The mixture was concentrated, and purified by HPLC to give the desired product (18 mg, 57%). MS (ESI) m/z 371 (M+H)⁺; ¹H NMR (400 MHz, DMSO-D₆) δ ppm 3.74 (s, 2H) 3.82 (s, 3H) 6.86 (d, J=8.90 Hz, 2H) 7.07 (s, 1H) 7.16 (s, 1H) 7.55 (d, J=8.59 Hz, 2H) 7.69 (d, J=8.29 Hz, 2H) 7.81 (d, J=8.59 Hz, 2H) 9.56 (s, 1H).

EXAMPLE 286

3-(4'-hydroxy-1,1'-biphenyl-4-yl)-6-methoxy-N-[2-(4-methylpiperazin-1-yl)ethyl]-1,4-dihydroindeno[1,2-c]pyrazole-7-carboxamide

EXAMPLE 286A 6-methoxy-3-(4'-{[2-(trimethylsilyl)ethoxy]methoxy}-1,1'-biphenyl-4-yl)-1-{[2-(trimethylsilyl)ethoxy]methyl}-1,4-dihydroindeno[1,2-c]pyrazol-7-yl trifluoromethanesulfonate To the solution of Example 267H (1.29 g, 2.04 mmol) in THF (10 mL) at room temperature was added 95% NaH (51.6 mg, 2.04 mmol). The mixture was stirred for half an hour, and N-phenyltrifluoromethane sulphonamide (0.88 g, 2.45 mmol) was added. The reaction mixture was stirred at 40° C. overnight. The reaction mixture was purified by flash chromatography to give the desired product (1.80 g, 100%). MS (APCI) m/z 763 (M+H)⁺.

EXAMPLE 286B 3-(4'-hydroxy-1,1'-biphenyl-4-yl)-6-methoxy-N-[2-(4-methylpiperazin-1-yl)ethyl]-1,4-dihydroindeno[1,2-c]pyrazole-7-carboxamide Example 286A (40 mg, 0.0524 mmol), 2-(4-methylpiperazin-1-yl)ethylamine (75 mg, 0.524 mmol), triethylamine (143 µL, 1.048 mmol), PdCl$_2$(dppf) (10 mg, 0.00132 mmol), and dichloromethane (5 mL) were mixed under CO (100 psi) at 100° C. for 5 days. The reaction was cooled, and the pressure was released. The solution was concentrated. Ethanol (2 mL) and concentrated hydrochloric acid (2 mL) were added. The reaction was shaken at 50° C. for 5 hours. The mixture was concentrated, and purified by HPLC to give the desired compound.

Examples 287 to 299 represented by FIG. (XVII) and shown in Table 17 were synthesized in a similar fashion as described in Example 286B using the appropriate amine instead of 2-(4-methylpiperazin-1-yl)ethylamine.

TABLE 17

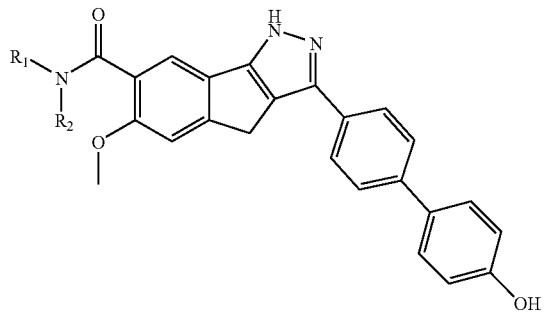

FIG. (XVII)

| Example # | —R$_1$ | —R$_2$ | $^1$H-NMR | MS m/z | Weight % Yield (%) |
|---|---|---|---|---|---|
| 286B | (piperazinyl-ethyl) | —H | $^1$H NMR (500 MHz, DMSO-D$_6$) δ ppm 2.85 (s, 3 H) 3.54-3.63 (m, 4 H) 3.73-3.79 (m, 8 H) 3.96 (s, 2 H) 3.99 (s, 3 H) 6.88 (d, J=8.54 Hz, 2 H) 7.44 (s, 1 H) 7.57 (d, J=8.54 Hz, 2 H) 7.73 (d, J=8.54 Hz, 2 H) 7.84 (d, J=8.54 Hz, 2 H) 8.11 (s, 1 H) 8.63 (s, 1 H) | MS (ESI) m/z 524 (M + H)$^+$ | 24 mg, 87% |
| 287 | (2-pyridylmethyl) | —H | $^1$H NMR (500 MHz, DMSO-D$_6$) δ ppm 3.96 (s, 2 H) 4.03 (s, 3 H) 4.72 (d, J=5.93 Hz, 2 H) 6.87 (d, J=8.73 Hz, 2 H) 7.45-7.48 (m, 2 H) 7.55-7.59 (m, 3 H) 7.72 (d, J=8.42 Hz, 2 H) 7.84 (d, J=8.11 Hz, 2 H) 8.00 (m, J=8.11 Hz, 1H) 8.11 (s, 1 H) 8.64 (d, J=4.99 Hz, 1 H) 9.09 (t, J=5.46 Hz, 1 H) 9.56 (s, 1 H) | MS (ESI) m/z 489 (M + H)$^+$ | 10 mg, 39% |
| 288 | (4-pyridylmethyl) | —H | $^1$H NMR (400 MHz, DMSO-D$_6$) δ ppm 3.95 (s, 2 H) 4.00 (s, 3 H) 4.71 (d, J=5.83 Hz, 2 H) 6.85-6.89 (m, 2 H) 7.46 (s, 1 H) 7.55-7.59 (m, 2 H) 7.71 (d, J=8.29 Hz, 2 H) 7.76 (d, J=6.14 Hz, 2 H) 7.83 (d, J=8.29 Hz, 2 H) 8.03 (s, 1 H) 8.74 (d, J=5.83 Hz, 2 H) 9.00 (t, J=5.98 Hz, 1 H) 9.57 (s, 1 H) | MS (ESI) m/z 489 (M + H)$^+$ | 10 mg, 39% |
| 289 | (diethylaminopropyl) | —H | $^1$H NMR (500 MHz, DMSO-D$_6$) δ ppm 1.24 (t, J=7.33 Hz, 6 H) 3.21-3.26 (m, 4 H) 3.29 (dd, J=11.54, 6.55 Hz, 2 H) 3.65-3.70 (m, 2 H) 3.95 (s, 2 H) 3.99 (s, 3 H) 6.87 (d, J=8.73 Hz, 2 H) 7.45 (s, 1 H) 7.57 (d, J=8.73 Hz, 2 H) 7.72 (d, J=8.42 Hz, 2 H) 7.84 (d, J=8.42 Hz, 2 H) 8.10 (s, 1 H) 8.55 (t, J=5.77 Hz, 1 H) 9.13 (s, 1 H) 9.58 (s, 1 H) | MS (ESI) m/z 497 (M + H)$^+$ | 6 mg, 23% |

TABLE 17-continued

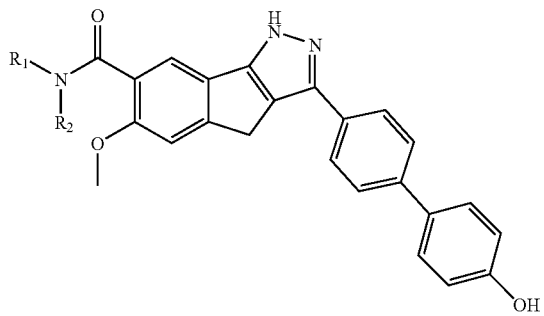

FIG. (XVII)

| Example # | —R₁ | —R₂ | ¹H-NMR | MS m/z | Weight % Yield (%) |
|---|---|---|---|---|---|
| 290 | diethylaminopropyl | —H | ¹H NMR (500 MHz, DMSO-D₆) δ ppm 1.21 (t, J=7.17 Hz, 6 H) 1.85-1.96 (m, 2H) 3.09-3.20 (m, 8 H) 3.94 (s, 2 H) 3.96 (s, 3 H) 6.87 (d, J=8.42 Hz, 1 H) 7.43 (s, 1 H) 7.57 (d, J= 8.73 Hz, 2 H) 7.72 (d, J=8.42 Hz, 2 H) 7.84 (d, J=8.11 Hz, 2 H) 8.00 (s, 1 H) 8.41 (t, J=5.93 Hz, 1 H) 9.00 (s, 1 H) 9.58 (s, 1 H) | MS (ESI) m/z 511 (M + H)⁺ | 6 mg, 22% |
| 291 | dimethylaminobutyl | —H | ¹H NMR (500 MHz, DMSO-D₆) δ ppm 1.54-1.61 (m, 2H) 1.65-1.71 (m, 2 H) 2.78 (s, H) 2.79 (s, 3 H) 3.06-3.14 (m, 2 H) 3.31-3.38 (m, 2 H) 3.94 (s, 2 H) 3.96 (s, 3 H) 6.87 (d, J= 8.42 Hz, 2 H) 7.42 (s, 1 H) 7.57 (d, J=8.73 Hz, 2 H) 7.72 (d, J=8.42 Hz, 2 H) 7.83 (d, J= 8.42 Hz, 2 H) 8.00 (s, 1 H) 8.29 (t, J=5.77 Hz, 1 H) 9.24 (s, 1 H) 9.57 (s, 1 H) | MS (ESI) m/z 524 (M + H)⁺ | 8 mg, 31% |
| 292 | dimethylaminoethyl | —H | ¹H NMR (500 MHz, DMSO-D₆) δ ppm 2.87 (s, 3 H) 2.88 (s, 3 H) 2.91-2.95 (m, 2 H) 3.64-3.70 (m, 2 H) 3.95 (s, 2 H) 3.98 (s, 3 H) 6.87 (d, J=8.73 Hz, 2 H) 7.45 (s, 1 H) 7.57 (d, J=8.42 Hz, 2 H) 7.72 (d, J= 8.11 Hz, 2 H) 7.83 (d, J=8.42 Hz, 2 H) 8.11 (s, 1 H) 8.52 (t, J= 5.77 Hz, 1 H) 9.29 (s, 1 H) 9.58 (s, 1 H) | MS (ESI) m/z 469 (M + H)⁺ | 9 mg, 37% |
| 293 | pyrrolidinylpropyl | —H | ¹H NMR (500 MHz, DMSO-D₆) δ ppm 1.83-1.92 (m, 2 H) 2.00-2.08 (m, 2 H) 3.04-3.14 (m, 2 H) 3.37 (dd, J=12.01, 6.08 Hz, 2 H) 3.64-3.68 (m, 4 H) 3.95 (s, 2 H) 3.99 (s, 3 H) 6.87 (d, J=8.73 Hz, 2 H) 7.45 (s, 1 H) 7.57 (d, J=8.42 Hz, 2 H) 7.72 (d, J=8.42 Hz, 2 H) 7.84 (d, J=8.42 Hz, 2 H) 8.11 (s, 1 H) 8.53 (t, J=5.77 Hz, 1 H) 9.43 (s, 1 H) 9.57 (s, 1 H) | MS (ESI) m/z 495 (M + H)⁺ | 14 mg, 54% |

TABLE 17-continued

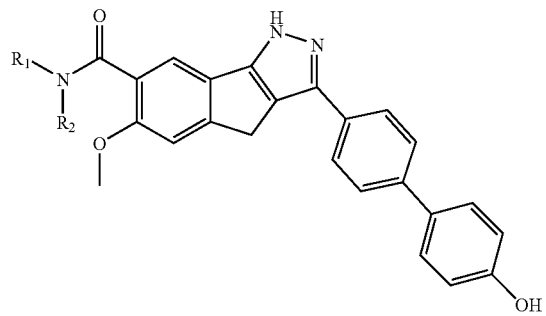

FIG. (XVII)

| Example # | —R$_1$ | —R$_2$ | $^1$H-NMR | MS m/z | Weight % Yield (%) |
|---|---|---|---|---|---|
| 294 | pyrrolidinyl-propyl | —H | $^1$H NMR (500 MHz, DMSO-D$_6$) δ ppm 1.84-1.96 (m, 4 H) 1.99-2.06 (m, 2 H) 2.97-3.06 (m, 2 H) 3.16-3.24 (m, 2 H) 3.55-3.60 (m, 4 H) 3.94 (s, 2 H) 3.97 (s, 3 H) 6.87 (d, J=8.73 Hz, 2 H) 7.43 (s, 1 H) 7.57 (d, J=8.73 Hz, 2 H) 7.72 (d, J=8.11 Hz, 2 H) 7.84 (d, J=8.11 Hz, 2 H) 8.02 (s, 1 H) 8.41 (t, J=5.77 Hz, 1 H) 9.40 (s, 1 H) 9.57 (s, 1 H) | MS (ESI) m/z 509 (M + H)$^+$ | 10 mg, 37% |
| 295 | piperidinyl-propyl | —H | $^1$H NMR (500 MHz, DMSO-D$_6$) δ ppm 1.40 (m, 1 H) 1.59-1.74 (m, 3 H) 1.80-1.89 (m, 2 H) 2.88-3.02 (m, 2 H) 3.17-3.30 (m, 2 H) 3.54-3.61 (m, 2 H) 3.67-3.72 (m, 2 H) 3.95 (s, 2 H) 3.98 (s, 3 H) 6.87 (d, J=8.42 Hz, 2 H) 7.45 (s, 1 H) 7.57 (d, J=8.42 Hz, 2 H) 7.72 (d, J=8.42 Hz, 2 H) 7.84 (d, J=8.42 Hz, 2 H) 8.09 (s, 1 H) 8.55 (t, J=5.93 Hz, 1 H) 9.07 (s, 1 H) 9.57 (s, 1 H) | MS (ESI) m/z 509 (M + H)$^+$ | 17 mg, 64% |
| 296 | piperidinyl-butyl | —H | $^1$H NMR (500 MHz, DMSO-D$_6$) δ ppm 1.40 (m, 1 H) 1.58-1.74 (m, 3 H) 1.79-1.87 (m, 2 H) 1.90-1.99 (m, 2 H) 2.83-2.95 (m, 2 H) 3.05-3.14 (m, 2 H) 3.44-3.49 (m, 4 H) 3.94 (s, 2 H) 3.97 (s, 3 H) 6.87 (d, J=8.73 Hz, 2 H) 7.43 (s, 1 H) 7.57 (d, J=8.73 Hz, 2 H) 7.72 (d, J=8.42 Hz, 2 H) 7.83 (d, J=8.42 Hz, 2 H) 8.02 (s, 1 H) 8.42 (t, J=5.93 Hz, 1 H) 8.93 (s, 1 H) 9.57 (s, 1 H) | MS (ESI) m/z 523 (M + H)$^+$ | 5 mg, 18% |
| 297 | morpholinyl-propyl | —H | $^1$H NMR (500 MHz, DMSO-D$_6$) δ ppm 3.18-3.22 (m, 2 H) 3.56-3.73 (m, 2 H) 3.65-3.74 (m, 4 H) 3.92-4.06 (m, 9 H) 6.87 (d, J=8.73 Hz, 2 H) 7.45 (s, 1 H) 7.57 (d, J=8.42 Hz, 2 H) 7.72 (d, J=8.42 Hz, 2 H) 7.84 (d, J=8.42 Hz, 2 H) (s, 1 H) 8.56 (t, J=5.93 Hz, 1 H) 9.58 (s, 1 H) | MS (ESI) m/z 511 (M + H)$^+$ | 13 mg, 49% |

TABLE 17-continued

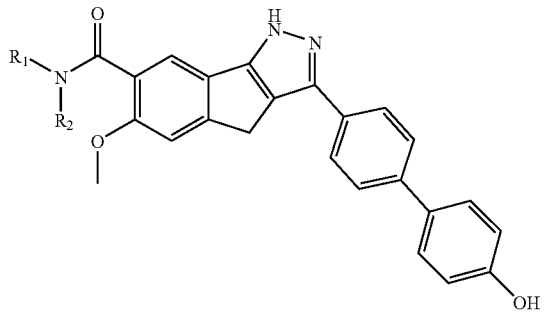

FIG. (XVII)

| Example # | —R$_1$ | —R$_2$ | $^1$H-NMR | MS m/z | Weight % Yield (%) |
|---|---|---|---|---|---|
| 298 | (dimethylamino-propyl group) | —CH$_3$ | $^1$H NMR (500 MHz, DMSO-D$_6$) δ ppm 2.83 (s, 3 H) 2.92 (s, 6 H) 3.24-3.34 (m, 2 H) 3.42-3.50 (m, 2 H) 3.87 (s, 2 H) 3.94 (s, 3 H) 6.88 (d, J= 8.42 Hz, 2 H) 7.38 (s, 1 H) 7.55-7.59 (m, 3 H) 7.73 (d, J=8.42 Hz, 2 H) 7.83 (d, J=8.11 Hz, 2 H) 9.61 (s, 1 H) | MS (ESI) m/z 483 (M + H)$^+$ | 18 mg, 71% |
| 299 | (dimethylamino-butyl group) | —CH$_3$ | $^1$H NMR (500 MHz, DMSO-D$_6$) δ ppm 1.94-2.02 (m, 2 H) 2.81 (s, 3 H) 2.84 (s, 3 H) 2.85 (s, 3 H) 3.07-3.16 (m, 2 H) 3.53-3.60 (m, 2H) 3.89 (s, 2 H) 3.93 (s, 3 H) 6.88 (d, J=8.73 Hz, 2 H) 7.38 (s, 1 H) 7.47 (s, 1 H) 7.57 (d, J=8.42 Hz, 2 H) 7.73 (d, J=8.42 Hz, 2 H) 7.84 (d, J=8.42 Hz, 2 H) 9.26 (s, 1 H) 9.57 (s, 1 H) | MS (ESI) m/z 497 (M + H)$^+$ | 6 mg, 23% |

EXAMPLE 300

4'-{6-methoxy-7-[(4-methyl-1,4-diazepan-1-yl)carbonyl]-1,4-dihydroindeno[1,2-c]pyrazol-3-yl}-1,1'-biphenyl-4-ol The title compound was synthesized in a similar fashion as described in Example 286B using 1-methyl-1,4-diazepane instead of 2-(4-methylpiperazin-1-yl)ethylamine, 22 mg 85% yield. MS (ESI) m/z 495 (M+H)$^+$; $^1$H NMR (500 MHz, DMSO-D$_6$) δ ppm 1.92-2.10 (m, 2H) 2.92 (s, 3H) 3.143.30 (m, 4H) 3.35-3.60 (m, 4H) 3.89 (s, 2H) 3.94 (s, 3H) 6.88 (d, J=8.42 Hz, 2H) 7.38 (s, 1H) 7.54-7.60 (m, 3H) 7.73 (d, J=8.42 Hz, 2H) 7.84 (d, J=8.42 Hz, 2H) 9.69 (s, 1H).

EXAMPLE 301

6-methoxy-3-{4-[3-(1-methylpyrrolidin-2-yl)propoxy]phenyl}-7-(2-piperidin-1-ylethoxy)-1,4-dihydroindeno[1,2-c]pyrazole

EXAMPLE 301A phenyl 4-(benzyloxy)benzoate

4-Hydroxy-benzoic acid phenyl ester (5 g, 23.3 mmol), benzyl bromide (5.54 mL, 46.7 mmol), K$_2$CO$_3$ (9.6 g, 70.0 mmol), and anhydrous acetone (200 mL) were mixed and reflux overnight. All acetone was removed. To the mixture was added water (300 mL). The solid was filtered, washed with methanol (50 mL×3), and dried to give the desired compound (6.63 g, 93%). MS (DCI) m/z 305 (M+H)$^+$; $^1$H NMR (300 MHz, CDCl$_3$) δ ppm 5.17 (s, 2H) 7.30-7.09 (m, 2H) 7.17-7.23 (m, 2H) 7.27 (m, 1H) 7.34-7.48 (m, 7H) 8.13-8.19 (m, 2H)

EXAMPLE 301B 5-methoxy-6-(2-piperidin-1-ylethoxy)indan-1-one

Example 144B (5.34 g, 30 mmol), 1-(2-chloro-ethyl)-piperidine hydrochloride (11.0 g, 60 mmol), K$_2$CO$_3$ (16.6 g, 120 mmol), and acetonitrile (150 mL) were mixed and refluxed 3 days. The reaction mixture was filtered. The filtrate was concentrated, and purified by flash chromatography to give the desired product (6.92 g, 80%). MS (ESI) m/z 290 (M+H)$^+$; $^1$H NMR (300 MHz, CDCl$_3$) δ ppm 1.40-1.49 (m, 2H) 1.55-1.65 (m, 4H) 2.45-2.57 (m, 4H) 2.63-2.70 (m, 2H) 2.84 (t, J=6.27 Hz, 2H) 3.01-3.08 (m, 2H) 3.94 (s, 3H) 4.18 (t, J=6.44 Hz, 2H) 6.88 (s, 1H) 7.20 (s, 1H).

EXAMPLE 301C

3-[4-(benzyloxy)phenyl]-6-methoxy-7-(2-piperidin-1-ylethoxy)-1,4-dihydroindeno[1,2-c]pyrazole Example 301A (7.16 g, 24.00 mmol), Example 301B (6.92 g, 23.92 mmol), 95% NaH (1.82 g, 72 mmol) and benzene (100 mL) were mixed and refluxed overnight. The reaction mixture was cooled to room temperature, and benzene was removed. Acetic acid (10 mL), ethanol (100 mL) and hydrazine monohydrate (10 mL) were added. The mixture was heated to reflux for 2 hours, and then cooled. All the solvents were removed. The residue was treated with water (200 mL). The precipitate was filtered, washed with water (100 mL×3) and ethyl acetate (100 mL×3), and dried to give the desired product (7.71 g, 85%). MS (ESI) m/z 496 (M+H)$^+$; $^1$H NMR (300 MHz, CD$_3$OD) δ ppm 1.44-1.55 (m, 2H) 1.59-1.70 (m, 4H) 2.60-2.67 (m, 4H) 2.87 (t, J=5.76 Hz, 2H) 3.75 (s, 2H) 3.89 (s, 3H) 4.23 (t, J=5.76 Hz, 2H) 5.15 (s, 2H) 7.11 (d, J=8.81 Hz, 2H) 7.24 (s, 1H) 7.29-7.41 (m, 4H) 7.43-7.48 (m, 2H) 7.69 (d, J=9.15 Hz, 2H).

EXAMPLE 301D

3-[4-(benzyloxy)phenyl]-6-methoxy-7-(2-piperidin-1-ylethoxy)-1-{[2-(trimethylsilyl)ethoxy]methyl}-1,4-dihydroindeno[1,2-c]pyrazole To the solution of Example 301C (7.71 g, 15.56 mmol) in DMF (200 mL) was added 95% NaH (0.412 g, 16.34 mmol). After 0.5 hour, 2-(trimethylsilyl)ethoxymethyl chloride (2.89 mL, 16.34 mmol) was added dropwise. Then the reaction was run at room temperature for 2 hours. All the DMF was removed. The residue was purified by flash chromatography to give the desired product (5.50 g, 56%). MS (APCI) m/z 626 (M+H)$^+$.

EXAMPLE 301E 4-(6-methoxy-7-(2-piperidin-1-ylethoxy)-1-{[2-(trimethylsilyl)ethoxy]methyl}-1,4-dihydroindeno[1,2-c]pyrazol-3-yl)phenol The mixture of Example 301D (5.50 g, 8.79 mmol) and 10% Pd/C (1.15 g, 1.09 mmol) in THF (100 mL) was treated with H$_2$ (60 psi) at room temperature for 2 days. The mixture was filtered. The solution was concentrated, and purified by flash chromatography to give the desired product (4.0 g, 85%). MS (ESI) m/z 536 (M+H)$^+$.

EXAMPLE 301F 6-methoxy-3-{4-[3-(1-methylpyrrolidin-2-yl)propoxy]phenyl}-7-(2-piperidin-1-ylethoxy)-1,4-dihydroindeno[1,2-c]pyrazole Example 301E (54 mg, 0.10 mmol), (1-methyl-pyrrolidin-2-yl)-propan-1-ol (29 mg, 0.20 mmol), PPh$_3$-polymer supported (50 mg, 0.15 mmol), di-tert-butyl azodicarboxylate (34.5 mg, 0.15 mmol), and THF (3 mL) were mixed and stirred at room-temperature for 4 days. The resin was filtered, and the solution was concentrated. To the residue were added 2N HCl solution (1 mL) and ethanol (1 mL). The reaction was at 50° C. for 8 hours, and concentrated. The residue was purified by HPLC give the desired product (24 mg, 46%). MS (ESI) m/z 517 (M+H)$^+$; $^1$H NMR (500 MHz, CD$_3$OD) δ ppm 1.58 (m, 1H) 1.79-1.91 (m, 5H) 1.96-2.05 (m, 3H) 2.06-2.20 (m, 3H) 3.08-3.15 (m, 3H) 3.35 (s, 3H) 3.55-3.62 (m, 4H) 3.703.77 (m, 4H) 3.82 (s, 2H) 3.94-3.98 (m, 3H) 4.39-4.44 (m, 2H) 7.08-7.13 (m, 2H) 7.34 (s, 1H) 7.40 (s, 1H) 7.71-7.75 (m, 2H).

EXAMPLE 302

1-{4-[6-methoxy-7-(2-piperidin-1-ylethoxy)-1,4-dihydroindeno[1,2-c]pyrazol-3-yl]phenoxy}acetone Example 302 was synthesized in a similar fashion as Example 301F, substituting (1-methyl-pyrrolidin-2-yl)-propan-1-ol with 1-hydroxy-propan-2-one (19 mg, 41%). MS (ESI) m/z 462 (M+H)$^+$; $^1$H NMR (500 MHz, CD$_3$OD) δ ppm 1.58 (m, 1H) 1.79-1.91 (m, 3H) 1.97-2.06 (m, 2H) 2.25 (s, 3H) 3.06-3.16 (m, 2H) 3.56-3.63 (m, 2H) 3.75 (d, J=12.16 Hz, 2H) 3.81 (s, 2H) 3.95 (s, 3H) 4.39-4.44 (m, 2H) 4.79 (s, 2H) 7.06 (d, J=9.04 Hz, 2H) 7.33 (s, 1H) 7.40 (s, 1H) 7.71 (d, J=8.73 Hz, 2H).

EXAMPLE 303

[4-(6,7-dimethoxy-1,4-dihydroindeno[1,2-c]pyrazol-3-yl)phenyl]methanol

Example 243B (70 mg, 0.20 mmol), bis(triphenylphosphine)dichloropalladium (14.3 mg, 0.020 mmol), 3-hydroxymethyl-phenylboronic acid (36 mg, 0.24 mmol), DME/EtOH/H$_2$O (7:2:3, 3 mL), and 1M Na$_2$CO$_3$ solution (1 mL) were mixed under N$_2$. The reaction mixture was heated to 160° C. for 600 s in a Smith Synthesizer. After the reaction, the mixture was dried, and purified by HPLC to give the desired product (17 mg, 26%). MS (ESI) m/z 323 (M+H)$^+$; $^1$H NMR (400 MHz, DMSO-D$_6$) δ ppm 3.76 (s, 2H) 3.82 (s, 3H) 3.84 (s, 3H) 4.54 (s, 2H) 7.21 (s, 1H) 7.24 (s, 1H) 7.61 (d, J=8.29 Hz, 2H) 7.74 (d, J=8.29 Hz, 2H).

EXAMPLE 304

3-(4-cyanophenyl)-6-methoxy-N-(pyridin-4-ylmethyl)-1,4-dihydroindeno[1,2-c]pyrazole-7-carboxamide

EXAMPLE 304A phenyl 4-cyanobenzoate

4-Cyano-benzoic acid (10.0 g, 68.0 mmol), phenol (6.40 g, 68.0 mmol), DCC (14.73 g, 71.4 mmol), DMAP (0.25 g, 2.04 mmol) and ether (200 mL) were mixed, and stirred at room temperature for 3 days. Ether was removed. To the residue was added CH$_2$Cl$_2$ (200 mL). The solid was filtered. The filtrate was concentrated, and purified by flash chromatography to give the desired product (12.41 g, 82%). MS (DCI/NH$_3$) m/z 224 (M+H)$^+$; $^1$H NMR (300 MHz, CDCl$_3$) δ ppm 7.19-7.25 (m, 2H) 7.31 (m, 1H) 7.41-7.50 (m, 2H) 7.807.85 (m, 2H) 8.29-8.34 (m, 2H).

EXAMPLE 304B 6-methoxy-3-oxo-2,3-dihydro-1H-inden-5-yl trifluoromethanesulfonate To the solution of Example 144B (4.86 g, 27.3 mmol) in THF (136 mL) at room temperature was added 95% NaH (0.690 g, 27.3 mmol). The temperature was raised to 40° C. After 0.5 hour, N-phenyltrifluoromethanesulfonimide (11.69 g, 27.3 mmol) was added. The temperature was maintained at 40° C. overnight under N$_2$. THF was removed. The residue was purified by flash chromatography to give the title compound (8.47 g, 100%). MS (DCI/NH$_3$) m/z 311

(M+H)⁺; ¹H NMR (300 MHz, CDCl₃) δ ppm 2.69-2.76 (m, 2H) 3.11-3.18 (m, 2H) 4.01 (s, 3H) 7.07 (s, 1H) 7.60 (s, 1H).

EXAMPLE 304C 6-methoxy-3-oxoindane-5-carboxylic acid

Example 304B (8.47 g, 27.3 mmol), PdCl₂(dppf) (0.21 g, 0.331 mmol), triethylamine (19.0 mL, 136.5 mmol), THF (200 mL) and water (50 mL) were mixed and stirred at room temperature under N₂ for 10 minutes. Then the reaction system was charged with CO (500 psi). The temperature was raised to 110° C. for 16 hours. The solvents were removed, and the residue was purified by flash chromatography to give the desired product (5.35 g, 95%). MS (ESI) m/z 207 (M+H)⁺; ¹H NMR (300 MHz, CD₃OD) δ ppm 2.63-2.69 (m, 2H) 3.10-3.16 (m, 2H) 3.99 (s, 3H) 6.99 (s, 1H) 8.26 (s, 1H).

EXAMPLE 304D methyl 6-methoxy-3-oxoindane-5-carboxylate

Example 304C (5.35 g, 25.94 mmol) was dissolved into methanol (100 mL). Concentrated H₂SO₄ (10 drops) was added. The mixture was refluxed overnight. The reaction was cooled, and methanol was removed. Saturated NaHCO₃ solution (100 mL) and CH₂Cl₂ (100 mL) were added. The organic layer was separated, and dried with MgSO₄. The organic solution was concentrated, and purified by flash chromatography to give the desired product (3.00 g, 48%). MS (DCI/NH₃) m/z 221 (M+H)⁺; ¹H NMR (300 MHz, CD₃OD) δ ppm 2.66-2.73 (m, 2H) 3.15-3.22 (m, 2H) 3.87 (s, 3H) 3.98 (s, 3H) 7.26 (s, 1H) 8.05 (s, 1H).

EXAMPLE 304E methyl 3-(4-cyanophenyl)-6-methoxy-1,4-dihydroindeno[1,2-c]pyrazole-7-carboxylate Example 304D (0.92 g, 4.18 mmol), Example 304A (1.74 g, 6.27 mmol), 95% NaH (0.32 g, 12.54 mmol) and benzene (50 mL) were mixed, and heated to reflux overnight. Benzene was removed. Eethanol (50 mL), acetic acid (3 mL) and hydrazine monohydrate (3 mL) was added. The mixture was heated to reflux for 2 hours. The mixture was cooled, and the solvents were removed. To the residue was added water (50 mL). The precipitate was filtered, washed with water (10 mL×3) and ethyl acetate (10 mL×3), and dried to give the above intermediate (0.925 g, 64%). MS (ESI) m/z 346 (M+H)⁺; ¹H NMR (400 MHz, DMSO-D₆) δ ppm 3.82 (s, 3H) 3.90 (s, 3H) 3.97 (s, 2H) 7.44 (m, 1H) 7.87-8.05 (m, 5H) 13.42 (m, 1H).

EXAMPLE 304F 3-(4-cyanophenyl)-6-methoxy-1,4-dihydroindeno[1,2-c]pyrazole-7-carboxylic acid Example 304E (0.925 g, 2.66 moles) was dissolved in DMF (90 mL). To this solution was added a solution of LiOH (1.28 g, 54 mmol) in water (10 mL). The solution was stirred at room temperature for 4 days. All the solvents were removed with vacuum pump. 2N HCl solution was added until pH equals 2. Yellow precipitate was filtered, washed with water (2 mL×2), and dried to give the above intermediate (0.75 g, 72%). MS (ESI) m/z 332 (M+H)⁺; ¹H NMR (500 MHz, DMSO-D₆) δ ppm 3.90 (s, 3H) 3.96 (s, 2H) 7.41 (s, 1H) 7.92 (s, 1H) 7.94-8.00 (m, 4H).

EXAMPLE 304G 3-(4-cyanophenyl)-6-methoxy-N-(pyridin-4-ylmethyl)-1,4-dihydroindeno[1,2-c]pyrazole-7-carboxamide Example 304F (50 mg, 0.136 mmol), PyBrop (65.3 mg, 0.140 mmol), O-pyridin-4-yl-methylamine (15 mg, 0.14 mmol), DIEA (49 μL, 0.28 mmol) and DMF (2 mL) were mixed, and stirred overnight. The solvent was removed. The residue was washed with water (2 mL×2), methanol (2 mL×2) and ethyl acetate (2 mL×2), and dried to give the title compound (20 mg, 35%). MS (ESI) m/z 422 (M+H)⁺; ¹H NMR (500 MHz, DMSO-D₆) δ ppm 3.89 (s, 2H) 3.99 (s, 3H) 4.56 (d, J=5.93 Hz, 2H) 7.34 (d, J=5.30 Hz, 2H) 7.45 (s, 1H) 7.948.00 (m, 5H) 8.52 (d, J=4.05 Hz, 2H) 8.86 (s, 1H) 13.39 (s, 1H).

EXAMPLE 305

3-(4-cyanophenyl)-N-(trans-4-hydroxycyclohexyl)-6-methoxy-1,4-dihydroindeno[1,2-c]pyrazole-7-carboxamide Example 305 was synthesized in similar fashion as Example 304G, substituting O-pyridin-4-yl-methylamine with trans-4-amino-cyclohexanol (9 mg, 15%). MS (ESI) m/z 429 (M+H)⁺; ¹H NMR (500 MHz, DMSO-D₆) δ ppm 1.22-1.40 (m, 4H) 1.81-1.93 (m, 4H) 3.43 (m, 1H) 3.75 (m, 1H) 3.90-4.05 (m, 5H) 7.40 (m, 1H) 7.948.00 (m, 5H) 13.37 (m, 1H).

EXAMPLE 306

4-[6-methoxy-7-(pyridin-3-ylmethoxy)-1,4-dihydroindeno[1,2-c]pyrazol-3-yl]benzonitrile

EXAMPLE 306A phenyl 4-bromobenzoate

4-Bromo-benzoic acid (32.83 g, 163.3 mmol), phenol (15.37 g, 163.3 mmol), DCC (35.38 g, 171.46 mmol), DMAP (0.40 g, 4.9 mmol) and ether (500 mL) were mixed, and stirred at room temperature for 3 days. Ether was removed. CH₂Cl₂ (1 L) was added. The suspension was filtered. The filtrate was concentrated, and purified by flash chromatography to give the above intermediate (33.14 g, 73%). MS (DCI/NH₃) m/z 278 (M+H)⁺; ¹H NMR (300 MHz, CDCl₃) δ ppm 7.18-7.23 (m, 2H) 7.29 (d, J=7.46 Hz, 1H) 7.40-7.47 (m, 2H) 7.63-7.69 (m, 2H) 8.04-8.09 (m, 2H).

EXAMPLE 306B 5-methoxy-6-(pyridin-3-ylmethoxy)indan-1-one

Example 144B (1.00 g, 5.61 mmol), 3-chloromethylpyridine hydrochloride (1.84 g, 11.22 mmol), K₂CO₃ (3.88 g, 28.10 mmol) and acetone (50 mL) were mixed, stirred, and heated to reflux overnight. The reaction mixture was then filtered. The filtrate was concentrated, and purified by flash chromatography to give the above intermediate (1.23 g, 81%). MS (ESI) m/z 270 (M+H)⁺; ¹H NMR (300 MHz, CD₃OD) δ ppm 2.62-2.67 (m, 2H) 3.04-3.11 (m, 2H) 3.95

(s, 3H) 5.19 (s, 2H) 7.13 (s, 1H) 7.27 (s, 1H) 7.46 (dd, J=7.80, 4.07 Hz, 1H) 7.96 (m, 1H) 8.50 (dd, J=4.92, 1.53 Hz, 1H) 8.65 (d, J=1.36 Hz, 1H).

EXAMPLE 306C 3-(4-bromophenyl)-6-methoxy-7-(pyridin-3-yl-methoxy)-1,4-dihydroindeno[1,2-c]pyrazole Example 306B (1.10 g, 4.08 mmol), Example 306A (2.26 g, 8.17 mmol), 95% NaH (0.41 g, 16.34 mmol) and benzene (100 mL) were mixed, stirred, and heated to reflux for 3 hours. The solvent was removed. Ethanol (100 mL), acetic acid (3 mL) and hydrazine monohydrate (3 mL) was added. The mixture was refluxed for another 2 hours. All the solvents were removed. To the residue was added water (100 mL). The suspension was filtered, washed with water (30 mL×3), ethyl acetate (30 mL×3), and dried to give the above product (1.70 g, 93%). MS (ESI) m/z 449 (M+H)$^+$; $^1$H NMR (400 MHz, DMSO-D$_6$) δ ppm 3.76 (s, 2H) 3.83 (s, 3H) 5.22 (s, 2H) 7.25 (s, 1H) 7.35 (s, 1H) 7.43 (dd, J=7.83, 4.76 Hz, 1H) 7.60-7.80 (m, 4H) 7.88 (d, J=7.98 Hz, 2H) 8.54 (dd, J=4.91, 1.53 Hz, 1H) 8.68 (d, J=1.84 Hz, 1H) 13.08 (s, 1H).

EXAMPLE 306D

4-[6-methoxy-7-(pyridin-3-ylmethoxy)-1,4-dihydroindeno[1,2-c]pyrazol-3-yl]benzonitrile Example 306C (75 mg, 0.167 mmol), Pd(PPh$_3$)$_4$ (20 mg, 0.0167 mmol), Zn(CN)$_2$ (230 mg, 2.00 mmol) and DMF (4 mL) were mixed, pumped with N$_2$, stirred, and heated to 18° C. for 5 minutes in a Smith Synthesizer. The reaction mixture was filtered, and the filtrate was concentrated. The residue was purified by HPLC to give the title compound (40.0 mg, 61%). MS (ESI) m/z 395 (M+H)$^+$; $^1$H NMR (400 MHz, DMSO-D$_6$) δ ppm 3.84 (s, 2H) 3.86 (s, 3H) 5.36 (s, 2H) 7.30 (s, 1H) 7.41 (s, 1H) 7.92 (dd, J=7.82, 5.37 Hz, 1H) 7.96 (s, 4H) 8.44 (d, J=7.98 Hz, 1H) 8.81 (d, J=4.91 Hz, 1H) 8.93 (s, 1H).

EXAMPLE 307

4-{7-[2-(dimethylamino)ethoxy]-6-methoxy-1,4-dihydroindeno[1,2-c]pyrazol-3-yl}benzonitrile

EXAMPLE 307A

6-[2-(dimethylamino)ethoxy]-5-methoxyindan-1-one

Example 144B (1.00 g, 5.61 mmol), (2-chloro-ethyl)-dimethyl-amine hydrochloride (1.62 g, 11.22 mmol), K$_2$CO$_3$ (3.88 g, 28.10 mmol) and acetone (50 mL) were mixed, stirred, and heated to reflux overnight. The reaction mixture was then filtered. The filtrate was concentrated, and purified by flash chromatography to give the above intermediate (1.20 g, 86%). MS (ESI) m/z 250 (M+H)$^+$; $^1$H NMR (300 MHz, CD$_3$OD) δ ppm 2.37 (s, 6H) 2.62-2.68 (m, 2H) 2.82 (t, J=5.43 Hz, 2H) 3.05-3.10 (m, 2H) 3.93 (s, 3H) 4.14 (t, J=5.43 Hz, 2H) 7.09 (s, 1H) 7.19 (s, 1H).

EXAMPLE 307B

N-(2-{[3-(4-bromophenyl)-6-methoxy-1,4-dihydroindeno[1,2-c]pyrazol-7-yl]oxy}ethyl)-N,N-dimethylamine Example 307A (0.67 g, 2.69 mmol), Example 306A (1.49 g, 5.38 mmol), 95% NaH (0.27 g, 10.7 mmol) and benzene (100 mL) were mixed, stirred, and heated to reflux for 3 hours. The solvent was removed. Ethanol (100 mL), acetic acid (3 mL) and hydrazine monohydrate (3 mL) were added. The mixture was refluxed for another 2 hours. All the solvents were removed by vacuum pump. To the residue was added methanol (100 mL) and K$_2$CO$_3$ (10 g). The suspension was stirred for 1 hour, and filtered. The filtrate was concentrated, and purified by flash chromatography to give the above intermediate (0.94 g, 82%). MS (ESI) m/z 429 (M+H)$^+$; $^1$H NMR (500 MHz, CD$_3$OD) δ ppm 2.39 (s, 6H) 2.83 (t, J=5.46 Hz, 2H) 3.71 (s, 2H) 3.88 (s, 3H) 4.18 (t, J=5.61 Hz, 2H) 7.20 (s, 1H) 7.30 (s, 1H) 7.61 (d, J=8.42 Hz, 2H) 7.65 (d, J=8.42 Hz, 2H).

EXAMPLE 307C

4-{7-[2-(dimethylamino)ethoxy]-6-methoxy-1,4-dihydroindeno[1,2-c]pyrazol-3-yl}benzonitrile Example 307B (73 mg, 0.170 mmol), Pd(PPh$_3$)$_4$ (20 mg, 0.0167 mmol), Zn(CN)$_2$ (230 mg, 2.00 mmol) and DMF (4 mL) were mixed, purged with N$_2$, stirred, and heated to 180° C. for 5 minutes in a Smith Synthesizer. The reaction mixture was filtered. The filtrate was concentrated. The residue was purified by HPLC to give the title compound (38.0 mg, 60%). MS (ESI) m/z 375 (M+H)$^+$; $^1$H NMR (400 MHz, CD$_3$OD) δ ppm 3.07 (s, 6H) 3.61-3.67 (m, 2H) 3.88 (s, 2H) 3.97 (s, 3H) 4.40-4.47 (m, 2H) 7.37 (s, 1H) 7.43 (s, 1H) 7.85 (d, J=8.29 Hz, 2H) 7.94 (d, J=8.29 Hz, 2H).

EXAMPLE 308

4-[6-methoxy-7-(pyridin-4-ylmethoxy)-1,4-dihydroindeno[1,2-c]pyrazol-3-yl]benzonitrile

EXAMPLE 308A 5-methoxy-6-(pyridin-4-ylmethoxy)indan-1-one

Example 144B (1.00 g, 5.61 mmol), 4 chloromethyl-pyridine hydrochloride (1.84 g, 11.22 mmol), K$_2$CO$_3$ (3.88 g, 28.10 mmol) and acetone (50 mL) were mixed, stirred, and heated to reflux overnight. The reaction mixture was then filtered. The filtrate was concentrated, and purified by flash chromatography to give the above intermediate (1.44 g, 95%). MS (ESI) m/z 270 (M+H)$^+$; $^1$H NMR (300 MHz, CD$_3$OD) δ ppm 2.62-2.68 (m, 2H) 3.06-3.10 (m, 2H) 3.98 (s, 3H) 5.22 (s, 2H) 7.14 (s, 1H) 7.21 (s, 1H) 7.54 (d, J=6.10 Hz, 2H) 8.51-8.55 (m, 2H).

EXAMPLE 308B 3-(4-bromophenyl)-6-methoxy-7-(pyridin-4-yl-methoxy)-1,4-dihydroindeno[1,2-c]pyrazole Example 308A (0.54 g, 2.00 mmol), Example 306A (1.11 g, 4.00 mmol), 95% NaH (0.38 g, 16.0 mmol) and benzene (70 mL) were mixed, stirred, and heated to reflux overnight. The solvent was removed. Ethanol (70 mL), acetic acid (3 mL) and hydrazine monohydrate (3 mL) was added. The mixture was refluxed for another 2 hours. All the solvents were removed by vacuum pump. To the residue was added water (100 mL). The suspension was filtered, washed with water (20 mL×3) and ethyl acetate (20 mL×3), and dried to give the above product (0.82 g, 91%). MS (ESI) m/z 449 (M+H)$^+$; $^1$H NMR (400 MHz, DMSO-D$_6$) δ ppm 3.76 (s, 2H) 3.87 (s, 3H) 5.27 (s, 2H) 7.25-7.33 (m, 2H) 7.47 (d, J=6.14 Hz, 2H) 7.71 (s, 4H) 8.558.62 (m, 2H) 13.08 (s, 1H).

EXAMPLE 308C

4-[6-methoxy-7-(pyridin-4-ylmethoxy)-1,4-dihydroindeno[1,2-c]pyrazol-3-yl]benzonitrile Example 308B (75 mg, 0.167 mmol), Pd(PPh$_3$)$_4$ (20 mg, 0.0167 mmol), Zn(CN)$_2$ (0.230 g, 2.00 mmol) and DMF (4 mL) were mixed, purged with N$_2$, stirred, and heated to 180° C. for 5 minutes in a Smith Synthesizer. The reaction mixture was filtered. The filtrate was concentrated. DMSO (2.5 mL) was added, and the suspension was stirred for 0.5 hour. The precipitate was then filtered, washed by water (5 mL×3) and ethyl acetate (5 mL×3), and dried in vacuo to give the title compound (35 mg, 53%). MS (ESI) m/z 395 (M+H)$^+$; $^1$H NMR (300 MHz, DMSO-D$_6$) δ ppm 3.84 (s, 2H) 3.88 (s, 3H) 5.28 (s, 2H) 7.28 (s, 1H) 7.33 (s, 1H) 7.47 (d, J=6.10 Hz, 2H) 7.92-8.01 (m, 4H) 8.60 (d, J=5.76 Hz, 2H) 13.30 (s, 1H)

EXAMPLE 309

4'-[6-methoxy-7-(trifluoromethoxy)-1,4-dihydroindeno[1,2-c]pyrazol-3-yl-1,1'-biphenyl-4-ol

EXAMPLE 309A

O-(6-methoxy-3-oxo-2,3-dihydro-1H-inden-5-yl) S-methyl dithiocarbonate

To a stirred solution of Example 144B (1.18 g, 6.6 mmol) in DMF (60 mL) was slowly added 95% NaH (0.20 g, 7.95 mmol) at 0° C. After the resulting mixture was stirred at room temperature for 1 hour, CS$_2$ (0.79 mL, 13.2 mmol) was added dropwise at 0° C. The resulting mixture was stirred for 10 hours at room temperature before iodomethane (0.49 mL, 7.92 mmol) was added dropwise to the reaction mixture at 0° C. The resulting mixture was stirred for 1 hour at room temperature. All solvents were removed. The residue was separated by flash chromatography to give the desired intermediate (0.80 g, 45%). MS (DCI/NH$_3$) m/z 269 (M+H)$^+$; $^1$H NMR (300 MHz, CDCl$_3$) δ ppm 2.65-2.74 (m, 5H) 3.09-3.17 (m, 2H) 3.90 (s, 3H) 7.01 (s, 1H) 7.44 (s, 1H).

EXAMPLE 309B 5-methoxy-6-(trifluoromethoxy)indan-1-one

To the suspension of 1,3-dibromo-5,5-dimethylhydantoin (0.83 g, 2.91 mmol) in CH$_2$Cl$_2$ in a flame-dried flask at −78° C. was added 70% HF/pyridine (2 mL) dropwise. To this mixture was added Example 309A (0.26 g, 0.97 mmol) in dichloromethane (5 mL). Then the dry-ice bath was replaced with ice-cold NaCl solution bath. The red-brown mixture was stirred for 0.5 hour, and diluted with ethyl ether. NaHSO$_3$/NaHCO$_3$/NaOH was used to adjust pH to 10. Ethyl ether (100 mL) was added to extract the product. The extraction solution was dried with MgSO$_4$ concentrated, and separated by flash chromatography to give the above intermediate (79.7 mg, 33%). MS (APCI) m/z 247 (M+H)$^+$.

EXAMPLE 309C 3-(4-bromophenyl)-6-methoxy-7-(trifluoromethoxy)-1,4-dihydroindeno[1,2-c]pyrazole Example 309B (80 mg, 0.325 mmol), Example 306A (180 mg, 0.65 mmol), 95% NaH (66 mg, 2.60 mmol), and benzene (10 mL) were mixed and reflux overnight. Then all the solvent was removed. To the residue were added ethanol (10 mL), acetic acid (2 mL), and hydrazine monohydrate (2 mL). The mixture was heated to reflux for 2 hours. Flash chromatography purification was used to give the above intermediate (45.3 mg, 33%). MS (APCI) m/z 425 (M+H)$^+$; $^1$H NMR (300 MHz, DMSO-D$_6$) δ ppm 3.89 (s, 2H) 3.92 (s, 3H) 7.68-7.75 (m, 4H) 7.83-7.89 (m, 2H).

EXAMPLE 309D

4'-[6-methoxy-7-(trifluoromethoxy)-1,4-dihydroindeno[1,2-c]pyrazol-3-yl]-1,1'-biphenyl-4-ol Example 309C (41.6 mg, 0.098 mmol), dichlorobis(triphenylphosphine)palladium (6.9 mg, 0.0098 mmol), (4-hydroxyphenyl)boronic acid (16.2 mg, 0.118 mmol), DME/EtOH/H$_2$O (7:2:3, 3 mL), and 1M Na$_2$CO$_3$ solution (1 mL) were mixed, heated to 160° C. for 10 minutes in a Smith Synthesizer. All the solvents were removed. The residue was purified by HPLC to give the title compound (9.0 mg, 42%). MS (ESI) m/z 439 (M+H)$^+$; $^1$H NMR (400 MHz, DMSO-D$_6$) δ ppm 3.88-3.95 (m, 5H) 6.87 (d, J=8.90 Hz, 2H) 7.52 (s, 1H) 7.557.58 (m, 3H) 7.72 (d, J=8.59 Hz, 2H) 7.84 (d, J=8.61 Hz, 2H).

EXAMPLE 312

4'-(6-morpholin-4-yl-1,4-dihydroindeno[1,2-c]pyrazol-3-yl)-1,1'-biphenyl-4-ol

EXAMPLE 312A 5-morpholin-4-ylindan-1-one

A mixture of 5-bromo-1-indanone (0.76 g, 3.60 mmol), Cs$_2$CO$_3$ (1.64 g, 5.04 mmol), Pd$_2$(dba)$_3$ (82 mg, 0.09 mmol), BINAP (112 mg, 0.18 mmol), morpholine (0.94 mL, 10.8 mmol) and THF (15 ml) was pumped with N$_2$ for 0.5 hour and then heated to reflux overnight. The reaction mixture was concentrated, and purified by flash chromatography to give the above intermediate (0.40 g, 51.1%). MS (ESI) m/z 218 (M+H)$^+$; $^1$H NMR (300 MHz, CD$_3$OD) δ ppm 2.59-2.65 (m, 2H) 3.03-3.10 (m, 2H) 3.34-3.40 (m, 4H) 3.79-3.85 (m, 4H) 6.95 (s, 1H) 6.99 (m, 1H) 7.57 (d, J=8.48 Hz, 1H).

EXAMPLE 312B 3-(4-bromophenyl)-6-morpholin-4-yl-1,4-dihydroindeno[1,2-c]pyrazole Example 312A (0.390 g, 1.80 mmol), Example 306A (0.746 g, 2.69 mmol), 95% NaH (0.136 g, 5.38 mmol) and bezene (40 mL) were mixed and reflux for 3 hours. Then all the benzene was removed. To the residue were added ethanol (30 mL), acetic acid (2.5 mL) and hydrazine monohydrate (2.5 mL). The mixture was refluxed for 2 hours. Once again, all the liquid reagents were removed using vacuum pump. Water (50 mL) was added. The precipitate was washed with water (20 mL×2) and ethyl acetate (10 mL×2), and dried in vacuo to give the above intermediate (0.464 g, 65%). MS (ESI) m/z 396 (M+H)$^+$; $^1$H NMR (300 MHz, DMSO-D$_6$) δ ppm 3.13-3.20 (m, 4H) 3.73-3.81 (m, 6H) 6.95 (dd, J=8.48, 2.37 Hz, 1H) 7.19 (d, J=2.03 Hz, 1H) 7.49 (d, J=8.14 Hz, 1H) 7.68 (d, J=8.48 Hz, 2H) 7.65-7.80 (m, 2H) 13.03 (s, 1H).

EXAMPLE 312C

4'-(6-morpholin-4-yl-1,4-dihydroindeno[1,2-c]pyrazol-3-yl)-1,1'-biphenyl-4-ol

Example 312B (60 mg, 0.151 mmol), (4-hydroxyphenyl)boronic acid (25 mg, 0.182 mmol), Pd(PPh$_3$)$_2$Cl$_2$ (10.6 mg, 0.015 mmol), DME/EtOH/H$_2$O (7:2:3, 3 mL) and 1M Na$_2$CO$_3$ solution (1 mL) were mixed, capped, and heated to 160° C. for 10 minutes in a Smith Synthesizer. All the solvents were removed. The residue was purified by HPLC to give the title compound (29 mg, 47%). MS (ESI) m/z 410 (M+H)$^+$; $^1$H NMR (500 MHz, DMSO-D$_6$) δ ppm 3.14-3.21 (m, 4H) 3.73-3.81 (m, 4H) 3.83 (s, 2H) 6.87 (d, J=8.73 Hz, 2H) 6.96 (dd, J=8.42, 2.18 Hz, 1H) 7.21 (s, 1H) 7.51 (d, J=8.42 Hz, 1H) 7.56 (d, J=8.73 Hz, 2H) 7.71 (d, J=8.42 Hz, 2H) 7.82 (d, J=8.42 Hz, 2H) 9.56 (s, 1H).

EXAMPLE 313

3-methoxy-4'-(6-morpholin-4-yl-1,4-dihydroindeno[1,2-c]pyrazol-3-yl)-1,1'-biphenyl-4-ol Example 313 was synthesized in similar fashion as Example 312C, submitting (4-hydroxyphenyl)boronic acid with 2-methoxy-4-(4,4,5,5-tetramethyl-1,3,2-dioxaborolan-2-yl)-phenol. (41 mg, 62%) MS (ESI) m/z 440 (M+H)$^+$; $^1$H NMR (500 MHz, DMSO-D$_6$) δ ppm 3.14-3.21 (m, 4H) 3.73-3.81 (m, 4H) 3.83 (s, 2H) 3.88 (s, 3H) 6.87 (d, J=8.11 Hz, 1H) 6.97 (dd, J=8.58, 2.03 Hz, 1H) 7.16 (dd, J=8.11, 2.18 Hz, 1H) 7.21 (s, 1H) 7.26 (d, J=1.87 Hz, 1H) 7.52 (d, J=8.42 Hz, 1H) 7.75 (d, J=8.42 Hz, 2H) 7.83 (d, J=8.42 Hz, 2H).

EXAMPLE 314

4-(6-morpholin-4-yl-1,4-dihydroindeno[1,2-c]pyrazol-3-yl)benzonitrile

Example 312B (60 mg, 0.151 mmol), Pd(PP$_3$)$_4$ (17.5 mg, 0.015 mmol), Zn(CN)$_2$ (213 mg, 1.82 mmol), and DMF (4 mL) were mixed, and purged with N$_2$ for 10 minutes. The reaction mixture was capped, stirred, and heated to 180° C. for 5 minutes in a Smith Synthesizer. After the reaction, the reaction mixture was filtered, and the filtrate was concentrated. The residue was purified by HPLC to give the title compound (33 mg, 64%). MS (ESI) m/z 343 (M+H)$^+$; $^1$H NMR (500 MHz, DMSO-D$_6$) δ ppm 3.17-3.24 (m, 4H) 3.743.82 (m, 4H) 3.85 (s, 2H) 7.00 (dd, J=8.42, 1.87 Hz, 2H) 7.23 (s, 1H) 7.52 (d, J=8.42 Hz, 1H) 7.908.01 (m, 4H).

EXAMPLE 315

4-[5-(6-morpholin-4-yl-1,4-dihydroindeno[1,2-c]pyrazol-3-yl)pyridin-2-yl]phenol

EXAMPLE 315A 3-(6-chloropyridin-3-yl)-6-morpholin-4-yl-1,4-dihydroindeno[1,2-c]pyrazole Example 312A (403 mg, 1.85 mmol), Example 230A (963 mg, 4.63 mmol), 95% NaH (187 mg, 7.40 mmol) and THF (20 mL) were mixed and stirred under N$_2$ overnight. THF was removed. To the residue was added ethanol (60 mL), acetic acid (3 mL) and hydrazine monohydrate (3 mL). The mixture was heated to reflux for 2 hours, and then cooled. The reaction mixture was concentrated. Water (30 mL) was added. The light yellow precipitate was washed with water (20 mL×2) and ethyl acetate (5 mL×2), and dried in vacuo to give the above intermediate (0.514 g, 79%). MS (ESI) m/z 353 (M+H)$^+$; $^1$H NMR (400 MHz, DMSO-D$_6$) δ ppm 3.13-3.19 (m, 4H) 3.72-3.78 (m, 4H) 3.82 (s, 2H) 6.95 (dd, J=8.59, 1.53 Hz, 1H) 7.18 (s, 1H) 7.48 (s, 1H) 7.64 (s, 1H) 8.20 (d, J=8.29 Hz, 1H) 8.81 (d, J=2.15 Hz, 1H) 13.17 (s, 1H).

EXAMPLE 315B

4-[5-(6-morpholin-4-yl-1,4-dihydroindeno[1,2-c]pyrazol-3-yl)pyridin-2-yl]phenol

Example 315A (60 mg, 0.151 mmol), (4-hydroxyphenyl)boronic acid (25 mg, 0.182 mmol), Pd(PPh$_3$)$_2$Cl$_2$ (10.6 mg, 0.015 mmol), DME/EtOH/H$_2$O (7/2/3, 3 mL) and 1M Na$_2$CO$_3$ (1 mL) were mixed, and heated to 160° C. for 10 minutes in a Smith Synthesizer. The solvents were removed. The residue was purified by HPLC to give the title compound (29 mg, 47%). MS (ESI) m/z 411 (M+H)$^+$; $^1$H NMR (500 MHz, DMSO-D$_6$) δ ppm 3.14-3.21 (m, 4H) 3.73-3.81 (m, 4H) 3.88 (s, 2H) 6.90 (d, J=8.73 Hz, 2H) 6.98 (dd, J=8.26, 2.03 Hz, 1H) 7.23 (s, 1H) 7.52 (d, J=8.42 Hz, 1H) 8.00 (t, J=9.04 Hz, 3H) 8.24 (dd, J=8.42, 2.18 Hz, 1H) 9.00 (d, J=1.87 Hz, 1H) 9.85 (s, 1H).

EXAMPLE 316

2-methoxy-4-[5-(6-morpholin-4-yl-1,4-dihydroindeno[1,2-c]pyrazol-3-yl)pyridin-2-yl]phenol Example 316 was synthesized in similar fashion as Example 315B, submitting (4-hydroxyphenyl)boronic acid with 2-methoxy-4-(4,4,5,5-tetramethyl-1,3,2-dioxaborolan-2-yl)-phenol. (76 mg, 61%) MS (ESI) m/z 441 (M+H)$^+$; $^1$H NMR (500 MHz, DMSO-D$_6$) δ ppm 3.14-3.21 (m, 4H) 3.73-3.81 (m, 4H) 3.88 (s, 2H) 3.89 (s, 3H) 6.91 (d, J=8.11 Hz, 1H) 6.98 (dd, J=8.42, 1.87 Hz, 1H) 7.23 (s, 1H) 7.52 (d, J=8.42 Hz, 1H) 7.60 (dd, J=8.26, 2.03 Hz, 1H) 7.74 (d, J=1.87 Hz, 1H) 8.05 (d, J=8.42 Hz, 1H) 8.23 (dd, J=8.42, 2.18 Hz, 1H) 9.01 (d, J=2.18 Hz, 1H).

EXAMPLE 317

5-(6-morpholin-4-yl-1,4-dihydroindeno[1,2-c]pyrazol-3-yl)pyridine-2-carbonitrile Example 315A (100 mg, 0.283 mmol), Pd(PPh$_3$)$_4$ (33 mg, 0.0283 mmol), Zn(CN)$_2$ (332 mg, 2.83 mmol), and DMF (4 mL) were mixed, and pumped with N$_2$ for 10 minutes. The reaction mixture was stirred, and heated to 180° C. for 5 minutes in a Smith Synthesizer. After the reaction, the solution was filtered, and the solvent was removed. The residue was purified by HPLC to give the title compound (39 mg, 40%). MS (ESI) m/z 344 (M+H)$^+$; $^1$H NMR (500 MHz, DMSO-D$_6$) δ ppm 3.14-3.21 (m, 4H) 3.73-3.81 (m, 4H) 3.89 (s, 2H) 6.98 (dd, J=8.42, 2.18 Hz, 1H) 7.22 (d, J=1.56 Hz, 1H) 7.51 (d, J=8.42 Hz, 1H) 8.13 (d, J=8.11 Hz, 1H) 8.35 (dd, J=8.11, 2.18 Hz, 1H) 9.15 (d, J=1.56 Hz, 1H).

EXAMPLE 318

5-(6,7-diisopropoxy-1,4-dihydroindeno[1,2-c]pyrazol-3-yl)pyridine-2-carbonitrile

EXAMPLE 318A 5,6-diisopropoxyindan-1-one

Example 144A (0.445 g, 2.70 mmol), 2-bromo-propane (0.64 mL, 6.77 mmol), Cs$_2$CO$_3$ (2.20 g, 6.77 mmol) and DMF (20 mL) were mixed, stirred, and heated to 60° C. for 8 hours. The reaction mixture was then filtered. The solution was concentrated, and dried to give the desired intermediate (0.67 g, 100%). MS (DCI/NH$_3$) m/z 249 (M+H)$^+$; $^1$H NMR (300 MHz, CD$_3$OD) δ ppm 1.32 (d, J=6.10 Hz, 6H) 1.38 (d, J=6.10 Hz, 6H) 2.612.68 (m, 2H) 3.03-3.09 (m, 2H) 4.51 (m, 1H) 4.75 (m, 1H) 7.08 (s, 1H) 7.18 (s, 1H).

EXAMPLE 318B 3-(6-chloropyridin-3-yl)-6,7-diisopropoxy-1,4-dihydroindenol 1,2-c]pyrazole Example 318A (0.67 g, 2.70 mmol), Example 230A (1.12 g, 5.40 mmol), 95% NaH (0.26 g, 10.8 mmol) and benzene (30 mL) were mixed, stirred, and heated to reflux for 4 hours. All the solvent was removed. To the residue were added ethanol (70 mL), acetic acid (5 mL) and hydrazine monohydrate (5 mL). The reaction mixture was heated to reflux for 2 hours. Then the solvents were removed. Water (50 mL) was added. The precipitate was filtered, washed with water (20 mL×3) and ethyl acetate (20 mL×3), and dried in vacuo to give the above intermediate (0.60 g, 58%). MS (ESI) m/z 384 (M+H)$^+$; $^1$H NMR (500 MHz, DMSO-D$_6$) δ ppm 1.25-1.33 (m, 12H) 3.72-3.85 (m, 2H) 4.45-4.60 (m, 2H) 7.15-7.28 (m, 2H) 7.63 (m, 1H) 8.21 (m, 1H) 8.81 (s, 1H) 13.23 (s, 1H).

EXAMPLE 318C 5-(6,7-diisopropoxy-1,4-dihydroindeno[1,2-c]pyrazol-3-yl)pyridine-2-carbonitrile Example 318B (100 mg, 0.261 mmol), Pd(PPh$_3$)$_4$ (30.1 mg, 0.0261 mmol), Zn(CN)$_2$ (0.367 g, 3.126 mmol) and DMF (5 mL) were mixed, purged with N$_2$, stirred, and heated to 180° C. for 5 minutes in the Smith Synthesizer. The reaction mixture was filtered. The solution was concentrated. DMSO (2.5 mL) was added. The suspension was filtered. The precipitate was washed with ethyl acetate (2 mL×3), and dried to give the title compound (19.4 mg, 20%). MS (ESI) m/z 375 (M+H)$^+$; $^1$H NMR (500 MHz, DMSO-D$_6$) δ ppm 1.25-1.31 (m, 12H) 3.86 (s, 2H) 4.45-4.60 (m, 2H) 7.17-7.30 (m, 2H) 8.13 (m, 1H) 8.34 (m, 1H) 9.13 (m, 1H) 13.39 (m, 1H).

EXAMPLE 319

4-[5-(6,7-diisopropoxy-1,4-dihydroindeno[1,2-c] pyrazol-3-yl)pyridin-2-yl]phenol Example 318B (100 mg, 0.26 mmol), (4-hydroxyphenyl) boronic acid (43 mg, 0.313 mmol), Pd(PPh$_3$)$_2$Cl$_2$ (18 mg, 0.026 mmol), DME/EtOH/H$_2$O (7:2:3, 3 mL) and 1M Na$_2$CO$_3$ solution (1 mL) were mixed, capped, and heated to 160° C. for 10 minutes in a Smith Synthesizer. Then all the solvents were removed. The residue was purified by HPLC to give the title compound (16.4 mg, 14%). MS (ESI) m/z 442 (M+H)$^+$; $^1$H NMR (500 MHz, DMSO-D$_6$) δ ppm 1.24-1.31 (m, 12H) 3.81 (s, 2H) 4.46-4.57 (m, 2H) 6.89 (d, J=8.73 Hz, 2H) 7.22 (d, J=9.36 Hz, 2H) 7.95-8.01 (m, 3H) 8.20 (dd, J=8.42, 2.18 Hz, 1H) 8.99 (d, J=1.87 Hz, 1H) 9.80 (s, 1H).

EXAMPLE 320

4-[5-(6,7-diisopropoxy-1,4-dihydroindeno[1,2-c] pyrazol-3-yl)pyridin-2-yl]-2-methoxyphenol Example 320 was synthesized in similar fashion as Example 319, submitting (4-hydroxyphenyl)boronic acid with 2-methoxy-4-(4,4,5,5-tetramethyl-1,3,2-dioxaborolan-2-yl)-phenol (65.4 mg, 53%). MS (ESI) m/z 472 (M+H)$^+$; $^1$H NMR (500 MHz, DMSO-D$_6$) δ ppm 1.23-1.30 (m, 12H) 3.82 (s, 2H) 3.88 (s, 3H) 4.464.57 (m, 2H) 6.89 (d, J=8.42 Hz, 1H) 7.22 (d, J=9.04 Hz, 2H) 7.56-7.62 (m, 3H) 7.73 (d, J=2.18 Hz, 1H) 8.03 (d, J=8.42 Hz, 1H) 8.20 (dd, J=8.42, 2.18 Hz, 1H) 8.99 (d, J=2.18 Hz, 1H).

EXAMPLE 321

5-[6-(tetrahydro-2H-pyran-4-yloxy)-1,4-dihydroindeno[1,2-c]pyrazol-3-yl]pyridine-2-carbonitrile

EXAMPLE 321A 5-(tetrahydro-2H-pyran-4-yloxy)indan-1-one

5-Hydroxy-1-indanone (0.636 g, 4.30 mmol), tetrahydropyran-4ol (1.22 mL, 12.80 mmol), PPh$_3$-polymer supported (2.864 g, 8.59 mmol), DBAD (1.978 g, 8.59 mmol) and THF (40 mL) were mixed, and shaken overnight. The mixture was filtered, and washed with THF (10 mL×3). The filtrate was concentrated. The residue was purified by flash chromatography to give the above intermediate (0.85 g, 85%). MS (APCI) m/z 233 (M+H)$^+$; $^1$H NMR (300 MHz, CD$_3$OD) δ ppm 1.79-1.89 (m, 2H) 2.01-2.12 (m, 2H) 2.62-2.69 (m, 2H) 3.07-3.15 (m, 2H) 3.85-4.00 (m, 4H) 4.75 (m, 1H) 6.97 (dd, J=8.65, 2.20 Hz, 1H) 7.08 (s, 1H) 7.63 (d, J=8.48 Hz, 1H).

EXAMPLE 321B 3-(6-chloropyridin-3-yl)-6-(tetrahydro-2H-pyran-4-yloxy)-1,4-dihydroindeno[1,2-c]pyrazole Example 321A (0.85 g, 3.66 mmol), Example 230A (1.52 g, 7.32 mmol), 95% NaH (0.37 g, 14.64 mmol) and benzene (40 mL) were mixed, stirred, and heated to reflux for 4 hours. The mixture was concentrated. To the residue was added ethanol (40 mL), acetic acid (5 mL) and hydrazine monohydrate (5 mL). The reaction mixture was heated to reflux for 2 hours. All the solvents were removed. To the residue was added water (50 mL). The precipitate was filtered, washed with water (30 mL×3) and ethyl acetate (30 mL×3), and dried in vacuo to give the desired intermediate (0.70 g, 28%). MS (ESI) m/z 368 (M+H)$^+$; $^1$H NMR (400 MHz, DMSO-D$_6$) δ ppm 1.56-1.62 (m, 2H) 1.95-2.04 (m, 2H) 3.46-3.55 (m, 2H) 3.82-3.91 (m, 4H) 4.62 (m, 1H) 6.99 (dd, J=8.59, 2.15 Hz, 1H) 7.23 (d, J=1.84 Hz, 1H) 7.54 (d, J=7.98 Hz, 1H) 7.64 (d, J=8.29 Hz, 1H) 8.22 (dd, J=8.29, 2.45 Hz, 1H) 8.82 (d, J=2.15 Hz, 1H) 13.25 (s, 1H).

EXAMPLE 321C

5-[6-(tetrahydro-2H-pyran-4-yloxy)-1,4-dihydroindeno[1,2-c]pyrazol-3-yl]pyridine-2-carbonitrile Example 321B (100 mg, 0.27 mmol), Pd(PPh$_3$)$_4$ (31 mg, 0.027 mmol), Zn(CN)$_2$ (0.383 g, 3.26 mmol) and DMF (5 mL) were mixed, purged with N, stirred, and heated to 180°

C. for 5 minutes in a Smith Synthesizer. The reaction mixture was filtered. The solution was concentrated. DMSO (2.5 mL) was added. The suspension was filtered. The precipitate was washed with ethyl acetate (2 mL×3), and dried to give the title compound (19.4 mg, 20%). MS (ESI) m/z 359 (M+H)$^+$; $^1$H NMR (500 MHz, DMSO-D$_6$) δ ppm 1.56-1.62 (m, 2H) 1.94-2.03 (m, 2H) 3.46-3.54 (m, 2H) 3.82-3.91 (m, 4H) 4.62 (m, 1H) 7.00 (d, J=7.49 Hz, 1H) 7.23 (s, 1H) 7.52 (m, 1H) 8.10 (m, 1H) 8.35 (d, J=7.49 Hz, 1H) 9.14 (s, 1H) 13.42 (m, 1H).

EXAMPLE 322

4-{5-[6-(tetrahydro-2H-pyran-4-yloxy)-1,4-dihydroindeno[1,2-c]pyrazol-3-yl]pyridin-2-yl}phenol Example 321B (100 mg, 0.27 mmol), (4-hydroxyphenyl)boronic acid (45 mg, 0.326 mmol), Pd(PPh$_3$)$_2$Cl$_2$ (19 mg, 0.027 mmol), DME/EtOH/H$_2$O (7:2:3, 3 mL) and 1M Na$_2$CO$_3$ (1 mL) were mixed, and heated to 160° C. for 10 minutes in a Smith Synthesizer. All the solvents were removed. The residue was purified by HPLC to give the title compound (31.7 mg, 28%). MS (ESI) m/z 426 (M+H)$^+$; $^1$H NMR (300 MHz, DMSO-D$_6$) δ ppm 1.57-1.64 (m, 2H) 1.95-2.04 (m, 2H) 3.47-3.54 (m, 2H) 3.82-3.91 (m, 4H) 4.63 (m, 1H) 6.87-6.71 (m, 2H) 6.99 (dd, J=8.48, 2.37 Hz, 1H) 7.24 (d, J=2.03 Hz, 1H) 7.55 (d, J=8.14 Hz, 1H) 7.94-8.02 (m, 3H) 8.19 (dd, J=8.48, 2.37 Hz, 1H) 9.01 (d, J=1.70 Hz, 1H).

EXAMPLE 323

2-methoxy-4-{5-[6-(tetrahydro-2H-pyran-4-yloxy)-1,4-dihydroindeno[1,2-c]pyrazol-3-yl]pyridin-2-yl}phenol Example 323 was synthesized in similar fashion as Example 322, submitting (4-hydroxyphenyl)boronic acid with 2-methoxy-4-(4,4,5,5-tetramethyl-1,3,2-dioxaborolan-2-yl)-phenol (56 mg, 46%). MS (ESI) m/z 456 (M+H)$^+$; $^1$H NMR (300 MHz, DMSO-D$_6$) δ ppm 1.58-1.66 (m, 2H) 1.94-2.04 (m, 2H) 3.46-3.53 (m, 2H) 3.843.92 (m, 4H) 4.63 (m, 1H) 6.90 (d, J=8.48 Hz, 1H) 6.99 (dd, J=8.48, 2.37 Hz, 1H) 7.25 (d, J=2.37 Hz, 1H) 7.56 (d, J=8.48 Hz, 1H) 7.60 (dd, J=8.14, 2.03 Hz, 1H) 7.75 (d, J=2.03 Hz, 1H) 8.04 (d, J=8.48 Hz, 1H) 8.20 (dd, J=8.65, 2.15 Hz, 1H) 9.01 (d, J=2.37 Hz, 1H) 9.35 (s, 1H).

EXAMPLE 324

5-(6-isopropoxy-1,4-dihydroindeno[1,2-c]pyrazol-3-yl)pyridine-2-carbonitrile

EXAMPLE 324A phenyl 6-chloronicotinate

6-Chloro-nicotinic acid (31.67 g, 201 mmol), phenol (18.92 g, 201 mmol), DCC (43.55 g, 211 mmol), DMAP (0.737 g, 6.03 mmol) and ether (500 mL) were mixed, and stirred under N$_2$ at room temperature for 3 days. Then the ether was removed. To the residue was added CH$_2$Cl$_2$ (1000 mL). The urea precipitate was filtered. The solution was concentrated, and purified by flash chromatography to give the desired intermediate (37 g, 79%). MS (DCI/NH$_3$) m/z 234 (M+H)$^+$; $^1$H NMR (300 MHz, CDCl$_3$) δ ppm 7.19-7.34 (m, 3H) 7.41-7.53 (m, 3H) 8.39 (dd, J=8.14, 2.37 Hz, 1H) 9.17 (d, J=2.03 Hz, 1H).

EXAMPLE 324B 5-isopropoxyindan-1-one 5-hydroxy-1-indanone (0.665 g, 4.68 mmol), 2-bromopropane (0.88 mL, 9.36 mmol), Cs$_2$CO$_3$ (3.05 g, 9.36 mmol) and DMF (50 mL) were mixed, stirred, and heated to 60° C. overnight. The reaction was filtered. The solution was concentrated, and dried to give the above intermediate (0.89 g, 100%). MS (DCI/NH$_3$) M/Z 191 (M+H)$^+$; $^1$H NMR (300 MHz, CD$_3$OD) δ ppm 1.35 (d, J=6.10 Hz, 6H) 2.62-2.69 (m, 2H) 3.07-3.15 (m, 2H) 4.75 (m, 1H) 6.91 (dd, J=8.48, 2.03 Hz, 1H) 7.01 (s, 1H) 7.61 (d, J=8.48 Hz, 1H).

EXAMPLE 324C (A-833748.0)

3-(6-chloropyridin-3-yl)-6-isopropoxy-1,4-dihydroindeno[1,2-c]pyrazole

Example 324B (0.89 g, 4.68 mmol), Example 324A (1.64 g, 7.02 mmol), 95% NaH (0.355 g, 14.64 mmol) and benzene (50 mL) were mixed, stirred, and heated to reflux for 4 hours. The mixture was concentrated. To the residue was added ethanol (150 mL), acetic acid (10 mL) and hydrazine monohydrate (10 mL). The reaction mixture was heated to reflux for 2 hours. All the solvents were removed. To the residue was added water (100 mL). The precipitate was filtered out, washed with water (30 mL×3) and ethyl acetate (30 mL×3), and dried in vacuo to give the intermediate 58C (1.01 g, 66%). MS (ESI) m/z 326 (M+H)$^+$; $^1$H NMR (500 MHz, DMSO-D6) δ ppm 1.30 (d, J=6.24 Hz, 6H) 3.85 (s, 2H) 4.66 (m, 1H) 6.93 (dd, J=8.11, 2.18 Hz, 1H) 7.16 (d, J=2.18 Hz, 1H) 7.53 (d, J=8.11 Hz, 1H) 7.64 (d, J=8.11 Hz, 1H) 8.22 (dd, J=8.11, 2.50 Hz, 1H) 8.82 (d, J=2.50 Hz, 1H) 13.24 (s, 1H).

EXAMPLE 324D 5-(6-isopropoxy-1,4-dihydroindeno[1,2-c]pyrazol-3-yl)pyridine-2-carbonitrile Example 324C (100 mg, 0.31 mmol), Pd(PPh$_3$)$_4$ (36 mg, 0.031 mmol), Zn(CN)$_2$ (0.43 g, 3.68 mmol) and DMF (5 mL) were mixed, pumped with N$_2$, stirred, and heated to 180° C. for 5 minutes in the Smith Synthesizer. The reaction mixture was filtered. The filtrate was concentrated. To the residue was added DMSO (2.5 mL). The suspension was filtered. The precipitate was washed with ethyl acetate (2 mL×3), and dried to give the title compound (53.6 mg, 55%). MS (ESI) m/z 317 (M+H)$^+$; $^1$H NMR (500 MHz, DMSO-D$_6$) δ ppm 1.30 (d, J=6.24 Hz, 6H) 3.89 (d, J=14.66 Hz, 2H) 4.67 (m, 1H) 6.94 (d, J=8.11 Hz, 1H) 7.17 (s, 1H) 7.54 (s, 1H) 8.11 (s, 1H) 8.36 (dd, J=8.11, 1.87 Hz, 1H) 9.15 (s, 1H) 13.43 (s, 1H).

EXAMPLE 325

4-[5-(6-isopropoxy-1,4-dihydroindeno[1,2-c]pyrazol-3-yl)pyridin-2-yl]phenol

Example 324C (100 mg, 0.31 mmol), (4-hydroxyphenyl)boronic acid (51 mg, 0.37 mmol), Pd(PPh$_3$)$_2$Cl$_2$ (22 mg, 0.031 mmol), DME/EtOH/H$_2$O (7/2/3, 3 mL) and 1M Na$_2$CO$_3$ (1 mL) were mixed, capped, and heated to 160° C. for 10 minutes in a Smith Synthesizer. All the solvents were removed. The residue was purified by HPLC to give the title compound (43 mg, 36%). MS (ESI) m/z 384 (M+H)$^+$; $^1$H NMR (500 MHz, DMSO-D$_6$) δ ppm 1.30 (d, J=5.93 Hz, 6H) 3.89 (s, 2H) 4.67 (m, 1H) 6.89 (d, J=8.73 Hz, 2H) 6.92 (dd, J=8.11, 2.18 Hz, 1H) 7.17 (s, 1H) 7.54 (d, J=8.11 Hz, 1H) 7.96 (d, J=8.42 Hz, 1H) 8.00 (d, J=8.73 Hz, 2H) 8.18 (dd, J=8.26, 2.34 Hz, 1H) 9.01 (d, J=2.18 Hz, 1H) 9.75 (s, 1H).

EXAMPLE 326

4-[5-(6-isopropoxy-1,4-dihydroindeno[1,2-c]pyrazol-3-yl)pyridin-2-yl]-2-methoxyphenol Example 326 was synthesized in a similar fashion as Example 325, submitting (4 hydroxyphenyl)boronic acid with 2-methoxy-4-(4,4,5,5-tetramethyl-1,3,2-dioxaborolan-2-yl)-phenol (72 mg, 56%). MS (ESI) m/z 414 (M+H)$^+$; $^1$H NMR (500 MHz, DMSO-D$_6$) δ ppm 1.30 (d, J=5.93 Hz, 6H) 3.89 (s, 5H) 4.66 (m, 1H) 6.90 (d, J=8.11 Hz, 1H) 6.93 (dd, J=8.26, 2.34 Hz, 1H) 7.17 (s, 1H) 7.55 (d, J=8.42 Hz, 1H) 7.60 (dd, J=8.26, 2.03 Hz, 1H) 7.74 (d, J=2.18 Hz, 1H) 8.03 (d, J=8.42 Hz, 1H) 8.21 (dd, J=8.42, 2.18 Hz, 1H) 9.01 (d, J=2.18 Hz, 1H) 9.35 (s, 1H).

EXAMPLE 327

5-(6,7-diethoxy-1,4-dihydroindeno[1,2-c]pyrazol-3-yl)pyridine-2-carbonitrile

EXAMPLE 327A 5,6-diethoxyindan-1-one

Example 144A (0.56 g, 3.41 mmol), bromoethane (2.55 mL, 34.1 mmol), Cs$_2$CO$_3$ (3.33 g, 10.23 mmol) and DMF (20 mL) were mixed, stirred, and heated to 60° C. in a capped high-pressure tube overnight. The reaction was then filtered. The solution was concentrated, and dried to give the desired intermediate (0.75 g, 100%). MS (APCI) m/z 221 (M+H)$^+$.

EXAMPLE 327B 3-(6-chloropyridin-3-yl)-6,7-diethoxy-1,4-dihydroindeno[1,2-c]pyrazole Example 327A (0.75 g, 3.41 mmol), Example 324A (1.60 g, 6.82 mmol), 95% NaH (0.344 g, 13.64 mmol) and benzene (50 mL) were mixed, stirred, and heated to reflux for 4 hours. The mixture was then concentrated. To the residue were added ethanol (150 mL), acetic acid (10 mL) and hydrazine monohydrate (10 mL). The reaction mixture was heated to reflux for 2 hours. All the solvents were removed. To the residue was added water (100 mL). The precipitate was filtered, washed with water (30 mL×3) and ethyl acetate (30 mL×3), and dried in vacuo to give the above intermediate (0.57 g, 47%). MS (ESI) m/z 356 (M+H)$^+$; $^1$H NMR (500 MHz, DMSO-D$_6$) δ ppm 1.36 (q, J=6.86 Hz, 6H) 3.78 (s, 2H) 4.00 4.13 (m, 4H) 7.21 (d, J=9.04 Hz, 2H) 7.64 (d, J=8.42 Hz, 1H) 8.20 (dd, J=8.27, 2.34 Hz, 1H) 8.81 (d, J=2.18 Hz, 1H) 13.17 (s, 1H).

EXAMPLE 327C 5-(6,7-diethoxy-1,4-dihydroindeno[1,2-c]pyrazol-3-yl)pyridine-2-carbonitrile Example 327B (100 mg, 0.281 mmol), Pd(PPh$_3$)$_4$ (32 mg, 0.028 mmol), Zn(CN)$_2$ (0.40 g, 3.37 mmol) and DMF (5 mL) were mixed, pumped with N$_2$, stirred, and heated to 180° C. for 5 minutes in a Smith Synthesizer. The reaction mixture was filtered. The solution was concentrated. To the residue was added DMSO (2.5 mL). The suspension was filtered. The precipitate was washed with ethyl acetate (2 mL×3), and dried to give the title compound (82.1 mg, 84%). MS (ESI) m/z 347 (M+H)$^+$; $^1$H NMR (400 MHz, DMSO-D$_6$) δ ppm 1.32-1.41 (m, 6H) 3.78-3.88 (m, 2H) 4.04-4.14 (m, 4H) 7.15-7.28 (m, 2H) 7.57 (m, 1H) 8.13 (m, 1H) 8.34 (t, J=7.52 Hz, 1H) 9.15 (m, 1H) 13.36 (s, 1H).

EXAMPLE 328

4-[5-(6,7-diethoxy-1,4-dihydroindeno[1,2-c]pyrazol-3-yl)pyridin-2-yl]phenol

Example 327B (100 mg, 0.281 mmol), (4-hydroxyphenyl)boronic acid (46 mg, 0.34 mmol), Pd(PPh$_3$)$_2$Cl$_2$ (20 mg, 0.0281 mmol), DME/EtOH/H$_2$O (7:2:3, 3 mL) and 1M Na$_2$CO$_3$ solution (1 mL) were mixed, and heated to 160° C. for 10 minutes in a Smith Synthesizer. All the solvents were removed. The residue was purified by HPLC to give the title compound (34 mg, 29%). MS (ESI) m/z 414 (M+H)$^+$; $^1$H NMR (400 MHz, DMSO-D$_6$) δ ppm 1.33-1.40 (m, 6H) 3.82 (s, 2H) 4.05-4.15 (m, 4H) 6.77-6.81 (m, 2H) 7.23 (d, J=6.14 Hz, 2H) 7.98-8.02 (m, 3H) 8.19 (dd, J=8.29, 2.46 Hz, 1H) 9.00 (d, J=1.53 Hz, 1H) 11.13 (s, 1H).

EXAMPLE 329

4-[5-(6,7-diethoxy-1,4-dihydroindeno[1,2-c]pyrazol-3-yl)pyridin-2-yl]-2-methoxyphenol Example 329 was synthesized in a similar fashion as Example 328, submitting (4-hydroxyphenyl)boronic acid with 2-methoxy-4-(4,4,5,5-tetramethyl-1,3,2-dioxaborolan-2-yl)-phenol (47 mg, 38%). MS (ESI) m/z 444 (M+H)$^+$; $^1$H NMR (400 MHz, DMSO-D$_6$) δ ppm 1.33-1.40 (m, 6H) 3.82 (s, 2H) 3.89 (s, 3H) 4.05-4.15 (m, 4H) 6.90 (d, J=8.29 Hz, 1H) 7.23 (d, J=6.14 Hz, 2H) 7.60 (dd, J=8.29, 2.15 Hz, 1H) 7.72 (m, 1H) 8.03 (d, J=8.29 Hz, 1H) 8.19 (dd, J=8.44, 2.30 Hz, 1H) 9.01 (d, J=1.84 Hz, 1H).

EXAMPLE 330

5-[6,7-bis(difluoromethoxy)-1,4-dihydroindeno[1,2-c]pyrazol-3-yl]pyridine-2-carbonitrile

EXAMPLE 330A 5,6-bis(difluoromethoxy)indan-1-one

Example 144A (1.266 g, 7.71 mmol), K$_2$CO$_3$ (4.26 g, 30.84 mmol) and DMF (100 mL) were mixed and stirred. ClCHF$_2$ (80 psi) was introduced to the reaction. The temperature was set to 85° C. for 2 hours. After the reaction, the high pressure was released. The solvent was removed. The residue was purified by flash chromatography to give the above intermediate (1.10 g, 54%). MS (ESI) m/z 265 (M+H)$^+$; $^1$H NMR (300 MHz, CD$_3$OD) δ ppm 2.69-2.76 (m, 2H) 3.13-3.20 (m, 2H) 6.61-7.27 (m, 2H) 7.46 (s, 1H) 7.55 (s, 1H).

EXAMPLE 330B (A-835801.0)

3-(6-chloropyridin-3-yl)-6,7-bis(difluoromethoxy)-1,4-dihydroindeno[1,2-c]pyrazole Example 330A (0.55 g, 2.08 mmol), Example 324A (0.974 g, 4.16 mmol), 95% NaH (0.21 g, 8.32 mmol) and benzene (50 mL) were mixed, stirred, and heated to reflux for 4 hours. The mixture was then concentrated. To the residue were added ethanol (50 mL), acetic acid (5 mL) and hydrazine monohydrate (5 mL). The reaction mixture was heated to reflux for 2 hours. All the solvents were removed. To the residue as added water (100 mL). The precipitate was filtered, and washed with water (30 mL×3). The solid was further purified by flash chromatography to give the above intermediate (89 mg, 11%). MS (ESI) m/z 400 (M+H)$^+$.

EXAMPLE 330C

5-[6,7-bis(difluoromethoxy)-1,4-dihydroindeno[1,2-c]pyrazol-3-yl]pyridine-2-carbonitrile Example 330B (30 mg, 0.075 mmol), Pd(PPh$_3$)$_4$ (8.7 mg, 0.0075 mmol), Zn(CN)$_2$ (106 g, 0.901 mmol) and DMF (2 mL) were mixed, pumped with N$_2$, stirred, and heated to 180° C. for 5 minutes in a Smith Synthesizer. The reaction mixture was filtered. The solution was concentrated. To the residue was added DMSO (2.5 mL). The suspension was filtered. The precipitate was purified by flash chromatography to give the title compound (22.7 mg, 78%). MS (ESI) m/z 400 (M+H)$^+$; $^1$H NMR (300 MHz, DMSO-D$_6$) δ ppm 4.02 (s, 2H) 6.99-7.57 (m, 2H) 7.62 (s, 2H) 8.18 (d, J=7.80 Hz, 1H) 8.39 (dd, J=8.14, 2.37 Hz, 1H) 9.18 (d, J=2.03 Hz, 1H) 13.74 (s, 1H).

EXAMPLE 331

4-{5-[6,7-bis(difluoromethoxy)-1,4-dihydroindeno[1,2-c]pyrazol-3-yl]pyridin-2-yl}phenol Example 330B (30 mg, 0.075 mmol), (4-hydroxyphenyl)boronic acid (12.4 mg, 0.090 mmol), Pd(PPh$_3$)$_2$Cl$_2$ (5.2 mg, 0.0075 mmol), DME/EtOH/H$_2$O (7/2/3, 2.25 mL) and 1M Na$_2$CO$_3$ (0.75 mL) were mixed, and heated to 160° C. for 10 minutes in a Smith Synthesizer. All the solvents were removed. The residue was purified by HPLC to give the title compound (24 mg, 70%). MS (ESI) m/z 458 (M+H)$^+$; $^1$H NMR (300 MHz, DMSO-D$_6$) δ ppm 3.99 (s, 2H) 6.85-6.92 (m, 2H) 6.98-7.57 (m, 2H) 7.60-7.64 (m, 2H) 7.98-8.04 (m, 2H) 8.18 (m, 1H) 9.03 (d, J=2.71 Hz, 1H) 9.79 (s, 1H).

EXAMPLE 332

5-[6-(1H-1,2,4-triazol-1-ylmethyl)-1,4-dihydroindeno[1,2-c]pyrazol-3-yl]pyridine-2-carbonitrile

EXAMPLE 332A

5'-bromo-2',3'-dihydrospiro[1,3-dioxolane-2,1'-indene]

A mixture of 5-bromo-1-indanone (13.0 g, 61.8 mmol), p-toluenesulfonic acid (23 mg, 0.12 mmol) and ethylene glycol (27.6 mL, 494.6 mmol) in benzene (140 mL) was refluxed for about 24 hours, using a Dean-Stark trap to remove water. The mixture was cooled, poured into excess 5% aqueous sodium bicarbonate and was extracted with toluene. The combined organic extracts were washed with brine, dried with MgSO$_4$, filtered, and evaporated in vacuum. The residue was purified by flash column chromatography using dichloromethane as the mobile phase to give the above intermediate. MS (DCI/NH$_3$): m/z 254, 256 (M)$^+$.

EXAMPLE 332B

2',3'-dihydrospiro[1,3-dioxolane-2,1'-inden]-5'-yl-methanol

To a solution of Example 332A (13 g, 50.9 mmol) in tetrahydrofuran (150 mL) was added a 2.5 M solution of n-butyllithium in hexanes (30.5 mL, 76.4 mmol) dropwise at about −78° C. Then a solution of N,N-dimethylformamide (39.4 mL, 509.0 mmol) in tetrahydrofuran (40 mL) was added dropwise and the mixture was allowed to warm to ambient temperature. The mixture was poured into water and was extracted with ethyl acetate. The combined organic extracts were washed with brine, dried over MgSO$_4$, filtered, and evaporated in vacuum. The residue was re-dissolved in a mixture of tetrahydrofuran (15 mL) and methanol (150 mL) and sodium borohydride (2.6 g, 68.7 mmol) was added in portions at about 0° C. The reaction mixture was stirred at room temperature for about 2 hours, then the mixture was concentrated in vacuum, diluted with water, and extracted with ethyl acetate. The combined organic extracts were washed with brine, dried (MgSO$_4$), filtered and evaporated under reduced pressure. The residue was purified by flash column chromatography on silica gel using hexane/ethyl acetate (2:1) as the mobile phase to give the above intermediate. MS (DCI/NH$_3$): m/z 207 (M+H)$^+$.

EXAMPLE 332C 5-(hydroxymethyl)indan-1-one

A solution of Example 332B (8.0 g, 38.7 mmol) and p-toluenesulfonic acid (7.4 g, 38.7 mmol) in a mixture of water (20 mL) and acetone (85 mL) was refluxed for about 1 hour. The mixture was concentrated in vacuum, diluted with water and was neutralized by careful addition of potassium carbonate (2.7 g, 19.4 mmol). The precipitate was filtered off, washed with a minimum of water and diethyl ether and was dried in vacuum to give the above intermediate. MS (DCI/NH$_3$): m/z 180 (M+NH$_4$)$^+$.

EXAMPLE 332D (1-oxo-2,3-dihydro-1H-inden-5-yl)methyl methanesulfonate

To a mixture of Example 332C (3.8 g, 23.6 mmol) and triethylamine (4.3 mL, 30.7 mmol) in tetrahydrofuran (50 mL) was added methanesulfonyl chloride (2.2 mL, 28.3 mmol) dropwise at about 0° C. After about 30 min stirring at about 0° C., the reaction mixture was diluted with water and was extracted with ethyl acetate. The combined organic extracts were washed with brine, dried (MgSO$_4$), filtered and evaporated under reduced pressure to give the above intermediate. MS (DCI/NH$_3$): m/z 258 (M+NH$_4$)$^+$.

EXAMPLE 332E 5-(1H-1,2,4-triazol-1-ylmethyl)indan-1-one

To a suspension of Example 332D (5.6 g, 23.3 mmol) and potassium carbonate (6.4 g, 46.6 mmol) in ethanol (200 mL) was added 1-methylpiperazine (5.2 mL, 46.6 mmol) dropwise at about 0° C. The mixture was stirred at room temperature for about 3 hours, concentrated in vacuum, diluted with water and was extracted with ethyl acetate. The combined organic extracts were dried (MgSO$_4$), filtered and evaporated under reduced pressure. The residue was purified by flash column chromatography on silica gel using dichloromethane/methanol (5:1) as the mobile phase to give the above intermediate. MS (DCI/NH$_3$): m/z 214 (M+H)$^+$; $^1$H NMR (500 MHz, CDCl$_3$) δ ppm 2.62 (t, J=8 Hz, 2H), 3.08 (t, J=8 Hz, 2H), 5.55 (s, 2H), 7.28 (d, J=9 Hz, 1H), 7.42 (s, 1H), 7.63 (d, J=9 Hz, 1H), 8.01 (s, 1H), 8.75 (s, 1H).

EXAMPLE 332F 3-(6-chloropyridin-3-yl)-6-(1H-1,2,4-triazol-1-ylmethyl)-1,4-dihydroindeno[1,2-c]pyrazole Example 332E (250 mg, 1.17 mmol), Example 324A (0.55 g, 2.35 mmol), 95% NaH (0.120 g, 4.69 mmol) and THF (50 mL) were mixed, and stirred under N$_2$ for 1 hour. The mixture was concentrated. To the residue was added ethanol (100 mL), acetic acid (5 mL) and hydrazine monohydrate (5 mL). The reaction mixture was heated to reflux for 2 hours, and then cooled to room temperature. All the solvents were removed. To the residue was added water (100 mL). The precipitate was filtered, washed with water (30 mL×3) and CCl$_4$ (30 mL×3), and dried in vacuo to give the above intermediate (200.5 mg, 49%). MS (ESI) m/z 349 (M+H)$^+$; $^1$H NMR (400 MHz, DMSO-D$_6$) δ ppm 3.89 (s, 2H) 5.47 (s, 2H) 7.31 (d, J=7.67 Hz, 1H) 7.42 (m, 1H) 7.50 (s, 1H) 7.64 (d, J=7.98 Hz, 2H) 7.97 (d, J=7.98 Hz, 1H) 8.22 (dd, J=8.44, 2.61 Hz, 1H), 8.68 (s, 1H) 8.83 (d, J=2.15 Hz, 1H).

EXAMPLE 332G

5-[6-(1H-1,2,4-triazol-1-ylmethyl)-1,4-dihydroindeno[1,2-c]pyrazol-3-yl]pyridine-2-carbonitrile Example 332F (50 mg, 0.143 mmol), Pd(PPh$_3$)$_4$ (16.5 mg, 0.0143 mmol), Zn(CN)$_2$ (0.200 g, 1.71 mmol) and DMF (2 mL) were mixed, pumped with N$_2$, stirred, and heated to 180° C. for 5 minutes in a Smith Synthesizer. The reaction mixture was filtered. The solution was concentrated. To the residue was added DMSO (2.5 mL). The suspension was filtered. The precipitate was washed with ethyl acetate (2 mL×3), and dried to give the title compound (33 mg, 68%). MS (ESI) m/z 340 (M+H)$^+$; $^1$H NMR (500 MHz, DMSO-D$_6$) δ ppm 3.91 (s, 2H) 5.45 (s, 2H) 7.28 (s, 1H) 7.45-7.65 (m, 3H) 7.95 (s, 1H) 8.33 (s, 1H) 8.65 (m, 1H) 9.11 (s, 1H) 13.60 (m, 1H).

EXAMPLE 333

4-{5-[6-(1H-1,2,4-triazol-1-ylmethyl)-1,4-dihydroindeno[1,2-c]pyrazol-3-yl]pyridin-2-yl}phenol Example 332F (50 mg, 0.143 mmol), (4-hydroxyphenyl) boronic acid (24 mg, 0.172 mmol), Pd(PPh$_3$)$_2$Cl$_2$ (10 mg, 0.0143 mmol), DME/EtOH/H$_2$O (7/2/3, 2 mL) and 1 M Na$_2$CO$_3$ (1 mL) were mixed, and heated to 160° C. for 10 minutes in a Smith Synthesizer. All the solvents were removed. The residue was purified by HPLC to give the title compound (29 mg, 50%). MS (ESI) m/z 407 (M+H)$^+$; $^1$H NMR (500 MHz, DMSO-D$_6$) δ ppm 3.93 (s, 2H) 5.48 (s, 2H) 6.87-6.90 (m, 2H) 7.31 (d, J=7.49 Hz, 1H) 7.51 (s, 1H) 7.65 (d, J=7.80 Hz, 1H) 7.96-8.01 (m, 4H) 8.20 (dd, J=8.42, 2.18 Hz, 1H) 8.69 (s, 1H) 9.01 (d, J=2.18 Hz, 1H).

EXAMPLE 334

4-[6-(1H-1,2,4-triazol-1-ylmethyl)-1,4-dihydroindeno[1,2-c]pyrazol-3-yl]benzonitrile

EXAMPLE 334A 3-(4-bromophenyl)-6-(1H-1,2,4-triazol-1-ylmethyl)-1,4-dihydroindeno[1,2-c]pyrazole Example 332E (250 mg, 117 mmol), phenyl 4-bromobenzoate (0.65 g, 2.35 mmol), 95% NaH (0.120 g, 4.69 mmol) and THF (50 mL) were mixed, and stirred for 3 hours. The mixture was then concentrated. To the residue was added ethanol (100 mL), acetic acid (5 mL) and hydrazine monohydrate (5 mL). The reaction mixture was heated to reflux for 2 hours. All the solvents were removed. To the residue was added water (100 mL). The precipitate was filtered, washed with water (30 mL×3) and CCl$_4$ (30 mL×3), and dried in vacuo to give the above intermediate (307 g, 67%). MS (ESI) m/z 393 (M+H)$^+$; $^1$H NMR (500 MHz, DMSO-D$_6$) δ ppm 3.85 (s, 2H) 5.48 (s, 2H) 7.30 (d, J=7.80 Hz, 1H) 7.50 (s, 1H) 7.64 (d, J=7.80 Hz, 1H) 7.69 (d, J=8.11 Hz, 2H) 7.76 (d, J=8.11 Hz, 2H) 7.99 (s, 1H) 8.68 (s, 1H) 13.30 (s, 1H).

EXAMPLE 334B

4-[6-(1H-1,2,4-triazol-1-ylmethyl)-1,4-dihydroindeno[1,2-c]pyrazol-3-yl]benzonitrile Example 334A (50 mg, 0.127 mmol), Pd(PPh$_3$)$_4$ (14.7 mg, 0.0127 mmol), Zn(CN)$_2$ (0.179 g, 1.524 mmol) and DMF (2 mL) were mixed, purged with N$_2$, stirred, and heated to 180° C. for 5 minutes in a Smith Synthesizer. The reaction mixture was filtered. The solution was concentrated. To the residue was added DMSO (2.5 mL). The suspension was filtered. The precipitate was washed with ethyl acetate (2 mL×3), and dried to give the title compound (40 mg, 93%). MS (ESI) m/z 339 (M+H)$^+$; $^1$H NMR (500 MHz, DMSO-D$_6$) δ ppm 3.92 (s, 2H) 5.49 (s, 2H) 7.31 (m, 1H) 7.51 (m, 1H) 7.66 (m, 1H) 7.868.03 (m, 5H) 8.70 (s, 1H) 13.49 (s, 1H).

EXAMPLE 335 835613

4'-[6-(1H-1,2,4-triazol-1-ylmethyl)-1,4-dihydroindeno[1,2-c]pyrazol-3-yl]-1,1'-biphenyl-4-ol Example 334A (50 mg, 0.127 mmol), (4-hydroxyphenyl) boronic acid (21 mg, 0.152 mmol), Pd(PPh$_3$)$_2$Cl$_2$ (9 mg, 0.0127 mmol), DME/EtOH/H$_2$O (7/2/3, 2 mL) and 1M Na$_2$CO$_3$ (1 mL) were mixed, and heated to 160° C. for 10 minutes in a Smith Synthesizer. All the solvents were removed. The residue was purified by HPLC to give the title compound (18 mg, 35%). MS (ESI) m/z 406 (M+H)$^+$; $^1$H NMR (500 MHz, DMSO-D$_6$) δ ppm 3.88 (s, 2H) 5.47 (s, 2H) 6.84-6.88 (m, 2H) 7.30 (d, J=8.11 Hz, 1H) 7.50 (s, 1H)

7.54-7.57 (m, 2H) 7.64 (d, J=7.17 Hz, 1H) 7.70 (d, J=8.42 Hz, 2H) 7.83 (d, J=8.42 Hz, 2H) 7.99 (s, 1H) 8.68 (s, 1H).

EXAMPLE 336

4-{5-[6-(diethylamino)-1,4-dihydroindeno[1,2-c]pyrazol-3-yl]pyridin-2-yl}phenol

EXAMPLE 336A 5-(diethylamino)indan-1-one

5-Amino-indan-1-one (408 mg, 2.77 mmol), iodoethane (0.89 mL, 11.1 mmol), NaCO$_3$ (0.88 g, 8.31 mmol) and water (10 mL) were mixed, and stirred at 100° C. in a high pressure tube overnight. The reaction was concentrated. The residue was purified by flash chromatography to give the above intermediate (0.40 g, 47%). MS (DCI/NH$_3$) m/z 204 (M+H)$^+$; $^1$H NMR (300 MHz, CD$_3$OD) δ ppm 1.21 (t, J=7.12 Hz, 6H) 2.56-2.62 (m, 2H) 2.99-3.06 (m, 2H) 3.50 (q, J=7.12 Hz, 4H) 6.67 (s, 1H) 6.73 (dd, J=8.82, 2.37 Hz, 1H) 7.52 (d, J=8.82 Hz, 1H).

EXAMPLE 336B 3-(6-chloropyridin-3-yl)-N,N-diethyl-1,4-dihydroindeno[1,2-c]pyrazol-6-amine Example 336A (0.40 g, 1.97 mmol), Example 324A (0.92 g, 3.94 mmol), 95% NaH (0.20 g, 7.88 mmol) and benzene (30 mL) were mixed, stirred, and heated to reflux overnight. The mixture was concentrated. To the residue was added ethanol (100 mL), acetic acid (5 mL) and hydrazine monohydrate (5 mL). The reaction mixture was heated to reflux for 2 hours. All the solvents were removed. To the residue was added water (100 mL). The precipitate was filtered, washed with water (30 mL×3) and ethyl acetate (30 mL×3), and dried in vacuo to give the above intermediate (0.50 g, 75%). MS (ESI) m/z 339 (M+H)$^+$; $^1$H NMR (300 MHz, DMSO-D$_6$) δ ppm 1.12 (t, J=6.95 Hz, 6H) 3.34-3.43 (m, 4H) 3.80 (s, 2H) 6.67 (dd, J=8.65, 2.20 Hz, 1H) 6.90 (s, 1H) 7.43 (s, 1H) 7.65 (s, 1H) 8.22 (s, 1H) 8.80 (d, J=2.37 Hz, 1H) 13.05 (s, 1H).

EXAMPLE 336C

5-[6-(diethylamino)-1,4-dihydroindeno[1,2-c]pyrazol-3-yl]pyridine-2-carbonitrile Example 336B (100 mg, 0.294 mmol), Pd(PPh$_3$)$_4$ (34 mg, 0.0294 mmol), Zn(CN)$_2$ (0.416 g, 3.54 mmol) and DMF (5 mL) were mixed, pumped with N$_2$, stirred, and heated to 180° C. for 5 minutes in a Smith Synthesizer. The reaction mixture was filtered. The solution was concentrated. To the residue was added DMSO (2.5 mL). The suspension was filtered. The precipitate was washed with ethyl acetate (2 mL×3), and dried to give the title compound (71 mg, 73%). MS (ESI) m/z 330 (M+H)$^+$; $^1$H NMR (400 MHz, DMSO-D$_6$) δ ppm 1.07 (t, J=6.90 Hz, 6H) 3.33-3.37 (m, 4H) 3.75-3.84 (m, 2H) 6.63 (d, J=8.59 Hz, 1H) 6.86 (d, J=1.23 Hz, 1H) 7.34 (m, 1H) 8.07 (m, 1H) 8.27 (s, 1H) 9.09 (s, 1H) 13.22 (s, 1H).

EXAMPLE 336D

4-{5-[6-(diethylamino)-1,4-dihydroindeno[1,2-c]pyrazol-3-yl]pyridin-2-yl}phenol

Example 336B (100 mg, 0.294 mmol), (4-hydroxyphenyl)boronic acid (49 mg, 0.0.353 mmol), Pd(PPh$_3$)$_2$Cl$_2$ (21 mg, 0.0294 mmol), DME/EtOH/H$_2$O (7/2/3, 3.5 mL) and 1M Na$_2$CO$_3$ (1.5 mL) were mixed, and heated to 160° C. for 10 minutes in a Smith Synthesizer. All the solvents were removed. The residue was purified by HPLC to give the title compound (29 mg, 25%). MS (ESI) m/z 397 (M+H)$^+$; $^1$H NMR (500 MHz, DMSO-D$_6$) δ ppm 1.07 (t, J=6.87 Hz, 6H) 3.61 (s, 2H) 4.02 (s, 4H) 6.90 (d, J=8.85 Hz, 2H) 7.99-8.03 (m, 3H) 8.23 (dd, J=8.54, 2.14 Hz, 1H) 9.03 (s, 1H).

EXAMPLE 337

4-{5-[6-(diethylamino)-1,4-dihydroindeno[1,2-c]pyrazol-3-yl]pyridin-2-yl}-2-methoxyphenol Example 337 was synthesized in a similar fashion as Example 336D, substituting (4-hydroxyphenyl)boronic acid with 2-methoxy-4-(4,4,5,5-tetramethyl-1,3,2-dioxaborolan-2-yl)-phenol (45 mg, 36%). MS (ESI) m/z 427 (M+H)$^+$; $^1$H NMR (500 MHz, DMSO-D$_6$) δ ppm 1.03-1.12 (m, 6H) 3.60 (s, 2H) 3.89 (s, 3H) 3.93-4.06 (m, 4H) 6.90 (d, J=8.24 Hz, 1H) 7.40-8.00 (m, 4H) 8.06 (d, J=8.54 Hz, 1H) 8.23 (dd, J=8.39, 1.98 Hz, 1H) 9.03 (s, 1H) 9.41 (s, 1H).

EXAMPLE 338

5-[6-(tetrahydrofuran-3-ylmethoxy)-1,4-dihydroindeno[1,2-c]pyrazol-3-yl]pyridine-2-carbonitrile

EXAMPLE 338A

1-[chloro(4-methoxyphenyl)methyl]-4-methoxybenzene

Bis-(4-methoxy-phenyl)-methanol (25 g, 102 mmol) and SOCl$_2$ (60 mL, 823 mmol) were mixed, and heated to reflux for 4 hours. The reaction mixture was concentrated under vacuum pump, and dried completely to give the above intermediate (26.5 g, 99%). MS (DCI/NH$_3$) m/z 263 (M+H)$^+$; $^1$H NMR (300 MHz, CDCl$_3$) δ ppm 3.80 (s, 6H) 6.12 (s, 1H) 6.82-6.91 (m, 4H) 7.29-7.36 (m, 4H).

EXAMPLE 338B 5-(cyclohex-2-en-1-yloxy)indan-1-one

5-Hydroxy-indan-1-one (6.60 g, 46.4 mmol), cyclohex-2-enol (7.68 mL, 77.00 mmol), PPh$_3$-polymer supported (18.93 g, 56.79 mmol), DBAD (13.08 g, 56.80 mmol) and THF (300 mL) were mixed, and shaken overnight. The reaction mixture was filtered. The solution was concentrated. The residue was purified by flash chromatography to give the above intermediate (6.75 g, 64%). MS (DCI/NH$_3$) m/z 229 (M+H)$^+$; $^1$H NMR (300 MHz, CD$_3$OD) δ ppm 1.70 (m, 1H) 1.77-1.91 (m, 2H) 1.99 (m, 1H) 2.04-2.15 (m, 2H) 2.62-2.68 (m, 2H) 3.07-3.14 (m, 2H) 4.99 (m, 1H) 5.85 (m, 1H) 6.00 (m, 1H) 6.93 (dd, J=8.48, 2.37 Hz, 1H) 7.05 (d, J=2.37 Hz, 1H) 7.61 (d, J=8.81 Hz, 1H).

EXAMPLE 338C

3-(6-chloropyridin-3-yl)-6-(cyclohex-2-en-1-yloxy)-1,4-dihydroindeno[1,2-c]pyrazole

Example 338B (6.70 g, 29.3 mmol), Example 324A (13.7 g, 58.7 mmol), 95% NaH (3.71 g, 146.7 mmol) and benzene (200 mL) were mixed, stirred, and heated to reflux overnight. The mixture was concentrated. To the residue was added ethanol (150 mL), acetic acid (25 mL) and hydrazine monohydrate (25 mL). The reaction mixture was heated to reflux for 3 hours. All the solvents were removed. To the residue was added water (300 mL). The precipitate was filtered, washed with water (100 mL×3) and ethyl acetate (50 mL×3), and dried in vacuo to give the above intermediate (8.54 g, 80%). MS (ESI) m/z 364 (M+H)$^+$; $^1$H NMR (300 MHz, DMSO-D$_6$) δ ppm 1.64 (m, 1H) 1.69-1.81 (m, 2H) 1.95 (m, 1H) 2.00-2.10 (m, 2H) 3.86 (s, 2H) 4.93 (s, 1H) 5.85 (m, 1H) 5.95 (m, 1H) 6.96 (m, 1H) 7.20 (s, 1H) 7.54 (s, 1H) 7.67 (s, 1H) 8.22 (dd, J=8.48, 2.03 Hz, 1H) 8.82 (d, J=2.37 Hz, 1H) 13.26 (s, 1H).

EXAMPLE 338D

1-[bis(4-methoxyphenyl)methyl]-3-(6-chloropyridin-3-y)-6-(cyclohex-2-en-1-yloxy)-1,4-dihydroindeno[1,2-c]pyrazole

Example 338C (8.54 g, 23.47 mmol), Example 338A (8.02 g, 30.51 mmol), triethylamine (6.54 mL, 46.94 mmol) and THF (200 mL) were mixed, stirred, and heated to 60° C. for 2 hours. The reaction mixture was cooled, filtered, and concentrated. The residue was purified by flash chromatography to give the above intermediate (12.96 g, 94%). MS (ESI) m/z 591 (M+H)$^+$; $^1$H NMR (300 MHz, CDCl$_3$) δ ppm 1.65 (m, 1H) 1.76-2.15 (m, 5H) 3.75 (s, 2H) 3.79 (s, 6H) 4.79 (m, 1H) 5.85 (m, 1H) 5.97 (m, 1H) 6.66 (d, J=8.48 Hz, 1H) 6.72 (m, 1H) 6.83-6.89 (m, 4H) 6.93 (s, 1H) 7.11 (s, 1H) 7.19-7.25 (m, 4H) 7.34 (d, J=8.14 Hz, 1H) 8.16 (dd, J=8.31, 2.20 Hz, 1H) 8.80 (d, J=2.03 Hz, 1H).

EXAMPLE 338E

5-{1-[bis(4-methoxyphenyl)methyl]-6-hydroxy-1,4-dihydroindeno[1,2-c]pyrazol-3-yl}pyridine-2-carbonitrile

Example 338D (3.18 g, 5.39 mmol), Pd(PPh$_3$)$_4$ (1.62 g, 0.147 mmol), Zn(CN)$_2$ (7.59 g, 64.67 mmol) and DMF (200 mL) were mixed, pumped with N$_2$, stirred, and heated to reflux for 6 hours. The reaction mixture was filtered. The filtrate was concentrated. The residue was purfied by flash chromatography to give the above intermediate (2.06 g, 76%). MS (ESI) m/z 501 (M+H)$^+$; $^1$H NMR (500 MHz, DMSO-D$_6$) δ ppm 3.73 (s, 6H) 3.87 (s, 2H) 6.68 (dd, J=8.11, 2.18 Hz, 1H) 6.90-6.95 (m, J=8.73 Hz, 4H) 7.00 (d, J=1.87 Hz, 1H) 7.12 (s, 1H) 7.26-7.30 (m, 4H) 8.07 (d, J=8.11 Hz, 1H) 8.28 (dd, J=8.11, 2.18 Hz, 1H) 9.09 (d, J=1.25 Hz, 1H) 9.66 (s, 1H).

EXAMPLE 338F

5-[6-(tetrahydrofuran-3-ylmethoxy)-1,4-dihydroindeno[1,2-c]pyrazol-3-yl]pyridine-2-carbonitrile

Example 338E (100 mg, 0.20 mmol), (tetrahydro-furan-3-yl)-methanol (82 mg, 0.80 mmol), DBAD (92 mg, 0.40 mmol), PPh$_3$-polymer supported (133 mg, 0.40 mmol) and THF (5 mL) were mixed, and shaken overnight. The mixture was filtered. The filtrate was concentrated. To the residue was added methanol (8.0 mL) and 4N HCl in dioxane (0.50 mL). The mixture was stirred at room temperature for 8 hours. All the solvents were removed. The residue was washed with ethyl acetate (10 mL×2), and dried to give the desired product (48 mg, 67%).

Examples 339 to 343 represented by FIG. (XVIII) and shown in Table 18 were synthesized in a similar fashion as described in Example 338F using the appropriate alcohol instead of (tetrahydro-furan-3-yl)-methanol.

TABLE 18

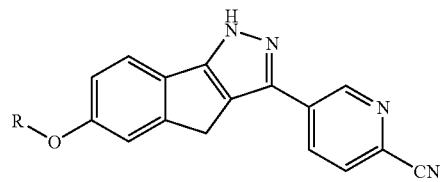

FIG. (XVIII)

| Example # | -R | 1H-NMR | MS m/z | Weight & Yield (%) |
|---|---|---|---|---|
| 338F | 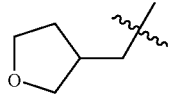 | $^1$H NMR (500 MHz, DMSO-D$_6$) δ ppm 1.67 (m, 1 H) 2.03 (m, 1 H) 2.67 (m, 1 H) 3.55 (m, 1 H) 3.66 (m, 1 H) 3.73-3.82 (m, 2 H) 3.90 (s, 2 H) 3.93 (m, 1 H) 4.00 (dd, J=9.36, 6.55 Hz, 1 H) 6.96 (dd, J=8.27, 2.34 Hz, 1 H) 7.20 (d, J=1.87 Hz, 1 H) 7.55 (d, J=8.42 Hz, 1 H) 8.13 (d, J=8.11 Hz, 1 H) 8.36 (dd, J=8.11, 2.18 Hz, 1 H) 9.15 (d, J=1.56 Hz, 1 H) | MS (ESI) m/z 359 (M+H)$^+$ | 48 mg, 67% |

TABLE 18-continued

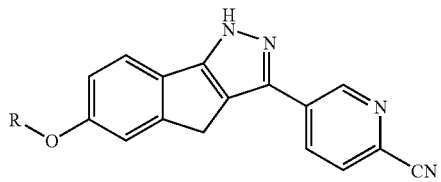

FIG. (XVIII)

| Example # | -R | 1H-NMR | MS m/z | Weight & Yield (%) |
|---|---|---|---|---|
| 339 | 3-methylcyclohexyl | ¹H NMR (400 MHz, DMSO-D₆) δ ppm 0.86 (m, 1 H) 0.93 (d, J=6.44 Hz, 3 H) 1.01 (m, 1 H) 1.24 (m, 1 H) 1.37 (m, 1 H) 1.51-1.65 (m, 2 H) 1.76 (m, 1 H) 2.04-2.12 (m, 2 H) 3.91 (s, 2 H) 4.33 (m, 1 H) 6.95 (d, J=8.29 Hz, 1 H) 7.19 (s, 1 H) 7.53 (d, J=7.35 Hz, 1 H) 8.13 (d, J=7.36 Hz, 1 H) 8.36 (d, J=7.98 Hz, 1 H) 9.15 (s, 1 H) | MS (ESI) m/z 371 (M+H)⁺ | 21 mg, 28% |
| 340 | cyclohexylmethyl | ¹H NMR (500 MHz, DMSO-D₆) δ ppm 1.00-1.33 (m, 5 H) 1.62-1.86 (m, 6 H) 3.84 (d, J=6.24 Hz, 2 H) 3.90 (s, 2 H) 6.94 (dd, J=8.42, 2.18 Hz, 1 H) 7.18 (d, J=1.87 Hz, 1 H) 7.55 (d, J=8.42 Hz, 1 H) 8.14 (d, J=8.11 Hz, 1 H) 8.37 (dd, J=8.11, 2.18 Hz, 1 H) 9.16 (d, J=1.56 Hz, 1 H) | MS (ESI) m/z 371 (M+H)⁺ | 34 mg, 46% |
| 341 | pyridin-2-ylmethyl | ¹H NMR (400 MHz, DMSO-D₆) δ ppm 3.95 (s, 2 H) 5.41 (s, 2 H) 7.10 (dd, J=8.59, 2.46 Hz, 1 H) 7.35 (d, J=2.15 Hz, 1 H) 7.61 (d, J=8.29 Hz, 1 H) 7.67 (m, 1 H) 7.84 (d, J=7.98 Hz, 1 H) 8.15 (dd, J=8.13, 0.77 Hz, 1 H) 8.21 (m, 1 H) 8.38 (dd, J=8.29, 2.15 Hz, 1 H) 8.76 (dd, J=5.98, 0.77 Hz, 1 H) 9.17 (dd, J=2.15, 0.92 Hz, 1 H) | MS (ESI) m/z 366 (M+H)⁺ | 29 mg, 40% |
| 342 | 2-(pyridin-2-yl)ethyl | ¹H NMR (400 MHz, DMSO-D₆) δ ppm 3.52 (t, J=5.98 Hz, 2 H) 3.91 (s, 2 H) 4.49 (t, J=6.29 Hz, 2 H) 6.96 (dd, J=8.13, 1.99 Hz, 1 H) 7.20 (d, J=1.23 Hz, 1 H) 7.56 (d, J=8.29 Hz, 1 H) 7.88 (m, 1 H) 8.04 (d, J=8.59 Hz, 1 H) 8.15 (d, J=7.98 Hz, 1 H) 8.37 (dd, J=8.13, 1.99 Hz, 1 H) 8.47 (t, J=7.83 Hz, 1 H) 8.83 (d, J=5.22 Hz, 1 H) 9.16 (d, J=1.23 Hz, 1 H) | MS (ESI) m/z 380 (M+H)⁺ | 11 mg, 14% |
| 343 | 2-[4-(dimethylamino)phenyl]ethyl | ¹H NMR (500 MHz, DMSO-D₆) δ ppm 2.70 (s, 6 H) 2.74 (t, J=6.71 Hz, 2 H) 3.65 (s, 2 H) 3.96 (t, J=6.71 Hz, 2 H) 6.67-6.73 (m, 3 H) 6.94 (d, J=1.87 Hz, 1 H) 7.01 (d, J=8.42 Hz, 2 H) 7.30 (d, J=8.42 Hz, 1 H) 7.89 (d, J=8.11 Hz, 1 H) 8.11 (dd, J=8.11, 2.18 Hz, 1 H) 8.90 (d, J=1.87 Hz, 1 H) | MS (ESI) m/z 422 (M+H)⁺ | 19 mg, 23% |

EXAMPLE 344

5-{6-[(4-hydroxycyclohexyl)oxy]-1,4-dihydroindeno[1,2-c]pyrazol-3-yl}pyridine-2-carbonitrile

EXAMPLE 344A

4-{[2-(trimethylsilyl)ethoxy]methoxy}cyclohexanol

Cyclohexane-1,4-diol (4 g, 34.8 mmol) was dissolved in THF (200 mL). To this solution was added 95% NaH (0.922 g, 36.6 mmol). The mixture was heated to reflux for 1 hour. Then 10 the reaction was cooled down. SEMCl (6.44 mL, 36.6 mmol) was added dropwise. The reaction mixture was heated to reflux again overnight. THF was removed. The residue was purified by flash chromatography to give the desired product (2.10 g, 16%). MS (DCI/NH₃) m/z 247 (M+H)⁺; ¹H NMR (400 MHz, CDCl₃) δ ppm 0.02 (s, 9H) 0.87-0.95 (m, 2H) 1.30-1.38 (m, 2H) 1.57 (m, 1H) 1.64-1.70 (m, 2H) 1.80 (m, 1H) 1.91-2.01 (m, 2H) 3.50-3.70 (m, 4H) 4.69 (s, 2H).

EXAMPLE 344B

5-{6-[(4-hydroxycyclohexyl)oxy]-1,4-dihydroindeno[1,2-c]pyrazol-3-yl}pyridine-2-carbonitrile Example 338E (20 mg, 0.040 mmol), Example 344A (20 mg, 0.080 mmol), DBAD (13.8 mg, 0.060 mmol), PPh$_3$-polymer supported (20 mg, 0.060 mmol) and THF (2 mL) were mixed and shaken overnight. The reaction mixture was filtered. The filtrate was concentrated. To the residue was added methanol (5 mL) and 4N HCl in dioxane (0.5 mL). After 4 hours, the reaction was completed. The solution was concentrated. The residue was purified by HPLC to give the title compound (4.0 mg, 27%). MS (ESI) m/z 373 (M+H)$^+$; $^1$H NMR (400 MHz, DMSO-D$_6$) δ ppm 1.57-1.76 (m, 2H) 1.77-1.95 (m, 4H) 1.98-2.10 (m, 2H) 3.92 (s, 2H) 4.56 (s, 1H) 5.15 (s, 1H) 7.01 (m, 1H) 7.25 (m, 1H) 7.56 (d, J=8.29 Hz, 1H) 8.14 (d, J=8.29 Hz, 1H) 8.36 (dd, J=8.29, 2.15 Hz, 1H) 9.16 (s, 1H).

EXAMPLE 345

5-{6-[2-(4-methyl-1,3-thiazol-5-yl)ethoxy]-1,4-dihydroindeno[1,2-c]pyrazol-3-yl}pyridine-2-carboxamide Example 338E (100 mg, 0.192 mmol), 2-(4-methyl-thiazol-5-yl)-ethanol (55 mg, 0.384 mmol), DBAD (66 mg, 0.288 mmol), PPh$_3$-polymer supported (96 mg, 0.288 mmol) and THF (5 mL) were mixed, and shaken overnight. The mixture was filtered. The filtrate was concentrated. To the residue was added 4N HCl in dioxane (4 mL). The mixture was stirred at room temperature overnight. All the solvents were removed. The residue was purified by HPLC to give the title compound (18 mg, 22%). MS (ESI) m/z 418 (M+H)$^+$; $^1$H NMR (400 MHz, DMSO-D$_6$) δ ppm 2.38 (s, 3H) 3.25 (t, J=6.29 Hz, 2H) 3.91 (s, 2H) 4.22 (t, J=5.98 Hz, 2H) 6.96 (dd, J=8.44, 1.99 Hz, 1H) 7.20 (d, J=1.53 Hz, 1H) 7.56 (d, J=8.29 Hz, 1H) 7.65 (s, 1H) 8.13 (s, 1H) 8.15 (s, 1H) 8.33 (dd, J=7.98, 2.15 Hz, 1H) 8.89 (s, 1H) 9.04 (d, J=1.53 Hz, 1H).

EXAMPLE 346

5-[6-(2-hydroxyethyl)-1,4-dihydroindeno[1,2-c]pyrazol-3-yl]pyridine-2-carbonitrile

EXAMPLE 346A

5'-bromo-2',3'-dihydrospiro[1,3-dioxolane-2, 1'-indene]

5-Bromo-indan-1-one (15 g, 71.1 mmol), ethylene glycol (19.8 mL, 355.2 mmol), p-toluene-sulfonic acid monohydrate (15 mg, 0.079 mmol) and benzene (400 mL) were mixed, stirred, and heated to reflux in a Dean-Stark apparatus overnight. The mixture was poured into saturated NaHCO$_3$ solution (200 mL) in a separatory funnel, and shaken. The organic layer was separated and dried over K$_2$CO$_3$ powder. The solution was concentrated, and purified by flash chromatography to give the above intermediate (10.50 g, 60%). MS (DCI/NH$_3$) m/z 256 (M+H)$^+$; $^1$H NMR (300 MHz, CDCl$_3$) δ ppm 2.24-2.34 (m, 2H) 2.93 (t, J=6.95 Hz, 2H) 4.04-4.20 (m, 4H) 7.22 (d, J=8.48 Hz, 1H) 7.35-7.40 (m, 2H).

EXAMPLE 346B

5'-vinyl-2',3'-dihydrospiro[1,3-dioxolane-2,1'-indene]

Example 346A (7.80 g, 30.58 mmol), tributyl(vinyl)tin (10.71 mL, 36.69 mmol), Pd(PPh$_3$)$_4$ (3.52 g, 3.06 mmol) and DMF (100 mL) were mixed, pumped with N$_2$ and heated to 80° C. overnight. All the solvent was removed. The residue was purified by flash chromatography to give the above intermediate (4.53 g, 66%). MS (DCI/NH$_3$) m/z 203 (M+H)$^+$; $^1$H NMR (300 MHz, CDCl$_3$) δ ppm 2.25-2.34 (m, 2H) 2.89-2.94 (m, 2H) 4.04.4.23 (m, 4H) 5.24 (d, J=10.85 Hz, 1H) 5.74 (d, J=17.63 Hz, 1H) 6.72 (dd, J=17.63, 10.85 Hz, 1H) 7.297.31 (m, 2H) 7.39 (s, 1H).

EXAMPLE 346C 2-(2',3'-dihydrospiro[1,3-dioxolane-2,1'-inden]-5'-yl)ethanol

To a solution of Example 346B (4.53 g, 22.39 mmol) in anhydrous THF (100 mL) was added 0.5 M 9-BBN in THF (54 mL, 26.88 mmol). The reaction was run at room temperature overnight. A solution of NaOH (1.08 g, 26.88 mmol) in water (5 mL) was added, followed by dropwise addition of 30% H$_2$O$_2$ solution (3.05 mL, 26.88 mmol). The mixture was stirred for 4 hours at room temperature. The reaction mixture was concentrated. Ethyl acetate (100 mL) and water (100 mL) was added to the residue. The organic layer was separated. To the water phase was added ethyl acetate (100 mL×5). The organic layers were combined, dried over K$_2$CO$_3$ powder, and concentrated. The residue was purified by flash chromatography to give the above intermediate (2.96 g, 60%). MS (DCI/NH$_3$) m/z 221 (M+H)$^+$; $^1$H NMR (300 MHz, CD$_3$OD) δ ppm 2.21-2.29 (m, 2H) 2.78-2.92 (m, 4H) 3.73 (t, J=7.12 Hz, 2H) 4.01-4.19 (m, 4H) 7.08-7.13 (m, 2H) 7.25 (d, J=8.14 Hz, 1H).

EXAMPLE 346D 5-(2-hydroxyethyl)indan-1-one

Example 346C (2.96 g, 13.43 mmol) was dissolved in THF (30 mL). To this solution was added 2N HCl solution (40 mL). The reaction mixture was stirred at room temperature overnight, concentrated, and extracted with ethyl acetate (50 mL×5). The organic solution was dried with MgSO$_4$, concentrated, and purified by flash chromatography to give above intermediate (1.63 g, 69%). MS (DCI/NH$_3$) m/z 177 (M+H)$^+$; $^1$H NMR (300 MHz, CD$_3$OD) δ ppm 2.64-2.70 (m, 2H) 2.92 (t, J=6.78 Hz, 2H) 3.11-3.17 (m, 2H) 3.80 (t, J=6.78 Hz, 2H) 7.29 (d, J=7.80 Hz, 1H) 7.43 (s, 1H) 7.63 (d, J=7.80 Hz, 1H).

EXAMPLE 346E

5-[2-(pyridin-4-yloxy)ethyl]indan-1-one

Example 346D (0.2933 g, 1.646 mmol), pyridin-4-ol (0.156 g, 1.646 mmol), PPh$_3$-polymer supported (1.097 g, 3.292 mmol), DBAD (0.758 g, 3.292 mmol) and THF (15 mL) were mixed, and shaken at room temperature overnight. The solution was filtered, concentrated, and purified by flash chromatography to give the above intermediate (213 mg, 51%). MS (DCI/NH$_3$) m/z 254 (M+H)$^+$; $^1$H NMR (300 MHz, CD$_3$OD) δ ppm 2.65-2.77 (m, 2H) 3.12-3.18 (m, 2H)

3.22 (t, J=6.44 Hz, 2H) 4.37 (t, J=6.44 Hz, 2H) 6.97 (dd, J=4.92, 1.53 Hz, 2H) 7.38 (d, J=7.46 Hz, 1H) 7.51 (s, 1H) 7.65 (d, J=7.80 Hz, 1H) 8.31 (dd, J=5.09, 1.70 Hz, 2H).

EXAMPLE 346F

2-[3-(6-chloropyridin-3-yl)-1,4-dihydroindeno[1,2-c]pyrazol-6-yl]ethanol

Example 346E (115.2 mg, 0.61 mmol), 324A (360.0 mg, 1.53 mmol), 95% NaH (77 mg, 3.05 mmol) and benzene (20 mL) were mixed, stirred, and heated to reflux 3 hours. The mixture was then concentrated. To the residue was added ethanol (20 mL), acetic acid (2 mL) and hydrazine monohydrate (2 mL). The reaction mixture was heated to reflux for 2 hours. All the solvents were removed. To the residue was added water (20 mL). The precipitate was filtered, washed with water (10 mL×3) and ethyl acetate (10 mL×3), and dried in vacuo to give the above intermediate (64 mg, 34%). MS (ESI) m/z 312 (M+H)$^+$; $^1$H NMR (400 MHz, DMSO-D$_6$) δ ppm 2.80 (t, J=7.06 Hz, 2H) 3.64-3.66 (m, 2H) 3.85-3.88 (m, 2H) 4.64 (t, J=5.22 Hz, 1H) 7.23 (s, 1H) 7.43 (s, 1H) 7.59 (d, J=5.52 Hz, 1H) 7.68 (m, 1H) 8.24 (m, 1H) 8.84 (s, 1H) 13.35 (s, 1H).

EXAMPLE 346G

5-[6-(2-hydroxyethyl)-1,4-dihydroindeno[1,2-c]pyrazol-3-yl]pyridine-2-carbonitrile Example 346F (64 mg, 0.205 mmol), Pd(PPh$_3$)$_4$ (24 mg, 0.0205 mmol), Zn(CN)$_2$ (0.29 g, 22.463 mmol) and DMF (4 mL) were mixed, pumped with N$_2$, stirred, and heated to 180° C. for 5 minutes in a Smith Synthesizer. The reaction mixture was filtered. The filtrate was concentrated. The residue was purified by HPLC to give the title product (30.5 mg, 49%). MS (ESI) m/z 303 (M+H)$^+$; $^1$H NMR (400 MHz, DMSO-D$_6$) δ ppm 2.80 (t, J=7.06 Hz, 2H) 3.66 (t, J=7.06 Hz, 2H) 3.92 (s, 2H) 4.65 (br s, 1H) 7.24 (d, J=7.36 Hz, 1H) 7.45 (s, 1H) 7.57 (s, 1H) 8.16 (s, 1H) 8.38 (dd, J=7.98, 2.15 Hz, 1H) 9.17 (s, 1H) 13.56 (s, 1H).

EXAMPLE 347

5-[6-(difluoromethoxy)-7-methoxy-1,4-dihydroindeno[1,2-c]pyrazol-3-yl]pyridine-2-carbonitrile

EXAMPLE 347A 5-(difluoromethoxy)-6-methoxyindan-1-one

5-Hydroxy-6-methoxy-indan-1-one (0.78 g, 4.38 mmol), ClCHF$_2$ (7.0 g, 80.95 mmol), K$_2$CO$_3$ (3.6 g, 26.04 mmol) and DMF (40 mL) were stirred, and heated to 100° C. for 2 hours. The reaction mixture was filtered. The filtrate was concentrated. The residue was purified by flash chromatography to give the above intermediate (0.59 g, 59%). MS (DCI/NH$_3$) m/z 229 (M+H)$^+$; $^1$H NMR (300 MHz, CD$_3$OD) δ ppm 2.67-2.73 (m, 2H) 3.06-3.13 (m, 2H) 3.91 (s, 3H) 6.90 (t, J=74.43 Hz, 1H) 7.31 (s, 1H) 7.32 (s, 1H).

EXAMPLE 347B 3-(6-chloropyridin-3-yl)-6-(difluoromethoxy)-7-methoxy-1,4-dihydroindeno[1,2-c]pyrazole Example 347A (0.59 g, 2.59 mmol), Example 324A (1.21 g, 5.17 mmol), 95% NaH (0.26 g, 10.34 mmol) and anhydrous THF (30 mL) were mixed, and stirred at room temperature for 1 hour. All the solvent was removed. To the residue was added ethanol (50 mL), acetic acid (2 mL) and hydrazine monohydrate (2 mL). The mixture was heated to reflux for 2 hours, and cooled. All the solvents were removed. To the residue was added water (50 mL). The precipitate was filtered, washed with water (5 mL×3) and ethyl acetate (5 mL×3), and dried to give the above intermediate (0.64 g, 68%). MS (ESI) m/z 364 (M+H)$^+$; $^1$H NMR (500 MHz, DMSO-D$_6$) δ ppm 3.83 (s, 2H) 3.91 (s, 3H) 7.06 (t, J=74.87 Hz, 1H) 7.40 (d, J=7.49 Hz, 2H) 7.64 (d, J=8.42 Hz, 1H) 8.20 (dd, J=8.42, 1.87 Hz, 1H) 8.81 (d, J=1.56 Hz, 1H) 13.41 (s, 1H).

EXAMPLE 347C

5-[6-(difluoromethoxy)-7-methoxy-1,4-dihydroindeno[1,2-c]pyrazol-3-yl]pyridine-2-carbonitrile Example 347B (100 mg, 0.282 mmol), Pd(PPh$_3$)$_4$ (33 mg, 0.0282 mmol), Zn(CN)$_2$ (0.331 g, 2.82 mmol) and DMF (5 mL) were mixed, pumped with N$_2$, stirred, and heated to 180° C. for 5 minutes in a Smith Synthesizer. The reaction mixture was filtered. The filtrate was concentrated. To the residue was added DMSO (2.5 mL). The suspension was stirred for 0.5 hour. The precipitate was then filtered, washed by water (5 mL×3) and ethyl acetate (5 mL×3), and dried in vacuo to give the title compound (32 mg, 32%). MS (ESI) m/z 355 (M+H)$^+$; $^1$H NMR (500 MHz, DMSO-D$_6$) δ ppm 3.84-3.92 (m, 5H) 7.08 (t, J=74.71 Hz, 1H) 7.34 7.52 (m, 2H) 8.13 (m, 1H) 8.35 (s, 1H) 9.15 (d, J=1.87 Hz, 1H).

EXAMPLE 348

4-{5-[6-(difluoromethoxy)-7-methoxy-1,4-dihydroindeno[1,2-c]pyrazol-3-yl]pyridin-2-yl}phenol Example 347B (100 mg, 0.275 mmol), (4-hydroxyphenyl)boronic acid (49 mg, 0.356 mmol), Pd(PPh$_3$)$_2$Cl$_2$ (17 mg, 0.0237 mmol), DME/EtOH/H$_2$O (7/2/3, 3.5 mL) and 1 M NaCO$_3$ (1.5 mL) were mixed, and heated to 160° C. for 10 minutes in a Smith Synthesizer. All the solvents were removed. The residue was purified by HPLC to give the title compound (42 mg, 36%). MS (ESI) m/z 422 (M+H)$^+$; $^1$H NMR (500 MHz, DMSO-D$_6$) δ ppm 3.89 (s, 2H) 3.93 (s, 3H) 6.89 (d, J=8.73 Hz, 2H) 7.08 (t, J=74.87 Hz, 1H) 7.43 (d, J=12.17 Hz, 2H) 7.98-8.02 (m, 3H) 8.20 (dd, J=8.42, 2.18 Hz, 1H) 9.02 (d, J=2.18 Hz, 1H).

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:
1. A compound of formula (I)

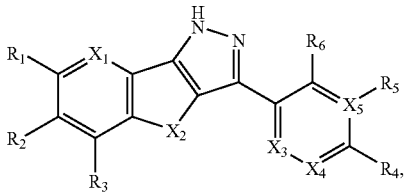

or a pharmaceutically acceptable salt, ester, amide, or prodrug thereof, wherein $R_1$ and $R_2$ are independently selected from the group consisting of hydrogen, alkenyl, alkenyloxy, alkoxy, alkoxyalkoxy, alkoxyalkoxyalkynyl, alkoxyalkyl, alkoxycarbonyl, alkoxycarbonylalkyl, alkoxysulfonyl, alkyl, alkylcarbonyl, alkylcarbonyloxy, alkylsulfinyl, alkylsulfonyl, alkylthio, alkylthioalkyl, alkynyl, carboxy, carboxyalkyl, cyano, cycloalkenylalkoxy, cycloalkylalkoxy, cycloalkylalkyl, cycloalkylcarbonyl, cycloalkyloxy, formyl, haloalkoxy, haloalkoxyalkynyl, haloalkyl, halogen, heteroarylalkoxy, heteroarylalkoxyalkoxy, heteroarylalkyl, heteroarylalkynyl, heteroaryloxyalkyl, hydroxy, hydroxyalkoxy, hydroxyalkyl, hydroxyalkynyl, hydroxysulfonyl, hydroxysulfonylalkyl, mercapto, mercaptoalkyl, nitro, —$NR_AR_B$, $(NR_AR_B)$alkoxy, $(NR_AR_B)$alkyl, $(NR_AR_B)$alkynyl, $(NR_AR_B)$carbonyl, $(NR_AR_B)$carbonylalkoxy, $(NR_AR_B)$carbonylalkyl, and $(NR_GR_H)$alkoxy; or $R_1$ and $R_2$ together with the carbon atoms to which they are attached form a 5, 6, 7, or 8-membered nonaromatic ring wherein the ring contains 0, 1, or 2 heteroatoms selected from the group consisting of O, $N(R_C)$, and $N(R_D)$, wherein the nonaromatic ring is substituted with 0, 1, or 2 substituents selected from the group consisting of alkyl and hydroxy;

$R_3$ is selected from the group consisting of hydrogen, alkenyl, alkenyloxy, alkoxy, alkoxyalkyl, alkoxycarbonyl, alkoxycarbonylalkyl, alkyl, alkylcarbonyl, alkylthio, alkylthioalkyl, alkynyl, carboxy, carboxyalkyl, cyano, formyl, haloalkoxy, haloalkyl, halogen, hydroxy, hydroxyalkyl, mercapto, nitro, —$NR_ER_F$, $(NR_ER_F)$alkoxy $(NR_ER_F)$alkyl, $(NR_ER_F)$carbonyl, and $(NR_ER_F)$carbonylalkyl;

$R_4$ is selected from the group consisting of hydrogen, alkoxycarbonyl, alkylcarbonylalkoxy, aryl, arylalkoxy, arylalkyl, aryloxy, carboxy, cyano, halogen, heteroaryl, heteroarylalkoxy, heteroarylalkyl, heteroaryloxy, hydroxy, —$NR_ER_F$, and $(NR_ER_F)$carbonyl;

$R_5$ is selected from the group consisting of hydrogen, alkoxycarbonyl, carboxy, or halogen, heteroaryl, hydroxy, nitro, —$NR_ER_F$, and $(NR_ER_F)$carbonyl;

provided that when $R_5$ is hydrogen, $R_4$ is other than hydrogen; or $R_4$ and $R_5$, together with the atoms to which they are attached, form a phenyl ring optionally substituted with 1, 2, 3, or 4 substituents independently selected from the group consisting of alkenyl, alkoxy, alkoxyalkyl, alkoxycarbonyl, alkoxycarbonylalkyl, alkoxysulfonyl, alkyl, alkylcarbonyl, alkylcarbonyloxy, alkylsulfmyl, alkylsulfonyl, alkylthio, alkylthioalkyl, alkynyl, carboxy, carboxyalkyl, cyano, formyl, haloalkoxy, haloalkyl, halogen, hydroxy, hydroxyalkyl, mercapto, nitro, —$NR_GR_H$, $(NR_GR_H)$alkoxy, $(NR_GR_H)$alkyl, $(NR_GR_H)$carbonyl, and $(NR_GR_H)$sulfonyl; or $R_4$ and $R_5$, together with the atoms to which they are attached, form a heterocycle optionally substituted with 1, 2, or 3 substituents independently selected from the group consisting of alkenyl, alkoxy, alkoxyalkyl, alkoxycarbonyl, alkyl, alkylcarbonyl, alkylcarbonyloxy, alkylthio, alkynyl, carboxy, cyano, formyl, haloalkoxy, haloalkyl, halogen, hydroxy, hydroxyalkyl, mercapto, nitro, oxo, —$NR_GR_H$, $(NR_GR_H)$alkoxy, $(NR_GR_H)$alkyl, and $(NR_GR_H)$carbonyl;

$R_6$ is selected from the group consisting of hydrogen, lower alkoxy, lower alkyl, halogen, hydroxy, and —$NR_ER_F$;

$R_A$ and $R_B$ are independently selected from the group consisting of hydrogen, alkenyl, alkoxyalkyl, alkoxyalkylcarbonyl, alkoxycarbonyl, alkoxycarbonylalkyl, alkoxycarbonylalkylcarbonyl, alkoxysulfonyl, alkoxysulfonylalkyl, alkoxysulfonylalkylcarbonyl, alkyl, alkylcarbonyl, alkynyl, aryl, carboxyalkyl, carboxyalkylcarbonyl, cycloalkyl, cycloalkylalkyl, cycloalkylalkylcarbonyl, cycloalkylcarbonyl, cycloalkylcarbonylalkyl, cycloalkylcarbonylalkylcarbonyl, heteroaryl, heteroarylalkyl, hydroxyalkyl, hydroxyalkylcarbonyl, hydroxysulfonyl, hydroxysulfonylalkyl, hydroxysulfonylalkylcarbonyl, $(NR_ER_F)$alkyl, $(NR_ER_F)$alkylcarbonyl, $(NR_ER_F)$carbonyl, $(NR_ER_F)$carbonylalkyl, $(NR_ER_F)$carbonylalkylcarbonyl, $(NR_ER_F)$sulfonyl, $(NR_ER_F)$sulfonylalkyl, and $(NR_ER_F)$sulfonylalkylcarbonyl;

$R_C$ and $R_D$ are independently selected from the group consisting of hydrogen, alkoxycarbonyl, alkyl, and alkylcarbonyl;

$R_E$ and $R_F$ are independently selected from the group consisting of hydrogen, alkyl, alkylcarbonyl, cycloalkyl, heteroarylalkyl, and hydroxyalkyl;

$X_1$ and $X_3$, are CH;

$X_4$ is N;

$X_2$ is $CH(R_7)$;

$X_5$ is C; and $R_7$ is selected from the group consisting of hydrogen, alkoxy, alkyl, hydroxy, lower alkoxy, lower alkyl, and hydroxyalkyl.

2. The compound according to claim 1 selected from the group consisting of
3-(6-cyanopyridin-3-yl)-N-(pyridin-2-ylmethyl)-1,4-dihydroindeno[1,2-c]pyrazole-6-carboxamide;
5-(6-{[(pyridin-2-ylmethyl)amino]methyl}-1,4-dihydroindeno[1,2-c]pyrazol-3-yl)pyridine-2-carbonitrile;
5-(6-{[(trans-4-hydroxycyclohexyl)amino]methyl}-1,4-dihydroindeno[1,2-c]pyrazol-3-yl)pyridine-2-carbonitrile;
3-(6-cyanopyridin-3-yl)-N-(trans-4-hydroxycyclohexyl)-1,4-dihydroindeno[1,2-c]pyrazole-6-carboxamide;
3-(6-cyanopyridin-3-yl)-N-{[6-(trifluoromethyl)pyridin-3-yl]methyl}-1,4-dihydroindeno[1,2-c]pyrazole-6-carboxamide;
5-[6-(hydroxymethyl)-1,4-dihydroindeno[1,2-c]pyrazol-3-yl]pyridine-2-carbonitrile;
5-{6-[(pyridin-3-yloxy)methyl]-1,4-dihydroindeno[1,2-c]pyrazol-3-yl}pyridine-2-carbonitrile;
5-{6-[(pyridin-4-yloxy)methyl]-1,4-dihydroindeno[1,2-c]pyrazol-3-yl}pyridine-2-carbonitrile;
5-[7-methoxy-6-(pyridin-2-ylmethoxy)-1,4-dihydroindeno[1,2-c]pyrazol-3-yl]pyridine-2-carbonitrile;
5-{7-[(6-chloropyridin-3-yl)methoxy]-6-methoxy-1,4-dihydroindeno[1,2-c]pyrazol-3-yl}pyridine-2-carbonitrile;

5-[6-methoxy-7-(pyridin-2-ylmethoxy)-1,4-dihydroindeno[1,2-c]pyrazol-3-yl]pyridine-2-carbonitrile;
5-[6-methoxy-7-(pyridin-3-ylmethoxy)-1,4-dihydroindeno[1,2-c]pyrazol-3-yl]pyridine-2-carbonitrile;
5-{6-methoxy-7-[2-(4-methyl-1,3-thiazol-5-yl)ethoxy]-1,4-dihydroindeno[1,2-c]pyrazol-3-yl}pyridine-2-carbonitrile;
5-[7-(2-hydroxyethoxy)-6-methoxy-1,4-dihydroindeno[1,2-c]pyrazol-3-yl]pyridine-2-carbonitrile;
5-{7-[(6-bromopyridin-2-yl)methoxy]-6-methoxy-1,4-dihydroindeno[1,2-c]pyrazol-3-yl}pyridine-2-carbonitrile;
5-[7-methoxy-6-(pyridin-3-ylmethoxy)-1,4-dihydroindeno[1,2-c]pyrazol-3-yl]pyridine-2-carbonitrile;
5-{6-[3-(dimethylamino)propoxy]-7-methoxy-1,4-dihydroindeno[1,2-c]pyrazol-3-yl}pyridine-2-carbonitrile;
5-{7-methoxy-6-[2-(4-methyl-1,3-thiazol-5-yl)ethoxy]-1,4-dihydroindeno[1,2-c]pyrazol-3-yl}pyridine-2-carbonitrile;
5-[6-(2-hydroxyethoxy)-7-methoxy-1,4-dihydroindeno[1,2-c]pyrazol-3-yl]pyridine-2-carbonitrile;
5-{6-[(6-bromopyridin-2-yl)methoxy]-7-methoxy-1,4-dihydroindeno[1,2-c]pyrazol-3-yl}pyridine-2-carbonitrile;
5-{6-[(6-chloropyridin-3-yl)methoxy]-7-methoxy-1,4-dihydroindeno[1,2-c]pyrazol-3-yl}pyridine-2-carbonitrile;
5-{6-[2-(5-ethylpyridin-2-yl)ethoxy]-7-methoxy-1,4-dihydroindeno[1,2-c]pyrazol-3-yl}pyridine-2-carbonitrile;
3-(6-chloropyridin-3-yl)-6,7-dimethoxy-1,4-dihydroindeno[1,2-c]pyrazole;
4-[5-(6,7-dimethoxy-1,4-dihydroindeno[1,2-c]pyrazol-3-yl)pyridin-2-yl]phenol;
4-[5-(6,7-dimethoxy-1,4-dihydroindeno[1,2-c]pyrazol-3-yl)pyridin-2-yl]-2-methoxyphenol;
4-[5-(6,7-dimethoxy-1,4-dihydroindeno[1,2-c]pyrazol-3-yl)pyridin-2-yl]-2-fluorophenol;
5-(6,7-dimethoxy-1,4-dihydroindeno[1,2-c]pyrazol-3-yl)pyridine-2-carbonitrile;
2-[3-(6-chloropyridin-3-yl)-1,4-dihydroindeno[1,2-c]pyrazol-6-yl]propan-2-ol;
4-{5-[6-(1-hydroxy-1-methylethyl)-1,4-dihydroindeno[1,2-c]pyrazol-3-yl]pyridin-2-yl}phenol;
3-(5,6-dichloropyridin-3-yl)-6,7-dimethoxy-1,4-dihydroindeno[1,2-c]pyrazole;
2-[3-(6-fluoropyridin-3-yl)-1,4-dihydroindeno[1,2-c]pyrazol-6-yl]propan-2-ol;
3-(6-chloropyridin-3-yl)-7-ethyl-6-methoxy-1,4-dihydroindeno[1,2-c]pyrazole;
5-(7-ethyl-6-methoxy-1,4-dihydroindeno[1,2-c]pyrazol-3-yl)pyridine-2-carbonitrile;
5-{7-ethyl-6-[(4-hydroxycyclohexyl)oxy]-1,4-dihydroindeno[1,2-c]pyrazol-3-yl}pyridine-2-carbonitrile;
5-[7-ethyl-6-(pyridin-2-ylmethoxy)-1,4-dihydroindeno[1,2-c]pyrazol-3-yl]pyridine-2-carbonitrile;
5-(6,7-diethyl-1,4-dihydroindeno[1,2-c]pyrazol-3-yl)pyridine-2-carbonitrile;
3-(6-chloropyridin-3-yl)-6,7-bis(2-methoxyethoxy)-1,4-dihydroindeno[1,2-c]pyrazole;
5-[6,7-bis(2-methoxyethoxy)-1,4-dihydroindeno[1,2-c]pyrazol-3-yl]pyridine-2-carbonitrile;
5-(6,7-diisopropoxy-1,4-dihydroindeno[1,2-c]pyrazol-3-yl)pyridine-2-carbonitrile;
3-(6-chloropyridin-3-yl)-6,7-diisopropoxy-1,4-dihydroindeno[1,2-c]pyrazole;
4-[5-(6,7-diisopropoxy-1,4-dihydroindeno[1,2-c]pyrazol-3-yl)pyridin-2-yl]phenol;
4-[5-(6,7-diisopropoxy-1,4-dihydroindeno[1,2-c]pyrazol-3-yl)pyridin-2-yl]-2-methoxyphenol;
5-(6-isopropoxy-1,4-dihydroindeno[1,2-c]pyrazol-3-yl)pyridine-2-carbonitrile;
5-(6-isopropoxy-1,4-dihydroindeno[1,2-c]pyrazol-3-yl)pyridine-2-carbonitrile;
4-[5-(6-isopropoxy-1,4-dihydroindeno[1,2-c]pyrazol-3-yl)pyridin-2-yl]phenol;
4-[5-(6-isopropoxy-1,4-dihydroindeno[1,2-c]pyrazol-3-yl)pyridin-2-yl]-2-methoxyphenol;
5-(6,7-diethoxy-1,4-dihydroindeno[1,2-c]pyrazol-3-yl)pyridine-2-carbonitrile;
3-(6-chloropyridin-3-yl)-6,7-diethoxy-1,4-dihydroindeno[1,2-c]pyrazole;
4-[5-(6,7-diethoxy-1,4-dihydroindeno[1,2-c]pyrazol-3-yl)pyridin-2-yl]phenol;
4-[5-(6,7-diethoxy-1,4-dihydroindeno[1,2-c]pyrazol-3-yl)pyridin-2-yl]-2-methoxyphenol;
5-[6,7-bis(difluoromethoxy)-1,4-dihydroindeno[1,2-c]pyrazol-3-yl]pyridine-2-carbonitrile;
3-(6-chloropyridin-3-yl)-6,7-bis(difluoromethoxy)-1,4-dihydroindeno[1,2-c]pyrazole;
4-{5-[6,7-bis(difluoromethoxy)-1,4-dihydroindeno[1,2-c]pyrazol-3-yl]pyridin-2-yl}phenol;
5-[6-(1H-1,2,4-triazol-1-ylmethyl)-1,4-dihydroindeno[1,2-c]pyrazol-3-yl]pyridine-2-carbonitrile;
3-(6-chloropyridin-3-yl)-6-(1H-1,2,4-triazol-1-ylmethyl)-1,4-dihydroindeno[1,2-c]pyrazole;
4-{5-[6-(1H-1,2,4-triazol-1-ylmethyl)-1,4-dihydroindeno[1,2-c]pyrazol-3-yl]pyridin-2-yl}phenol;
4-{5-[6-(diethylamino)-1,4-dihydroindeno[1,2-c]pyrazol-3-yl]pyridin-2-yl}phenol;
3-(6-chloropyridin-3-yl)-N,N-diethyl-1,4-dihydroindeno[1,2-c]pyrazol-6-amine;
5-[6-(diethylamino)-1,4-dihydroindeno[1,2-c]pyrazol-3-yl]pyridine-2-carbonitrile;
4-{5-[6-(diethylamino)-1,4-dihydroindeno[1,2-c]pyrazol-3-yl]pyridin-2-yl}-2-methoxyphenol;
5-{6-[(3-methylcyclohexyl)oxy]-1,4-dihydroindeno[1,2-c]pyrazol-3-yl}pyridine-2-carbonitrile;
5-[6-(cyclohexylmethoxy)-1,4-dihydroindeno[1,2-c]pyrazol-3-yl]pyridine-2-carbonitrile;
5-[6-(pyridin-2-ylmethoxy)-1,4-dihydroindeno[1,2-c]pyrazol-3-yl]pyridine-2-carbonitrile;
5-[6-(2-pyridin-2-ylethoxy)-1,4-dihydroindeno[1,2-c]pyrazol-3-yl]pyridine-2-carbonitrile;
5-(6-{2-[4-(dimethylamino)phenyl]ethoxy}-1,4-dihydroindeno[1,2-c]pyrazol-3-yl)pyridine-2-carbonitrile;
5-{6-[(4-hydroxycyclohexyl)oxy]-1,4-dihydroindeno[1,2-c]pyrazol-3-yl}pyridine-2-carbonitrile;
5-{6-[2-(4-methyl-1,3-thiazol-5-yl)ethoxy]-1,4-dihydroindeno[1,2-c]pyrazol-3-yl}pyridine-2-carboxamide;
5-[6-(2-hydroxyethyl)-1,4-dihydroindeno[1,2-c]pyrazol-3-yl]pyridine-2-carbonitrile;
5-[6-(difluoromethoxy)-7-methoxy-1,4-dihydroindeno[1,2-c]pyrazol-3-yl]pyridine-2-carbonitrile;
3-(6-chloropyridin-3-yl)-6-(difluoromethoxy)-7-methoxy-1,4-dihydroindeno[1,2-c]pyrazole; and
4-{5-[6-(difluoromethoxy)-7-methoxy-1,4-dihydroindeno[1,2-c]pyrazol-3-yl]pyridin-2-yl}phenol.

3. A pharmaceutical composition comprising a compound of formula (I) or a therapeutically acceptable salt thereof in combination with a therapeutically acceptable carrier.

4. The compound according to claim 1 wherein
$X_1$ and $X_3$ are CH;
$X_2$ is CH($R_7$);
$X_4$ is N;
$X_5$ is C;
$R_1$ is selected from the group consisting of hydrogen, alkoxy, alkyl, hydroxyalkoxy, and hydroxyalkyl;
$R_2$ is selected from the group consisting of alkoxy, alkoxyalkoxyalkynyl, alkyl, haloalkoxyalkynyl, heteroarylalkoxy, heteroarylalkynyl, heteroaryloxyalkyl, heteroaryloxy, heterocyclealkoxy, heterocyclecarbonyl, heterocycleoxy, heterocycleoxyalkyl, hydroxyalkoxy, hydroxalkyl, hydroxyalkynyl, ($NR_AR_B$)alkynyl, and ($NR_AR_B$)carbonyl;
$R_3$ is selected from the group consisting of hydrogen, —$NR_ER_F$, and hydroxyalkyl;
$R_4$ is selected from the group consisting of cyano, halogen, and aryl wherein the aryl is phenyl optionally substituted with 1 or 2 substituents independently selected from alkoxy and hydroxy;
$R_5$ and $R_6$ are hydrogen;
$R_7$ is selected from the group consisting of hydrogen, lower alkoxy, lower alkyl, and hydroxy;
$R_E$ and $R_F$ are independently selected from the group consisting of hydrogen, alkyl, and alkylcarbonyl; and
$R_A$ and $R_B$ are as defined in formula (I).

\* \* \* \* \*

UNITED STATES PATENT AND TRADEMARK OFFICE
CERTIFICATE OF CORRECTION

PATENT NO. : 7,320,986 B2  Page 1 of 7
APPLICATION NO. : 10/792564
DATED : January 22, 2008
INVENTOR(S) : Tong et al.

It is certified that error appears in the above-identified patent and that said Letters Patent is hereby corrected as shown below:

Title Page, item (73), under "Assignee", in Column 1, Line 1, delete "Labortories," and insert -- Laboratories, --.

Column 3, line 39, delete "emobidment," and insert -- embodiment, --.

Column 4, lines 27-28, delete "heteroaryl,hydroxy," and insert -- heteroaryl, hydroxy, --.

Column 8, line 23, delete "heteraryl" and insert -- heteroaryl --.

Column 9, line 62, delete "hydroxalkyl," and insert -- hydroxyalkyl, --.

Column 10, line 14, delete "hydroxalkyl," and insert -- hydroxyalkyl, --.

Column 10, line 32, delete "hydroxalkyl," and insert -- hydroxyalkyl, --.

Column 10, line 52, delete "hydroxalkyl," and insert -- hydroxyalkyl, --.

Column 11, line 4, delete "hydroxalkyl," and insert -- hydroxyalkyl, --.

Column 11, line 24, delete "hydroxalkyl," and insert -- hydroxyalkyl, --.

Column 11, line 43, delete "hydroxalkyl," and insert -- hydroxyalkyl, --.

Column 11, line 63, delete "hydroxalkyl," and insert -- hydroxyalkyl, --.

Column 12, line 15, delete "hydroxalkyl," and insert -- hydroxyalkyl, --.

Column 12, line 35, delete "hydroxalkyl," and insert -- hydroxyalkyl, --.

Column 12, line 53, delete "hydroxalkyl," and insert -- hydroxyalkyl, --.

Signed and Sealed this

Twentieth Day of July, 2010

David J. Kappos
*Director of the United States Patent and Trademark Office*

Column 13, line 6, delete "hydroxalkyl," and insert -- hydroxyalkyl, --.

Column 14, line 18, delete "appended appended" and insert -- appended --.

Column 14, line 24, delete "appended appended" and insert -- appended --.

Column 14, line 33, delete "appended appended" and insert -- appended --.

Column 15, line 46, delete "sulfonyl" and insert -- sulfonyl. --.

Column 15, lines 56-57, delete "4 carboxyphenylmethyl," and insert -- 4-carboxyphenylmethyl, --.

Column 19, line 59, delete "4 piperidinyloxy," and insert -- 4-piperidinyloxy, --.

Column 21, line 30, delete "2-methylamino)" and insert -- 2-(methylamino) --.

Column 24, line 30, delete "yl 1,4'-" and insert -- yl-1,4' --.

Column 25, line 26, delete "controlled;" and insert -- controlled. --.

Column 26, line 35, delete "µM." and insert -- nM. --.

Column 27, line 5, delete "$CH_2$—," and insert -- $CH_2$—; --.

Column 27, line 12, delete "trifluoracetic" and insert -- trifluoroacetic --.

Column 29, line 20, delete "(triphenylphoshine)" and insert -- (triphenylphosphine) --.

Column 29, line 21, delete "(triphenylphoshine)" and insert -- (triphenylphosphine) --.

Column 29, lines 35-36, delete "(triphenylphoshine)" and insert -- (triphenylphosphine) --.

Column 29, line 36, delete "(triphenylphoshine)" and insert -- (triphenylphosphine) --.

Column 30, line 37, delete "Aid," and insert -- acid, --.

Column 31, lines 60-61, delete "1 '-biphenyl" and insert -- 1'-biphenyl --.

Column 32, line 11, delete "et. al.," and insert -- et al., --.

Column 34, line 27, delete "4 carboxybenzene" and insert -- 4-carboxybenzene --.

Column 34, line 50, delete "procudure" and insert -- procedure --.

Column 35, line 23, delete "4-tethylcyclohexylamine" and insert -- 4-methylcyclohexylamine --.

Column 36, line 58, delete "Dynamx" and insert -- Dynamax --.

CERTIFICATE OF CORRECTION (continued)
U.S. Pat. No. 7,320,986 B2

Column 36, line 64, delete "254 nm)." and insert -- 254 nm. --.

Column 38, line 65, delete "2.742.89" and insert -- 2.74-2.89 --.

Column 42, line 45, delete "promixed" and insert -- pre-mixed --.

Column 44, line 29, delete "1,4 dioxane" and insert -- 1,4-dioxane --.

Column 45, line 3, delete "8.038.08" and insert -- 8.03-8.08 --.

Column 45, line 19, delete "D6)" and insert -- $D_6$) --.

Column 45, line 31, delete "2H," and insert -- 2H), --.

Column 45, line 44, delete "D6)" and insert -- $D_6$) --.

Column 49, line 28, delete "1,4 dihydro" and insert -- 1,4-dihydro --.

Column 49, line 56, delete "1H," and insert -- 1H), --.

Column 50, line 5, delete "7.787.88" and insert -- 7.78-7.88 --.

Column 51, line 65, delete "6 bromo" and insert -- 6-bromo --.

Column 53, line 4, delete "2H," and insert -- 2H), --.

Column 55, line 20, delete "1H," and insert -- 1H), --.

Column 56, line 30, delete "neophentylamine" and insert -- neopentylamine --.

Column 57, line 60, delete "pyrazolC3-" and insert -- pyrazol-3- --.

Column 58, line 54, delete "7.167.28" and insert -- 7.16-7.28 --.

Column 60, line 9, delete "mmol))," and insert -- mmol), --.

Column 60, line 27, delete "mmol))," and insert -- mmol), --.

Column 60, line 29, delete "heard" and insert -- heated --.

Column 61, line 41, delete "NaBH" and insert -- $NaBH_4$ --.

Column 64, line 7, delete "C. 18" and insert -- C18 --.

Column 71, line 41, delete "1,4 dioxane" and insert -- 1,4-dioxane --.

Column 72, line 58, delete "(0.22 mL" and insert -- (0.22 mL, --.

CERTIFICATE OF CORRECTION (continued)
U.S. Pat. No. 7,320,986 B2

Column 72, line 62, delete "MgSO$_4$" and insert -- MgSO$_4$, --.

Column 72, line 64, delete "DMSO$_{46}$)" and insert -- DMSO-D$_6$) --.

Column 82, line 7, delete "(2 ML)" and insert -- (2 mL) --.

Column 86, line 43, delete "$^{266.9}$" and insert -- 266.9 --.

Column 106, line 8, delete "3.83 t, t," and insert -- 3.83 (t, --.

Column 106, line 42, delete "concertrate" and insert -- concentrate --.

Column 106, line 66, delete "7.147.31" and insert -- 7.14-7.31 --.

Column 107, line 36, delete "(concentracted," and insert -- (concentrated, --.

Column 111, line 53, delete "2H) H)" and insert -- 2H) --.

Column 124, line 27, delete "carbonyldimidazole" and insert -- carbonyldiimidazole --.

Column 124, line 61, delete "procudure" and insert -- procedure --.

Column 125, line 49, delete "4 iodo" and insert -- 4-iodo --.

Column 126, line 53, delete "yl 1,4'-" and insert -- yl-1,4'- --.

Column 127, line 5, delete "yl 1,4'-" and insert-- yl-1,4'- --.

Column 127, line 20, delete "yl 1,4'-" and insert -- yl-1,4'- --.

Columns 145-146 (Table 11), line 2 (Example 206B), delete "395.7" and insert -- 395.07 --.

Column 151, line 51, delete "±35° C." and insert -- -35° C. --.

Column 151, line 63, delete "PdC$_2$" and insert -- PdCl$_2$ --.

Column 157, line 1, above "EXAMPLE 228A" insert
-- Example 228
4-(6-{[trans(4-hydroxycyclohexyl)amino]methyl}-7-methoxy-1,4-dihydroindeno[1,2-c]
pyrazol-3-yl)benzonitrile --.

Column 157, line 5, delete "trans4" and insert -- trans-4 --.

Column 160, line 16, delete "7.21" and insert -- 7.24 --.

Column 163, line 63, delete "ML)" and insert -- mL) --.

Column 165, line 5, delete "tributylvinyltin" and insert -- tributyl(vinyl)tin --.

Column 174, line 42, delete "concentarted." and insert -- concentrated. --.

Columns 175-176 (Table 14), line 12 (Example 259), delete "9.34 9.34" and insert -- 9.34 --.

Column 182, line 55, delete "pyrolidone" and insert -- pyrrolidone --.

Column 189, line 58, delete "corcentrated" and insert -- concentrated --.

Column 192, line 4, delete "shakenat" and insert -- shaken at --.

Columns 191-192 (Table 17), lines 2-3 (Below Figure), delete "Weight % Yield (%)" and insert -- Weight & Yield (%) --.

Columns 193-194 (Table 17), lines 2-3 (Below Figure), delete "Weight % Yield (%)" and insert -- Weight & Yield (%) --.

Columns 193-194 (Table 17), line 3 (Example 291), delete "2.78 (s, H)" and insert -- 2.78 (s, 3H) --.

Columns 193-194 (Table 17), line 3 (Example 291), delete "m/z 524" and insert -- m/z 497 --.

Columns 195-196 (Table 17), lines 2-3 (Below Figure), delete "Weight % Yield (%)" and insert -- Weight & Yield (%) --.

Columns 197-198 (Table 17), lines 2-3 (Below Figure), delete "Weight % Yield (%)" and insert -- Weight & Yield (%) --.

Column 199, line 65, delete "3.703.77" and insert -- 3.70-3.77 --.

Column 200, line 53, delete "7.807.85" and insert -- 7.80-7.85 --.

Column 201, line 25, delete "Concertrated" and insert -- Concentrated --.

Column 201, line 44, delete "Eethanol" and insert -- Ethanol --.

Column 202, line 19, delete "7.948.00" and insert -- 7.94-8.00 --.

Column 202, line 33, delete "7.948.00" and insert -- 7.94-8.00 --.

Column 203, lines 31-32, delete "18° C." and insert -- 180° C. --.

Column 204, lines 39-40, delete "4 chloromethyl-pyridine" and insert -- 4-chloromethyl-pyridine --.

Column 205, line 18, delete "(s, 1H)" and insert -- (s, 1H). --.

CERTIFICATE OF CORRECTION (continued)
U.S. Pat. No. 7,320,986 B2

Column 205, line 23, delete "yl-" and insert -- yl]- --.

Column 205, line 57, delete "MgSO$_4$" and insert -- MgSO$_4$, --.

Column 206, line 24, delete "7.557.58" and insert -- 7.55-7.58 --.

Column 206, line 40, delete "ml)" and insert -- mL) --.

Column 206, line 55, delete "bezene" and insert -- benzene --.

Column 207, line 46, delete "3.743.82" and insert -- 3.74-3.82 --.

Column 209, line 6, delete "2.612.68" and insert -- 2.61-2.68 --.

Column 209, lines 12-13, delete "dihydroindenol 1," and insert -- dihydroindeno[1, --.

Column 210, line 11, delete "4.464.57" and insert -- 4.46-4.57 --.

Column 210, line 26, delete "pyran-4ol" and insert -- pyran-4-ol --.

Column 210, line 67, delete "N," and insert -- N$_2$, --.

Column 211, line 41, delete "3.843.92" and insert -- 3.84-3.92 --.

Column 212, line 10, delete "M/Z" and insert -- m/z --.

Column 213, line 13, delete "(4 hydroxyphenyl)" and insert -- (4-hydroxyphenyl) --.

Column 213, line 57, delete "4.004.13" and insert -- 4.00-4.13 --.

Column 215, line 13, delete "as" and insert -- was --.

Column 218, line 20, delete "117" and insert -- 1.17 --.

Column 218, line 51, delete "7.868.03" and insert -- 7.86-8.03 --.

Column 219, line 1, delete "7.547.57" and insert -- 7.54-7.57 --.

Column 219, line 16, delete "NaCO$_3$" and insert -- Na$_2$CO$_3$ --.

Column 219, line 38, delete "filtred," and insert -- filtered, --.

Column 221, line 26, delete "3-y)" and insert -- 3-yl) --.

Column 222, line 12, delete "purfied" and insert -- purified --.

CERTIFICATE OF CORRECTION (continued)
U.S. Pat. No. 7,320,986 B2

Column 224, line 56, delete "Then 10 the" and insert -- Then the --.

Column 225, line 52, delete "2, 1'" and insert -- 2,1' --.

Column 226, line 8, delete "$N_2$" and insert -- $N_2$, --.

Column 228, line 39, delete "7.347.52" and insert -- 7.34-7.52 --.

Column 228, line 50, delete "$NaCO_3$" and insert -- $Na_2CO_3$ --.

Column 229, line 64, in claim 1, delete "alkylsulfmyl," and insert -- alkylsulfinyl, --.

Column 230, line 37, in claim 1, delete "$X_4$is" and insert -- $X_4$ is --.

Column 233, line 2, in claim 4, delete "$X_3$are" and insert -- $X_3$ are --.

Column 233, line 13, in claim 4, delete "hydroxalkyl" and insert -- hydroxyalkyl --.